(12) United States Patent
Liu et al.

(10) Patent No.: US 11,459,394 B2
(45) Date of Patent: Oct. 4, 2022

(54) BISPECIFIC BINDING MOLECULES THAT ARE CAPABLE OF BINDING CD137 AND TUMOR ANTIGENS, AND USES THEREOF

(71) Applicant: MacroGenics, Inc., Rockville, MD (US)

(72) Inventors: Liqin Liu, Germantown, MD (US); Chia-Ying Kao Lam, San Jose, CA (US); Gundo Diedrich, North Potomac, MD (US); Leslie S. Johnson, Rockville, MD (US); Paul A. Moore, North Potomac, MD (US); Ezio Bonvini, Potomac, MD (US)

(73) Assignee: MACROGENICS, INC., Rockville, MD (US)

( * ) Notice: Subject to any disclaimer, the term of this patent is extended or adjusted under 35 U.S.C. 154(b) by 31 days.

(21) Appl. No.: 16/488,025

(22) PCT Filed: Feb. 22, 2018

(86) PCT No.: PCT/US2018/019188
§ 371 (c)(1),
(2) Date: Aug. 22, 2019

(87) PCT Pub. No.: WO2018/156740
PCT Pub. Date: Aug. 30, 2018

(65) Prior Publication Data
US 2020/0062854 A1    Feb. 27, 2020

Related U.S. Application Data

(60) Provisional application No. 62/597,594, filed on Dec. 12, 2017, provisional application No. 62/463,353, filed on Feb. 24, 2017.

(51) Int. Cl.
| | | |
|---|---|---|
| C07K 16/28 | (2006.01) | |
| A61P 35/00 | (2006.01) | |
| A61K 39/395 | (2006.01) | |
| A61K 45/06 | (2006.01) | |
| C07K 16/32 | (2006.01) | |
| A61K 39/00 | (2006.01) | |

(52) U.S. Cl.
CPC ...... *C07K 16/2878* (2013.01); *A61K 39/3955* (2013.01); *A61K 39/39558* (2013.01); *A61K 45/06* (2013.01); *A61P 35/00* (2018.01); *C07K 16/32* (2013.01); *A61K 2039/505* (2013.01); *C07K 2317/24* (2013.01); *C07K 2317/31* (2013.01); *C07K 2317/35* (2013.01); *C07K 2317/565* (2013.01); *C07K 2317/626* (2013.01); *C07K 2317/73* (2013.01); *C07K 2317/75* (2013.01); *C07K 2317/92* (2013.01); *C07K 2317/94* (2013.01)

(58) Field of Classification Search
CPC ............... C07K 16/2878; C07K 16/32; C07K 2317/35; A61K 39/3955
See application file for complete search history.

(56) References Cited

U.S. PATENT DOCUMENTS

| | | |
|---|---|---|
| 4,816,567 A | 3/1989 | Cabilly et al. |
| 5,624,821 A | 4/1997 | Winter et al. |
| 5,807,715 A | 9/1998 | Morrison et al. |
| 5,821,337 A | 10/1998 | Carter et al. |
| 5,843,749 A | 12/1998 | Maisonpierre et al. |
| 5,866,692 A | 2/1999 | Shitara et al. |
| 5,952,136 A | 9/1999 | Daems et al. |
| 5,997,867 A | 12/1999 | Waldmann et al. |
| 6,054,297 A | 4/2000 | Carter et al. |
| 6,180,377 B1 | 1/2001 | Morgan et al. |

(Continued)

FOREIGN PATENT DOCUMENTS

| | | |
|---|---|---|
| EP | 0519596 A1 | 12/1992 |
| EP | 2158221 A2 | 3/2010 |

(Continued)

OTHER PUBLICATIONS

Rudikoff et al., Single amino acid substitution altering antigen-binding specificity, PNAS, USA, 1982, 79: 1979-1983 (Year: 1982).*

(Continued)

*Primary Examiner* — Peter J Reddig
*Assistant Examiner* — Cheng Lu
(74) *Attorney, Agent, or Firm* — Grant IP, Inc.

(57) ABSTRACT

The present invention is directed to binding molecules that possess one or more epitope-binding sites specific for an epitope of CD137 and one or more epitope-binding sites specific for an epitope of a tumor antigen ("TA") (e.g., a "CD137×TA Binding Molecule"). In one embodiment, such CD137×TA Binding Molecules will be bispecific molecules, especially bispecific tetravalent diabodies, that are composed of two, three, four or more than four polypeptide chains and possessing two epitope-binding sites each specific for an epitope of CD137 and two epitope-binding sites each specific for an epitope of a TA. Alternatively, such CD137×TA Binding Molecules will be bispecific molecules, especially bispecific trivalent binding molecules composed of three or more polypeptide chains and possessing one or two epitope-binding sites each specific for an epitope of CD137 and one or two epitope-binding sites each specific for an epitope of a TA. The CD137×TA Binding Molecules of the invention are capable of simultaneous binding to CD137, and a TA. The invention is directed to pharmaceutical compositions that contain any such CD137×TA Binding Molecules. The invention is additionally directed to methods for the use of such molecules in the treatment of cancer and other diseases and conditions. The invention also provides novel CD137-binding molecules, and HER2/neu-binding molecules, as well as derivatives thereof and uses thereof.

8 Claims, 48 Drawing Sheets

Specification includes a Sequence Listing.

(56) References Cited

U.S. PATENT DOCUMENTS

| | | |
|---|---|---|
| 6,277,375 B1 | 8/2001 | Ward |
| 6,331,415 B1 | 12/2001 | Cabilly et al. |
| 6,803,192 B1 | 10/2004 | Chen |
| 7,083,784 B2 | 8/2006 | Dall'Acqua et al. |
| 7,101,976 B1 | 9/2006 | Kilpatrick et al. |
| 7,112,324 B1 | 9/2006 | Dorken et al. |
| 7,148,038 B2 | 12/2006 | Mather |
| 7,192,698 B1 | 3/2007 | Kinch et al. |
| 7,217,797 B2 | 5/2007 | Hinton et al. |
| 7,405,061 B2 | 7/2008 | Mather et al. |
| 7,488,802 B2 | 2/2009 | Collins et al. |
| 7,521,051 B2 | 4/2009 | Collins et al. |
| 7,527,969 B2 | 5/2009 | Mather et al. |
| 7,569,672 B2 | 8/2009 | Mather et al. |
| 7,572,895 B2 | 8/2009 | Mather et al. |
| 7,572,896 B2 | 8/2009 | Mather et al. |
| 7,666,424 B2 | 2/2010 | Cheung et al. |
| 7,737,258 B2 | 6/2010 | Cheung |
| 7,740,845 B2 | 6/2010 | Cheung |
| 7,794,710 B2 | 9/2010 | Chen et al. |
| 7,892,554 B2 | 2/2011 | Marks et al. |
| 8,008,449 B2 | 8/2011 | Korman et al. |
| 8,044,180 B2 | 10/2011 | Koenig et al. |
| 8,084,249 B2 | 12/2011 | Kingsman et al. |
| 8,088,376 B2 | 1/2012 | Chamberlain et al. |
| 8,088,905 B2 | 1/2012 | Collins et al. |
| 8,133,982 B2 | 3/2012 | Johnson et al. |
| 8,137,667 B2 | 3/2012 | Jure-Kunkel et al. |
| 8,148,154 B2 | 4/2012 | Cheung et al. |
| 8,173,424 B2 | 5/2012 | Marks et al. |
| 8,187,593 B2 | 5/2012 | Koenig et al. |
| 8,193,318 B2 | 6/2012 | Koenig et al. |
| 8,337,850 B2 | 12/2012 | Ahrens et al. |
| 8,350,011 B2 | 1/2013 | Cartlidge et al. |
| 8,354,509 B2 | 1/2013 | Carven et al. |
| 8,409,577 B2 | 4/2013 | Thompson et al. |
| 8,414,892 B2 | 4/2013 | Cheung |
| 8,460,927 B2 | 6/2013 | Chen |
| 8,501,471 B2 | 8/2013 | Cheung |
| 8,530,627 B2 | 9/2013 | Koenig et al. |
| 8,552,154 B2 | 10/2013 | Freeman et al. |
| 8,609,089 B2 | 12/2013 | Langermann et al. |
| 8,669,349 B2 | 3/2014 | Johnson et al. |
| 8,759,495 B2 | 6/2014 | Boghaert et al. |
| 8,778,339 B2 | 7/2014 | Tuaillon et al. |
| 8,779,098 B2 | 7/2014 | Mather et al. |
| 8,779,105 B2 | 7/2014 | Korman et al. |
| 8,779,108 B2 | 7/2014 | Queva et al. |
| 8,784,808 B2 | 7/2014 | Johnson et al. |
| 8,795,667 B2 | 8/2014 | Johnson et al. |
| 8,802,091 B2 | 8/2014 | Johnson et al. |
| 8,802,093 B2 | 8/2014 | Johnson et al. |
| 8,858,942 B2 | 10/2014 | Cartlidge et al. |
| 8,900,587 B2 | 12/2014 | Carven et al. |
| 8,946,387 B2 | 2/2015 | Koenig et al. |
| 8,968,730 B2 | 3/2015 | Koenig et al. |
| 8,974,792 B2 | 3/2015 | Marks et al. |
| 8,981,063 B2 | 3/2015 | Chen |
| 8,993,730 B2 | 3/2015 | Johnson et al. |
| 9,062,110 B2 | 6/2015 | Cheung |
| 9,062,112 B2 | 6/2015 | Chen |
| 9,084,776 B2 | 7/2015 | Korman et al. |
| 9,273,135 B2 | 3/2016 | Korman et al. |
| 9,617,338 B1 | 4/2017 | Campbell et al. |
| 2002/0147311 A1 | 10/2002 | Gillies et al. |
| 2003/0105000 A1* | 6/2003 | Pero ............... C07K 14/47 514/19.3 |
| 2003/0223989 A1 | 12/2003 | Pluenneke |
| 2004/0058400 A1 | 3/2004 | Holliger et al. |
| 2004/0220388 A1 | 11/2004 | Mertens et al. |
| 2005/0013811 A1 | 1/2005 | Chen et al. |
| 2005/0059051 A1 | 3/2005 | Chen |
| 2006/0121030 A1 | 6/2006 | Schwarz et al. |
| 2006/0166291 A1 | 7/2006 | Mather et al. |
| 2006/0172349 A1 | 8/2006 | Mather et al. |
| 2006/0172350 A1 | 8/2006 | Mather et al. |
| 2006/0182744 A1 | 8/2006 | Strome et al. |
| 2006/0188439 A1 | 8/2006 | Strome et al. |
| 2007/0004909 A1 | 1/2007 | Johnson et al. |
| 2007/0148164 A1 | 6/2007 | Farrington et al. |
| 2008/0019905 A9 | 1/2008 | Strome et al. |
| 2008/0166336 A1 | 7/2008 | Pluenneke |
| 2009/0055944 A1 | 2/2009 | Korman et al. |
| 2009/0060910 A1 | 3/2009 | Johnson et al. |
| 2009/0081239 A1 | 3/2009 | Staunton et al. |
| 2009/0274666 A1 | 11/2009 | Chen |
| 2009/0313687 A1 | 12/2009 | Popp et al. |
| 2010/0143245 A1 | 6/2010 | Cheung |
| 2010/0174053 A1 | 7/2010 | Johnson et al. |
| 2011/0081347 A1 | 4/2011 | Gorlatov |
| 2011/0097313 A1 | 4/2011 | Schonbrunn et al. |
| 2011/0097323 A1 | 4/2011 | Johnson et al. |
| 2011/0104049 A1 | 5/2011 | Strome et al. |
| 2011/0117089 A1 | 5/2011 | Johnson et al. |
| 2012/0009186 A1 | 1/2012 | Koenig et al. |
| 2012/0034221 A1 | 2/2012 | Bonvini et al. |
| 2012/0058047 A9 | 3/2012 | Strome et al. |
| 2012/0141476 A1 | 6/2012 | Johnson et al. |
| 2012/0294796 A1 | 11/2012 | Johnson et al. |
| 2013/0017114 A1 | 1/2013 | Nakamura et al. |
| 2013/0071403 A1 | 3/2013 | Rolland et al. |
| 2013/0078234 A1 | 3/2013 | Takahashi et al. |
| 2013/0149236 A1 | 6/2013 | Johnson et al. |
| 2013/0273078 A1 | 10/2013 | Rolland et al. |
| 2013/0280265 A1 | 10/2013 | Rolland et al. |
| 2013/0295121 A1 | 11/2013 | Johnson et al. |
| 2014/0017237 A1 | 1/2014 | Johnson et al. |
| 2014/0044738 A1 | 2/2014 | Langermann et al. |
| 2014/0099318 A1 | 4/2014 | Huang et al. |
| 2014/0274909 A1 | 9/2014 | Orentas et al. |
| 2014/0328750 A1 | 11/2014 | Johnson et al. |
| 2014/0328836 A1 | 11/2014 | Johnson et al. |
| 2014/0356363 A1 | 12/2014 | Zhou et al. |
| 2015/0197571 A1 | 7/2015 | Freeman et al. |
| 2015/0203579 A1 | 7/2015 | Papadopoulos et al. |
| 2016/0075782 A1 | 3/2016 | Korman et al. |
| 2016/0130360 A1 | 5/2016 | Johnson et al. |
| 2016/0159905 A1 | 6/2016 | Abdiche et al. |
| 2016/0257761 A1 | 9/2016 | Koenig et al. |
| 2016/0319019 A1 | 11/2016 | Amirina et al. |
| 2017/0044259 A1 | 2/2017 | Tipton et al. |
| 2017/0081424 A1 | 3/2017 | Bernett et al. |
| 2017/0319690 A1 | 11/2017 | Wang et al. |

FOREIGN PATENT DOCUMENTS

| | | |
|---|---|---|
| EP | 1868650 A4 | 12/2010 |
| EP | 2328934 A1 | 6/2011 |
| EP | 2376109 A1 | 10/2011 |
| EP | 2601216 A1 | 6/2013 |
| EP | 2714079 A2 | 4/2014 |
| EP | 2839842 A1 | 2/2015 |
| EP | 2840091 A1 | 2/2015 |
| EP | 2998319 A1 | 3/2016 |
| EP | 2252631 B1 | 4/2016 |
| EP | 2247304 B1 | 5/2016 |
| EP | 2282770 B1 | 3/2018 |
| EP | 2714733 B1 | 1/2019 |
| EP | 2786762 B1 | 1/2019 |
| EP | 2542256 B1 | 5/2019 |
| JP | 2013-534809 A | 9/2013 |
| JP | 2016-518368 A | 6/2016 |
| KR | 2004-0083918 A | 10/2004 |
| TW | 201632559 A | 9/2016 |
| WO | WO 91/03493 A1 | 3/1991 |
| WO | WO 92/22583 A2 | 12/1992 |
| WO | WO 98/02463 A1 | 1/1998 |
| WO | WO 98/23289 A1 | 6/1998 |
| WO | WO 99/55367 A1 | 11/1999 |
| WO | WO 01/00245 A2 | 1/2001 |
| WO | WO 01/36005 A2 | 5/2001 |
| WO | WO 01/39722 A2 | 6/2001 |
| WO | WO 02/02781 A1 | 1/2002 |
| WO | WO 02/14870 A2 | 2/2002 |

(56) References Cited

FOREIGN PATENT DOCUMENTS

| | | |
|---|---|---|
| WO | WO 02/086083 A2 | 10/2002 |
| WO | WO 03/012069 A2 | 2/2003 |
| WO | WO 03/024191 A2 | 3/2003 |
| WO | WO 03/025018 A2 | 3/2003 |
| WO | WO 03/032814 A2 | 4/2003 |
| WO | WO 03/087340 A2 | 10/2003 |
| WO | WO 03/093443 A2 | 11/2003 |
| WO | WO 03/094859 A2 | 11/2003 |
| WO | WO 2004/001381 A2 | 12/2003 |
| WO | WO 2004/043239 A2 | 5/2004 |
| WO | WO 2004/056875 A1 | 7/2004 |
| WO | WO 2005/028498 A2 | 3/2005 |
| WO | 2005/035584 A1 | 4/2005 |
| WO | WO 2005/070966 A2 | 8/2005 |
| WO | WO 2005/121179 A2 | 12/2005 |
| WO | WO 2006/076584 A2 | 7/2006 |
| WO | WO 2006/083852 A2 | 8/2006 |
| WO | WO 2006/084075 A2 | 8/2006 |
| WO | WO 2006/084078 A2 | 8/2006 |
| WO | WO 2006/084092 A2 | 8/2006 |
| WO | WO 2006/084226 A2 | 8/2006 |
| WO | WO 2006/107617 A2 | 10/2006 |
| WO | WO 2006/107786 A2 | 10/2006 |
| WO | WO 2006/113665 A2 | 10/2006 |
| WO | WO 2006/121168 A1 | 11/2006 |
| WO | WO 2007/024715 A2 | 3/2007 |
| WO | WO 2007/046893 A2 | 4/2007 |
| WO | WO 2007/075270 A2 | 7/2007 |
| WO | WO 2007/106744 A2 | 9/2007 |
| WO | WO 2007/146968 A2 | 12/2007 |
| WO | WO 2008/003103 A2 | 1/2008 |
| WO | WO 2008/003116 A2 | 1/2008 |
| WO | WO 2008/019290 A2 | 2/2008 |
| WO | WO 2008/024188 A2 | 2/2008 |
| WO | WO 2008/027236 A2 | 3/2008 |
| WO | WO 2008/116219 A2 | 9/2008 |
| WO | WO 2008/156712 A1 | 12/2008 |
| WO | WO 2008/157379 A2 | 12/2008 |
| WO | WO 2009/018386 A1 | 2/2009 |
| WO | WO 2009/058492 A2 | 5/2009 |
| WO | WO 2009/132876 A1 | 11/2009 |
| WO | WO 2010/027797 A1 | 3/2010 |
| WO | WO 2010/028795 A1 | 3/2010 |
| WO | WO 2010/028796 A1 | 3/2010 |
| WO | WO 2010/028797 A1 | 3/2010 |
| WO | WO 2010/033279 A2 | 3/2010 |
| WO | WO 2010/080538 A1 | 7/2010 |
| WO | WO 2010/108127 A1 | 9/2010 |
| WO | WO 2010/136172 A1 | 12/2010 |
| WO | WO 2011/034660 A1 | 3/2011 |
| WO | 2011/071871 A1 | 6/2011 |
| WO | WO 2011/086091 A1 | 7/2011 |
| WO | WO 2011/109400 A2 | 9/2011 |
| WO | WO 2011/133886 A2 | 10/2011 |
| WO | 2011/147982 A2 | 12/2011 |
| WO | WO 2011/147986 A1 | 12/2011 |
| WO | WO 2012/009544 A2 | 1/2012 |
| WO | WO 2012/018687 A1 | 2/2012 |
| WO | 2012/032433 A1 | 3/2012 |
| WO | WO 2012/135408 A1 | 10/2012 |
| WO | WO 2012/145493 A1 | 10/2012 |
| WO | WO 2012/145549 A1 | 10/2012 |
| WO | WO 2012/147713 A1 | 11/2012 |
| WO | WO 2012/156430 A1 | 11/2012 |
| WO | WO 2012/162067 A2 | 11/2012 |
| WO | WO 2012/162068 A2 | 11/2012 |
| WO | WO 2012/162583 A1 | 11/2012 |
| WO | WO 2013/003652 A1 | 1/2013 |
| WO | WO 2013/006544 A1 | 1/2013 |
| WO | WO 2013/014668 A1 | 1/2013 |
| WO | WO 2013/026835 A1 | 2/2013 |
| WO | WO 2013/041687 A1 | 3/2013 |
| WO | WO 2013/070565 A1 | 5/2013 |
| WO | WO 2013/079174 A1 | 6/2013 |
| WO | WO 2013/119903 A1 | 8/2013 |
| WO | WO 2013/158856 A2 | 10/2013 |
| WO | WO 2013/163427 A1 | 10/2013 |
| WO | WO 2013/174873 A1 | 11/2013 |
| WO | WO 2014/022540 A1 | 2/2014 |
| WO | WO 2014/047231 A1 | 3/2014 |
| WO | WO 2014/055897 A2 | 4/2014 |
| WO | WO 2014/110601 A1 | 7/2014 |
| WO | WO 2014/131711 A1 | 9/2014 |
| WO | WO 2014/137931 A1 | 9/2014 |
| WO | WO 2014/159940 A1 | 10/2014 |
| WO | WO 2014/179664 A2 | 11/2014 |
| WO | WO 2014/194302 A2 | 12/2014 |
| WO | WO 2015/021089 A1 | 2/2015 |
| WO | WO 2015/026892 A1 | 2/2015 |
| WO | WO 2015/026894 A2 | 2/2015 |
| WO | WO 2015/109124 A2 | 7/2015 |
| WO | WO 2015/112800 A1 | 7/2015 |
| WO | WO 2015/112805 A1 | 7/2015 |
| WO | WO 2015/184203 A1 | 12/2015 |
| WO | WO 2016/000619 A1 | 1/2016 |
| WO | WO 2016/007235 A1 | 1/2016 |
| WO | WO 2016/014688 A2 | 1/2016 |
| WO | WO 2016/022939 A1 | 2/2016 |
| WO | WO 2016/036937 A1 | 3/2016 |
| WO | WO 2016/048938 A1 | 3/2016 |
| WO | WO 2016/061142 A1 | 4/2016 |
| WO | WO 2016/073860 A1 | 5/2016 |
| WO | WO 2016/077397 A2 | 5/2016 |
| WO | WO 2016/111645 A1 | 7/2016 |
| WO | WO 2016/115274 A1 | 7/2016 |
| WO | 2016/134358 A1 | 8/2016 |
| WO | 2016/177802 A1 | 11/2016 |
| WO | WO 2016/182751 A1 | 11/2016 |
| WO | 2016/200782 A1 | 12/2016 |
| WO | WO 2016/210262 A1 | 12/2016 |
| WO | WO 2017/019846 A1 | 2/2017 |
| WO | WO 2017/021893 A1 | 2/2017 |
| WO | WO 2017/030926 A1 | 2/2017 |
| WO | WO 2017/079112 A1 | 5/2017 |
| WO | WO 2017/087547 A1 | 5/2017 |
| WO | WO 2017/091656 A1 | 6/2017 |
| WO | WO 2017/106656 A1 | 6/2017 |
| WO | WO 2017/118675 A1 | 7/2017 |
| WO | WO 2017/123650 A2 | 7/2017 |
| WO | WO 2017/142928 A1 | 8/2017 |
| WO | WO 2017/180913 A2 | 10/2017 |
| WO | WO 2017/220990 A1 | 12/2017 |
| WO | WO 2018/056821 A1 | 3/2018 |
| WO | WO 2018/156740 A1 | 8/2018 |
| WO | WO 2019/025545 A1 | 2/2019 |
| WO | WO 2019/072868 A1 | 4/2019 |
| WO | WO 2019/072870 A1 | 4/2019 |
| WO | WO 2019/104716 A1 | 6/2019 |
| WO | WO 2019/182878 A1 | 9/2019 |

OTHER PUBLICATIONS

Abaza et al., Effects of Amino Acid Substitutions Outside an Antigenic Site on Protein Binding to Monoclonal Antibodies of Predetermined Specificity Obtained by Peptide Immunization, Journal of Protein Chemistry, vol. 11, No. 5, 1992, pp. 433-444 (Year: 1992).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*
"International Preliminary Report on Patentability dated Sep. 6, 2019 in International Patent Application No. PCT/US2018/019188, filed on Feb. 22, 2018", 10 pages.
"International Search Report and Written Opinion dated Jun. 29, 2018 in International Patent Application No. PCT/US2018/019188, filed on Feb. 22, 2018", 14 pages.
"WHO Drug Information", Recommended International Nonproprietary Names: List 72, 2014, 28(3):407.
"WHO Drug Information", Recommended International Nonproprietary Names: List 62, 2009, 23(3):240-241.

(56) References Cited

OTHER PUBLICATIONS

"WHO Drug Information", Recommended International Nonproprietary Names: List 116, 2016, 30(4):627-629.
"WHO Drug Information", Recommended International Nonproprietary Names: List 74, 2015, 29(3):387.
"WHO Drug Information", Recommended International Nonproprietary Names: List 74, 2015, 29(3):393-394.
"WHO Drug Information", Recommended International Nonproprietary Names: List 74, 2016, 30(1):100-101.
"WHO Drug Information", Recommended International Nonproprietary Names: List 69, 2013, 27(1):68-69.
"WHO Drug Information", Recommended International Nonproprietary Names: List 71, 2014, 28(1):93-94.
Abdulghani, et al., "TRAIL Receptor Signaling and Therapeutics", Expert Opinion on Therapeutic Targets, Oct. 2010, 14(10):1091-1108.
Adenis, et al., "Inhibitors of Epidermal Growth Factor Receptor and Colorectal Cancer", Bull Cancer, 2003, 90:S228-S232.
Adkins, et al., "Edrecolomab (Monoclonal Antibody 17-1A)", Drugs, Oct. 1998, 56(4):619-626.
Akcakanat, et al., "Heterogeneous Expression of GAGE, NY-ESO-1, MAGE-A and SSX Proteins in Esophageal Cancer: Implications for Immunotherapy", International Journal of Cancer, Jan. 1, 2006, 118(1):123-128.
Almqvist, "In Vitro and In Vivo Characterization of 177Lu-huA33 a Radioimmunoconjugate Against Colorectal Cancer", Nuclear Medicine and Biology, Nov. 2006, 33(8):991-998.
Alt, et al., "Novel Tetravalent and Bispecific IgG-Like Antibody Molecules Combining Single-Chain Diabodies With the Immunoglobin Gamma 1 Fc or CH3 Region", FEBS Letters, 1999, 454(1-2):90-94.
Andera, L., "Signaling Activated by the Death Receptors of the TNFR Family", Biomedical papers of the Medical Faculty of the University Palacky, Olomouc, Czechoslovakia, 2009, 153(3):173-180.
Asano, et al., "A Diabody for Cancer Immunotherapy and its Functional Enhancement by Fusion of Human Fc Domain", Abstract 3P-683, Journal of Biochemistry, 2004, 76(8):992.
Atwell, et al., "Stable Heterodimers from Remodeling the Domain Interface of a Homodimer Using a Phage Display Library", Journal of Molecular Biology, 1997, 270:26-35.
Baeuerle, et al., "Bispecific T-Cell Engaging Antibodies for Cancer Therapy", Cancer Research, 2009, 69(12):4941-4944.
Bartkowiak, et al., "4-1 BB Agonists: Multi-Potent Potentiators of Tumor Immunity", Frontiers in Oncology, 2015, 5(117):1-16.
Bast, et al., "New Tumor Markers: CA125 and Beyond", International Journal of Gynecological Cancer, Nov.-Dec. 2005, 15(3):274-281.
Bataille, et al., "The Phenotype of Normal, Reactive and Malignant Plasma Cells. Identification of "Many and Multiple Myelomas" and of New Targets for Myeloma Therapy", Haematologica, Sep. 2006, 91(9):1234-1240.
Bedzyk, et al., "Comparison of Variable Region Primary Structures Within an Anti-Fluorescein Idiotype Family", Journal of Biological Chemistry, 1989, 264(3):1565-1569.
Berezhnoy, et al., "Converting PD-L1-induced T-lymphocyte inhibition into CD137-mediated costimulation via PD-L1×CD137 bispecific DART® molecules", European Journal of Cancer, ENA Abstract 216, 2018, 1 page.
Berezhnoy, et al., "Converting PD-L1-induced T-lymphocyte Inhibition into CD137-mediated Costimulation via PD-L1×CD137 Bispecific DART® Molecules", Presented at the 30th EORTC/AACR/NCI Symposium, Dublin, Ireland, Nov. 13-16, 2018.
Berezhnoy, et al., "Tumor-targeted T-cell Activation via an Investigational PD-L1×CD137 Bispecific Molecule", SITC 2019 Abstract, Nov. 2019, 2 pages.
Berezhnoy, et al., "Tumor-targeted T-cell Activation via an Investigational PD-L1×CD137 Bispecific Molecule", Poster Presented at the Society for Immunotherapy of Cancer's (SITC) 34th Annual Meeting, National Harbor, MD, Nov. 6-10, 2019, 01 page.

Bhattacharya-Chatterjee, et al., "Idiotype vaccines against human T cell leukemia. II. Generation and characterization of a monoclonal idiotype cascade (Ab1, Ab2, and Ab3)", The Journal of Immunology, Aug. 15, 1988, 141(4):1398-1403.
Blumenthal, et al., "Expression Patterns of CEACAM5 and CEACAM6 in Primary and Metastatic Cancers", BMC Cancer, 2007, 7(2):15 pages.
Bodey, B., "Cancer-Testis Antigens: Promising Targets for Antigen Directed Antineoplastic Immunotherapy", Expert Opinion on Biological Therapy, 2002, 2(6):577-584.
Bodhinayake, et al., "Targeting a Heterogeneous Tumor: The Promise of the Interleukin-13 Receptor A2", Neurosurgery, Aug. 2014, 75(2):N18-N19.
Boghaert, et al., "The Oncofetal Protein, 5T4, Is a Suitable Target for Antibody-Guided Anti-Cancer Chemotherapy with Calicheamicin", International Journal of Oncology, Jan. 2008, 32(1):221-234.
Brown, et al., "Tumor-Specific Genetically Engineered Murine-Human Chimeric Monoclonal Antibody", Cancer Research, 1987, 47(13):3577-3583.
Calin, et al., "Genomics of Chronic Lymphocytic Leukemia MicroRNAs as New Players with Clinical Significance", Seminars in Oncology, May 2006, 33(2):167-173.
Cambier, et al., "M19 Modulates Skeletal Muscle Differentiation and Insulin Secretion in Pancreatic β-Cells through Modulation of Respiratory Chain Activity", PLOS One, Feb. 2012, 7(2):11 pages.
Cameron, et al., "Focal overexpression of CEACAM6 contributes to enhanced tumourigenesis in head and neck cancer via suppression of apoptosis", Molecular Cancer, Sep. 2012, 11(74):11 pages.
Cang, et al., "Novel CD20 Monoclonal Antibodies for Lymphoma Therapy", Journal of Hematology & Oncology, Oct. 11, 2012, 5(64):9 pages.
Cao, et al., "Bispecific Antibody Conjugates in Therapeutics", Advanced Drug Delivery Reviews, 2003, 55(2):171-197.
Carlo-Stella, et al., "Targeting TRAIL Agonistic Receptors for Cancer Therapy", Clinical Cancer Research, Apr. 2007, 13(8):2313-2317.
Carter, et al., "Humanization of an Anti-p185her2 Antibody for Human Cancer Therapy", Proceedings of the National Academy of Sciences, 1992, 89:4285-4289.
Castelli, et al., "T-Cell Recognition of Melanoma-Associated Antigens", Journal of Cellular Physiology, Mar. 2000, 182(3):323-331.
Castillo, et al., "Newer Monoclonal Antibodies for Hematological Malignancies", Experimental Hematology, 2008, 36(7):755-768.
Chan, et al., "The Use of Antibodies in the Treatment of Infectious Diseases", Singapore Medical Journal, 2009, 50(7):663-666.
Chapin, et al., "Distribution and Surfactant Association of Carcinoembryonic Cell Adhesion Molecule 6 in Human Lung", American Journal of Physiology—Lung Cellular and Molecular Physiology, Jan. 15, 2012, 302(2):L216-L225.
Chaudhari, et al., "Following the TRAIL to Apoptosis", Immunologic Research, 2006, 35(3):249-262.
Chen, et al., "EphA2 Enhances the Proliferation and Invasion Ability of LnCap Prostate Cancer Cells", Oncology Letters, Jul. 2014, 8(1):41-46.
Chen, et al., "Molecular Mechanisms of T-Cell Co-Stimulation and Co-Inhibition", Nature Reviews Immunology, Apr. 2013, 13(4):227-242.
Cheson, et al., "Monoclonal Antibody Therapy for B-Cell Non-Hodgkin's Lymphoma", The New England Journal of Medicine, 2008, 359(6):613-626.
Chichili, et al., "A CD3×CD123 Bispecific DART for Redirecting Host T Cells to Myelogenous Leukemia: Preclinical Activity and Safety in Nonhuman Primates", Science Translational Medicine, 2015, 7(289):14 pages.
Chothia, et al., "Canonical Structures for the Hypervariable Regions of Immunoglobulins", Journal of Molecular Biology, 1987, 196:901-917.
Chu, et al., "CD79: A Review", Applied Immunohistochemistry Molecular Morphology, 2001,9(2):97-106.
Chu, et al., "Nonviral Oncogenic Antigens and the Inflammatory Signals Driving Early Cancer Development as Targets for Cancer Immunoprevention", Clinical Cancer Research, Apr. 1, 2015, 21(7):1549-1557.

(56) References Cited

OTHER PUBLICATIONS

Co, et al., "Chimeric and Humanized Antibodies with Specificity for the CD33 Antigen", The Journal of Immunology, 1992, 148(4):1149-1154.
Co, et al., "Humanized Antibodies for Antiviral Therapy", Proceedings of the National Academy of Sciences, 1991,88:2869-2873.
Cracco, et al., "Immune Response in Prostate Cancer", Minerva Urologica e Nefrologica, Dec. 2005, 57(4):301-311.
Croft, "The Role of TNF Superfamily Members In T-Cell Function and Diseases", Nature Reviews Immunology, 2009, 9(4):271-285.
Dall'Acqua, et al., "Properties of Human IgG1s Engineered for Enhanced Binding to the Neonatal Fc Receptor (Fcrn)", The Journal of Biological Chemistry, 2006, 281(33):23514-23524.
Dao, et al., "Identification of a Human Cyclin D1-Derived Peptide that Induces Human Cytotoxic CD4 T Cells", PLoS One, Aug. 2009, 4(8):9 pages.
Daugherty, et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.
Davis, et al., "Therapy of B-Cell Lymphoma with Anti-CD20 Antibodies Can Result in the Loss of CD20 Antigen Expression", Clinical Cancer Research, Mar. 1999, 5(3):611-615.
Deng, et al., "Expression Profiling of CEACAM6 Associated with the Tumorigenesis and Progression in Gastric Adenocarcinoma", Genetics and Molecular Research, Sep. 26, 2014, 13(3):7686-7697.
Dennis, et al., "Glycoprotein Glycosylation and Cancer Progression", Biochimica et Biophysica Acta, 1999, 1473(1):21-34.
Dimaio, et al., "Human Papillomaviruses and Cervical Cancer", Advances in Virus Research, 2006, 66:125-159.
Dougall, et al., "The Neu-Oncogene: Signal Transduction pathways, transformation mechanisms and Evolving Therapies", Oncogene, Aug. 1994, 9(8):2109-2123.
Durrant, et al., "Development of an ELISA to Detect Early Local Relapse of Colorectal Cancer", British Journal of Cancer, Oct. 1, 1989, 60(4):533-537.
Edelson, "Cutaneous T-cell lymphoma: a model for selective immunotherapy", The cancer journal from Scientific American, Mar.-Apr. 1998, 4(2):62-71.
Egloff, et al., "Cyclin B1 and other Cyclins as Tumor Antigens in Immunosurveillance and Immunotherapy of Cancer", Cancer Research, Jan. 1, 2006, 66(1):6-9.
Eisen, et al., "Naptumomab Estafenatox: Targeted Immunotherapy with a Novel Immunotoxin", Current Oncology Reports, Feb. 2014, 16(370):6 pages.
Feizi, T., "Demonstration by Monoclonal Antibodies that Carbohydrate Structures of Glycoproteins and Glycolipids are Onco-Developmental Antigens", Nature, Mar. 7-13, 1985, 314(6006):53-57.
Fitzgerald, et al., "Improved Tumour Targeting by Disulphide Stabilized Diabodies Expressed in Pichia pastoris", Protein Engineering, 1997, 10(10):1221-1225.
Flies, et al., "The New B7s: Playing a Pivotal Role in Tumor Immunity", Journal of Immunotherapy, 2007, 30(3):251-260.
Foell, et al., "CD137 Costimulatory T Cell Receptor Engagement Reverses Acute Disease in Lupus-Prone NZBxNZW F1 Mice", The Journal of Clinical Investigation, 2003, 111(10):1505-1518.
Foell, et al., "Engagement of the CD137 (4-1BB) Costimulatory Molecule Inhibits and Reverses the Autoimmune Process in Collagen-Induced Arthritis and Establishes Lasting Disease Resistance", Immunology, 2004, 113(1):89-98.
Gardnerova, et al., "The Use of TNF Family Ligands and Receptors and Agents which Modify their Interaction as Therapeutic Agents", Current Drug Targets, Dec. 2000, 1(4):327-364.
Garratty, G., "Blood Group Antigens as Tumor Markers, Parasitic/Bacterial/Viral Receptors, and Their Association with Immunologically Important Proteins", Immunological Investigations, Jan.-Feb. 1995, 24(1-2):213-232.
Ge, et al., "CD36: A Multiligand Molecule", Laboratory Hematology, 2005, 11(1):31-37.
Gil, et al., "Regulation of the INK4b-ARF-INK4a Tumour Suppressor Locus: All for one or one for all", Nature Reviews Molecular Cell Biology, Sep. 2006, 7(9):667-677.
Gooi, et al., "Monoclonal Antibody Reactive with the Human Epidermal-Growth-Factor Receptor Recognizes the Blood-Group-A Antigen", Bioscience Reports, Nov. 1983, 3(11):1045-1052.
Gorman, et al., "Reshaping a Therapeutic CD4 Antibody", Proceedings of the National Academy of Sciences, 1991, 88:4181-4185.
Greulich, et al., "Functional Analysis of Receptor Tyrosine Kinase Mutations in Lung Cancer Identifies Oncogenic Extracellular Domain Mutations of ERBB2", Proceedings of the National Academy of Sciences, Sep. 4, 2012, 109(36):14476-14481.
Grosjean, H., et al., "Preferential Codon Usage in Prokaryotic Genes: The Optimal Codon-Anticodon Interaction Energy and the Selective Codon Usage in Efficiently Expressed Genes", Gene, Jun. 1982, 18(3):199-209 (Abstract only).
Gruber, et al., "Efficient Tumor Cell Lysis Mediated by a Bispecific Single Chain Antibody Expressed in *Escherichia coli*", Journal of Immunology, 1994, 152(11):5368-5374.
Hakomori, S., "Cancer-Associated Glycosphingolipid Antigens: their Structure, Organization, and Function", Acta Anatomica, 1998, 161(1-4):79-90.
Heath, et al., "The Human A33 Antigen is a Transmembrane Glycoprotein and a Novel Member of the Immunoglobulin Superfamily", Proceedings of the National Academy of Sciences, Jan. 21, 1997, 94(2):469-474.
Hellstrom, et al., "Monoclonal Antibodies to Cell Surface Antigens Shared by Chemically Induced Mouse Bladder Carcinomas", Cancer Research, May 1985, 45:2210-2218.
Hellstrom, et al., "Monoclonal Mouse Antibodies Raised against Human Lung Carcinoma", Cancer Research, Aug. 1986, 46(8):3917-3923.
Herlyn, et al., "Monoclonal Antibody Detection of a Circulating Tumor-Associated Antigen. I. Presence of Antigen in Sera of Patients with Colorectal, Gastric, and Pancreatic Carcinoma", Journal of Clinical Immunology, Apr. 1982, 2(2):135-140.
Hernandez-Chacon, et al., "Costimulation Through the CD137/4-1BB Pathway Protects Human Melanoma Tumor-Infiltrating Lymphocytes from Activation-Induced Cell Death and Enhances Antitumor Effector Function," Journal of Immunotherapy, 2011, 34(3):236-250.
Hoelzer, D., "Targeted Therapy with Monoclonal Antibodies in Acute Lymphoblastic Leukemia", Current Opinion in Oncology, Nov. 2013, 25(6):701-706.
Hofmeyer, et al., "The Contrasting Role of B7-H3", Proceedings of the National Academy of Sciences of the United States of America, Jul. 29, 2008, 105(30):10277-10278.
Hogg, et al., "A Monoclonal Antibody Exhibiting Reactivity with both X-Hapten- and Lactose-Bearing Glycolipids", Tissue Antigens, Jan. 1991, 37(1):33-38.
Holliger, et al., "Carcinoembryonic Antigen (CEA)-specific T-Cell Activation in Colon Carcinoma Induced by Anti-CD3xAnti-CEA Bispecific Diabodies and B7xAnti-CEA Bispecific Fusion Proteins", Cancer Research, 1999, 59(12):2909-2916.
Holliger, et al., "'Diabodies': Small Bivalent and Bispecific Antibody Fragments", Proceedings of the National Academy of Sciences, 1993, 90:6444-6448.
Holliger, et al., "Specific Killing of Lymphoma Cells by Cytotoxic T-Cells Mediated by a Bispecific Diabody", Protein Engineering, 1996, 9(3):299-305.
Holmberg, et al., "Theratope Vaccine (STn-KLH)," Expert Opinion on Biological Therapy, Sep. 2001, 1(5):881-891.
Horssen, et al., "TNF-α in Cancer Treatment: Molecular Insights, Antitumor Effects, and Clinical Utility", Oncologist, Apr. 2006, 11(4):397-408.
Houot, et al., "Boosting Antibody-Dependant Cellular Cytotoxicity Against Tumor Cells with A CD137 Stimulatory Antibody", Oncoimmunology, Sep. 2012, 1:957-958.
Hynes, et al., "The Biology of erbB-2/neu/HER-2 and its Role in Cancer", Biochimica et Biophysica Acta (BBA)—Reviews on Cancer, Dec. 30, 1994, 1198(2-3):165-184.

(56) References Cited

OTHER PUBLICATIONS

Jennings, Veronica M., "Review of Selected Adjuvants Used in Antibody Production", ILAR Journal, 1995, 37(3):119-125.
Johansson, et al., "Structure, Specificity, and Mode of Interaction for Bacterial Albumin-binding Modules", Journal of Biological Chemistry, Mar. 2002, 277(10):8114-8120.
Johnson, et al., "Effector Cell Recruitment with Novel Fv-Based Dual-Affinity Re-Targeting Protein Leads to Potent Tumor Cytolysis and In vivo B-Cell Depletion", Journal of Molecular Biology, 2010, 399(3):436-449.
Jones, et al., "Replacing the Complementarity-Determining Regions in a Human Antibody With Those From a Mouse", Nature, 1986, 321:522-525.
Jurcic, Joseph G., "Immunotherapy for Acute Myeloid Leukemia", Current Oncology Reports, 2005, 7(5):339-346.
Kammer, et al., "Immunotherapy Tackles Lupus", Nature Medicine, 2002, 8(12):1356-1358.
Kettleborough, et al., "Humanization of a Mouse Monoclonal Antibody by CDR-Grafting: The Importance of Framework Residues on Loop Conformation", Protein Engineering, 1991, 4(7):773-783.
Kohler, et al., "Continuous Cultures of Fused Cells Secreting Antibody of Predefined Specificity", Nature, 1975, 256:495-497.
Kohrt, et al., "Targeting CD137 Enhances the Efficacy of Cetuximab", The Journal of Clinical Investigation, Jun. 2014, 124(6):2668-2682.
Kounalakis, et al., "Tumor Cell and Circulating Markers in Melanoma: Diagnosis, Prognosis, and Management", Current Oncology Reports, Sep. 2005, 7(5):377-382.
Kreitman, "Immunotoxins for Targeted Cancer Therapy", The AAPS Journal, Sep. 2006, 8(3):E532-E551.
Kwon, et al., "Cdna Sequences of Two Inducible T-Cell Genes", Proceedings of the National Academy of Sciences, Mar. 1989, 86:1963-1967.
Kwon, Byungsuk, "Is CD137 Ligand (CD137L) Signaling a Fine Tuner of Immune Responses?" Immune Network, Jun. 2015, 15(3):121-124.
Lee, et al., "4-1 BB as a Therapeutic Target for Human Disease", Advances in Experimental Medicine and Biology, 2009, 647:120-129.
Lee, et al., "Requirement for Neuregulin Receptor erbB2 in Neural and Cardiac Development", Nature, Nov. 23, 1995, 378(6555):394-398.
Lee, et al., "Targeting Cyclins and Cyclin-Dependent Kinases in Cancer: Lessons from Mice, Hopes for Therapeutic Applications in Humans", Cell Cycle, Sep. 2006, 5(18):2110-2114.
Lefranc, et al., "Gm, Am and Km immunoglobulin allotypes of two populations in Tunisia", Human Genetics, 1979, 50:199-211.
Lefranc, et al., "Molecular Genetics of Immunoglobulin Allotype Expression", The Human IgG Subclasses: Molecular Analysis of Structure, Function and Regulation, Pergamon Press, 1990, 43-78.
Legendre, et al., "Prognostic Stratification of Dukes B Colon Cancer by a Neoglycoprotein", International Journal of Oncology, Sep. 2004, 25(2):269-276.
Lewis-Wambi, et al., "Overexpression of CEACAM6 promotes migration and invasion of oestrogen-deprived breast cancer cells", European Journal of Cancer, Aug. 2008, 44(12):1770-1779.
Li, et al., "Immunotherapy of Melanoma with the Immune Costimulatory Monoclonal Antibodies Targeting CD137", Clinical Pharmacology, Aug. 30, 2013, 5:47-53.
Lin, et al., "Fc-Dependent Expression of CD137 on Human NK Cells: Insights Into "Agonistic" Effects of Anti-CD137 Monoclonal Antibodies", Blood, 2008, 112(3):699-707.
Livingston, et al., "Selection of GM2, Fucosyl GM1, Globo H and Polysialic Acid as Targets on Small Cell Lung Cancers for Antibody Mediated Immunotherapy", Cancer Immunology Immunotherapy, Oct. 2005, 54(10):1018-1025.
Lobuglio, et al., "Mouse-Human Chimeric Monoclonal Antibody in Man: Kinetics and Immune Response", Proceedings of the National Academy of Sciences, 1989, 86:4220-4224.
Long, et al., "4-1BB Costimulation Ameliorates T Cell Exhaustion Induced by Tonic Signaling of Chimeric Antigen Receptors", Nature Medicine, 2015, 21(6):581-590.
Loo, et al., "Development of an Fc-Enhanced Anti-B7-H3 Monoclonal Antibody with Potent Antitumor Activity", Clinical Cancer Research, Jul. 15, 2012, 18(14):3834-3845.
Lotem, et al., "Presentation of Tumor Antigens by Dendritic Cells Genetically Modified with Viral and Nonviral Vectors", Journal of Immunotherapy, Nov.-Dec. 2006, 29(6):616-627.
Loveless, et al., "Developmental Patterning of the Carbohydrate Antigen FC10.2 during Early Embryogenesis in the Chick", Development, 1990, 108(1):97-106.
Lu, et al., "A Fully Human Recombinant IgG-Like Bispecific Antibody to Both the Epidermal Growth Factor Receptor and the Insulin-Like Growth Factor Receptor for Enhanced Antitumor Activity", Journal of Biological Chemistry, 2005, 280(20):19665-19672.
Maeda, et al., "Construction of Reshaped Human Antibodies With HIV-Neutralizing Activity", Human Antibodies Hybridoma, 1991, 2:124-134.
Malaguarnera, et al., "Serum Markers of Hepatocellular Carcinoma", Digestive Diseases and Sciences, 2010, 55(10):2744-2755.
Mathelin, et al., "Circulating Proteinic Biomarkers and Breast Cancer", Gynecologie, Obstetrique & Fertilite, 2006, 34(7-8):638-646.
Melero, et al., "Monoclonal Antibodies Against The 4-1BB T-Cell Activation Molecule Eradicate Established Tumors", Nature Medicine, 1997, 3(6):682-685.
Melero, et al., "Multi-Layered Action Mechanisms of CD137 (4-1BB)-Targeted Immunotherapies", Trends in Pharmacological Sciences, Aug. 2008, 29(8):383-390.
Messmer, et al., "CD154 Gene Therapy for Human B-Cell Malignancies", Annals of the New York Academy of Sciences, 2005, 1062:51-60.
Miao, et al., "EphA2 is a Mediator of Vemurafenib Resistance and a Novel Therapeutic Target in Melanoma", Cancer Discovery, Mar. 2015, 5(3):274-287.
Mittal, et al., "Tumor-Unrelated CD4 T Cell Help Augments CD134 plus CD137 Dual Costimulation Tumor Therapy", The Journal of Immunology, Dec. 2015, 195(12):5816-5826.
Mittelman, et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies", Journal of Clinical Investigation, Dec. 1990, 86(6):2136-2144.
Mittler, et al., "Anti-CD137 Antibodies in the Treatment of Autoimmune Disease and Cancer", Immunologic Research, 2004, 29(1-3):197-208.
Moller, et al., "Bispecific-Monoclonal-Antibody-Directed Lysis of Ovarian Carcinoma Cells by Activated Human T Lymphocytes", Cancer Immunology, Immunotherapy, 1991, 33(4):210-216.
Moore, et al., "Application of Dual Affinity Retargeting Molecules to Achieve Optimal Redirected T-Cell Killing of B-Cell Lymphoma", Blood, 2011, 117(17):4542-4551.
Morales-Kastresana, et al., "Combinations of Immunostimulatory Antibodies with Synergistic Effects Against Spontaneous Cancer", Oncoimmunology, e27812, 2014, 3(2):04 pages.
Munoz, et al., "Interleukin-3 Receptor Alpha Chain (CD123) is Widely Expressed in Hematologic Malignancies", Haematologica, Dec. 2001, 86(12):1261-1269.
Muramatsu, et al., "Carbohydrate Antigens Expressed on Stem Cells and Early Embryonic Cells", Glycoconjugate Journal, 2004, 21(1-2):41-45.
Muta, et al., "CD30: from Basic Research to Cancer Therapy", Immunologic Research, Dec. 2013, 57(1-3):151-158.
Natali, et al., "Immunohistochemical Detection of Antigen in Human Primary and Metastatic Melanomas by the Monoclonal Antibody 140.240 and its possible Prognostic Significance", Cancer, 1987, 59(1):55-63.
O'Dwyer, P., "The Present and Future of Angiogenesis-Directed Treatments of Colorectal Cancer", Oncologist, Oct. 2006, 11(9):992-998.

(56) References Cited

OTHER PUBLICATIONS

Olafsen, et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.
Pal, et al., "Targeting HER2 Epitopes", Seminars in Oncology, Aug. 2006, 33(4):386-391.
Palma, et al., "Plasmacytoids Dendritic Cells are a Therapeutic Target in Anticancer Immunity", Biochimica et Biophysica Acta (BBA)—Reviews on Cancer, Dec. 2012, 1826(2):407-414.
Peggs, et al., "Principles and Use of Anti-CTLA4 Antibody in Human Cancer Immunotherapy", Current Opinion in Immunology, 2006, 18(2):206-213.
Perez, et al., "Isolation and Characterization of a Cdna Encoding the KS1/4 Epithelial Carcinoma Marker", Journal of Immunology, May 15, 1989, 142(10):3662-3667.
Prange, et al., "Beta-Catenin Accumulation in the Progression of Human Hepatocarcinogenesis Correlates with loss of E-Cadherin and Accumulation of P53, but not with Expression of Conventional WNT-1 Target Genes", The Journal of Pathology, 2003, 201(2):250-259.
Pui, et al., "Characterization of Childhood Acute Leukemia with Multiple Myeloid and Lymphoid Markers at Diagnosis and at Relapse", Blood, Sep. 1991, 78(5):1327-1337.
Qian, et al., "CD137 Ligand-Mediated Reverse Signaling Inhibits Proliferation and Induces Apoptosis in Non-Small Cell Lung Cancer", Medical Oncology, 2015, 32(44):1-10.
Rabbani, et al., "Expression of ROR1 in Patients with Renal Cancer—A Potential Diagnostic Marker", Iranian Biomedical Journal, Jul. 2010, 14(3):77-82.
Ragupathi, et al., "Antibody Inducing Polyvalent Cancer Vaccines", Cancer Treatment and Research, Feb. 2005, 123:157-180.
Ramakrishna, et al., "Characterization of the Human T Cell Response to In Vitro CD27 Costimulation With Varlilumab", Journal for Immunotherapy for Cancer, 2015, 3(37):1-13.
Reff, et al., "Depletion of B Cells In vivo by a Chimeric Mouse Human Monoclonal Antibody to CD20", Blood, Jan. 15, 1994, 83(2):435-445.
Ridgway, et al., "'Knobs-Into-Holes' Engineering of Antibody CH3 Domains for Heavy Chain Heterodimerization", Protein Engineering, 1996, 9(7):617-621.
Riechmann, et al., "Reshaping Human Antibodies for Therapy", Nature, 1988, 332:323-327.
Riley, et al., "Design and Activity of a Murine and Humanized anti-CEACAM6 scFv in the Treatment of Pancreatic Cancer", Cancer research, Mar. 2009, 69(5):1933-1940.
Rimon, et al., "Gonadotropin-Induced Gene Regulation in Human Granulosa Cells Obtained from IVF Patients: Modulation of Genes Coding for Growth Factors and their Receptors and Genes Involved in Cancer and other Diseases", International Journal of Oncology, May 2004, 24(5):1325-1338.
Ritter, et al., "Characterization of Posttranslational Modifications of Human A33 Antigen, a Novel Palmitoylated Surface Glycoprotein of Human Gastrointestinal Epithelium", Biochemical and Biophysical Research Communications, Jul. 30, 1997, 236(3):682-686.
Rosati, et al., "Chronic Lymphocytic Leukaemia: A Review of the Immuno-Architecture", Current Topics in Microbiology and Immunology, 2005, 294:91-107.
Russell, S., "CD46: A Complement Regulator and Pathogen Receptor that Mediates Links Between Innate and Acquired Immune Function", Tissue Antigens, Aug. 2004, 64(2):111-118.
Sallin, et al., "The Anti-Lymphoma Activities of Anti-CD 137 Monoclonal Antibodies Are Enhanced in FcγRIII Mice", Cancer Immunology, Immunotherapy, 2014, 63(9):947-958.
Sánchez-Paulete, et al., "Cancer Immunotherapy with Immunomodulatory Anti-CD137 and Anti-PD-1 Monoclonal Antibodies Requires Batf3-Dependent Dendritic Cells", Cancer Discovery, 2015, 6(1):71-79.
Sanmamed, et al., "Agonists of Co-stimulation in Cancer Immunotherapy Directed Against CD137, OX40, GITR, CD27, CD28, and ICOS", Seminars in Oncology, 2015, 42(4):640-655.
Sato, et al., "Reshaping a Human Antibody to Inhibit the Interleukin 6-dependent Tumor Cell Growth", Cancer Research, 1993, 53:851-856.
Schwarz, et al., "A Receptor Induced by Lymphocyte Activation (ILA): A New Member of the Human Nerve-Growth-Factor/Tumor-Necrosis-Factor Receptor Family", Gene, Dec. 8, 1993, 134(2):295:298.
Seo, et al., "4-1BB-Mediated Immunotherapy of Rheumatoid Arthritis. ", Nature Medicine, 2004, 10:1088-1094.
Shaw, et al., "Characterization of a Mouse-Human Chimeric Monoclonal Antibody (17-1A) to a Colon Cancer Tumor-Associated Antigen", Journal of Immunology, 1987, 138(12):4534-4538.
Shuford, et al., "4-1BB Costimulatory Signals Preferentially Induce CD8+ T Cell Proliferation and Lead to the Amplification In Vivo of Cytotoxic T Cell Responses", Journal of Experimental Medicine, Jul. 1997, 186(1):47-45.
So, et al., "Immune Regulation and Control of Regulatory T Cells by OX40 and 4-1BB", Cytokine & Growth Factor Reviews, 2008, 19(3-4):253-262.
Staerz, et al., "Hybrid Antibodies Can Target Sites for Attack by T Cells", Nature, 1985, 314:628-631.
Stavenhagen, et al., "Fc Optimization of Therapeutic Antibodies Enhances Their Ability to Kill Tumor Cells In Vitro and Controls Tumor Expansion In Vivo Via Low-Affinity Activating Fcgamma Receptors", Cancer Research, 2007, 67(18):8882-8890.
Stomski, et al., "Human interleukin-3 (IL-3) induces disulfide-linked IL-3 receptor alpha-and beta-chain heterodimerization, which is required for receptor activation but not high-affinity binding", Molecular and Cellular Biology, Jun. 1996, 16(6):3035-3046.
Sun, et al., "Costimulatory Molecule-Targeted Antibody Therapy of a Spontaneous Autoimmune Disease", Nature Medicine, 2002, 8:1405-1413.
Sytwu, et al., "Anti-4-1BB-Based Immunotherapy for Autoimmune Diabetes:Lessons From a Transgenic Non-Obese Diabetic (NOD) Model", Journal of Autoimmunity, 2003, 21(3):247-254.
Tailor, et al., "Nucleotide Sequence of Human Prostatic Acid Phosphatase Determined from a Full-Length CDNA Clone", Nucleic Acids Research, 1990, 18(16):1 page.
Takahashi, M., "A Study on Clinical Significance of Oncofetal Antigen-1 in Gynecologic Tumors", Nihon Sanka Fujinka Gakkai Zasshi, Dec. 1984, 36(12):2613-2618 (Abstract only).
Takeda, et al., "Combination Antibody-Based Cancer Immunotherapy", Cancer Science, 2007, 98(9):1297-1302.
Takemura, et al., "Construction of a Diabody (Small Recombinant Bispecific Antibody) Using A Refolding System", Protein Engineering, 2000, 13(8):583-588.
Taussig, et al., "Hematopoietic Stem Cells Express Multiple Myeloid Markers: Implications for the Origin and Targeted Therapy of Acute Myeloid Leukemia", Blood, Dec. 15, 2005, 106(13):4086-4092.
Tedder, "CD19: A Promising B Cell Target for Rheumatoid Arthritis", Nature Reviews Rheumatology, Oct. 2009, 5(10):572-577.
Tellez-Avila, et al., "The carcinoembryonic antigen: apropos of an old friend", Revista de investigacion clinica; organo del Hospital de Enfermedades de la Nutricion, Nov. 2005, 57(6):814-819.
Tempest, et al., "Reshaping a Human Monoclonal Antibody to Inhibit Human Respiratory Syncytial Virus Infection in Vivo", Bio-Technology, 1991, 9:266-271.
Tettamanti, et al., "Targeting of Acute Myeloid Leukaemia by Cytokine-induced Killer Cells Redirected with A Novel CD123-specific Chimeric Antigen Receptor", British Journal of Haematology, May 2013, 161(3):389-401.
Thomas, et al., "Monoclonal Antibody Therapy for Hairy Cell Leukemia", Hematology/Oncology Clinics of North America, Oct. 2006, 20(5):1125-1136.
Thompson, et al., "Carcinoembryonic Antigen Gene Family: Molecular Biology and Clinical Perspectives", Journal of Clinical Laboratory Analysis, 1991, 5(5):344-366.
Thum, et al., "CD137, Implications in Immunity and Potential for Therapy", Frontiers in Bioscience, Jan. 2009, 14:4173-4188.

(56) References Cited

OTHER PUBLICATIONS

Tongu, et al., "Intermittent Chemotherapy Can Retain the Therapeutic Potential of Anti-CD 137 Antibody During the Late Tumor-Bearing State", Cancer Science, 2015, 106(1):9-17.
Troussard, et al., "Hairy Cell Leukemia. What is New Forty Years after the First Description?" Hematology and Cell Therapy, Aug. 1998, 40(4):139-148.
Velázquez-Márquez, et al., "Sialyl Lewis X Expression in Cervical Scrapes of Premalignant Lesions", Journal of Biosciences, Dec. 2012, 37(6):999-1004.
Verhoeyen, et al., "Reshaping Human Antibodies: Grafting an Antilysozyme Activity", Science, 1988, 239:1534-1536.
Veri, et al., "Therapeutic Control of B Cell Activation Via Recruitment of Fcgamma Receptor IIb (CD32B) Inhibitory Function with A Novel Bispecific Antibody Scaffold", Arthritis & Rheumatology, 2010, 62(7):1933-1943.
Vijayasardahl, et al., "The Melanoma Antigen Gp75 is the Human Homologue of the Mouse B (Brown) Locus Gene Product", Journal of Experimental Medicine, Apr. 1, 1990, 171 (4):1375-1380.
Vinay, et al., "Immunotherapy of Cancer with 4-1BB", Molecular Cancer Therapeutics, May 2012, 11(5):1062-1070.
Vinay, et al., "Role of 4-1BB in Immune Responses", Seminars in Immunology, 1998, 10:481-489.
Vinay, et al., "Therapeutic Potential of Anti-CD137 (4-1BB) Monoclonal Antibodies", Expert Opinion on Therapeutic Targets, Oct. 1, 2015, 20(3):361-373.
Walter, et al., "Acute Myeloid Leukemia Stem Cells and CD33-Targeted Immunotherapy", Blood, Jun. 28, 2012, 119(26):6198-6208.
Wang, et al., "Immune Regulation by 4-1BB and 4-1BBL: Complexities and Challenges", Immunological Reviews, 2009, 229:192-215.
Wei, et al., "Dual Targeting of CD137 Co-Stimulatory and PD-1 Co-Inhibitory Molecules for Ovarian Cancer Immunotherapy", Oncoimmunology, e28248, 2014, 3(4):4 pages.
Williams, et al., "Biochemical and Genetic Analysis of the Oka Blood Group Antigen", Immunogenetics, 1988, 27(5):322-329.
Winter, et al., "Man-made Antibodies", Nature, 1991, 349:293-299.
Wong, et al., "EpCAM and gpA33 are markers of Barrett's metaplasia", Journal of Clinical Pathology, Mar. 2006, 59(3):260-263.
Wu, et al., "Multimerization of a Chimeric Anti-CD20 Single Chain Fv-Fv Fusion Protein Is Mediated Through Variable Domain Exchange", Protein Engineering, 2001, 14(12):1025-1033.
Wu, et al., "Receptor-Mediated In Vitro Gene Transformation by a Soluble DNA Carrier System", Journal of Biological Chemistry, 1987, 262(10):4429-4432.
Xie, et al., "A New Format of Bispecific Antibody: Highly Efficient Heterodimerization, Expression and Tumor Cell Lysis", Journal of Immunological Methods, 2005, 296:95-101.

Xu, et al., "High EphA2 Protein Expression in Renal Cell Carcinoma Is Associated with a Poor Disease Outcome", Oncology Letters, Aug. 2014, 8(2):687-692.
Yao, et al., "Advances in Targeting Cell Surface Signaling Molecules for Immune Modulation", Nature Reviews Drug Discovery, Feb. 2013, 12(2):130-146.
Yokota, et al., "Rapid Tumor Penetration of a Single-Chain Fv and Comparison with Other Immunoglobulin Forms", Cancer Research, Jul. 1992, 52(12):3402-3408.
Yonezawa, et al., "Boosting Cancer Immunotherapy with Anti-CD137 Antibody Therapy", Clinical Cancer Research, Jul. 15, 2015, 21(14):3113-3120.
Zang, et al., "The B7 Family and Cancer Therapy: Costimulation and Coinhibition", Clinical Cancer Research, Sep. 15, 2007, 13(18):5271-5279.
Zheng, et al., "A Novel Anti-CEACAM5 Monoclonal Antibody, CC4, Suppresses Colorectal Tumor Growth and Enhances NK Celis-Mediated Tumor Immunity", Plos One, e21146, Jun. 2011, 6(6):11 pages.
Zhou, et al., "Constitutive Overexpression of a Novel 21 Kda Protein by Hodgkin Lymphoma and Aggressive Non-Hodgkin Lymphomas", Molecular Cancer, 2008, 7(12):11 pages.
Zhou, et al., "Lung Tumorigenesis Associated with Erb-B-2 and Erb-B-3 Overexpression in Human Erb-B-3 Transgenic Mice is Enhanced by Methylnitrosourea", Oncogene, 2002, 21(57):8732-8740.
Dondelinger et al., "Understanding the Significance and Implications of Antibody Numbering and Antigen-Binding Surface/Residue Definition", Frontiers in Immunology, Oct. 16, 2018, 9(2278):15 pages.
Hinner et al., "Costimulatory T-Cell Engagement by PRS-343, a 4-1BB (CD137)/HER2 Bispecific, Leads to Tumor Growth Inhibition and TIL Expansion in Humanized Mouse Model", Retrieved via https://d1io3yog0oux5.cloudfront.net/pierisag/files/posters/1609+CRI+Poster+2016+Final.pdf, Sep. 26, 2016, 1 page.
Liu et al., "Tumor Antigen Expression-dependent Activation of the CD137 Costimulatory Pathway by Bispecific DART® Proteins", American Association for Cancer Research Annual Meeting 2017, Washington, DC, Abstract 3642, Apr. 1-5, 2017, 1 page.
Stern et al., "5T4 Oncofoetal Antigen: An Attractive Target for Immune Intervention in Cancer", Cancer Immunology Immunotherapy, DOI 10.1007/S00262-016-1917-3, Oct. 18, 2016, 12 pages.
Flower, Darren R., "The Lipocalin Protein Family: Structure and Function", Biochemical Journal, 1996, 318:1-14.
DART® and TRIDENT® Multi-Specific Platforms, MacroGenics, Retrieved via: https://macrogenics.com/dart-and-tridentplatforms/, Jun. 7, 2016, 4 pages.
Kohrt et al., "Stimulation of Natural Killer Cells with a CD137-Specific Antibody Enhances Trastuzumab Efficacy in Xenotransplant Models of Breast Cancer", The Journal of Clinical Investigation, Mar. 2012, 122(3):1066-1075.

\* cited by examiner

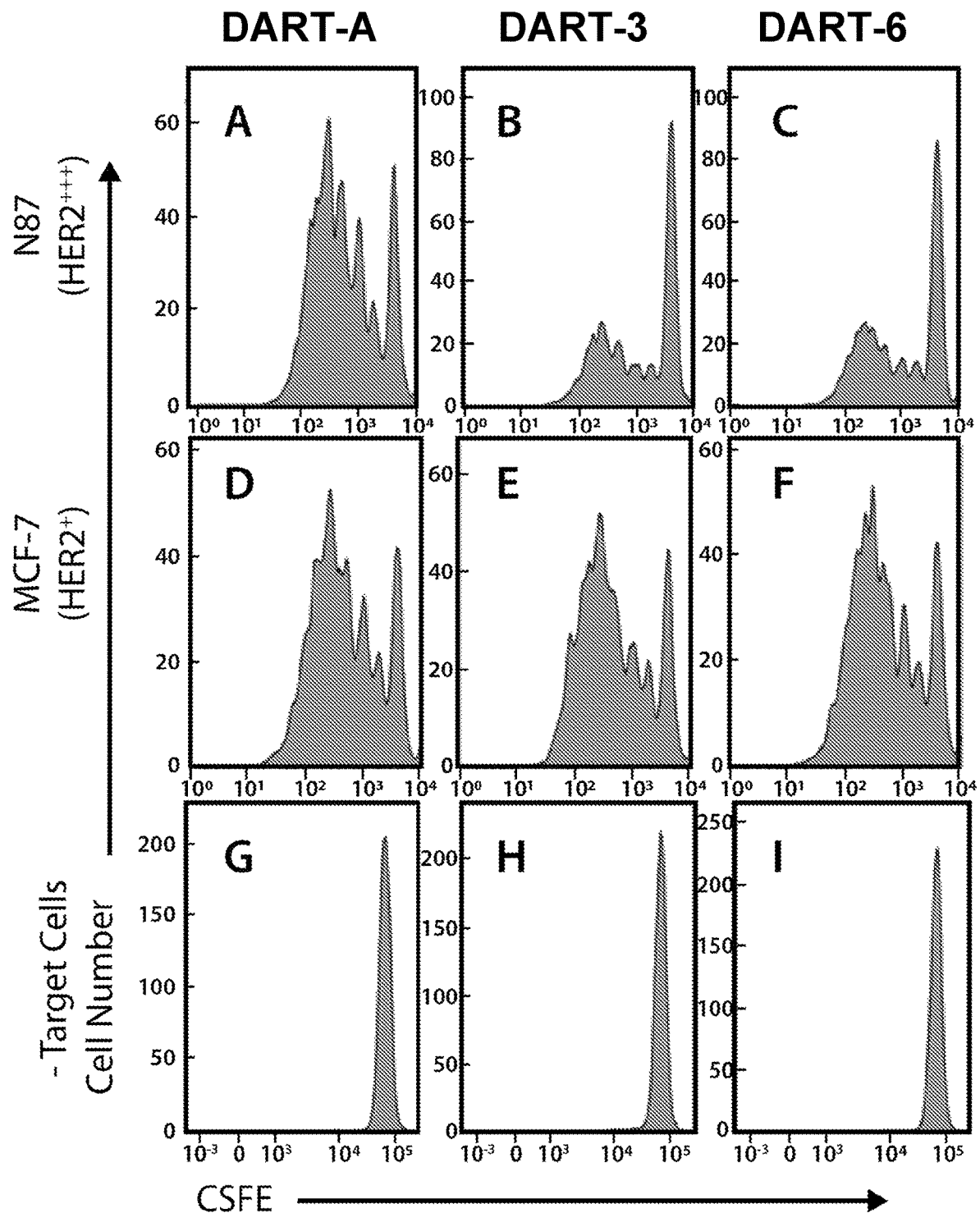
Figure 17, Panels A-I

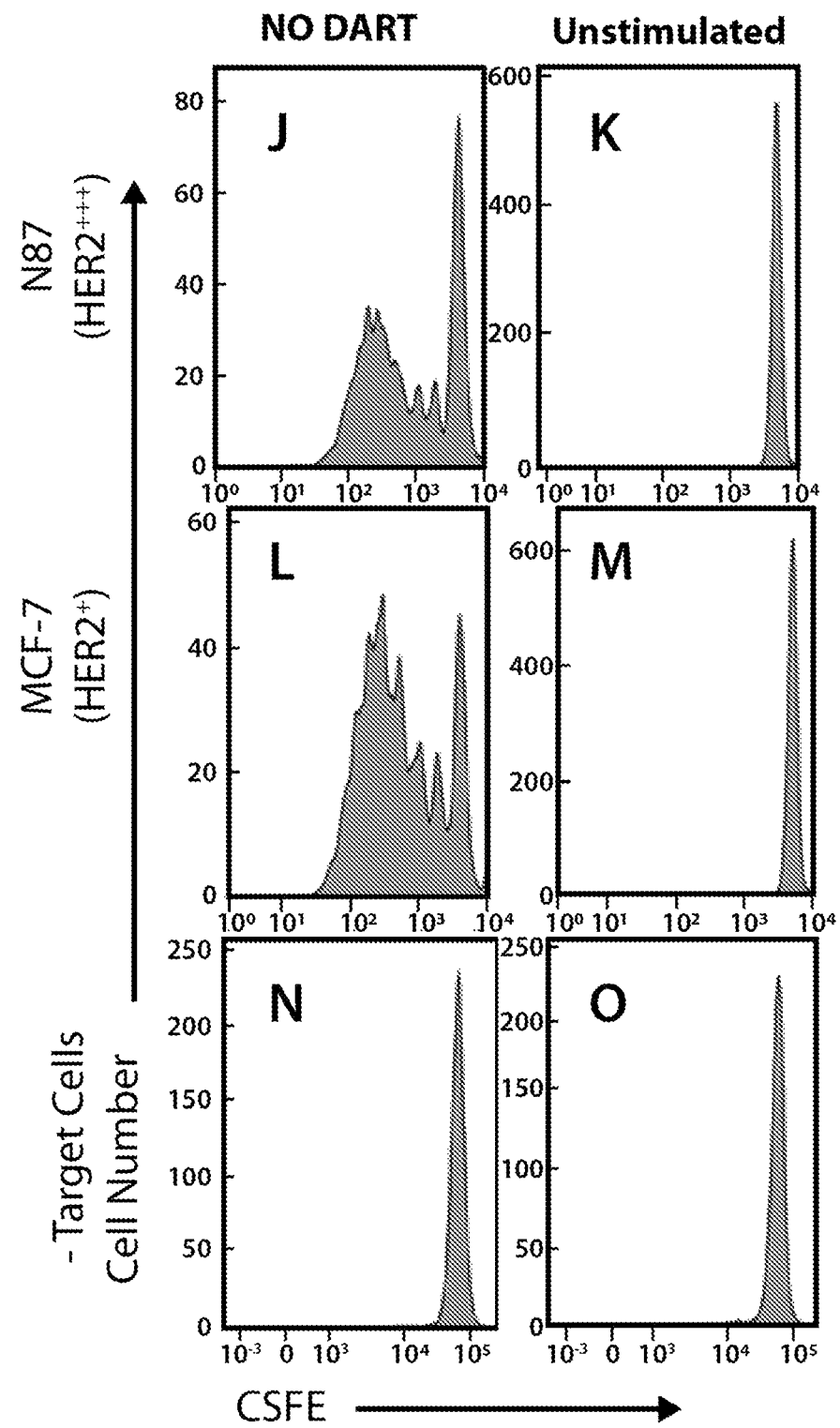
Figure 17, Panels J-O

```
         10          20          30          40          50
         |           |           |           |           |
QVQLVQSGAE VKKPGASVKV SCKASGYTFT SYWINWV|K|QA PGQGLEW|I|GN
                                        ↑           ↑
                                        38          48

60          70          80          90         100
         |           |           |           |           |
IYPSDSYTNY NQKFKDKATI TADKSTSTAY MELSSLRSED TAVYYCTRDY 110         119
         |           |
GSAYSMSTWG QGTTVTVSS    (SEQ ID NO:84)
```

Figure 31A

```
         10          20          30          40          50
         |           |           |           |           |
DIQMTQSPSS LSASVGDRVT ITC|R||P|SQDIS NYLNWYQQKP DKT|V|KLLI|Y|Y
                         ↑ ↑                       ↑    ↑
                        24 25                      44   48

60          70          80          90         100
         |           |           |           |           |
T|S|R|L|RSGVPS RFSGSGSGTD FTFTISSLQP EDIATYFCQQ GDTLPYTFGQ
 ↑   ↑
 52  54

107
         |
GTKLEIK    (SEQ ID NO:89)
```

Figure 31B

BISPECIFIC BINDING MOLECULES THAT ARE CAPABLE OF BINDING CD137 AND TUMOR ANTIGENS, AND USES THEREOF

CROSS-REFERENCE TO RELATED APPLICATIONS

This patent application is a national stage of International Patent Application No. PCT/US2018/019188, filed on Feb. 22, 2018, which claims the benefit of U.S. Patent Application Nos. 62/463,353 (filed on Feb. 24, 2017) and 62/597,594 (filed on Dec. 12, 2017), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_0149PCT_ST25_amended_2022-05-18, created on May 13, 2022, and having a size of 309,246 bytes), which file is herein incorporated by reference in its entirety.

FIELD OF THE INVENTION

The present invention is directed to binding molecules that possess one or more epitope-binding sites specific for an epitope of CD137 and one or more epitope-binding sites specific for an epitope of a tumor antigen ("TA") (e.g., a "CD137×TA Binding Molecule"). In one embodiment, such CD137×TA Binding Molecules will be bispecific molecules, especially bispecific tetravalent diabodies, that are composed of two, three, four or more than four polypeptide chains and possessing two epitope-binding sites each specific for an epitope of CD137 and two epitope-binding sites each specific for an epitope of a TA. Alternatively, such CD137×TA Binding Molecules will be bispecific molecules, especially bispecific trivalent binding molecules composed of three or more polypeptide chains and possessing one or two epitope-binding sites each specific for an epitope of CD137 and one or two epitope-binding sites each specific for an epitope of a TA. The CD137×TA Binding Molecules of the invention are capable of simultaneous binding to CD137, and a TA. The invention is directed to pharmaceutical compositions that contain any such CD137×TA Binding Molecules. The invention is additionally directed to methods for the use of such molecules in the treatment of cancer and other diseases and conditions. The invention also provides novel CD137-binding molecules, and HER2/neu-binding molecules, as well as derivatives thereof and uses thereof.

BACKGROUND OF THE INVENTION

CD137 (also known as 4-1BB and "TNF receptor superfamily member 9" ("TNFRSF9")) is a costimulatory receptor member of the tumor necrosis factor receptor superfamily, mediating CD28-dependent and independent T-cell costimulation (Vinay, D. S. and Kwon, B. S. (1998) "*Role of 4-1BB in immune responses*," Semin Immunol. 10:481-489; Bartkowiak, T. et al. (2015) "*4-1BB Agonists: Multi-Potent Potentiators Of Tumor Immunity*," Frontiers Oncol. 5:117; pp. 1-16; So, T., et al. (2008) "*Immune Regulation And Control Of Regulatory T Cells By OX40And 4-1BB*," Cytokine & Growth Factor Rev. 19:253-262; Croft, M. (2009) "*The Role Of TNF Superfamily Members In T-Cell Function And Diseases*," Nat. Rev. Immunol. 9:271-285; Yonezawa, A. et al. (2015) "*Boosting cancer immunotherapy with Anti-CD137 antibody therapy*," Clin. Cancer Res. 21(14): 3113-3120; Li, S. Y. et al. (2013) "*Immunotherapy Of Melanoma With The Immunecostimulatory Monoclonal Antibodies Targeting CD137*," Clin. Pharmacol. 5:47-53; Vinay, D. S. et al. (2012) "*Immunotherapy Of Cancer With 4-1BB*," Mol. Cancer Ther. 11:1062-1070; Houot, R. et al. (2012) "*Boosting Antibody-Dependent Cellular Cytotoxicity Against Tumor Cells With A CD137 Stimulatory Antibody*," Oncoimmunology. 1:957-958; Kwon, B. S. et al. (1989) "*cDNA Sequences Of Two Inducible T-Cell Genes*," Proc. Natl. Acad. Sci. (U.S.A.) 86:1963-1967; Chen, L. et al. (2013) "*Molecular Mechanisms Of T Cell Co-Stimulation And Coinhibition*," Nat. Rev. Immunol. 13:227-242; Yao S. et al. "*Advances In Targeting Cell Surface Signaling Molecules For Immune Modulation*," Nat. Rev. Drug Discov. 12:130-146).

CD137 is inducibly expressed by T cells, natural killer (NK) cells, dendritic cells (DC), B cells, and other cells of the immune system (Vinay, D. S. et al. (2015) "*Therapeutic Potential Of Anti-CD137 (4-1BB) Monoclonal Antibodies, Expert Opinion On Therapeutic Targets*," DOI:10.1517/14728222.2016.1091448; pp. 11-14; Wang, C. et al. (2009) "*Immune Regulation By 4-1BB And 4-1BBL: Complexities And Challenges*," Immunol. Rev. 229:192-215; Sallin, M. A. et al. (2014) "*The Anti-Lymphoma Activities Of Anti-CD137 Monoclonal Antibodies Are Enhanced In FcγRIII$^{-/-}$ Mice*," Cancer Immunol. Immunother. 63:947-958; Melero, I. et al. (2008) "*Multilayered Action Mechanisms Of CD137 (4-1BB)-Targeted Immunotherapies*," Trends Pharmacol Sci. 29:383-390; Ramakrishna, V. et al. (2015) "*Characterization Of The Human T Cell Response To In Vitro CD27 Costimulation With Varlilumab*," J. Immunother. Canc. 2:37; pp. 1-13). The protein is composed of a 255-amino acid protein having a short N-terminal cytoplasmic portion, a transmembrane region, and an extracellular domain that possesses 3 cysteine-rich motifs (Schwarz, H. et al. (1993) "*A Receptor Induced By Lymphocyte Activation (ILA): A New Member Of The Human Nerve-Growth-Factor/Tumor-Necrosis-Factor Receptor Family*," Gene 134:295-298).

Ligation of CD137 by its ligand CD137L (4-1BBL; TNFSF9), which is mainly, though not exclusively, expressed on Antigen-Presenting Cells (APCs), evokes various T cell responses such as cell expansion, increased cytokine secretion and the prevention of activation-induced cell death (Qian, Y. et al. (2015) "*CD137Ligand-Mediated Reverse Signaling Inhibits Proliferation And Induces Apoptosis In Non-Small Cell Lung Cancer*," Med. Oncol. 32:44; pp. 1-10); Sallin, M. A. et al. (2014) "*The Anti-Lymphoma Activities Of Anti-CD137 Monoclonal Antibodies Are Enhanced In FcγRIII$^{-/-}$ Mice*," Cancer Immunol. Immunother. 63:947-958; Lee, S. W. et al. (2009) "*4-1BB As A Therapeutic Target For Human Disease*," Adv. Exp. Med. Biol. 647:120-129; Thum, E. et al. (2009) "*CD137, Implications In Immunity And Potential For Therapy*," Front. Biosci. (Landmark Ed). 14:4173-4188; Wang, C. et al. (2009) "*Immune Regulation By 4-1BB And 4-1BBL: Complexities And Challenges*," Immunol. Rev. 229(1):192-215; Long, A. H. et al. (2015) "*4-1BB Costimulation Ameliorates T Cell Exhaustion Induced By Tonic Signaling Of Chimeric Antigen Receptors*," Nature Med. 21(6):581; pp. 1-13). Thus, such ligation serves to activate the immune system. However, cis-interactions between CD137 and CD137L also potently downregulate the expression of CD137L (Kwon, B. (2015) "*Is CD137 Ligand (CD137L) Signaling a Fine Tuner of Immune Responses?*," Immune Network. 15(3): 121-124). The CD137 ligand thus functions to control the extent and kinetics of CD137-mediated immune system activation (Kwon, B. (2015) "*Is CD137Ligand (CD137L) Signaling a Fine Tuner of Immune Responses?*," Immune Network. 15(3): 121-124; Shuford W W et al. (1997) "*4-1BB Costimulatory Signals Preferentially Induce CD8+ T Cell Proliferation And Lead To The Amplification In Vivo Of Cytotoxic T Cell Responses*," J. Exp. Med. 186:47-55).

Significantly, CD137 expressed on human NK cells becomes upregulated upon binding to anti-tumor antibodies (i.e., antibodies that bind a tumor antigen ("TA")) that have become bound to tumor cells (Houot, R. et al. (2012) "*Boosting Antibody-Dependent Cellular Cytotoxicity Against Tumor Cells With A CD137 Stimulatory Antibody*," Oncoimmunology. 1:957-958; Kohrt, H. E. et al. (2014) "*Targeting CD137Enhances The Efficacy Of Cetuximab*," J. Clin. Invest. 124(4):2668-2682; Lin, W. et al. (2008) "*Fc-Dependent Expression Of CD137 On Human NK Cells: Insights Into "Agonistic" Effects Of Anti-CD137 Monoclonal Antibodies*," Blood 112(3):699-707; Mittal, P. et al. (2015) "*Tumor-Unrelated CD4 T Cell Help Augments CD134 Plus CD137 Dual Costimulation Tumor Therapy*," J. Immunol. November 11. pii: 1502032; pp. 11-14; Sdnchez-Paulete, A. R. et al. (2015) "*Cancer Immunotherapy With Immunomodulatory Anti-CD137 And Anti-PD-1 Monoclonal Antibodies Requires Batf3-Dependent Dendritic Cells*," Cancer Discov. October 22. pii: CD-15-0510; pp. 1-28; Wei, H. et al. (2014) "*Dual Targeting Of CD137 Co-Stimulatory And PD-1 Co-Inhibitory Molecules For Ovarian Cancer Immunotherapy*," Oncolmmunology 3:e28248; pp. 1-3; Seo, S. K. et al. (2004) "*4-1BB-Mediated Immunotherapy Of Rheumatoid Arthritis*," Nat. Med. 10:1088-1094).

Such recognitions have led to the proposal that antibodies that are immunospecific for CD137 could be used to activate the immune system and thereby provide a therapy for cancer (Melero I. et al. (1997) "*Monoclonal Antibodies Against The 4-1BB T-Cell Activation Molecule Eradicate Established Tumors*," Nat Med. 3:682-385; Sun, Y. et al. (2002) "*Costimulatory Molecule-Targeted Antibody Therapy Of A Spontaneous Autoimmune Disease*," Nature Med. 8:1405-1413; Kammer, G. M. et al. (2002) "*Immunotherapy Tackles Lupus*," Nat. Med. 8(12):1356-1358; Foell, J. et al. (2003) "*CD137 Costimulatory T Cell Receptor Engagement Reverses Acute Disease In Lupus-Prone NZBxNZW F1 Mice*," J. Clin. Invest. 111(10):1505-1518; Mittler, R. S. et al. (2004) "*Anti-CD137 Antibodies In The Treatment Of Autoimmune Disease And Cancer*," Immunol. Res. 29(1-3): 197-208; Foell, J. L. et al. (2004) "*Engagement of The CD137 (4-1BB) Costimulatory Molecule Inhibits And Reverses The Autoimmune Process In Collagen-Induced Arthritis And Establishes Lasting Disease Resistance*," Immunology 113(1):89-98; Sytwu, H. K. et al. (2003) "*Anti-4-1BB-Based Immunotherapy For Autoimmune Diabetes: Lessons From A Transgenic Non-Obese Diabetic (NOD) Model*," J. Autoimmun. 21(3):247-254; Hernandez-Chacon J A et al. (2011) "*Costimulation Through The CD137/4-1BB Pathway Protects Human Melanoma Tumor-Infiltrating Lymphocytes From Activation Induced Cell Death And Enhances Antitumor Effector Function*," J. Immunother. 34:236-250; Morales-Kastresana, A. et al. (2014) "*Combinations Of Immunostimulatory Antibodies With Synergistic Effects Against Spontaneous Cancer*," OncoImmunology 3:2, e27812, pp. 11-4; Sanmamed, M. F. et al. (2015) "*Agonists of Co-stimulation in Cancer Immunotherapy Directed Against CD137, OX40, GITR, CD27, CD28, and ICOS*," Seminars Oncol. 42(4):640-655; Tongu, M. et al. (2015) "*Intermittent Chemotherapy Can Retain The Therapeutic Potential Of Anti-CD137 Antibody During The Late Tumor-Bearing State*," Cancer Sci. 106(1):9-17; Takeda, K. et al. (2007) "*Combination Antibody-Based Cancer Immunotherapy*," Cancer Sci. 98(9):1297-1302). Anti-CD137 antibodies are disclosed in US Patent Nos. 2014/0274909; 2013/0280265; 2013/0273078; 2013/0071403; 2012/0058047; 2011/0104049; 2011/0097313; 2008/0166336; 2008/0019905; 2006/0188439; 2006/0182744; 2006/0121030; and 2003/0223989.

However, despite all such prior advances, a need remains for improved compositions capable of more vigorously directing the body's immune system to attack cancer cells or pathogen-infected cells, especially at lower therapeutic concentrations. For although the adaptive immune system can be a potent defense mechanism against cancer and disease, it is often hampered by immune suppressive/evasion mechanisms in the tumor microenvironment, mediated by the reduced/absent co-stimulatory activity of CD137. Furthermore, co-inhibitory molecules expressed by tumor cells, immune cells, and stromal cells in the tumor milieu can dominantly attenuate T-cell responses against cancer cells.

As described in detail below, the present invention addresses this need by providing CD137×TA Binding Molecules. Such bispecific molecules are capable of binding to tumor antigens that are expressed on the surfaces of tumor cells, and of co-localizing CD137-expressing NK cells to such tumor cells. Such co-localization upregulates the NK cells so as to promote the activation or continued activation of the immune system (e.g., stimulating a cytotoxic T cell response, against tumor cells). These attributes permit such bispecific molecules to have utility in stimulating the immune system and particularly in the treatment of cancer and pathogen-associated diseases and conditions. The present invention is directed to these and other goals.

SUMMARY OF THE INVENTION

The present invention is directed to binding molecules that possess one or more epitope-binding sites specific for an epitope of CD137 and one or more epitope-binding sites specific for an epitope of a tumor antigen ("TA") (e.g., a "CD137×TA Binding Molecule"). In one embodiment, such CD137×TA Binding Molecules will be bispecific molecules, especially bispecific tetravalent diabodies, that are composed of two, three, four or more than four polypeptide chains and possessing two epitope-binding sites each specific for an epitope of CD137 and two epitope-binding sites each specific for an epitope of a TA. Alternatively, such CD137×TA Binding Molecules will be bispecific molecules, especially bispecific trivalent binding molecules composed of three or more polypeptide chains and possessing one or two epitope-binding sites each specific for an epitope of CD137 and one or two epitope-binding sites each specific for an epitope of a TA. The CD137×TA Binding Molecules of the invention are capable of simultaneous binding to CD137, and a TA. The invention is directed to pharmaceutical compositions that contain any such CD137×TA Binding Molecules. The invention is additionally directed to methods for the use of such molecules in the treatment of cancer and other diseases and conditions. The invention also provides novel CD137-binding molecules, and HER2/neu-binding molecules, as well as derivatives thereof and uses thereof.

The present invention provides CD137×TA Binding Molecules that are monovalent in that they are capable of binding to only one copy of an epitope of CD137 and to only one copy of an epitope of a TA, but are bispecific in that a single such diabody is able to bind simultaneously to the epitope of CD137 and to the epitope of a TA. The present invention is, however, particularly directed to CD137×TA Binding Molecules that are composed of polypeptide chains that associate with one another in a heterodimeric manner to form two binding sites each specific for an epitope of CD137 and two binding sites each specific for an epitope of a TA. Such preferred CD137×TA Binding Molecules of the invention are termed "bispecific tetravalent." The present invention is also particularly directed to CD137×TA Binding Molecules that are composed of polypeptide chains that associate with one another in a heterodimeric manner to form two binding sites each specific for an epitope of CD137 and one binding sites each specific for an epitope of a TA. Such preferred CD137×TA Binding Molecules of the invention are termed "bispecific trivalent."

The present invention provides CD137×TA Binding Molecules that comprise three polypeptide chains (a "first," "second" and "third" polypeptide chain), wherein the first and second polypeptide chains are covalently bonded to one another and the first and third polypeptide chains are covalently bonded to one another. The preferred CD137×TA Binding Molecules of the invention comprise four polypeptide chains (a "first," "second," "third," and "fourth" polypeptide chain), wherein the first and second polypeptide chains are covalently bonded to one another, the third and fourth polypeptide chains are covalent bonded to one another, and the first and third polypeptide chains are covalently bonded to one another. Also preferred are CD137×TA Binding Molecules of the invention comprising five polypeptide chains (a "first," "second," "third," "fourth," and "fifth" polypeptide chain), wherein the first and second polypeptide chains are covalently bonded to one another, the third and fourth polypeptide chain are covalent bonded to one another, the third and fifth polypeptide chains are covalent bonded to one another, and the first and third polypeptide chains are covalently bonded to one another.

In detail, the invention provides a CD137×TA Binding Molecule, wherein said Binding Molecule is capable of specific binding to an epitope of CD137 and an epitope of a tumor antigen (TA), and wherein said CD137×TA Binding Molecule comprises a first Light Chain Variable Domain that comprises a $CDR_L1$, $CDR_L2$ and $CDR_L3$, and a first Heavy Chain Variable Domain that comprises a $CDR_H1$, $CDR_H2$ and $CDR_H3$; and wherein:

(A) (1) said first Light Chain Variable Domain $CDR_L1$, $CDR_L2$, and $CDR_L3$ are the Light Chain CDRs of CD137 MAB-3 VL15 (SEQ ID NO:222); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(B) (1) said first Light Chain Variable Domain $CDR_L1$, $CDR_L2$, and $CDR_L3$ are the Light Chain CDRs of CD137 MAB-3 VL14 (SEQ ID NO:221); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(C) (1) said first Light Chain Variable Domain $CDR_L1$, $CDR_L2$, and $CDR_L3$ are the Light Chain CDRs of CD137 MAB-3 VL11 (SEQ ID NO:218); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(D) (1) said first Light Chain Variable Domain $CDR_L1$, $CDR_L2$, and $CDR_L3$ are the Light Chain CDRs of CD137 MAB-3 VL10 (SEQ ID NO:217); and (2) said first Heavy Chain Variable Domain $CDR_H1$, $CDR_H2$, and $CDR_H3$ are the Heavy Chain CDRs of CD137 MAB-3 VH1B (SEQ ID NO:84);

(E) (1) said first Light Chain Variable Domain $CDR_L1$, $CDR_L2$, and $CDR_L3$ are the Light Chain CDRs of CD137 MAB-3 VL6 (SEQ ID NO:213); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(F) (1) said first Light Chain Variable Domain $CDR_L1$, $CDR_L2$, and $CDR_L3$ are the Light Chain CDRs of CD137 MAB-3 VL4 (SEQ ID NO:211); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(G) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH (SEQ ID NO:74);

(H) (1) said first Light Chain Variable Domain $CDR_L1$, $CDR_L2$, and $CDR_L3$ are the Light Chain CDRs of CD137 MAB-4 VL (SEQ ID NO:91); and
(2) said first Heavy Chain Variable Domain $CDR_H1$, $CDR_H2$, and $CDR_H3$ are the Heavy Chain CDRs of CD137 MAB-4 VH (SEQ ID NO:90);

(I) (1) said first Light Chain Variable Domain $CDR_L1$, $CDR_L2$, and $CDR_L3$ are the Light Chain CDRs of CD137 MAB-5 VL (SEQ ID NO:97); and
(2) said first Heavy Chain Variable Domain $CDR_H1$, $CDR_H2$, and $CDR_H3$ are the Heavy Chain CDRs of CD137 MAB-5 VH (SEQ ID NO:96);

(J) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1A (SEQ ID NO:83);

(K) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1B (SEQ ID NO:84);

(L) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1C (SEQ ID NO:85);
or
(M) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1D (SEQ ID NO:86).

The invention further concerns such a CD137×TA Binding Molecule, wherein the first Heavy Chain Variable Domain comprises the amino acid sequence of:
(A) hCD137 MAB-3 (SEQ ID NO:77); or
(B) hCD137 MAB-4 (SEQ ID NO:92);
and/or wherein the first Light Chain Variable Domain comprises the amino acid sequence of:
(A) hCD137 MAB-3 (SEQ ID NO:82); or
(B) hCD137 MAB-4 (SEQ ID NO:93).

The invention further concerns such a CD137×TA Binding Molecule, wherein the first Heavy Chain Variable Domain comprises the amino acid sequence of:
(A) hCD137 MAB-3 VH1E (SEQ ID NO:208);
(B) hCD137 MAB-3 VH1B (SEQ ID NO:84);
(C) hCD137 MAB-3 VH1A (SEQ ID NO:83);
(D) hCD137 MAB-3 VH1 (SEQ ID NO:76);
(E) hCD137 MAB-3 VH1C (SEQ ID NO:85);
(F) hCD137 MAB-3 VH1D (SEQ ID NO:86);
(G) hCD137 MAB-3 VH1F (SEQ ID NO:209);
(H) hCD137 MAB-3 VH1G (SEQ ID NO:210); or
(I) hCD137 MAB-4 VH1 (SEQ ID NO:92).

The invention further concerns such CD137×TA Binding Molecules, wherein the first Light Chain Variable Domain comprises the amino acid sequence of:
(A) hCD137 MAB-3 VL15 (SEQ ID NO:222);
(B) hCD137 MAB-3 VL14 (SEQ ID NO:221);
(C) hCD137 MAB-3 VL1 (SEQ ID NO:87);
(D) hCD137 MAB-3 VL2 (SEQ ID NO:88);
(E) hCD137 MAB-3 VL3 (SEQ ID NO:89);
(F) hCD137 MAB-3 VL4 (SEQ ID NO:211);
(G) hCD137 MAB-3 VL5 (SEQ ID NO:212);
(H) hCD137 MAB-3 VL6 (SEQ ID NO:213);
(I) hCD137 MAB-3 VL7 (SEQ ID NO:214);
(J) hCD137 MAB-3 VL8 (SEQ ID NO:215);
(K) hCD137 MAB-3 VL9 (SEQ ID NO:216);
(L) hCD137 MAB-3 VL10 (SEQ ID NO:217);
(M) hCD137 MAB-3 VL11 (SEQ ID NO:218);
(N) hCD137 MAB-3 VL12 (SEQ ID NO:219);
(O) hCD137 MAB-3 VL13 (SEQ ID NO:220);
(P) hCD137 MAB-4 VL1 (SEQ ID NO:94); or
(Q) hCD137 MAB-4 VL2 (SEQ ID NO:95).

The invention further concerns such a CD137×TA Binding Molecule, wherein the tumor antigen (TA) is selected from the group of tumor antigens consisting of: 19.9; oncofetal protein 5T4; antigen 4.2; A33; AFP; ALCAM; BAGE; beta-catenin; CA125; Carboxypeptidase M; B1; CD5; CD19; CD20; CD22; CD23; CD25; CD27; CD30; CD33; CD36; CD46; CD52; CD79a/CD79b; CD123; CD317; CEA; CEACAM5; CEACAM6; CO-43; CO-514; CTLA-1; CTLA-4; Cytokeratin 8; E1 series; EGF-R; an Ephrin receptor; Erb; F3; FC10.2; a GAGE GD2; GD3; GD49; GM2; GM3; GICA 19-9; gp37; gp75; gp100; HER-2/neu; human B-lymphoma antigen-CD20; human milk fat globule antigen; human papillomavirus-E6/human papillomavirus-E7; HMW-MAA; I antigen; ITGB6; IL13Rα2; JAM-3; KID3; KID31; KS 1/4 pan-carcinoma antigen; KS 1/4; KSA; L6; L20; LEA; LUCA-2; M1:22:25:8; M18; M39; a MAGE; MART; Myl; MUC-1; MUM-1; N-acetylglucosaminyltransferase; neoglycoprotein; NS-10; OFA-1; OFA-2; Oncostatin M; p15; PSA; PSMA; PEMA; PIPA; prostatic acid phosphate; R24; ROR1; SSEA-1; SSEA-3; SSEA-4; sTn; T cell receptor derived peptide; TAG-72; TL5; TNF-α receptor; TNF-β receptor; TNF-γ receptor; TRA-1-85; Transferrin Receptor; TSTA; and VEGF-R.

The invention further concerns such a CD137×TA Binding Molecule, wherein the tumor antigen (TA) is selected from the tumor antigens of Table 1, and particularly wherein the tumor antigen (TA) is: HER2/neu, EphA2 or 5T4.

The invention further concerns such a CD137×TA Binding Molecule, wherein the tumor antigen (TA) is HER2/neu and wherein the CD137×TA Binding Molecule comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$; and wherein (A) the second Light Chain Variable Domain $CDR_L1$, $CDR_L2$, and $CDR_L3$ are the Light Chain CDRs of HER2 MAB-1 VL (SEQ ID NO:63); and
(B) the second Heavy Chain Variable Domain $CDR_H1$, $CDR_H2$, and $CDR_H3$ are the Heavy Chain CDRs of HER2 MAB-1 VH (SEQ ID NO:62).

The invention further concerns such a CD137×TA Binding Molecule, wherein:
(A) (1) the second Light Chain Variable Domain $CDR_L1$, $CDR_L2$, and $CDR_L3$ are the Light Chain CDRs of hHER2 MAB-1 VL1 (SEQ ID NO:67);
(2) the second Light Chain Variable Domain $CDR_L1$, $CDR_L2$, and $CDR_L3$ are the Light Chain CDRs of hHER2 MAB-1 VL2 (SEQ ID NO:68); or
(3) the second Light Chain Variable Domain $CDR_L1$, $CDR_L2$, and $CDR_L3$ are the Light Chain CDRs of hHER2 MAB-1 VL3 (SEQ ID NO:69); and
(B) (1) the second Heavy Chain Variable Domain $CDR_H1$, $CDR_H2$, and $CDR_H3$ are the Heavy Chain CDRs of hHER2 MAB-1 VH1 (SEQ ID NO:64);
(2) the second Heavy Chain Variable Domain $CDR_H1$, $CDR_H2$, and $CDR_H3$ are the Heavy Chain CDRs of hHER2 MAB-1 VH2 (SEQ ID NO:65); or
(3) the second Heavy Chain Variable Domain $CDR_H1$, $CDR_H2$, and $CDR_H3$ are the Heavy Chain CDRs of hHER2 MAB-1 VH3 (SEQ ID NO:66).

The invention further concerns such a CD137×TA Binding Molecule, wherein the second Heavy Chain Variable Domain comprises the amino acid sequence of:
(A) hHER2 MAB-1 VH1 (SEQ ID NO:64);
(B) hHER2 MAB-1 VH2 (SEQ ID NO:65); or
(C) hHER2 MAB-1 VH3 (SEQ ID NO:66).

The invention further concerns such a CD137×TA Binding Molecule, wherein the second Light Chain Variable Domain comprises the amino acid sequence of:
(A) hHER2 MAB-1 VL1 (SEQ ID NO:67);
(B) hHER2 MAB-1 VL2 (SEQ ID NO:68); or
(C) hHER2 MAB-1 VL3 (SEQ ID NO:69).

The invention further concerns such a CD137×TA Binding Molecule, wherein the tumor antigen (TA) is 5T4 and wherein the CD137×TA Binding Molecule comprises a second Light Chain Variable Domain that comprises a CDRL1, CDRL2 and CDRL3, and a second Heavy Chain Variable Domain that comprises a CDRH1, CDRH2 and CDRH3; and wherein:
(I) (A) the second Light Chain Variable Domain $CDR_L1$, $CDR_L2$, and $CDR_L3$ are the Light Chain CDRs of 5T4 MAB-1 VL (SEQ ID NO:135); and
(B) the second Heavy Chain Variable Domain $CDR_H1$, $CDR_H2$, and $CDR_H3$ are the Heavy Chain CDRs of 5T4 MAB-1 VH (SEQ ID NO:134); or
(II) (A) the second Light Chain Variable Domain $CDR_L1$, $CDR_L2$, and $CDR_L3$ are the Light Chain CDRs of 5T4 MAB-2 VL (SEQ ID NO:137); and
(B) the second Heavy Chain Variable Domain $CDR_H1$, $CDR_H2$, and $CDR_H3$ are the Heavy Chain CDRs of 5T4 MAB-2 VH (SEQ ID NO:136).

The invention further concerns such a CD137×TA Binding Molecule, wherein the second Heavy Chain Variable Domain comprises the amino acid sequence of: MAB-1 VH1 (SEQ ID NO:135).

The invention further concerns such a CD137×TA Binding Molecule, wherein the second Light Chain Variable Domain comprises the amino acid sequence of MAB-1 VH1 (SEQ ID NO:136).

The invention further concerns such a CD137×TA Binding Molecule, wherein the molecule is a bispecific tetravalent Fc-bearing diabody comprising a first, a second, a third, and a fourth polypeptide chain, wherein the polypeptide chains form a covalently bonded complex.

The invention further concerns such a CD137×TA Binding Molecule, wherein the tumor antigen (TA) is HER2/neu and wherein:
(I) (A) the first and the third polypeptide chain have the amino acid sequence of SEQ ID NO:100; and
(B) the second and the fourth polypeptide chain have the amino acid sequence of SEQ ID NO:101;
or
(II) (A) the first and the third polypeptide chain have the amino acid sequence of SEQ ID NO:102; and
(B) the second and the fourth polypeptide chain have the amino acid sequence of SEQ ID NO:103.

The invention further concerns such CD137×TA Binding Molecules, wherein the molecule is bispecific and tetravalent, and comprises a first, a second, a third, a fourth, and a fifth polypeptide chain, wherein the polypeptide chains form a covalently bonded complex.

The invention further concerns such a CD137×TA Binding Molecule, wherein the tumor antigen (TA) is HER2/neu and wherein:
(I) (A) the first polypeptide chain has the amino acid sequence of SEQ ID NO:104;
(B) the second and the fifth polypeptide chain have the amino acid sequence of SEQ ID NO:105;
(C) the third polypeptide chain has the amino acid sequence of SEQ ID NO:106; and
(D) the fourth polypeptide chain has the amino acid sequence of SEQ ID NO:107;
or
(II) (A) the first polypeptide chain has the amino acid sequence of SEQ ID NO:104;
(B) the second and the fifth polypeptide chain have the amino acid sequence of SEQ ID NO:105;
(C) the third polypeptide chain has the amino acid sequence of SEQ ID NO:114, SEQ ID NO:115, SEQ ID NO:116, SEQ ID NO:117, or SEQ ID NO:118; and
(D) the fourth polypeptide chain has the amino acid sequence of SEQ ID NO:119, SEQ ID NO:120, SEQ ID NO:121, SEQ ID NO:122, or SEQ ID NO:123.

The invention further concerns such a CD137×TA Binding Molecule, wherein said molecule is bispecific and tri-valent, and comprises a first, a second, a third, and a fourth, polypeptide chain, wherein said polypeptide chains form a covalently bonded complex.

The invention further concerns such a CD137×TA Binding Molecule, wherein said tumor antigen (TA) is HER2/neu and wherein:
(A) said first polypeptide chain has the amino acid sequence of SEQ ID NO:192, SEQ ID NO:193, SEQ ID NO:194, SEQ ID NO:195, or SEQ ID NO:196;
(B) said second polypeptide chain has the amino acid sequence of SEQ ID NO:197, SEQ ID NO:198, SEQ ID NO:199, SEQ ID NO:200, or SEQ ID NO:201;
(C) said third polypeptide chain has the amino acid sequence of SEQ ID NO:104; and
(D) said fourth polypeptide chain has the amino acid sequence of SEQ ID NO:105.

The invention further concerns such a CD137×TA Binding Molecule, wherein said tumor antigen (TA) is 5T4 and wherein:

(A) said first polypeptide chain has the amino acid sequence of SEQ ID NO:192, SEQ ID NO:193, SEQ ID NO:194, SEQ ID NO:195, SEQ ID NO:196, or SEQ ID NO:229;
(B) said second polypeptide chain has the amino acid sequence of SEQ ID NO:197, SEQ ID NO:198, SEQ ID NO:199, SEQ ID NO:200, SEQ ID NO:201, or SEQ ID NO:230;
(C) said third polypeptide chain has the amino acid sequence of SEQ ID NO:231; and
(D) said fourth polypeptide chain has the amino acid sequence of SEQ ID NO:232.

The invention further concerns a pharmaceutical composition comprising any of the above-described CD137×TA Binding Molecules and a physiologically acceptable carrier.

The invention further concerns the use of any of the above-described CD137×TA Binding Molecules or such pharmaceutical composition in the treatment of a disease or condition associated with or characterized by the expression of the tumor antigen (TA), and particularly wherein the disease or condition associated with or characterized by the expression of the tumor antigen (TA) is cancer.

The invention further concerns a CD137 binding molecule that comprises a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:
(A) (1) said first Light Chain Variable Domain $CDR_L1$, $CDR_L2$, and $CDR_L3$ are the Light Chain CDRs of CD137 MAB-3 VL15 (SEQ ID NO:222); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(B) (1) said first Light Chain Variable Domain $CDR_L1$, $CDR_L2$, and $CDR_L3$ are the Light Chain CDRs of CD137 MAB-3 VL14 (SEQ ID NO:221); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(C) (1) said first Light Chain Variable Domain $CDR_L1$, $CDR_L2$, and $CDR_L3$ are the Light Chain CDRs of CD137 MAB-3 VL11 (SEQ ID NO:218); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(D) (1) said first Light Chain Variable Domain $CDR_L1$, $CDR_L2$, and $CDR_L3$ are the Light Chain CDRs of CD137 MAB-3 VL10 (SEQ ID NO:217); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(E) (1) said first Light Chain Variable Domain $CDR_L1$, $CDR_L2$, and $CDR_L3$ are the Light Chain CDRs of CD137 MAB-3 VL6 (SEQ ID NO:213); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(F) (1) said first Light Chain Variable Domain $CDR_L1$, $CDR_L2$, and $CDR_L3$ are the Light Chain CDRs of CD137 MAB-3 VL4 (SEQ ID NO:211); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(G) (1) the Light Chain Variable Domain $CDR_L1$, $CDR_L2$, and $CDR_L3$ are the Light Chain CDRs of CD137 MAB-3 VL (SEQ ID NO:75); and (2) the Heavy Chain Variable Domain $CDR_H1$, $CDR_H2$, and $CDR_H3$ are the Heavy Chain CDRs of CD137 MAB-3 VH (SEQ ID NO:74);

(H) (1) the Light Chain Variable Domain $CDR_L1$, $CDR_L2$, and $CDR_L3$ are the Light Chain CDRs of CD137 MAB-4 VL (SEQ ID NO:91); and (2) the Heavy Chain Variable Domain $CDR_H1$, $CDR_H2$, and $CDR_H3$ are the Heavy Chain CDRs of CD137 MAB-4 VH (SEQ ID NO:90);

(I) (1) the Light Chain Variable Domain $CDR_L1$, $CDR_L2$, and $CDR_L3$ are the Light Chain CDRs of CD137 MAB-5 VL (SEQ ID NO:97); and (2) the Heavy Chain Variable Domain $CDR_H1$, $CDR_H2$, and $CDR_H3$ are the Heavy Chain CDRs of CD137 MAB-5 VH (SEQ ID NO:96);

(J) (1) the Light Chain Variable Domain $CDR_L1$, $CDR_L2$, and $CDR_L3$ are the Light Chain CDRs of CD137 MAB-3 VL (SEQ ID NO:75); and (2) the Heavy Chain Variable Domain $CDR_H1$, $CDR_H2$, and $CDR_H3$ are the Heavy Chain CDRs of CD137 MAB-3 VH1A (SEQ ID NO:83);

(K) (1) the first Light Chain Variable Domain $CDR_L1$, $CDR_L2$, and $CDR_L3$ are the Light Chain CDRs of CD137 MAB-3 VL (SEQ ID NO:75); and (2) the first Heavy Chain Variable Domain $CDR_H1$, $CDR_H2$, and $CDR_H3$ are the Heavy Chain CDRs of CD137 MAB-3 VH1B (SEQ ID NO:84);

(L) (1) the first Light Chain Variable Domain $CDR_L1$, $CDR_L2$, and $CDR_L3$ are the Light Chain CDRs of CD137 MAB-3 VL (SEQ ID NO:75); and (2) the first Heavy Chain Variable Domain $CDR_H1$, $CDR_H2$, and $CDR_H3$ are the Heavy Chain CDRs of CD137 MAB-3 VH1C (SEQ ID NO:85); or (M) (1) the first Light Chain Variable Domain $CDR_L1$, $CDR_L2$, and $CDR_L3$ are the Light Chain CDRs of CD137 MAB-3 VL (SEQ ID NO:75); and (2) the first Heavy Chain Variable Domain $CDR_H1$, $CDR_H2$, and $CDR_H3$ are the Heavy Chain CDRs of CD137 MAB-3 VH1D (SEQ ID NO:86).

The invention further concerns the embodiment of such a CD137 binding molecule, wherein the Heavy Chain Variable Domain comprises the amino acid sequence of:
(A) hCD137 MAB-3 (SEQ ID NO:77); or
(B) hCD137 MAB-4 (SEQ ID NO:92).

The invention further concerns the embodiment of such a CD137 binding molecule, wherein the Light Chain Variable Domain comprises the amino acid sequence of:
(A) hCD137 MAB-3 (SEQ ID NO:82); or
(B) hCD137 MAB-4 (SEQ ID NO:93).

The invention further concerns the embodiment of such CD137 binding molecules, wherein the Heavy Chain Variable Domain comprises the amino acid sequence of:
(A) hCD137 MAB-3 VH1 (SEQ ID NO:76);
(B) hCD137 MAB-3 VH1A (SEQ ID NO:83);
(C) hCD137 MAB-3 VH1B (SEQ ID NO:84);
(D) hCD137 MAB-3 VH1C (SEQ ID NO:85);
(E) hCD137 MAB-3 VH1D (SEQ ID NO:86);
(F) hCD137 MAB-3 VH1E (SEQ ID NO:208);
(G) hCD137 MAB-3 VH1F (SEQ ID NO:209);
(H) hCD137 MAB-3 VH1G (SEQ ID NO:210); or
(I) hCD137 MAB-4 VH1 (SEQ ID NO:92).

The invention further concerns the embodiment of such CD137 binding molecules, wherein the Light Chain Variable Domain comprises the amino acid sequence of:
(A) hCD137 MAB-3 VL15 (SEQ ID NO:222);
(B) hCD137 MAB-3 VL14 (SEQ ID NO:221);
(C) hCD137 MAB-3 VL1 (SEQ ID NO:87);
(D) hCD137 MAB-3 VL2 (SEQ ID NO:88);
(E) hCD137 MAB-3 VL3 (SEQ ID NO:89);
(F) hCD137 MAB-3 VL4 (SEQ ID NO:211);
(G) hCD137 MAB-3 VL5 (SEQ ID NO:212);
(H) hCD137 MAB-3 VL6 (SEQ ID NO:213);
(I) hCD137 MAB-3 VL7 (SEQ ID NO:214);
(J) hCD137 MAB-3 VL8 (SEQ ID NO:215);
(K) hCD137 MAB-3 VL9 (SEQ ID NO:216);
(L) hCD137 MAB-3 VL10 (SEQ ID NO:217);
(M) hCD137 MAB-3 VL11 (SEQ ID NO:218);
(N) hCD137 MAB-3 VL12 (SEQ ID NO:219);
(O) hCD137 MAB-3 VL13 (SEQ ID NO:220);
(P) hCD137 MAB-4 VL1 (SEQ ID NO:94); or
(Q) hCD137 MAB-4 VL2 (SEQ ID NO:95).

The invention further concerns the embodiment of such CD137 binding molecules, wherein the molecule is an antibody or an antigen binding fragment thereof The invention further concerns a pharmaceutical composition comprising any of the above-described CD137 Binding Molecules, and a physiologically acceptable carrier.

The invention further concerns the use of any of the above-described CD137 Binding Molecules, or such pharmaceutical composition, in the treatment of a disease or condition associated with a suppressed immune system or characterized by the expression of a tumor antigen (TA).

The invention further concerns such use wherein the condition associated with a suppressed immune system or characterized by the expression of the tumor antigen (TA) is cancer.

The invention further concerns a HER2/neu Binding Molecule that comprises a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:
(A) the Light Chain Variable Domain $CDR_L1$, $CDR_L2$, and $CDR_L3$ are the Light Chain CDRs of HER2 MAB-1 VL (SEQ ID NO:63); and
(B) the Heavy Chain Variable Domain $CDR_H1$, $CDR_H2$, and $CDR_H3$ are the Heavy Chain CDRs of HER2 MAB-1 VH (SEQ ID NO:62).

The invention further concerns the embodiment of such HER2/neu Binding Molecules wherein:
(A) (1) the Light Chain Variable Domain $CDR_L1$, $CDR_L2$, and $CDR_L3$ are the Light Chain CDRs of hHER2 MAB-1 VL1 (SEQ ID NO:67);
(2) the Light Chain Variable Domain $CDR_L1$, $CDR_L2$, and $CDR_L3$ are the Light Chain CDRs of hHER2 MAB-1 VL2 (SEQ ID NO:68); or
(3) the Light Chain Variable Domain $CDR_L1$, $CDR_L2$, and $CDR_L3$ are the Light Chain CDRs of hHER2 MAB-1 VL3 (SEQ ID NO:69);
and
(B) (1) the Heavy Chain Variable Domain $CDR_H1$, $CDR_H2$, and $CDR_H3$ are the Heavy Chain CDRs of hHER2 MAB-1 VH1 (SEQ ID NO:64);
(2) the Heavy Chain Variable Domain $CDR_H1$, $CDR_H2$, and $CDR_H3$ are the Heavy Chain CDRs of hHER2 MAB-1 VH2 (SEQ ID NO:65); or
(3) the Heavy Chain Variable Domain $CDR_H1$, $CDR_H2$, and $CDR_H3$ are the Heavy Chain CDRs of hHER2 MAB-1 VH3 (SEQ ID NO:66).

The invention further concerns the embodiment of such HER2/neu Binding Molecules wherein the Heavy Chain Variable Domain comprises the amino acid sequence of:
(A) hHER2 MAB-1 VH1 (SEQ ID NO:64);
(B) hHER2 MAB-1 VH2 (SEQ ID NO:65); or
(C) hHER2 MAB-1 VH3 (SEQ ID NO:66).

The invention further concerns the embodiment of such HER2/neu Binding Molecules wherein the Light Chain Variable Domain comprises the amino acid sequence of:
(A) hHER2 MAB-1 VL1 (SEQ ID NO:67);
(B) hHER2 MAB-1 VL2 (SEQ ID NO:68); or
(C) hHER2 MAB-1 VL3 (SEQ ID NO:69).

The invention further concerns the embodiment of such HER2/neu Binding Molecules wherein the molecule is an antibody or an antigen binding fragment thereof.

The invention further concerns a pharmaceutical composition comprising any of the above-described HER2/neu Binding Molecules and a physiologically acceptable carrier The invention further concerns the use of any of the above-described HER2/neu Binding Molecule, or such pharmaceutical composition, in the treatment of a disease or condition associated with or characterized by the expression of HER2/neu, and particularly wherein the condition associated with or characterized by the expression of HER2/neu is cancer.

The invention further concerns methods of enhancing the activity of a tumor targeting agent comprising administering such tumor target agent in combination with the any of the above-described CD137×TA Binding Molecules, or a pharmaceutical composition comprising the same. The invention further concerns such methods further comprising administering a PD-1/PD-L1 checkpoint inhibitor and particularly wherein such checkpoint inhibitor is an anti-PD-1 antibody or an anti-PD-L1 antibody. The invention particularly concerns such methods wherein the tumor target agent is an antibody, an epitope binding fragment of an antibody, or an agent that mediates T-cell redirected killing of a target cell.

The invention further concerns methods method of treating a disease or condition associated with a suppressed immune system or characterized by the expression of a tumor antigen (TA) comprising administering to a subject in need thereof any of the above-described CD137×TA Binding Molecules, or a pharmaceutical composition comprising the same. The invention particularly, concerns such methods wherein the condition associated with a suppressed immune system or characterized by the expression of the tumor antigen (TA) is cancer. The invention also concerns such methods further comprising administering a tumor targeting agent, and particularly wherein the tumor target agent is an antibody, an epitope binding fragment of an antibody, or an agent that mediates T-cell redirected killing of a target cell. The invention further concerns such methods further comprising administering a PD-1/PD-L1 checkpoint inhibitor, and particularly wherein such checkpoint inhibitor is an anti-PD-1 antibody or an anti-PD-L1 antibody.

The invention further concerns the above uses and methods wherein the cancer is selected from the group consisting of: an acute myeloid leukemia, an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, a glioblastoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a malignant mesothelioma, a multiple endocrine neoplasia, a multiple myeloma, a myelodysplastic syndrome, a neuroblastoma, a neuroendocrine tumors, a non-small cell lung cancer, an ovarian cancer, a pancreatic cancer, a pharyngeal cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal cell carcinoma, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention particularly concerns the above uses and methods wherein the cancer is selected from the group consisting: bladder cancer, breast cancer, colorectal cancer, gastric cancer, glioblastoma, kidney cancer, lung cancer, melanoma, neuroblastoma, ovarian cancer, pancreatic cancer, pharyngeal cancer, prostate cancer, renal cell carcinoma, rhabdomyosarcoma, and squamous cell cancer of the head and neck (SCCHN).

BRIEF DESCRIPTION OF THE DRAWINGS

FIG. 3A shows an Fc Region-containing diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains. FIGS. 3D-3E illustrate how selection of the binding domains shown in FIG. 3B can result in a CD137×TA Binding Molecule having two binding sites specific for an epitope of CD137 and two binding sites specific for an epitope of a TA. FIGS. 3D-3E illustrate how domains may be selected to yield CD137×TA Binding Molecules having differing orientations (i.e., FIG. 3D employs, a VL CD137 Domain as the VL1 Domain of the Binding Molecule, a VH CD137 Domain as the VH1 Domain of the Binding Molecule, a VL TA Domain as the VL2 Domain of the Binding Molecule, and a VH TA Domain as the VH2 Domain of the Binding Molecule. In contrast, FIG. 3E employs, a VL TA Domain as the VL1 Domain of the Binding Molecule, a VH TA Domain as the VH1 Domain of the Binding Molecule, a VL CD137 Domain as the VL2 Domain of the Binding Molecule, and a VH CD137 Domain as the VH2 Domain of the Binding Molecule). As provided below, the VL/VH binding sites formed by the association of the polypeptide chains may be the same or different so as to permit tetravalent binding that is monospecific, bispecific, trispecific or tetraspecific.

FIG. 5A shows the general structure of such a CD137×TA Binding Molecule. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern. FIG. 5B shows the structure of an alternative preferred CD137×TA Binding Molecule in which the variable domains shown in FIG. 5A have been selected to yield a resultant CD137×TA Binding Molecule that possesses two non-diabody type binding domains specific for an illustrative TA, HER2/neu, and two diabody-type binding domains specific for CD137. FIG. 5C shows the structure of an alternative preferred CD137×TA Binding Molecule in which the variable domains shown in FIG. 5A have been selected to yield a resultant CD137×TA Binding Molecule that possesses two non-diabody type binding domains specific for CD137 and two diabody-type binding domains specific for HER2/neu. FIG. 5D shows the structure of an alternative preferred CD137×TA Binding Molecule in which the variable domains shown in FIG. 5A have been selected to yield a resultant CD137×TA Binding Molecule that possesses two non-diabody type binding domains specific for an epitope of CD137, one diabody-type binding domains specific for an epitope of HER2/neu and a second diabody-type binding domain specific for an epitope of CD137. Such CD137 epitopes may be the same or different. As will be appreciated, by proper selection of the binding domains shown in FIG. 5A, any three of the binding domains could have been selected to bind an epitope of CD137. Likewise, any three of the binding domains could have been selected to bind an epitope of HER2/neu. As provided below, the VL/VH binding sites formed by the association of the polypeptide chains may be the same or different so as to permit tetravalent binding that is monospecific, bispecific, trispecific or tetraspecific.

FIG. 6A illustrates schematically the domains of trivalent binding molecules comprising two diabody-type binding domains and a Fab-type binding domain having different domain orientations in which the diabody-type binding domains are C-terminal to an Fc Region. FIGS. 6B-6C show the structure of illustrative preferred CD137×TA Binding Molecule in which the variable domains shown in FIG. 6A have been selected to yield a resultant CD137×TA Binding Molecule that possesses a non-diabody type binding domains specific for CD137, a diabody-type binding domain that is specific for an illustrative TA, HER2/neu, and a second diabody-type binding domain that is specific for CD137. FIG. 6D illustrates schematically the domains of trivalent binding molecules comprising two diabody-type binding domains and a Fab-type binding domain having different domain orientations in which the diabody-type binding domains are C-terminal to an Fc Region. The molecules in FIGS. 6A-6D comprise four chains. FIGS. 6E and 6F, respectively, illustrate schematically the domains of trivalent binding molecules comprising two diabody-type binding domains N-terminal to an Fc Region, and a Fab-type binding domain in which the light chain and heavy chain are linked via a polypeptide spacer, or an scFv-type binding domain. The trivalent binding molecules in FIGS. 6G and 6H, respectively, illustrate schematically the domains of trivalent binding molecules comprising two diabody-type binding domains C-terminal to an Fc Region, and a Fab-type binding domain in which the light chain and heavy chain are linked via a polypeptide spacer, or an scFv-type binding domain. The trivalent binding molecules in FIGS. 6E-6H comprise three chains. VL and VH Domains that recognize the same epitope are shown using the same shading or fill pattern.

FIG. 10A: DART-B and DART-C (comprising hCD137 MAB-3 and hHER2 MAB-1 domains), DART-D and DART-E (comprising CD137 MAB-3 and hHER2 MAB-1 domains), and control molecules, DART-3 (comprising hHER2 MAB-1 and variant palivizumab domains) and DART-6 (comprising variant palivizumab and CD137 MAB-3 domains). FIG. 10B: DART-D (comprising CD137 MAB-3 and hHER2 MAB-1 domains), DART-F (comprising CD137 MAB-4 and hHER2 MAB-1 domains), DART-1, and DART-4 (comprising CD137 MAB-1 and hHER2 MAB-1 domains), DART-2 and DART-5 (comprising CD137 MAB-2 and hHER2 MAB-1 domains) and control binding molecule DART-6 (comprising CD137 MAB-3 and variant palivizumab domains).

FIG. 11A: DART-B, DART-C, DART-D, DART-E, and the control binding molecules DART-3 and DART-6. FIG. 11B: DART-D, DART-F, DART-1, DART-2, DART-4, DART-5, and DART-6.

FIG. 17, Panels A-O show the ability of CD137×TA Binding Molecules to enhance T cell proliferation in co-culture with TA expressing target cells. CFSE-labeled human T cells ±sub-optimal αCD3/αCD28 stimulation co-cultured with HER2/neu-high N87 target cells (FIG. 17, Panels A-C and J-K), HER2/neu-low MCF-7 target cells (FIG. 17, Panels D-F and L-M), or no target cells (FIG. 17, Panels G-I and N-O) in the presence of DART-A (FIG. 17, Panels A, D and G), DART-3 (FIG. 17, Panels B, E and H), DART-6 (FIG. 17, Panels C, F and I), or no molecule (FIG. 17, Panels J, L and N) and monitored for T cell proliferation.

FIG. 23A: binding to N87 (HER2$^{+++}$) gastric cancer cells. FIG. 23B: binding to JIMT-1 (HER2++) breast carcinoma cells. FIG. 23C: binding to MCF-7 (HER2+) breast cancer cells. Binding for TRIDENT-A, TRIDENT-A2, TRIDENT-A3, TRIDENT-A4, DART-G, DART-G2, DART-G3, DART-G4, and the control binding molecules TRIDENT-1 and TRIDENT-2 is shown in both panels.

FIG. 24A: TRIDENT-A, TRIDENT-A2, TRIDENT-A3, TRIDENT-A4, and the control binding molecules TRIDENT-1 and TRIDENT-2. FIG. 24B: DART-G, DART-G2, DART-G3, DART-G4, and the control binding molecules TRIDENT-1 and TRIDENT-2.

FIG. 25A: Cell-cell conjugation with N87 (HER2+++) gastric cancer cells. FIG. 25B: Cell-cell conjugation with JIMT-1 (HER2++) breast carcinoma cells. FIG. 25C: Cell-cell conjugation with MCF-7 (HER2+) breast cancer cells. The activity of TRIDENT-A, TRIDENT-A2, TRIDENT-A3, TRIDENT-A4, DART-G4, and the TRIDENT-2 control binding molecule is shown in both panels.

FIG. 28A: CD4 expression, FIG. 28B: CD8 expression, FIG. 28C: CD69 expression.

FIGS. 31A-31B depict the amino acid sequences of hCD137 MAB-3 VH1B (FIG. 30A, SEQ ID NO:84) and hCD137 MAB-3 VL3 (FIG. 30B, SEQ ID NO:89). underlining indicate CDR residues. Positions of substitution are boxed and the Kabat numbers are indicated with arrows; sequential amino acid residue numbering is indicated above the sequences.

DETAILED DESCRIPTION OF THE INVENTION

Figure 1A:
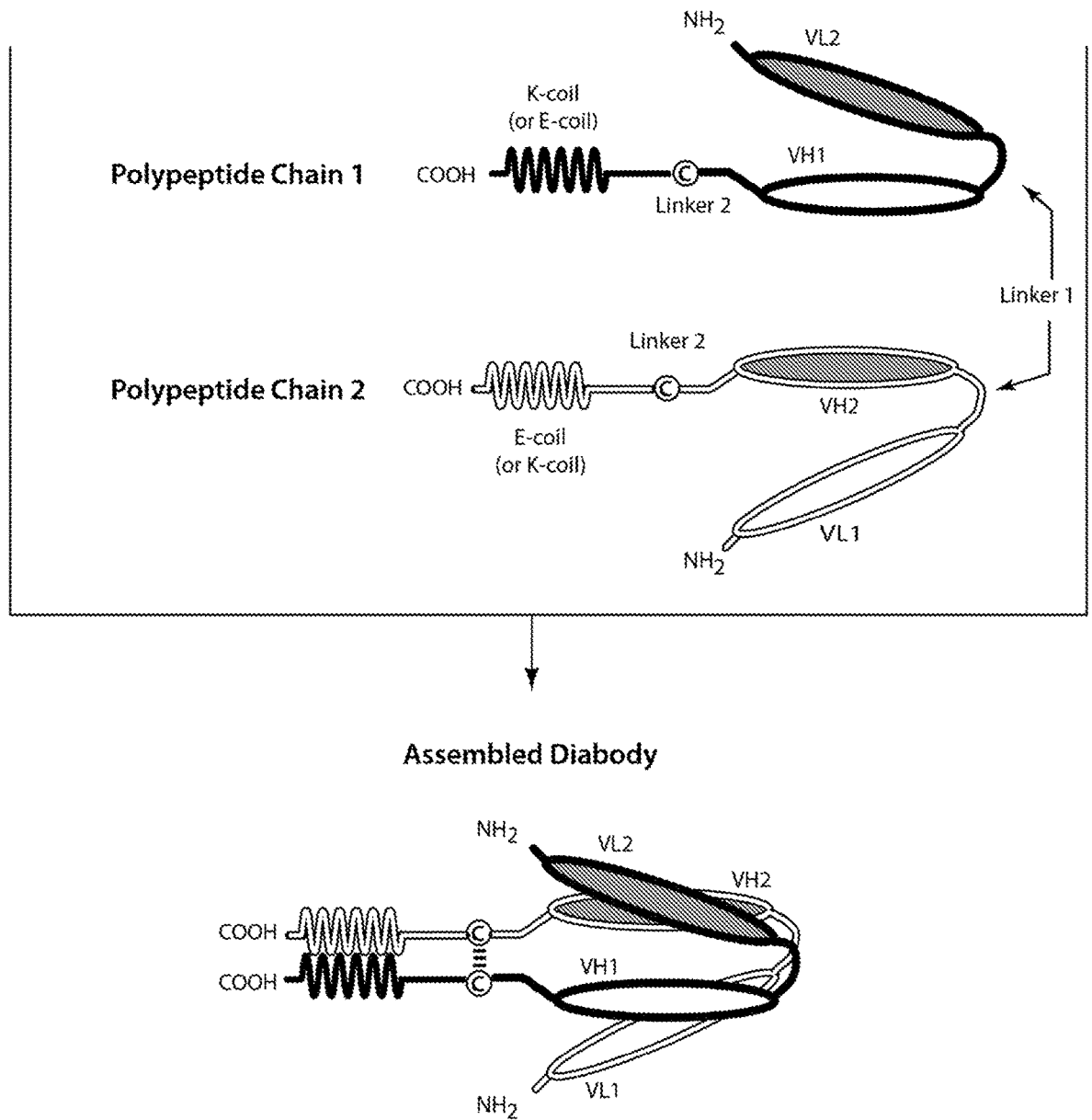
FIGS. 1A-1B provide schematics of a representative covalently bonded diabody having two epitope-binding sites composed of two polypeptide chains, each having an E-coil or K-coil Heterodimer-Promoting Domain (alternative Heterodimer-Promoting Domains are provided below). A cysteine residue may be present in a linker (FIG. 1A) and/or in the Heterodimer-Promoting Domain (FIG. 1B). VL and VH Domains that recognize the same epitope are shown using the same shading or fill pattern. The wavy line ( WWW ) in this and all of the Figures providing schematic presentations of binding molecule domains represents one or more optional Heterodimer-Promoting Domains, that is/are preferably present.

The present invention is directed to binding molecules that possess one or more epitope-binding sites specific for an epitope of CD137 and one or more epitope-binding sites specific for an epitope of a tumor antigen ("TA") (e.g., a "CD137×TA Binding Molecule"). In one embodiment, such CD137×TA Binding Molecules will be bispecific molecules, especially bispecific tetravalent diabodies, that are composed of two, three, four or more than four polypeptide chains and possessing two epitope-binding sites each specific for an epitope of CD137 and two epitope-binding sites each specific for an epitope of a TA. Alternatively, such CD137×TA Binding Molecules will be bispecific molecules, especially bispecific trivalent binding molecules composed of three or more polypeptide chains and possessing one or two epitope-binding sites each specific for an epitope of CD137 and one or two epitope-binding sites each specific for an epitope of a TA. The CD137×TA Binding Molecules of the invention are capable of simultaneous binding to CD137, and a TA. The invention is directed to pharmaceutical compositions that contain any such CD137×TA Binding Molecules. The invention is additionally directed to methods for the use of such molecules in the treatment of cancer and other diseases and conditions. The invention also provides novel CD137-binding molecules, and HER2/neu-binding molecules, as well as derivatives thereof and uses thereof.

I. Antibodies and Other Binding Molecules

Antibodies are immunoglobulin molecules capable of specific binding to a target region ("epitope") of a molecule, such as a carbohydrate, polynucleotide, lipid, polypeptide, etc. ("antigen"), through at least one "epitope-binding site" located in the Variable Region of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, the term "antibody"

includes immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. Antibodies are capable of "immunospecifically binding" to a polypeptide or protein or a non-protein molecule due to the presence on such molecule of a particular domain or moiety or conformation (an "epitope"). As used herein, an "epitope-binding fragment of an antibody" is intended to denote a portion of an antibody capable of immunospecifically binding to an epitope. As used herein, such term encompasses fragments (such as Fab, Fab', $F(ab')_2$ Fv), and single chain (scFv), as well as the epitope-binding domain of a diabody. As used herein, an antibody or an epitope-binding fragment thereof is said to "immunospecifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or an epitope-binding fragment thereof that immunospecifically binds to a first target may or may not specifically or preferentially bind to a second target. An epitope-containing molecule may have immunogenic activity, such that it elicits an antibody production response in an animal; such molecules are termed "antigens". Natural antibodies are capable of binding to only one epitope species (i.e., they are "monospecific"), although they can bind multiple copies of that species (i.e., exhibiting "bivalency" or "multivalency").

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', $F(ab')_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity,*" Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production,*" ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freund's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced, and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and/or predicted amino acid sequence of the light and heavy chain Variable Domains of the starting antibody; (2) designing the humanized antibody or caninized antibody, i.e., deciding which antibody framework region(s) to use during the humanizing or caninizing process; (3) application of the actual humanizing or caninizing methodologies/techniques; and (4) the transfection and expression of the humanized or caninized antibody (see, for example, U.S. Pat. Nos. 4,816,567; 5,807,715; 5,866,692; and 6,331,415).

The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases,*" Singapore Med. J. 50(7):663-666). Over 200 antibody-based drugs have been approved for use or are under development.

A. General Structural Attributes of Antibodies

The basic structural unit of naturally occurring immunoglobulins (e.g., IgG) is a tetramer composed of two shorter "Light Chains" complexed with two longer "Heavy Chains" and is usually expressed as a glycoprotein of about 150,000 Da. Each chain is composed of an amino-terminal ("N-terminal") portion that comprises a "Variable Domain" and a carboxy-terminal ("C-terminal") portion that comprises at least one "Constant Domain." An IgG Light Chain is composed of a single "Light Chain Variable Domain" ("VL") and a single "Light Chain Constant Domain" ("CL"). Thus, the structure of the light chains of an IgG molecule is n-VL-CL-c (where n and c represent, respectively, the N-terminus and the C-terminus of the polypeptide). An IgG Heavy Chain is composed of a single "Heavy Chain Variable Domain" ("VH"), three "Heavy Chain Constant Domains" ("CH1," "CH2" and "CH3"), and a "Hinge" Region ("H"), located between the CH1 and CH2 Domains. Thus, the structure of an IgG heavy chain is n-VH-CH1-H-CH2-CH3-c (where n and c represent, respectively, the N-terminus and the C-terminus of the polypeptide). The ability of an intact, unmodified antibody (e.g., an IgG antibody) to bind an epitope of an antigen depends upon the presence and sequences of the Variable Domains.

1. Constant Domains
(a) Light Chain Constant Domain
A preferred CL Domain is a human IgG CL Kappa Domain. The amino acid sequence of an exemplary human CL Kappa Domain is (SEQ ID NO:1):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG CL Lambda Domain. The amino acid sequence of an exemplary human CL Lambda Domain is (SEQ ID NO:2):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

(b) Heavy Chain CH1 Domains
An exemplary CH1 Domain is a human IgG1 CH1 Domain. The amino acid sequence of an exemplary human IgG1 CH1 Domain is (SEQ ID NO:3):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV
```

An exemplary CH1 Domain is a human IgG2 CH1 Domain. The amino acid sequence of an exemplary human IgG2 CH1 Domain is (SEQ ID NO:4):

```
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV
```

An exemplary CH1 Domain is a human IgG3 CH1 Domain. The amino acid sequence of an exemplary human IgG3 CH1 Domain is (SEQ ID NO:5):

```
ASTKGPSVFP LAPCSRSTSG GTAALGCLVK DYFPEPVTVS

WNSGALTSGV HTFPAVLQSS GLYSLSSVVT VPSSSLGTQT

YTCNVNHKPS NTKVDKRV
```

An exemplary CH1 Domain is a human IgG4 CH1 Domain. The amino acid sequence of an exemplary human IgG4 CH1 Domain is (SEQ ID NO:6):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV
```

(c) Heavy Chain Hinge Regions
An exemplary Hinge Region is a human IgG1 Hinge Region. The amino acid sequence of an exemplary human IgG1 Hinge Region is (SEQ ID NO:7):

```
EPKSCDKTHT CPPCP
```

Another exemplary Hinge Region is a human IgG2 Hinge Region. The amino acid sequence of an exemplary human IgG2 Hinge Region is (SEQ ID NO:8):

```
ERKCCVECPP CP
```

Another exemplary Hinge Region is a human IgG3 Hinge Region. The amino acid sequence of an exemplary human IgG3 Hinge Region is (SEQ ID NO:9):

```
ELKTPLGDTT HTCPRCPEPK SCDTPPPCPR CPEPKSCDTP

PPCPRCPEPK SCDTPPPCPR CP
```

Another exemplary Hinge Region is a human IgG4 Hinge Region. The amino acid sequence of an exemplary human IgG4 Hinge Region is (SEQ ID NO:10):

```
ESKYGPPCPS CP
```

As described herein, an IgG4 Hinge Region may comprise a stabilizing mutation such as the S228P substitution (as numbered by the EU index as set forth in Kabat). The amino acid sequence of an exemplary stabilized IgG4 Hinge Region is (SEQ ID NO:11):

```
ESKYGPPCPP CP
```

(d) Heavy Chain CH2 and CH3 Domains
The CH2 and CH3 Domains of the two heavy chains interact to form the "Fc Region" of IgG antibodies that is recognized by cellular Fc Receptors, including but not limited to Fc gamma Receptors (FcγRs). As used herein, the term "Fc Region" is used to define a C-terminal region of an IgG heavy chain. A portion of an Fc Region (including a portion that encompasses an entire Fc Region) is referred to herein as an "Fc Domain." An Fc Region is said to be of a particular IgG isotype, class or subclass if its amino acid sequence is most homologous to that isotype relative to other IgG isotypes. In addition to their known uses in diagnostics, antibodies have been shown to be useful as therapeutic agents.

The amino acid sequence of the CH2-CH3 Domain of an exemplary human IgG1 is (SEQ ID NO:12).

```
        231         240         250         260         270
        APELLGGPSV  FLFPPKPKDT  LMISRTPEVT  CVVVDVSHED 280         290         300         310
        PEVKFNWYVD  GVEVHNAKTK  PREEQYNSTY  RVVSVLTVLH 320         330         340         350
        QDWLNGKEYK  CKVSNKALPA  PIEKTISKAK  GQPREPQVYT 360         370         380         390
        LPPSREEMTK  NQVSLTCLVK  GFYPSDIAVE  WESNGQPENN 400         410         420         430
        YKTTPPVLDS  DGSFFLYSKL  TVDKSRWQQG  NVFSCSVMHE 440         447
        ALHNHYTQKS  LSLSPGX
as numbered by the EU index as set forth in Kabat,
wherein X is a lysine (K) or is absent.
```

The amino acid sequence of the CH2-CH3 Domain of an exemplary human IgG2 is (SEQ ID NO:13):

```
231        240        250        260        270
APPVA-GPSV FLFPPKPKDT LMISRTPEVT CVVVDVSHED 280        290        300        310
PEVQFNWYVD GVEVHNAKTK PREEQFNSTF RVVSVLTVVH 320        330        340        350
QDWLNGKEYK CKVSNKGLPA PIEKTISKTK GQPREPQVYT 360        370        380        390
LPPSREEMTK NQVSLTCLVK GFYPSDISVE WESNGQPENN 400        410        420        430
YKTTPPMLDS DGSFFLYSKL TVDKSRWQQG NVFSCSVMHE 440        447
ALHNHYTQKS LSLSPGX
as numbered by the EU index as set forth in Kabat,
wherein X is a lysine (K) or is absent.
``` as numbered by the EU index as set forth in Kabat, wherein X is a lysine (K) or is absent.

The amino acid sequence of the CH2-CH3 Domain of an exemplary human IgG3 is (SEQ ID NO:14):

```
231        240        250        260        270
APELLGGPSV FLFPPKPKDT LMISRTPEVT CVVVDVSHED 280        290        300        310
PEVQFKWYVD GVEVHNAKTK PREEQYNSTF RVVSVLTVLH 320        330        340        350
QDWLNGKEYK CKVSNKALPA PIEKTISKTK GQPREPQVYT 360        370        380        390
LPPSREEMTK NQVSLTCLVK GFYPSDIAVE WESSGQPENN 400        410        420        430
YNTTPPMLDS DGSFFLYSKL TVDKSRWQQGN IFSCSVMHE 440        447
ALHNRFTQKS LSLSPGX
as numbered by the EU index as set forth in Kabat,
wherein X is a lysine (K) or is absent.
```

The amino acid sequence of the CH2-CH3 Domain of an exemplary human IgG4 is (SEQ ID NO:15):

```
231        240        250        260        270
APEFLGGPSV FLFPPKPKDT LMISRTPEVT CVVVDVSQED 280        290        300        310
PEVQFNWYVD GVEVHNAKTK PREEQFNSTY RVVSVLTVLH 320        330        340        350
QDWLNGKEYK CKVSNKGLPS SIEKTISKAK GQPREPQVYT 360        370        380        390
LPPSQEEMTK NQVSLTCLVK GFYPSDIAVE WESNGQPENN 400        410        420        430
YKTTPPVLDS DGSFFLYSRL TVDKSRWQEG NVFSCSVMHE 440        447
ALHNHYTQKS LSLSLGX
as numbered by the EU index as set forth in Kabat,
wherein X is a lysine (K) or is absent.
```

Throughout the present specification, the numbering of the residues in the constant region of an IgG heavy chain is that of the EU index as in Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by reference. The term "EU index as in Kabat" refers to the numbering of the constant domains of human IgG1 EU antibody.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation.*" Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the CD137×TA Binding Molecules of the invention. Specifically encompassed by the instant invention are CD137×TA Binding Molecules lacking the C-terminal residue of the CH3 Domain. Also specifically encompassed by the instant invention are such constructs comprising the C-terminal lysine residue of the CH3 Domain.

2. Variable Domains

The Variable Domains of an IgG molecule consist of three "complementarity determining regions" ("CDRs"), which contain the amino acid residues of the antibody that will be in contact with the epitope, as well as intervening non-CDR segments, referred to as "framework regions" ("FR"), which, in general maintain the structure and determine the positioning of the CDR loops so as to permit such contacting (although certain framework residues may also contact the epitope). Thus, the VL and VH Domains have the structure n-FR1-CDR1-FR2-CDR2-FR3-CDR3-FR4-c. The amino acid sequences of the CDRs determine whether an antibody will be able to bind to a particular epitope. Interaction of an antibody light chain with an antibody heavy chain and, in particular, interaction of their VL and VH Domains, forms an epitope-binding site of the antibody.

Amino acids from the Variable Domains of the mature heavy and light chains of immunoglobulins are designated by the position of an amino acid in the chain. Kabat (SEQUENCES OF PROTEINS OF IMMUNOLOGICAL INTEREST, 5$^{th}$ Ed. Public Health Service, NH1, MD (1991)) described numerous amino acid sequences for antibodies, identified an amino acid consensus sequence for each subgroup, and assigned a residue number to each amino acid, and the CDRs and FRs are identified as defined by Kabat (it will be understood that CDR$_H$1 as defined by Chothia, C. & Lesk, A. M. ((1987) "*Canonical Structures For The Hypervariable Regions Of Immunoglobulins,*" J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or is a diabody or a single-chain binding molecule (e.g., an scFv, a BiTe, etc.), or is another type of protein. Accordingly, as used herein, the term "Epitope-Binding Fragment" denotes a fragment of a molecule capable of immunospecifically binding to an epitope. An epitope-binding fragment may contain any 1, 2, 3, 4, or 5 the CDR Domains of an antibody, or may contain all 6 of the CDR Domains of an antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an $Fab_2$ fragment, etc.). Unless specifically noted, the order of domains of the protein molecules described herein is in the "N-Terminal to C-Terminal" direction.

The epitope-binding site may comprise either a complete Variable Domain fused onto Constant Domains or only the complementarity determining regions (CDRs) of such Variable Domain grafted to appropriate framework regions. Epitope-binding sites may be wild-type or modified by one or more amino acid substitutions. This eliminates the constant region as an immunogen in human individuals, but the possibility of an immune response to the foreign variable domain remains (LoBuglio, A. F. et al. (1989) "*Mouse Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable domains as well so as to reshape them as closely as possible to human form. It is known that the variable domains of both heavy and light chains contain three Complementarity Determining Regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991)"*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

B. Humanization of Antibodies

The invention particularly encompasses binding molecules (including antibodies and diabodies) that comprise a VL and/or VH Domain of a humanized antibody. The term "humanized" antibody refers to a chimeric molecule, generally prepared using recombinant techniques, having an epitope-binding site of an immunoglobulin from a non-human species and a remaining immunoglobulin structure of the molecule that is based upon the structure and/or sequence of a human immunoglobulin. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

A number of humanized antibody molecules comprising an epitope-binding site derived from a non-human immunoglobulin have been described, including chimeric antibodies having rodent or modified rodent Variable Domain and their associated complementarity determining regions (CDRs) fused to human constant domains (see, for example, Winter et al. (1991) "*Man-made Antibodies*," Nature 349: 293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody* (17-4A) *To A Colon Cancer Tumor-Associated Antigen*," J. Immunol. 138:4534-4538, and Brown et al. (1987) "*Tumor-Specific Genetically Engineered Murine/Human Chimeric Monoclonal Anti-* body," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

Notwithstanding such successes, the production of stable, functional heterodimeric, non-monospecific diabodies optimized for therapeutic use can be further improved by the careful consideration and placement of the domains employed in the polypeptide chains. The present invention is thus directed to the provision of specific polypeptides that are particularly designed to form, via covalent bonding, stable and therapeutically useful heterodimeric diabodies and heterodimeric Fc diabodies that are capable of simultaneously binding CD137 and a TA.

C. Bispecific Antibodies, Multi-Specific Diabodies and DART® Diabodies

As indicated above, natural antibodies are capable of binding to only one epitope species, although they can bind multiple copies of that species. The art has recognized the desirability of producing bispecific antibodies, and a wide variety of recombinant bispecific antibody formats have been developed to produce such bispecific antibodies (see, e.g., PCT Publication Nos. WO 2008/003116, WO 2009/132876, WO 2008/003103, WO 2007/146968, WO 2009/018386, WO 2012/009544, WO 2013/070565). Most of such approaches use linker peptides to fuse a further binding domain (e.g. an scFv, VL, VH, etc.) to, or within the antibody core (IgA, IgD, IgE, IgG or IgM), or to fuse multiple antibody binding portions to one another (e.g. two Fab fragments or scFv). Alternative formats use linker peptides to fuse a binding protein (e.g., an scFv, VL, VH, etc.) to a dimerization domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publication Nos. WO 2013/174873, WO 2011/133886 and WO 2010/136172 disclose that the use of linkers may cause problems in therapeutic settings, and teaches a tri-specific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publication Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publication Nos. WO 2010/028797, WO2010028796 and WO 2010/028795 disclose recombinant antibodies whose Fc Regions have been replaced with additional VL and VH Domains, so as to form trivalent binding molecules. PCT Publication Nos. WO 2003/025018 and WO2003012069 disclose recombinant diabodies whose individual chains contain scFv domains. PCT Publication No. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publication Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional Binding Domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability of producing diabodies that differ from natural antibodies in being capable of binding two or more different epitope species (i.e., exhibiting bispecificity or multispecificity in addition to bi-valency or multi-valency) (see, e.g., Holliger et al. (1993) "'*Diabodies': Small Bivalent And Bispecific Antibody Fragments*," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20): 19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng Des Sel. 17(1): 21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T cell Engaging Antibodies For Cancer Therapy*," Cancer Res. 69(12):4941-4944).

The provision of non-monospecific "diabodies" provides a significant advantage over antibodies: the capacity to co-ligate and co-localize cells that express different epitopes. Bispecific diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their bivalency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T cells Mediated By A Bispecific Diabody*," Protein Eng. 9:299-305) to thereby co-localize T cells to the sites of tumor cells.

Alternatively to targeting such diabodies to bind to T cells, diabody epitope binding domains may be directed to a surface determinant of a B cell, such as CD19, CD20, CD22, CD30, CD37, CD40, and CD74 (Moore, P. A. et al. (2011) "*Application Of Dual Affinity Retargeting Molecules To Achieve Optimal Redirected T cell Killing Of B-Cell Lymphoma*," Blood 117(17):4542-4551; Cheson, B. D. et al. (2008) "*Monoclonal Antibody Therapy For B-Cell Non-Hodgkin's Lymphoma*," N. Engl. J. Med. 359(6):613-626; Castillo, J. et al. (2008) "*Newer Monoclonal Antibodies For Hematological Malignancies*," Exp. Hematol. 36(7):755-768). In many studies, diabody binding to effector cell determinants, e.g., Fcγ receptors (FcγR), was also found to activate the effector cell (Holliger et al. (1996) "*Specific Killing Of Lymphoma Cells By Cytotoxic T cells Mediated By A Bispecific Diabody*," Protein Eng. 9:299-305; Holliger et al. (1999) "*Carcinoembryonic Antigen (CEA)-Specific T cell Activation In Colon Carcinoma Induced By Anti-CD3× Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen-bound antibody to an effector cell via an Fc Domain-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of a tumor cell but leads to effective tumor killing (see e.g., Cao et al. (2003) "*Bispecific Antibody Conjugates In Therapeutics*," Adv. Drug. Deliv. Rev. 55:171-197).

However, the above advantages come at a salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-mono-specific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to address covalent bonding between polypeptides of the same species (i.e., so as to minimize their homodimerization) (Takemura, S. et al. (2000) "*Construction Of A Diabody (Small Recombinant Bispecific Antibody) Using A Refolding System*," Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bispecific diabodies composed of non-covalently associated polypeptides are unstable and readily dissociate into non-functional single polypeptide chain monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-mono-specific diabodies, termed DART® diabodies, see, e.g., Chichili, G. R. et al. (2015) "*A CD3×CD123 Bispecific DART For Redirecting Host T Cells To Myelogenous Leukemia: Preclinical Activity And Safety In Nonhuman Primates*," Sci. Transl. Med. 7(289):289ra82; Johnson, S. et al. (2010) "*Effector Cell Recruitment With Novel Fv-Based Dual-Affinity Re-Targeting Protein Leads To Potent Tumor Cytolysis And In Vivo B-Cell Depletion*," J. Molec. Biol. 399(3):436-449; Veri, M. C. et al. (2010) "*Therapeutic Control Of B Cell Activation Via Recruitment Of Fcgamma Receptor IIB (CD32B) Inhibitory Function With A Novel Bispecific Antibody Scaffold*," Arthritis Rheum. 62(7):1933-1943; Moore, P. A. et al. (2011) "*Application Of Dual Affinity Retargeting Molecules To Achieve Optimal Redirected T cell Killing Of B-Cell Lymphoma*," Blood 117(17): 4542-4551; U.S. Pat. Nos. 8,044,180; 8,133,982; 8,187,593; 8,193,318; 8,530,627; 8,669,349; 8,778,339; 8,784,808; 8,795,667; 8,802,091; 8,802,093; 8,946,387; 8,968,730; and 8,993,730; US Patent Publication Nos. 2009/0060910; 2010/0174053; 2011/0081347; 2011/0097323; 2011/0117089; 2012/0009186; 2012/0034221; 2012/0141476; 2012/0294796; 2013/0149236; 2013/0295121; 2014/0017237; and 2014/0099318; European Patent Documents No. EP 1868650; EP 2158221; EP 2247304; EP 2252631; EP 2282770; EP 2328934; EP 2376109; EP 2542256; EP 2601216; EP 2714079; EP 2714733; EP 2786762; EP 2839842; EP 2840091; and PCT Publication Nos. WO 2006/113665; WO 2008/157379; WO 2010/027797; WO 2010/033279; WO 2010/080538; WO 2011/109400; WO 2012/018687; WO 2012/162067; WO 2012/162068; WO 2014/159940; WO 2015/021089; WO 2015/026892; and WO 2015/026894). Such diabodies comprise two or more covalently complexed polypeptides and involve engineering one or more cysteine residues into each of the employed polypeptide species. For example, the addition of a cysteine residue to the C-terminus of such constructs has been shown to allow disulfide bonding between the polypeptide chains, stabilizing the resulting heterodimer without interfering with the binding characteristics of the bivalent molecule.

Figure 1B:
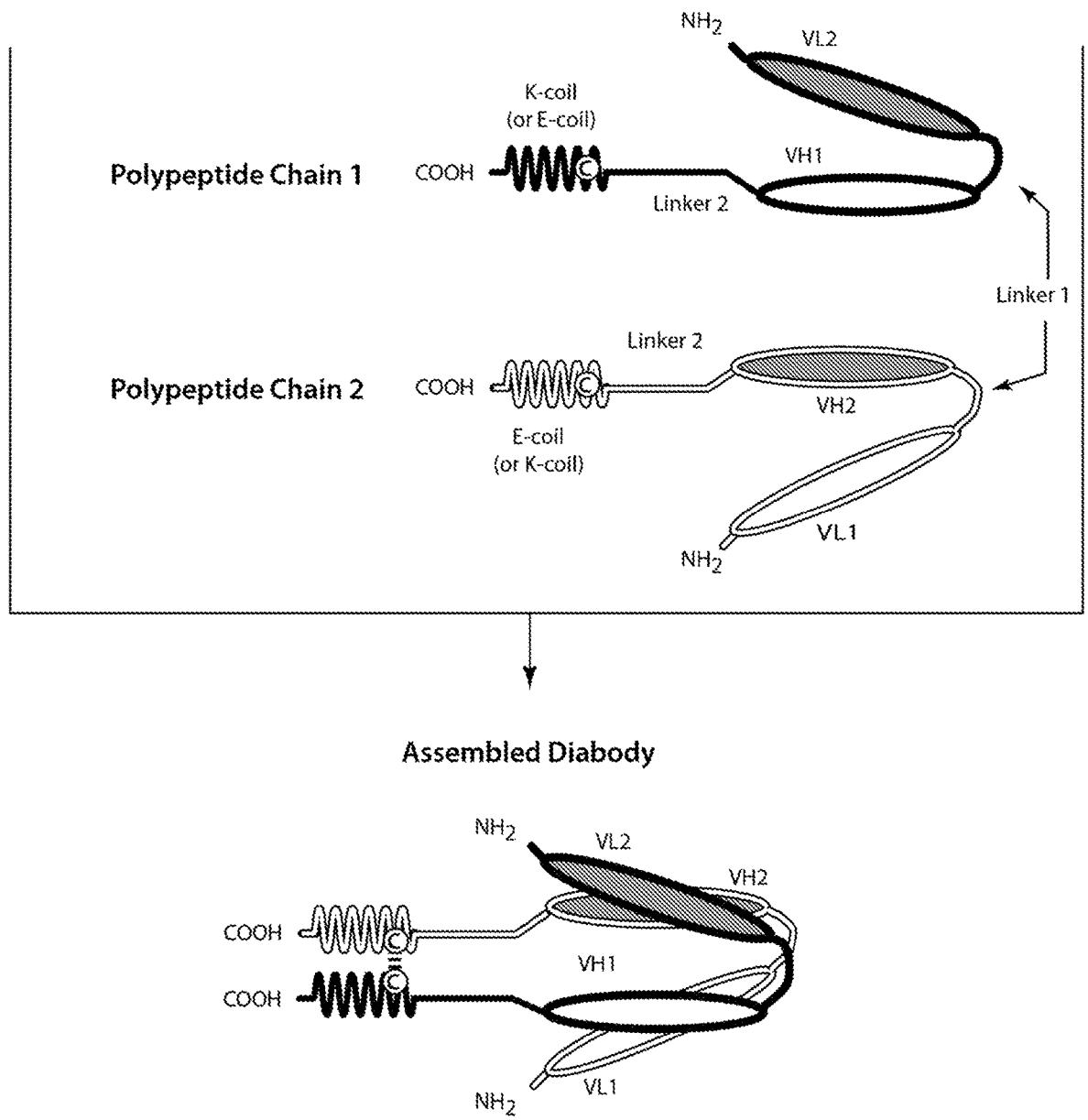

The simplest DART® diabody comprises two polypeptide chains each comprising three Domains (FIG. 1). The first polypeptide chain comprises: (i) a first Domain that comprises a binding region of a light chain variable Domain of a first immunoglobulin (VL1), (ii) a second Domain that comprises a binding region of a heavy chain variable Domain of a second immunoglobulin (VH2), and (iii) a third Domain that serves to promote heterodimerization (a "Heterodimer-Promoting Domain") with the second polypeptide chain and to covalently bond the first polypeptide to the second polypeptide chain of the diabody. The second polypeptide chain contains a complementary first Domain (a VL2 Domain), a complementary second Domain (a VH1 Domain) and a third Domain that complexes with the third Domain of the first polypeptide chain in order to promote heterodimerization (a "Heterodimer-Promoting Domain") and covalent bonding with the first polypeptide chain. Such molecules are stable, potent and have the ability to simultaneously bind two or more antigens. In one embodiment, the third Domains of the first and second polypeptide chains each contain a cysteine ("ⓒ") residue, which serves to bind the polypeptides together via a disulfide bond. The third Domain of one or both of the polypeptide chains may additionally possesses the sequence of a CH2-CH3 Domain, such that complexing of the diabody polypeptides forms an Fc Domain that is capable of binding to the Fc receptor of cells (such as B lymphocytes, dendritic cells, natural killer cells, macrophages, neutrophils, eosinophils, basophils and mast cells). Many variations of such molecules have been described (see, e.g., United States Patent Publication Nos. 2013-0295121; 2010-0174053; 2007-0004909; 2009-0060910; European Patent Publication No. EP 2714079; EP 2601216; EP 2376109; EP 2158221 and PCT Publication Nos. WO 2012/162068; WO 2012/018687; WO 2010/080538; WO 2006/113665) and are provided herein.

II. Components of the Preferred CD137×TA Binding Molecules of the Present Invention The CD137×TA Binding Molecules of the present invention are composed of polypeptides, and may be composed of two, three, four or more than four polypeptide chains. As used herein, the term "composed of" is intended to be open-ended, such that a CD137×TA Binding Molecules of the present invention that is composed of two polypeptide chains may possess additional polypeptide chains. Such chains may have the same sequence as another polypeptide chain of the Binding Molecule, or may be different in sequence from any other polypeptide chain of the Binding Molecule.

A. Preferred "Linker" Peptides

The polypeptides of the CD137×TA Binding Molecules of the present invention comprise domains that are preceded by, followed by, and/or linked to one another by "linker" peptides, such as Linker 1, Linker 2, Linker 3, etc. Although the invention utilizes certain preferred "linker" peptides, in light of the teachings provided herein, alternative linkers could readily be identified and employed to achieve CD137× TA Binding Molecules.

Most preferably, the length of Linker 1, which separates such VL and VH domains of a polypeptide chain is selected to substantially or completely prevent such VL and VH domains from binding to one another (e.g., 12 or less amino acid residues in length). Thus, the VL1 and VH2 domains of the first polypeptide chain are substantially or completely incapable of binding to one another, and do not form an epitope-binding site that is capable of substantially binding to either the first or second antigen. Likewise, the VL2 and VH1 domains of the second polypeptide chain are substantially or completely incapable of binding to one another, and do not form an epitope-binding site that is capable of substantially binding to either the first or second antigen. A preferred intervening spacer peptide (Linker 1) has the sequence (SEQ ID NO:16): GGGS GGGG, which is too short to allow the VL and VH Domains of the same polypeptide chain to complex together (in contrast to the longer intervening spacer peptide that is employed to produce scFv molecules (e.g., GGGGSGGGGSGGGGS (SEQ ID NO:17)).

The purpose of Linker 2 is to separate the VH Domain of a polypeptide chain from the optionally present Heterodimer-Promoting Domain of that polypeptide chain. Any of a variety of linkers can be used for the purpose of Linker 2. A preferred sequence for such Linker 2 has the amino acid sequence: GGCGGG (SEQ ID NO:18), which possesses a cysteine residue that may be used to covalently bond the first and second polypeptide chains to one another via a disulfide bond, or ASTKG (SEQ ID NO:19), which is derived from the IgG CH1 domain. Since the Linker 2, ASTKG (SEQ ID NO:19) does not possess such a cysteine, the use of such Linker 2 is preferably associated with the use of a cysteine-containing Heterodimer-Promoting Domain, such as the E-coil of SEQ ID NO:38 or the K-coil of SEQ ID NO:39 (see below).

One purpose of Linker 3 is to separate the Heterodimer-Promoting Domain of a polypeptide chain from the Fc Domain of that polypeptide chain. A second purpose is to provide a cysteine-containing polypeptide domain. Any of a variety of linkers can be used for the purpose of Linker 3. A preferred sequence for such Linker 3 has the amino acid sequence: DKTHTCPPCP (SEQ ID NO:20). Another preferred sequence for Linker 3 has the amino acid sequence: GGGDKTHTCPPCP (SEQ ID NO:21).

The purpose of Linker 4 is to separate the C-terminus of the CH2-CH3 domains of an Fc Region ("Fc Domain") from the N-terminus of a VL Domain. Any of a variety of linkers can be used for the purpose of Linker 4. A preferred sequence for such Linker 4 has the amino acid sequence: APSSS (SEQ ID NO:22) or the amino acid sequence APSSSPME (SEQ ID NO:23) or the amino acid sequence GGGSGGGSGGG (SEQ ID NO:24), The Fc Region-containing molecules of the present invention may include additional intervening spacer peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Region (preferably a cysteine-containing portion of an IgG Hinge Region). Linkers that may be employed in the bispecific Fc Region-containing diabody molecules of the present invention include: GGC, GGG, ASTKG (SEQ ID NO:19), DKTHTCPPCP (SEQ ID NO:20), APSSS (SEQ ID NO:22), APSSSPME (SEQ ID NO:23), GGGSGGGSGGG (SEQ ID NO:24), LGGGSG (SEQ ID NO:25), GGGS (SEQ ID NO:26), LEPKSS (SEQ ID NO:27), VEPKSADKTHTCPPCP (SEQ ID NO:28), LEPKSADKTHTCPPCP (SEQ ID NO:29). LEPKSS (SEQ ID NO:27) may be used in lieu of GGG or GGC for ease of cloning. Additionally, the amino acids GGG, or LEPKSS (SEQ ID NO:27) may be immediately followed by DKTHTCPPCP (SEQ ID NO:20) to form the alternate linkers: GGGDKTHTCPPCP (SEQ ID NO:21); and LEPKSSDKTHTCPPCP (SEQ ID NO:30). Bispecific Fc Region-containing molecules of the present invention may incorporate an IgG Hinge Region, such as the IgG Hinge Region of a human IgG1, IgG2, IgG3 or IgG4 antibody, or a portion thereof.

B. Preferred Heterodimer-Promoting Domains

As indicated above, the formation of the CD137×TA Binding Molecules of the present invention involves the assembly of two or more different polypeptide chains (i.e., heterodimerization). The formation of heterodimers of the first and second polypeptide chains can be driven by the inclusion of "Heterodimer-Promoting Domains." The Heterodimer-Promoting Domains may be a domain of a Hinge Region of an IgG (or a polypeptide derived from a Hinge Region, such as, for example, GVEPKSC (SEQ ID NO:31), VEPKSC (SEQ ID NO:32) or AEPKSC (SEQ ID NO:33)) on one polypeptide chain, and a CL Domain (or a polypeptide derived from the CL Domain, such as, for example, GFNRGEC (SEQ ID NO:34) or FNRGEC (SEQ ID NO:35)) on the other polypeptide chain (US2007/0004909).

More preferably, however, the Heterodimer-Promoting Domains of the present invention will comprise tandemly repeated coil domains of opposing charge, for example "E-coil" helical domains (SEQ ID NO:36: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:37: KVAALKE-KVAALKE-KVAALKE-KVAALKE), whose lysine residues will form a positive charge at pH 7. The presence of such charged domains promotes association between the first and second polypeptides, and thus fosters heterodimerization. In another preferred embodiment, a Heterodimer-Promoting Domain in which one of the four tandem "E-coil" helical domains of SEQ ID NO:36 has been modified to contain a cysteine residue: EVAACEK-EVAALEK-EVAALEK-EVAALEK (SEQ ID NO:38) is utilized. Likewise, in another preferred embodiment, a Heterodimer-Promoting Domain in which one of the four tandem "K-coil" helical domains of SEQ ID NO:37 has been modified to contain a cysteine residue: KVAACKE-KVAALKE-KVAALKE-KVAALKE (SEQ ID NO:39) is utilized.

C. Covalent Bonding of the Polypeptide Chains

The CD137×TA Binding Molecules of the present invention are engineered so that pairs of their polypeptide chains covalently bond to one another via one or more cysteine residues positioned along their length to produce a covalently associated molecular complex. Such cysteine residues may be introduced into the intervening linker that separates the VL and VH domains of the polypeptides. Alternatively, Linker 2 or Linker 3, or an alternative linker may contain a cysteine residue. Most preferably, one or more coil domains of a coil-containing Heterodimer-Promoting Domain will comprise an amino acid substitution that incorporates a cysteine residue as in SEQ ID NO:38 or SEQ ID NO:39.

D. Preferred Fc Domains

The Fc Domain of an Fc-bearing CD137×TA Binding Molecule of the present invention may comprise a complete Fc region (e.g., a complete IgG Fc region) or only a fragment of a complete Fc region. The Fc Domain of the Fc-bearing CD137×TA Binding Molecules of the present invention may thus include some or all of the CH2 Domain and/or some or all of the CH3 Domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bispecific Fc diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 Domain linked to a CH2 Domain, etc.).

Although the Fc Domain of an Fc-bearing CD137×TA Binding Molecule of the present invention may comprise the amino acid sequence of a naturally occurring FC Domain, it is preferred for the CH2-CH3 Domains that form such Fc Domain to comprise one or more substitutions such that the resultant FC Domain exhibits decreased (e.g., less than 50%, less than 40%, less than 30%, less than 20%, or less than 10%, of the binding exhibited by such molecule if having an Fc Domain having the amino acid sequence of a naturally-occurring Fc Region), or substantially no detectable, binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region). Fc variants and mutant forms capable of mediating such altered binding are well known in the art and include amino acid substitutions at one or more positions elected from the group consisting of: 234, 235, 265, and 297, wherein said numbering is that of the EU index as in Kabat (see, for example, U.S. Pat. No. 5,624,821, herein incorporated by reference). In one embodiment, the CH2-CH3 Domain of the first and/or third polypeptide chains of the Fc-bearing molecules of the invention include any 1, 2, 3, or 4 of the substitutions: L234A, L235A, D265A, N297Q, and N297G. Alternatively, a CH2-CH3 Domain of a naturally occurring Fc region that inherently exhibits decreased (or substantially no) binding to FcγRIIIA (CD16a) and/or reduced effector function (relative to the binding and effector function exhibited by the wild-type IgG1 Fc Region (SEQ ID NO:12)) is utilized. In a specific embodiment, the Fc-bearing molecules of the present invention comprise an IgG2 Fc Region (SEQ ID NO:13) or an IgG4 Fc Region (SEQ ID:NO:15). When an IgG4 Fc Region is utilized, the instant invention also encompasses the introduction of a stabilizing mutation, such as the Hinge Region S228P substitution described above (see, e.g., SEQ ID NO:11).

In a preferred embodiment, the employed CH2-CH3 Domain of Fc-bearing CD137×TA Binding Molecules of the present invention include a substitution at position 234 with alanine and 235 with alanine, wherein said numbering is that of the EU index as in Kabat (SEQ ID NO:40):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX wherein, X is a lysine (K) or is absent.
```

The serum half-life of proteins comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., a human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the Fc-bearing CD137×TA Binding Molecules of the present invention comprise a variant Fc Region, wherein said variant Fc Region comprises at least one amino acid modification relative to a wild-type Fc Region, such that said molecule has an increased half-life (relative to a molecule comprising a wild-type Fc Region). In some embodiments, the Fc-bearing CD137×TA Binding Molecules of the present invention comprise a variant IgG Fc Region, wherein said variant Fc Region comprises a half-live extending amino acid substitution. Numerous amino acid substitutions capable of increasing the half-life of an Fc-bearing molecule are known in the art see for example the amino acid substitutions described in U.S. Pat. Nos. 6,277,375, 7,083,784; 7,217,797, 8,088,376; U.S. Publication Nos. 2002/0147311; 2007/0148164; and PCT Publication Nos. WO 98/23289; WO 2009/058492; and WO 2010/033279, which are herein incorporated by reference in their entireties. A Fc-bearing CD137×TA Binding Molecule having enhanced half-life may comprise two or more substitutions selected from: T250Q, M252Y, S254T, T256E, K288D, T307Q, V308P, A378V, M428L, N434A, H435K, and Y436I, wherein said numbering is that of the EU index as in Kabat.

In particular, the employed CH2-CH3 Domain may comprise the substitutions:
(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y436I;
(H) V308P and N434A; or
(I) K288D and H435K,
wherein said numbering is that of the EU index as in Kabat.

A preferred sequence for the CH2 and CH3 Domains comprises the triple amino acid substitution: M252Y/S254T/T256E (YTE), which significantly enhances serum-half life (Dall'Acqua, W. F. et al. (2006) *"Properties of Human IgGs Engineered for Enhanced Binding to the Neonatal Fc Receptor (FcRn),"* J. Biol. Chem. 281(33):23514-23524), as in SEQ ID NO:41 or SEQ ID NO:42, which are variants of the IgG1 CH2-CH3 domain, or as in SEQ ID NO:43, which is a variant of the IgG4 CH2-CH3 Domain:

```
SEQ ID NO: 41:
APELLGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX wherein, X is a lysine (K) or is absent.

SEQ ID NO: 42:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX wherein, X is a lysine (K) or is absent.

SEQ ID NO: 43:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX wherein, X is a lysine (K) or is absent.
```

The invention also encompasses Fc-bearing CD137×TA Binding Molecules comprising variant Fc Domains that exhibit altered effector function, altered serum half-life, altered stability, altered susceptibility to cellular enzymes or altered effector function as assayed in an NK dependent or macrophage dependent assay, etc. Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) *"Fc Optimization Of Therapeutic Antibodies Enhances Their Ability To Kill Tumor Cells In Vitro And Controls Tumor Expansion In Vivo Via Low-Affinity Activating Fcgamma Receptors,"* Cancer Res. 57(18):8882-8890). Exemplary variants of human IgG1 Fc Domains with reduced binding to CD32B and/or increased binding to CD16A contain F243L, R292P, Y300L, V305I or P296L substitutions. These amino acid substitutions may be present in a human IgG1 Fc Domain in any combination. In one embodiment, the human IgG1 Fc Domain variant contains a F243L, R292P and Y300L substitution, wherein said numbering is that of the EU index as in Kabat. In another embodiment, the human IgG1 Fc Domain variant contains a F243L, R292P, Y300L, V305I and P296L substitution, wherein said numbering is that of the EU index as in Kabat.

The CH2 and/or CH3 Domains of the CD137×TA Binding Molecules of the present invention need not be identical in sequence, and advantageously are modified to promote heterodimerization between the two CH2-CH3-bearing polypeptide chains. For example, an amino acid substitution (preferably a substitution with an amino acid comprising a bulky side group forming a "knob," e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., a "hole" (e.g., a substitution with glycine). Such sets of mutations can be engineered into any pair of polypeptides comprising the bispecific Fc-bearing diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) *"'Knobs-Into-Holes' Engineering Of Antibody CH3 Domains For Heavy Chain Heterodimeriza-* tion," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which documents is hereby incorporated herein by reference in its entirety). In one embodiment, the knob is engineered into the CH2-CH3 Domains of the first polypeptide chain and the hole is engineered into the CH2-CH3 Domains of the third polypeptide chain. Thus, the knob will help in preventing two molecules of the first polypeptide chain from homodimerizing via their CH2 and/or CH3 Domains. As the third polypeptide chain of this embodiment preferably contains the hole substitution it will have the ability to heterodimerize with the first polypeptide chain as well as homodimerize with itself (however, such homodimerization does not form a molecule possessing epitope-binding sites). A preferred knob is created by modifying a native IgG Fc Domain to contain the modification T366W. A preferred hole is created by modifying a native IgG Fc Domain to contain the modification T366S, L368A and Y407V. To aid in purifying the third polypeptide chain homodimer from the final bispecific Fc-bearing diabody comprising heterodimers of the first and third polypeptide chains, the protein A binding site of the CH2 and CH3 Domains of the third polypeptide chain is preferably mutated by amino acid substitution at position 435 (H435R). Thus, the third polypeptide chain homodimer will not bind to protein A, whereas the properly assembled bispecific Fc-bearing diabody will retain its ability to bind protein A via the protein A binding site on the first polypeptide chain.

SEQ ID NO:44, SEQ ID NO:45 and SEQ ID NO:46 provide exemplary preferred sequences for "knob-bearing" CH2 and CH3 Domains that may be used in the CD137×TA Binding Molecules of the present invention:

```
SEQ ID NO: 44:
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX wherein X is a lysine (K) or is absent,

SEQ ID NO: 45:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLWCLVK GFYPSDIAVE WESNGQPENN

YKTTPPVLDS DGSFFLYSRL TVDKSRWQEG NVFSCSVMHE

ALHNHYTQKS LSLSLGX wherein X is a lysine (K) or is absent,

SEQ ID NO: 46:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX wherein X is a lysine (K) or is absent,
```

SEQ ID NO:47, SEQ ID NO:48 and SEQ ID NO:49 provide exemplary preferred sequences for "hole-bearing" CH2 and CH3 Domains that may be used in the CD137×TA Binding Molecules of the present invention:

```
SEQ ID NO: 47:
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX wherein X is a lysine (K) or is absent,

SEQ ID NO: 48:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLSCAVK GFYPSDIAVE WESNGQPENN

YKTTPPVLDS DGSFFLVSRL TVDKSRWQEG NVFSCSVMHE

ALHNRYTQKS LSLSLGX wherein X is a lysine (K) or is absent,

SEQ ID NO: 49:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX wherein X is a lysine (K) or is absent,
```

As will be noted, the CH2-CH3 Domains of SEQ ID NOs:45 and 48 are IgG4 Domains, while the CH2-CH3 Domains of SEQ ID NOs:44, 46 47 and 49 are IgG1 Domains. SEQ ID NOs:44, 46 47 and 49 include a substitution at position 234 with alanine and 235 with alanine, and thus form an Fc Domain that exhibits decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO:12). Furthermore, specifically encompassed by the instant invention are CD137×TA Binding Molecule constructs lacking the above-indicated C-terminal lysine residue.

In the embodiment described above, the first polypeptide chain will have a "knob-bearing" CH2-CH3 sequence, such as that of SEQ ID NO:44. However, as will be recognized, a "hole-bearing" CH2-CH3 Domain (e.g., SEQ ID NO:47) could be employed in the first polypeptide chain, in which case, a "knob-bearing" CH2-CH3 Domain (e.g., SEQ ID NO:44) would be employed in the third polypeptide chain.

E. Albumin-Binding Domain

As disclosed in WO 2012/018687, in order to improve the in vivo pharmacokinetic properties of diabodies, a diabody may be modified to contain a polypeptide portion of a serum-binding protein at one or more of the termini of the diabody. Such considerations are also applicable to the Tri-Specific Binding Molecules of the present invention. Most preferably, when a polypeptide portion of a serum-binding protein is desired to be incorporated into the Tri-Specific Binding Molecules of the present invention, such polypeptide portion will be installed at the C-terminus of one of the polypeptide chains of the Tri-Specific Binding Molecule.

Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules*," J. Biol. Chem. 277 (10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:50):

```
LAEAKVLANR ELDKYGVSDY YKNLIDNAKS AEGVKALIDE
ILAALP.
```

As disclosed in WO 2012/162068 (herein incorporated by reference), "deimmunized" variants of SEQ ID NO:50 have the ability to attenuate or eliminate MHC class II binding. Based on combinational mutation results, the following combinations of substitutions are considered to be preferred substitutions for forming such a deimmunized Albumin-Binding Domain: 66S/70S+71A; 66S/70S+79A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence of SEQ ID NOs:51, 52 or 53 are particularly preferred as such deimmunized Albumin-Binding Domains exhibit substantially wild-type binding while providing attenuated MHC class II binding:

```
SEQ ID NO: NO: 51:
LAEAKVLANR ELDKYGVSDY YKNLID66NAKS70 A71EGVKALIDE

ILAALP

SEQ ID NO: NO: 52:
LAEAKVLANR ELDKYGVSDY YKNA64A65NNAKT VEGVKALIA79E

ILAALP

SEQ ID NO: NO: 53:
LAEAKVLANR ELDKYGVSDY YKNLIS66NAKS70 VEGVKALIA79E

ILAALP
```

Although such Albumin-Binding Domains may be incorporated into any of the polypeptide chains of the Tri-Specific Binding Molecules of the present invention, it is preferred to position such Domain C-terminally to the E-coil (or K-coil) Domain of the first or third polypeptide chain (via a linker that intervenes between the E-coil (or K-coil) Domain and the Albumin-Binding Domain (which is preferably a deimmunized Albumin-Binding Domain)). A preferred sequence for such a linker is SEQ ID NO:26: GGGS.

F. Preferred Tumor Antigens (TA) and Exemplary Variable Domains

The CD137xTA Binding Molecules of the present invention comprise at least one epitope-binding site specific for an epitope of a tumor antigen. Exemplary Tumor Antigens ("TAs"), which may be bound by the CD137xTA Binding Molecules of the present invention include, but are not limited to: colon cancer antigen 19.9; oncofetal protein 5T4; gastric cancer mucin antigen 4.2; colorectal carcinoma antigen A33 (Almqvist, Y. 2006, *Nucl Med Biol*. November; 33(8):991-998); ADAM-9 (United States Patent Publication No. 2006/0172350; PCT Publication No. WO 06/084075; AFP oncofetal antigen-alpha-fetoprotein (Malaguarnera, G. et al. (2010) "*Serum markers of hepatocellular carcinoma*," Dig. Dis. Sci. 55(10):2744-2755); ALCAM (PCT Publication No. WO 03/093443); BAGE (Bodey, B. 2002 *Expert Opin Biol Ther.* 2(6):577-84); beta-catenin (Prange W. et al. 2003 *J Pathol.* 201(2):250-9); CA125 (Bast, R. C. Jr. et al. 2005 *Int J Gynecol Cancer* 15 Suppl 3:274-81); Carboxypeptidase M (United States Patent Publication No. 2006/0166291); 1 (Egloff, A. M. et al. 2006, *Cancer Res.* 66(1): 6-9); CD5 (Calin, G. A. et al. 2006 *Semin Oncol.* 33(2):167-73; CD19 (Troussard, X. et al. 1998 *Hematol Cell Ther.* 40(4):139-48); CD20 (Thomas, D. A. et al. 2006 Hematol Oncol Clin North Am. 20(5):1125-36); CD20 (Cang, S. et al. (2012) "*Novel CD20Monoclonal Antibodies For Lymphoma Therapy*," J. Hematol. Oncol. 5:64 pp. 1-9); CD22 (Kreitman, R. J. 2006 AAPS J. 18; 8(3):E532-51); CD23 (Rosati, S. et al. 2005 *Curr Top Microbiol Immunol.* 5; 294:91-107); CD25 (Troussard, X. et al. 1998 *Hematol Cell Ther.* 40(4): 139-48); CD27 (Bataille, R. 2006 *Haematologica* 91(9): 1234-40); CD28 (Bataille, R. 2006 *Haematologica* 91(9): 1234-40); CD30 (Muta, H. et al. (2013) "*CD30: From Basic Research To Cancer Therapy*," Immunol. Res. 57(1-3):151-158); CD33 (Walter, R. B. et al. (2012) "Acute myeloid leukemia stem cells and CD33-targeted immunotherapy," Blood 119(26):6198-6208); CD36 (Ge, Y. 2005 *Lab Hematol.* 11(1):31-7); CD40/CD154 (Messmer, D. et al. 2005 *Ann NY Acad Sci.* 1062:51-60); CD45 (Jurcic, J. G. 2005 *Curr Oncol Rep.* 7(5):339-46); CD56 (Bataille, R. 2006 *Haematologica* 91(9):1234-40); CD46 (U.S. Pat. No. 7,148,038; PCT Publication No. WO 03/032814; Russell, S. et al. (2004) "*CD46: A Complement Regulator And Pathogen Receptor That Mediates Links Between Innate And Acquired Immune Function*," Tissue Antigens 64(2):111-118); CD52 (Hoelzer, D. et al. (2013) "Targeted therapy with monoclonal antibodies in acute lymphoblastic leukemia," Curr. Opin. Oncol. 25(6):701-706); CD79a/CD79b (Troussard, X. et al. 1998 *Hematol Cell Ther.* 40(4):139-48; Chu, P. G. et al. 2001 Appl Immunohistochem Mol Morphol. 9(2):97-106); CD103 (Troussard, X. et al. 1998 *Hematol Cell Ther.* 40(4):139-48); CD123 (Taussig, D. et al. (2005) "*Hematopoietic Stem Cells Express Multiple Myeloid Markers: Implications For The Origin And Targeted Therapy Of Acute Myeloid Leukemia*," Blood 106:4086-4092); CD317 (Palma, G. et al. (2012) "*Plasmacytoids Dendritic Cells Are A Therapeutic Target In Anticancer Immunity*," Biochim. Biophys. Acta. 1826(2):407-414; CDK4 (Lee, Y. M. et al. 2006

Cell Cycle 5(18):2110-4); CEA (carcinoembryonic antigen; Mathelin, C. 2006 Gynecol Obstet Fertil. 34(7-8):638-46; Tellez-Avila, F. I. et al. 2005 Rev Invest Clin. 57(6):814-9); CEACAM5 and CEACAM6 (PCT Publication No. WO 2011/034660; Zheng, C. et al. (2011) "A Novel Anti-CEACAM5 Monoclonal Antibody, CC4, Suppresses Colorectal Tumor Growth and Enhances NK Cells-Mediated Tumor Immunity," PLoS One 6(6):e21146, pp. 1-11); CO17-1A (Adkins, J. C. et al. (1998) "Edrecolomab (Monoclonal Antibody 17-1A)," Drugs 56(4):619-626; CO-43 (blood group Leb) and CO-514 (blood group Lea) (Garratty, G. (1995) "Blood Group Antigens As Tumor Markers, Parasitic/Bacterial/Viral Receptors, And Their Association With Immunologically Important Proteins," Immunol. Invest. 24(1-2):213-232; CTLA-1 and CTLA-4 (Peggs, K. S. et al. 2006 Curr Opin Immunol. 18(2):206-13); Cytokeratin 8 (PCT Publication No. WO 03/024191); antigen D1.1 (Dao, T. et al. (2009) "Identification Of A Human Cyclin D1-Derived Peptide That Induces Human Cytotoxic CD4 T Cells," PLoS One. 4(8):e6730); DR5 (Abdulghani, J. et al. (2010) "TRAIL Receptor Signaling And Therapeutics," Expert Opin. Ther. Targets 14(10):1091-1108; Andera, L. (2009) "Signaling Activated By The Death Receptors Of The TNFR Family," Biomed. Pap. Med. Fac. Univ. Palacky Olomouc Czech. Repub. 153(3):173-180; Carlo-Stella, C. et al. (2007) "Targeting TRAIL Agonistic Receptors for Cancer Therapy," Clin, Cancer 13(8):2313-2317; Chaudhari, B. R. et al. (2006) "Following the TRAIL to Apoptosis," Immunologic Res. 35(3):249-262); E1 series (blood group B); EGF-R (epidermal growth factor receptor; Adenis, A. et al. 2003 Bull Cancer. 90 Spec No: S228-32); Ephrin receptors (and in particular EphA2 (U.S. Pat. No. 7,569,672; PCT Publication No. WO 06/084226); Erb (ErbB1; ErbB3; ErbB4; Zhou, H. et al. 2002 Oncogene 21(57):8732-40; Rimon, E. et al. 2004 Int J Oncol. 24(5):1325-38); lung adenocarcinoma antigen F3 (Greulich, H. et al. (2012) "Functional analysis of receptor tyrosine kinase mutations in lung cancer identifies oncogenic extracellular domain mutations of ERBB2," Proc. Natl. Acad. Sci. (U.S.A.) 109(36):14476-14481); antigen FC10.2 (Loveless, W. et al. (1990) "Developmental Patterning Of The Carbohydrate Antigen FC10.2 During Early Embryogenesis In The Chick," Development 108(1):97-106); GAGE (GAGE-1; GAGE-2; Akcakanat, A. et al. 2006 Int J Cancer. 118(1):123-8); GD2/GD3/GD49/GM2/GM3 (Livingston, P. O. et al. 2005 Cancer Immunol Immunother. 54(10):1018-25); GICA 19-9 (Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2:135-140); gp37 (human leukemia T cell antigen ((Bhattacharya-Chatterjee et al. (1988) "Idiotype Vaccines Against Human T Cell Leukemia. II Generation And Characterization Of A Monoclonal Idiotype Cascade (Ab1, Ab2, and Ab3)," J. Immunol. 141:1398-1403); gp75 (melanoma antigen) (Vijayasardahl et al. (1990) "The Melanoma Antigen Gp75 Is The Human Homologue Of The Mouse B (Brown) Locus Gene Product," J. Exp. Med. 171(4):1375-1380); gp100 (Lotem, M. et al. 2006J Immunother. 29(6):616-27); HER-2/neu (Kumar, Pal S et al. 2006 Semin Oncol. 33(4):386-91); human B-lymphoma antigen-CD20 (Reff et al. (1994) "Depletion Of B Cells In Vivo By A Chimeric Mouse Human Monoclonal Antibody To CD20," Blood 83:435-445); human milk fat globule antigen; human papillomavirus-E6/human papillomavirus-E7 (DiMaio, D. et al. 2006 Adv Virus Res. 66:125-59; HMW-MAA (high molecular weight melanoma antigen) (Natali et al. (1987) "Immunohistochemical Detection Of Antigen In Human Primary And Metastatic Melanomas By The Monoclonal Antibody 140.240 And Its Possible Prognostic Significance," Cancer 59:55-63; Mittelman et al. (1990) "Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies," J. Clin. Invest. 86:2136-2144); I antigen (differentiation antigen) (Feizi (1985) "Demonstration By Monoclonal Antibodies That Carbohydrate Structures Of Glycoproteins And Glycolipids Are Onco-Developmental Antigens," Nature 314:53-57) such as I(Ma) as found in gastric adenocarcinomas; Integrin Alpha-V-Beta-6 Integrinβ6 (ITGB6) (PCT Publication No. WO 03/087340); JAM-3 (PCT Publication No. WO 06/084078); Interleukin-13 Receptor α2 (IL13Ra2) (Bodhinayake, I. et al. (2014) "Targeting A Heterogeneous Tumor: The Promise Of The Interleukin-13 Receptor α2," Neurosurgery 75(2):N18-9); JAM-3 (PCT Publication No. WO 06/084078); KID3 (PCT Publication No. WO 05/028498); KID31 (PCT Publication No. WO 06/076584); KS 1/4 pan-carcinoma antigen (Perez et al. (1989) "Isolation And Characterization Of A cDNA Encoding The Ks1/4 Epithelial Carcinoma Marker," J. Immunol. 142:3662-3667; Möller et al. (1991) "Bispecific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); KS 1/4 pan-carcinoma antigen (Perez et al. (1989) "Isolation And Characterization Of A cDNA Encoding The Ks1/4 Epithelial Carcinoma Marker," J. Immunol. 142:3662-3667; Möller et al. (1991) "Bispecific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); KSA (17-1A) (Ragupathi, G. 2005 Cancer Treat Res. 123:157-80); human lung carcinoma antigens L6 and L20 (Hellström et al. (1986) "Monoclonal Mouse Antibodies Raised Against Human Lung Carcinoma," Cancer Res. 46:3917-3923); LEA (Velázquez-Márquez, N. et al. (2012) "Sialyl Lewisx expression in cervical scrapes of premalignant lesions," J. Biosci. 37(6):999-1004); LUCA-2 (United States Patent Publication No. 2006/0172349; PCT Publication No. WO 06/083852); M1:22:25:8, M18, M39 (Cambier, L. et al. (2012) "M19 Modulates Skeletal Muscle Differentiation And Insulin Secretion In Pancreatic B-Cells Through Modulation Of Respiratory Chain Activity," PLoS One 7(2):e31815; Pui, C. H. et al. (1991) "Characterization of childhood acute leukemia with multiple myeloid and lymphoid markers at diagnosis and at relapse," Blood 78(5):1327-1337); MAGE (MAGE-1; MAGE-3; (Bodey, B. 2002 Expert Opin Biol Ther. 2(6):577-84); MART (Kounalakis, N. et al. 2005 Curr Oncol Rep. 7(5):377-82; Myl, MUC-1 (Mathelin, C. 2006 Gynecol Obstet Fertil. 34(7-8):638-46; MUM-1 (Castelli, C. et al. 2000 J Cell Physiol. 182(3):323-31); N-acetylglucosaminyltransferase (Dennis, J. W. 1999 Biochim Biophys Acta. 6; 1473(1):21-34); neoglycoprotein (Legendre, H. et al. (2004) "Prognostic Stratification Of Dukes B Colon Cancer By A Neoglycoprotein," Int. J. Oncol. 25(2):269-276); NS-10; OFA-1 and OFA-2 (Takahashi, M. (1984) "A Study On Clinical Significance Of Oncofetal Antigen-1 In Gynecologic Tumors," Nihon Sanka Fujinka Gakkai Zasshi. 36(12):2613-2618); Oncostatin M (Oncostatin Receptor Beta) (U.S. Pat. No. 7,572,896; PCT Publication No. WO 06/084092); p15 (Gil, J. et al. 2006 Nat Rev Mol Cell Biol. 7(9):667-77); PSA (prostate specific antigen; Cracco, C. M. et al. 2005 Minerva Urol Nefrol. 57(4):301-11); PSMA (Ragupathi, G. 2005 Cancer Treat Res. 123:157-80); PEMA (polymorphic epithelial mucin antigen) (Chu, N. J. et al. (2015) "*Nonviral Oncogenic Antigens and the Inflammatory Signals Driving Early Cancer Development as Targets for Cancer Immunoprevention*," Clin. Cancer Res. 21(7):1549-1557); PIPA (U.S. Pat. No. 7,405,061; PCT Publication No. WO 04/043239); prostatic acid phosphate (Tailor et al. (1990) "*Nucleotide Sequence Of Human Prostatic Acid Phosphatase Determined From A Full-Length cDNA Clone*," Nucl. Acids Res. 18(16):4928); R24 (Zhou, M. et al. (2008) "*Constitutive Overexpression Of A Novel 21 Kda Protein By Hodgkin Lymphoma And Aggressive Non-Hodgkin Lymphomas*," Mol. Cancer 7:12); ROR1 (U.S. Pat. No. 5,843,749); Rabbani, H. et al. (2010) "*Expression Of ROR1 In Patients With Renal Cancer—A Potential Diagnostic Marker*," Iran Biomed. J. 14(3):77-82); sphingolipids (Hakomori, S. (1998) "*Cancer-Associated Glycosphingolipid Antigens: Their Structure, Organization, And Function*," Acta Anat. (Basel) 161(1-4):79-90; SSEA-1, SSEA-3 and SSEA-4 (Muramatsu, T. et al. (2004) "*Carbohydrate Antigens Expressed On Stem Cells And Early Embryonic Cells*," Glycoconj. J. 21(1-2):41-45); sTn (Holmberg, L. A. 2001 *Expert Opin Biol Ther.* 1(5):881-91); T cell receptor derived peptide (Edelson (1998) "*Cutaneous T-Cell Lymphoma: A Model For Selective Immunotherapy*," Cancer J Sci Am. 4:62-71); T5A7 (Hogg, R. J. et al. (1991) "*A monoclonal antibody exhibiting reactivity with both X-hapten-and lactose-bearing glycolipids*," Tissue Antigens 37(1):33-38); TAG-72 (Yokota et al. (1992) "*Rapid Tumor Penetration Of A Single-Chain Fv And Comparison With Other Immunoglobulin Forms*," Cancer Res. 52:3402-3408); TL5 (blood group A) (Gooi, H. C. et al. (1983) "Monoclonal antibody reactive with the human epidermal-growth-factor receptor recognizes the blood-group-A antigen," Biosci. Rep. 3(11): 1045-1052); TNF-ß receptor (TNF-α receptor, TNF-β receptor; or TNF-γ receptor (van Horssen, R. et al. 2006 *Oncologist.* 11(4):397-408; Gardnerova, M. et al. 2000 *Curr Drug Targets.* 1(4):327-64); TRA-1-85 (blood group H) (Williams, B. P. et al. (1988) "Biochemical and genetic analysis of the OKa blood group antigen," Immunogenetics 27(5):322-329); Transferrin Receptor (U.S. Pat. No. 7,572,895; PCT Publication No. WO 05/121179); TSTA tumor-specific transplantation antigen (Hellström et al. (1985) "*Monoclonal Antibodies To Cell Surface Antigens Shared By Chemically Induced Mouse Bladder Carcinomas*," Cancer. Res. 45:2210-2188); VEGF-R (O'Dwyer. P. J. 2006 *Oncologist.* 11(9):992-8); and Y hapten, Le$^y$ (Durrant, L. G. et al. (1989) "*Development Of An ELISA To Detect Early Local Relapse Of Colorectal Cancer*," Br. J. Cancer 60(4):533-537).

Antibodies that recognize such Tumor Antigens are known in the art or can be generated using well-known methods, including those described in WO 2002/014870. Exemplary antibodies that comprise VL and VH Domains capable of binding to a Tumor Antigen, and whose sequences or polypeptide chains may thus be employed in the construction of the CD137×TA Binding Molecules of the present invention, are listed in Table 1. Exemplary VH and VL Domains for antibodies binding to several Tumor Antigens are presented below.

TABLE 1

| Antibody Name | Tumor Antigen(s) | Therapeutic Target Application |
| --- | --- | --- |
| 3F8 | Gd2 | Neuroblastoma |
| 8H9 | B7-H3 | Neuroblastoma, Sarcoma, Metastatic Brain Cancers |

TABLE 1-continued

| Antibody Name | Tumor Antigen(s) | Therapeutic Target Application |
| --- | --- | --- |
| Abagovomab | CA-125 | Ovarian Cancer |
| Adecatumumab | Epcam | Prostate And Breast Cancer |
| Afutuzumab | CD20 | Lymphoma |
| Alacizumab | VEGFR2 | Cancer |
| Altumomab | CEA | Colorectal Cancer |
| Amatuximab | Mesothelin | Cancer |
| Anatumomab Mafenatox | TAG-72 | Non-Small Cell Lung Carcinoma |
| Anifrolumab | Interferon A/B Receptor | Systemic Lupus Erythematosus |
| Anrukinzumab | IL-13 | Cancer |
| Apolizumab | HLA-DR | Hematological Cancers |
| Arcitumomab | CEA | Gastrointestinal Cancer |
| Atinumab | RTN4 | Cancer |
| Bectumomab | CD22 | Non-Hodgkin's Lymphoma (Detection) |
| Belimumab | BAFF | Non-Hodgkin Lymphoma |
| Bevacizumab | VEGF-A | Metastatic Cancer, Retinopathy Of Prematurity |
| Bivatuzumab | CD44 V6 | Squamous Cell Carcinoma |
| Blinatumomab | CD19 | Cancer |
| Brentuximab | CD30 (TNFRSF8) | Hematologic Cancers |
| Cantuzumab | MUC1 | Cancers |
| Cantuzumab Mertansine | Mucin Canag | Colorectal Cancer |
| Caplacizumab | VWF | Cancers |
| Capromab | Prostatic Carcinoma Cells | Prostate Cancer (Detection) |
| Carlumab | MCP-1 | Oncology/Immune Indications |
| Catumaxomab | Epcam, CD3 | Ovarian Cancer, Malignant Ascites, Gastric Cancer |
| Cc49 | Tag-72 | Tumor Detection |
| Cetuximab | EGFR | Metastatic Colorectal Cancer And Head And Neck Cancer |
| Ch. 14.18 | Undetermined | Neuroblastoma |
| Citatuzumab | Epcam | Ovarian Cancer And Other Solid Tumors |
| Cixutumumab | IGF-1 Receptor | Solid Tumors |
| Clivatuzumab | MUC1 | Pancreatic Cancer |
| Conatumumab | TRAIL-R2 | Cancer |
| Dacetuzumab | CD40 | Hematologic Cancers |
| Dalotuzumab | Insulin-Like Growth Factor I Receptor | Cancer |
| Daratumumab | CD38 | Cancer |
| Demcizumab | DLL4 | Cancer |
| Detumomab | B-Lymphoma Cell | Lymphoma |
| Drozitumab | DR5 | Cancer |
| Duligotumab | HER3 | Cancer |
| Dusigitumab | ILGF2 | Cancer |
| Ecromeximab | GD3 Ganglioside | Malignant Melanoma |
| Eculizumab | C5 | Paroxysmal Nocturnal Hemoglobinuria |
| Edrecolomab | Epcam | Colorectal Carcinoma |
| Elotuzumab | SLAMF7 | Multiple Myeloma |
| Elsilimomab | IL-6 | Cancer |
| Enavatuzumab | TWEAK Receptor | Cancer |
| Enlimomab | ICAM-1 (CD54) | Cancer |
| Enokizumab | IL9 | Asthma |
| Enoticumab | DLL4 | Cancer |
| Ensituximab | 5AC | Cancer |
| Epitumomab Cituxetan | Episialin | Cancer |
| Epratuzumab | CD22 | Cancer, SLE |
| Ertumaxomab | HER2/Neu, CD3 | Breast Cancer |
| Etaracizumab | Integrin A$_v$β$_3$ | Melanoma, Prostate Cancer, Ovarian Cancer |
| Faralimomab | Interferon Receptor | Cancer |
| Farletuzumab | Folate Receptor 1 | Ovarian Cancer |
| Fasinumab | HNGF | Cancer |
| Fbta05 | CD20 | Chronic Lymphocytic Leukemia |
| Ficlatuzumab | HGF | Cancer |
| Figitumumab | IGF-1 Receptor | Adrenocortical Carcinoma, Non-Small Cell Lung Carcinoma |
| Flanvotumab | TYRP1 (Glycoprotein 75) | Melanoma |
| Fontolizumab | IFN-γ | Crohn's Disease |

TABLE 1-continued

| Antibody Name | Tumor Antigen(s) | Therapeutic Target Application |
| --- | --- | --- |
| Fresolimumab | TGF-B | Idiopathic Pulmonary Fibrosis, Focal Segmental Glomerulosclerosis, Cancer |
| Futuximab | EGFR | Cancer |
| Galiximab | CD80 | B Cell Lymphoma |
| Ganitumab | IGF-I | Cancer |
| Gemtuzumab Ozogamicin | CD33 | Acute Myelogenous Leukemia |
| Gevokizumab | IL-1β | Diabetes |
| Girentuximab | Carbonic Anhydrase 9 (CA-IX) | Clear Cell Renal Cell Carcinoma |
| Glembatumumab Vedotin | GPNMB | Melanoma, Breast Cancer |
| Golimumab | TNF-A | Rheumatoid Arthritis, Psoriatic Arthritis, Ankylosing Spondylitis |
| Ibritumomab Tiuxetan | CD20 | Non-Hodgkin's Lymphoma |
| Icrucumab | VEGFR-1 | Cancer |
| Igovomab | CA-125 | Ovarian Cancer (Diagnosis) |
| Imab362 | Cldn18.2 | Gastrointestinal Adenocarcinomas And Pancreatic Tumor |
| Imgatuzumab | EGFR | Cancer |
| Inclacumab | Selectin P | Cancer |
| Inclatuximab Ravtansine | SDC1 | Cancer |
| Inotuzumab Ozogamicin | CD22 | Cancer |
| Intetumumab | CD51 | Solid Tumors (Prostate Cancer, Melanoma) |
| Ipilimumab | CD152 | Melanoma |
| Iratumumab | CD30 (TNFRSF8) | Hodgkin's Lymphoma |
| Itolizumab | CD6 | Cancer |
| Labetuzumab | CEA | Colorectal Cancer |
| Lambrolizumab | PDCD1 | Antineoplastic Agent |
| Lampalizumab | CFD | Cancer |
| Lexatumumab | TRAIL-R2 | Cancer |
| Libivirumab | Hepatitis B Surface Antigen | Hepatitis B |
| Ligelizumab | IGHE | Cancer |
| Lintuzumab | CD33 | Cancer |
| Lirilumab | KIR2D | Cancer |
| Lorvotuzumab | CD56 | Cancer |
| Lucatumumab | CD40 | Multiple Myeloma, Non-Hodgkin's Lymphoma, Hodgkin's Lymphoma |
| Lumiliximab | CD23 | Chronic Lymphocytic Leukemia |
| Mapatumumab | TRAIL-R1 | Cancer |
| Margetuximab | Ch4d5 | Cancer |
| Matuzumab | EGFR | Colorectal, Lung And Stomach Cancer |
| Milatuzumab | CD74 | Multiple Myeloma And Other Hematological Malignancies |
| Minretumomab | TAG-72 | Cancer |
| Mitumomab | GD3 Ganglioside | Small Cell Lung Carcinoma |
| Mogamulizumab | CCR4 | Cancer |
| Morolimumab | Rhesus Factor | Cancer |
| Moxetumomab Pasudotox | CD22 | Cancer |
| Nacolomab Tafenatox | C242 Antigen | Colorectal Cancer |
| Namilumab | CSF2 | Cancer |
| Naptumomab Estafenatox | 5T4 | Non-Small Cell Lung Carcinoma, Renal Cell Carcinoma |
| Narnatumab | RON | Cancer |
| Nebacumab | Endotoxin | Sepsis |
| Necitumumab | EGFR | Non-Small Cell Lung Carcinoma |
| Nerelimomab | TNF-A | Cancer |
| Nesvacumab | Angiopoietin 2 | Cancer |
| Nimotuzumab | EGFR | Squamous Cell Carcinoma, Head And Neck Cancer, Nasopharyngeal Cancer, Glioma |
| Nivolumab | PD-1 | Cancer |
| Nofetumomab Merpentan | Undetermined | Cancer |
| Ocaratuzumab | CD20 | Cancer |
| Ofatumumab | CD20 | Chronic Lymphocytic Leukemia |
| Olaratumab | PDGF-R A | Cancer |
| Olokizumab | IL6 | Cancer |
| Onartuzumab | Human Scatter Factor Receptor Kinase | Cancer |
| Ontuxizumab | TEM1 | Cancer |
| Oportuzumab Monatox | Epcam | Cancer |
| Oregovomab | CA-125 | Ovarian Cancer |
| Orticumab | Oxldl | Cancer |
| Otlertuzumab | CD37 | Cancer |
| Panitumumab | EGFR | Colorectal Cancer |
| Pankomab | Tumor Specific Glycosylation Of MUC1 | Ovarian Cancer |
| Parsatuzumab | EGFL7 | Cancer |
| Patritumab | HER3 | Cancer |
| Pembrolizumab | PD-1 | Cancer |
| Pemtumomab | MUC1 | Cancer |
| Perakizumab | IL17A | Arthritis |
| Pertuzumab | HER2/Neu | Cancer |
| Pidilizumab | PD-1 | Cancer And Infectious Diseases |
| Pinatuzumab Vedotin | CD22 | Cancer |
| Pintumomab | Adenocarcinoma Antigen | Adenocarcinoma |
| Placulumab | Human TNF | Cancer |
| Polatuzumab Vedotin | CD79B | Cancer |
| Pritoxaximab | E. Coli Shiga Toxin Type-1 | Cancer |
| Pritumumab | Vimentin | Brain Cancer |
| Quilizumab | IGHE | Cancer |
| Racotumomab | N-Glycolylneuraminic Acid | Cancer |
| Radretumab | Fibronectin Extra Domain-B | Cancer |
| Ramucirumab | VEGFR2 | Solid Tumors |
| Rilotumumab | HGF | Solid Tumors |
| Rituximab | CD20 | Lymphomas, Leukemias, Some Autoimmune Disorders |
| Robatumumab | IGF-1 Receptor | Cancer |
| Roledumab | RHD | Cancer |
| Samalizumab | CD200 | Cancer |
| Satumomab Pendetide | TAG-72 | Cancer |
| Seribantumab | ERBB3 | Cancer |
| Setoxaximab | E. Coli Shiga Toxin Type-1 | Cancer |
| Sgn-CD19a | CD19 | Acute Lymphoblastic Leukemia And B Cell Non-Hodgkin Lymphoma |
| Sgn-CD33a | CD33 | Acute Myeloid Leukemia |
| Sibrotuzumab | FAP | Cancer |
| Siltuximab | IL-6 | Cancer |
| Solitomab | Epcam | Cancer |
| Sontuzumab | Episialin | Cancer |
| Tabalumab | BAFF | B Cell Cancers |
| Tacatuzumab Tetraxetan | Alpha-Fetoprotein | Cancer |
| Taplitumomab Paptox | CD19 | Cancer |
| Telimomab | Undetermined | Cancer |
| Tenatumomab | Tenascin C | Cancer |
| Teneliximab | CD40 | Cancer |
| Teprotumumab | CD221 | Hematologic Tumors |
| Ticilimumab | CTLA-4 | Cancer |
| Tigatuzumab | TRAIL-R2 | Cancer |
| Tnx-650 | Il-13 | Hodgkin's Lymphoma |
| Tositumomab | CD20 | Follicular Lymphoma |
| Tovetumab | CD140a | Cancer |
| Trastuzumab | HER2/Neu | Breast Cancer |
| Trbs07 | Gd2 | Melanoma |
| Tremelimumab | CTLA-4 | Cancer |
| Tucotuzumab Celmoleukin | Epcam | Cancer |
| Ublituximab | MS4A1 | Cancer |

TABLE 1-continued

| Antibody Name | Tumor Antigen(s) | Therapeutic Target Application |
| --- | --- | --- |
| Urelumab | 4-1BB | Cancer |
| Vantictumab | Frizzled Receptor | Cancer |
| Vapaliximab | AOC3 (VAP-1) | Cancer |
| Vatelizumab | ITGA2 | Cancer |
| Veltuzumab | CD20 | Non-Hodgkin's Lymphoma |
| Vesencumab | NRP1 | Cancer |
| Volociximab | Integrin A5β1 | Solid Tumors |
| Vorsetuzumab | CD70 | Cancer |
| Votumumab | Tumor Antigen CTAA16.88 | Colorectal Tumors |
| Zalutumumab | EGFR | Squamous Cell Carcinoma Of The Head And Neck |
| Zatuximab | HER1 | Cancer |
| Ziralimumab | CD147 | Cancer |

1. Antibodies that Bind to HER2/Neu

HER2/neu is a 185 kDa receptor protein that was originally identified as the product of the transforming gene from neuroblastomas of chemically treated rats. HER2/neu has been extensively investigated because of its role in several human carcinomas and in mammalian development (Hynes et al. (1994) "*The Biology of erbB-21neu/HER-2 and its Role in Cancer*," Biochim. Biophys. Acta 1198:165-184; Dougall et al. (1994) "*The neu-Oncogene: Signal Transduction Pathways, Transformation Mechanisms and Evolving Therapies*," Oncogene 9:2109-2123; Lee et al. (1995) "*Requirement for Neuregulin Receptor erbB2 in Neural and Cardiac Development*," Nature 378:394-398).

The epitope-binding site of any anti-HER2/neu antibody may be used in accordance with the present invention, and the principles of the present invention are illustrated with respect to the HER2/neu tumor antigen. Exemplary antibodies that bind human HER2/neu include "Margetuximab," "Trastuzumab" and "Pertuzumab." Margetuximab (also known as MGAH22; CAS Reg No. 1350624-75-7, see, for example, U.S. Pat. No. 8,802,093) is an Fc-optimized monoclonal antibody that binds to HER2/neu and mediates enhanced ADCC activity. Trastuzumab (also known as rhuMAB4D5, and marketed as HERCEPTIN®; CAS Reg No 180288-69-1; see, U.S. Pat. No. 5,821,337) is the humanized version of antibody 4D5, having IgG1/kappa constant regions. Pertuzumab (also known as rhuMAB2C4, and marketed as PERJETA™; CAS Reg No 380610-27-5; see for example, WO2001/000245) is a humanized version of antibody 2C4 having IgG1/kappa constant regions. Additional anti-HER2/neu antibodies are also provided.

(a) Margetuximab

The amino acid sequence of the VH Domain of Margetuximab is (SEQ ID NO:54) (CDR$_H$ residues are shown underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS
```

The amino acid sequence of the VL Domain of Margetuximab is (SEQ ID NO:55) (CDR$_L$ residues are shown underlined):

```
DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIK
```

The amino acid sequences of the complete Heavy and Light Chains of Margetuximab are known in the art (see., e.g., WHO Drug Information, 2014, Recommended INN: List 71, 28(1):93-94).

(b) Trastuzumab

The amino acid sequence of the VH Domain of Trastuzumab is (SEQ ID NO:56) (CDR$_H$ residues are shown underlined):

```
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDYW GQGTLVTVSS
```

The amino acid sequence of the VL Domain of Trastuzumab is (SEQ ID NO:57) (CDR$_L$ residues are shown underlined):

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIK
```

(c) Pertuzumab

The amino acid sequence of the VH Domain of Pertuzumab is (SEQ ID NO:58) (CDR$_H$ residues are shown underlined):

```
EVQLVESGGG LVQPGGSLRL SCAASGFTFT DYTMDWVRQA

PGKGLEWVAD VNPNSGGSIY NQRFKGRFTL SVDRSKNTLY

LQMNSLRAED TAVYYCARNL GPSFYFDYWG QGTLVTVSS
```

The amino acid sequence of the VL Domain of Pertuzumab is (SEQ ID NO:59) (CDR$_L$ residues are shown underlined):

```
DIQMTQSPSS LSASVGDRVT ITCKASQDVS IGVAWYQQKP

GKAPKLLIYS ASYRYTGVPS RFSGSGSGTD FTLTISSLQP

EDFATYYCQQ YYIYPYTFGQ GTKVEIK
```

(d) HER2-MAB-1

Antibody HER2-MAB-1 is a murine anti-HER2/neu monoclonal antibody that binds an epitope of HER2/neu that is distinct from the epitope recognized by Margetuximab, Trastuzumab and Pertuzumab. The amino acid sequence of the VH Domain of HER2-MAB-1 (referred to herein as HER2 MAB-1 VH) is (SEQ ID NO:60) (CDR$_H$ residues are shown underlined):

```
EVQLQESGPE LKKPGETVKI SCKASGYTFT NYGMNWVKQA

PGKGLKWMGW INTNIGEPTY TEEFKGRFAF SLGTSASTAF

LQINNLKNED TATYFCARDD GYGNRVSYWG QGTLVTVSA
```

The amino acid sequences of the $CDR_H$s of HER2 MAB-1 VH are:

```
CDR_H1:
                              (SEQ ID NO: 177)
NYGMN

CDR_H2:
                              (SEQ ID NO: 178)
WINTNIGEPTYTEEFKG

CDR_H3:
                              (SEQ ID NO: 179)
DDGYGNRVSY
```

The amino acid sequence of the VL Domain of HER2-MAB-1 (referred to herein as HER2 MAB-1 VL) is (SEQ ID NO:61) ($CDR_L$ residues are shown underlined):

```
DILMTQSPLS MYTSLGERVT ITCKASQDIN SYLSWFQQKP

GKSPKTLIYR ANRLVDGVPS RFSGSGSGQD YSLTISSLEY

EDMGIYYCLQ HDEFPWTFGG GTKLEIK
```

The amino acid sequences of the $CDR_L$S of HER2 MAB-1 VL are:

```
CDR_L1 (SEQ ID NO: 180):
KASQDINSYLS

CDR_L2 (SEQ ID NO: 181):
RANRLVD

CDR_L3 (SEQ ID NO: 182):
LQHDEFPWT
```

(e) Humanized HER2-MAB-1

Antibody HER2-MAB-1 was humanized to form antibody hHER2-MAB-1. The amino acid sequence of the VH Domain of such humanized antibody (hHER2-MAB-1 VH) is (SEQ ID NO:62) ($CDR_H$ residues are shown underlined):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDX_1 X_2YGNRVSYWG QGTLVTVSS wherein: X_1 is D or E and X_2 is G or I
```

The amino acid sequence of the VL Domain of such humanized antibody (hHER2 MAB-1 VL) is (SEQ ID NO:63) ($CDR_L$ residues are shown underlined):

```
DIQMTQSPSS LSASVGDRVT ITCKASQDIX_3 X_4YLSWFQQKP

GKAPKTLIYR ANRLX_5X_6 GVPS RFSGSGSGTD FTLTISSLQP

EDFATYYCLQ HDEFPWTFGQ GTKLEIK wherein: X_3 is N or S; X_4 is S, T or N; X_5 is

V or Q and X_6 is D, E or S
```

Three variant hHER2-MAB-1 VH Domains were isolated: hHER2 MAB-1 VH1, hHER2 MAB-1 VH2, and hHER2 MAB-1 VH3. The amino acid sequences of such variant hHER2-MAB-1 VH Domains are presented below.

The amino acid sequence of hHER2 MAB-1 VH1 is (SEQ ID NO:64) ($CDR_H$ residues are shown underlined; note that the second and third residues of $CDR_H3$ are D and G, respectively):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSS
```

The amino acid sequence of hHER2 MAB-1 VH2 is (SEQ ID NO:65) ($CDR_H$ residues are shown underlined; note that the second and third residues of $CDR_H3$ are E and G, respectively):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDE GYGNRVSYWG QGTLVTVSS
```

The amino acid sequence of hHER2 MAB-1 VH3 is (SEQ ID NO:66) ($CDR_H$ residues are shown underlined; note that the second and third residues of $CDR_H3$ are D and I, respectively):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD IYGNRVSYWG QGTLVTVSS
```

Thus, the amino acid sequence of $CDR_H1$ of hHER2 MAB-1 VH1, hHER2 MAB-1 VH2 and hHER2 MAB-1 VH3 are the same (NYGMN; SEQ ID NO:177) and the amino acid sequence of $CDR_H2$ of hHER2 MAB-1 VH1, hHER2 MAB-1 VH2 and hHER2 MAB-1 VH3 are the same (SEQ ID NO:178). However, the amino acid sequences of $CDR_H3$ of hHER2 MAB-1 VH1, hHER2 MAB-1 VH2 and hHER2 MAB-1 VH3 differ:

```
hHER2 MAB-1 VH1 CDR_H3 (SEQ ID NO: 183):
DDGYGNRVSY hHER2 MAB-1 VH2 CDR_H3 (SEQ ID NO: 184):
DEGYGNRVSY hHER2 MAB-1 VH3 CDR_H3 (SEQ ID NO: 185):
DDIYGNRVSY
```

Three variant hHER2-MAB-1 VL Domains were isolated: hHER2 MAB-1 VL1, hHER2 MAB-1 VL2, and hHER2 MAB-1 VL3. The amino acid sequences of such variant hHER2 MAB-1 VH Domains are presented below.

The amino acid sequence of hHER2 MAB-1 VL1 is (SEQ ID NO:67) ($CDR_L$ residues are shown underlined; note that the seventh and eighth residues of $CDR_L1$ are N and S, respectively, and that the sixth and seventh residues of $CDR_L2$ are V and D, respectively):

```
DIQMTQSPSS LSASVGDRVT ITCKASQDIN SYLSWFQQKP

GKAPKTLIYR ANRLVDGVPS RFSGSGSGTD FTLTISSLQP

EDFATYYCLQ HDEFPWTFGQ GTKLEIK
```

The amino acid sequence of hHER2 MAB-1 VL2 is (SEQ ID NO:68) ($CDR_L$ residues are shown underlined; note that the seventh and eighth residues of $CDR_L1$ are N and T, respectively, and that the sixth and seventh residues of $CDR_L2$ are V and E, respectively):

```
DIQMTQSPSS LSASVGDRVT ITCKASQDIN TYLSWFQQKP

GKAPKTLIYR ANRLVEGVPS RFSGSGSGTD FTLTISSLQP

EDFATYYCLQ HDEFPWTFGQ GTKLEIK
```

The amino acid sequence of hHER2 MAB-1 VL3 is (SEQ ID NO:69) (CDR$_L$ residues are shown underlined; note that the seventh and eighth residues of CDR$_L$1 are S and N, respectively, and that the sixth and seventh residues of CDR$_L$2 are Q and S, respectively):

```
DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIK
```

Thus, the amino acid sequence of CDR$_L$3 of hHER2 MAB-1 VL1, hHER2 MAB-1 VL2 and hHER2 MAB-1 VL3 are the same (LQHDEFPWT; SEQ ID NO:182). However, the amino acid sequences of CDR$_L$1 and CDR$_L$2 of hHER2 MAB-1 VL1, hHER2 MAB-1 VL2 and hHER2 MAB-1 VL3 differ:

```
hHER2 MAB-1 VL1 CDR_L1 (SEQ ID NO: 186):
KASQDINSYLS hHER2 MAB-1 VL2 CDR_L1 (SEQ ID NO: 187):
KASQDINTYLS hHER2 MAB-1 VL3 CDR_L1 (SEQ ID NO: 188):
KASQDISNYLS hHER2 MAB-1 VL1 CDR_L2 (SEQ ID NO: 189):
RANRLVD hHER2 MAB-1 VL2 CDR_L2 (SEQ ID NO: 190):
RANRLVE hHER2 MAB-1 VL3 CDR_L2 (SEQ ID NO: 191):
RANRLQS
```

Any of such humanized VH and VL hHER2-MAB-1 Domains, including any embraced within the generic sequence(s) of the hHER2-MAB-1 VH and/or VL Domains presented above may be used to form an antibody, diabody or binding molecule capable of binding Her2/neu.

(f) Other Anti-HER2/Neu Antibodies

In addition to the above-identified preferred anti-HER2/neu Binding Molecules, the invention contemplates the use of any of the following anti-Her-2 Binding Molecules: 1.44.1; 1.140; 1.43; 1.14.1; 1.100.1; 1.96; 1.18.1; 1.20; 1.39; 1.24; and 1.71.3 (U.S. Pat. Nos. 8,350,011; 8,858,942; and PCT Patent Publication WO 2008/019290); F5 and C1 (U.S. Pat. Nos. 7,892,554; 8,173,424; 8,974,792; and PCT Patent Publication WO 99/55367); and also the anti-Her-2 Binding Molecules of US Patent Publication 2011/0097323, 2013/017114, 2014/0328836, 2016/0130360 and 2016/0257761, and PCT Patent Publication WO2011/147986), all of which publications are herein incorporated by reference for their disclosures of anti-HER2/neu Binding Molecules.

The present invention specifically includes and encompasses CD137×HER2/neu Binding Molecules that comprise the VL and/or VH Domain, and/or 1, 2 or all 3 of the CDRLs of the VL Region and/or 1, 2 or all 3 of the CDRHs of the VH Domain of any of Margetuximab, Trastuzumab, Pertuzumab, hHER2-MAB-1, or any of the other anti-HER2/neu antibodies provided herein; and more preferably possess 1, 2 or all 3 of the CDRLs of the VL Region and/or 1, 2 or all 3 of the CDRHs of the VH Domain of such anti-HER2/neu monoclonal antibodies.

2. Antibodies that Bind to EphA2

The receptor tyrosine kinase, ephrin type-A receptor 2 (EphA2) is normally expressed at sites of cell-to-cell contact in adult epithelial tissues, however, recent studies have shown that it is also overexpressed in various types of epithelial carcinomas, with the greatest level of EphA2 expression observed in metastatic lesions. High expression levels of EphA2 have been found in a wide range of cancers and in numerous tumor cell lines, including prostate cancer, breast cancer, non-small cell lung cancer and melanoma (Xu, J. et al. (2014) "*High EphA2 Protein Expression In Renal Cell Carcinoma Is Associated With A Poor Disease Outcome*," Oncol. Lett. August 2014; 8(2): 687-692; Miao, B. et al. (2014) "*EphA2 is a Mediator of Vemurafenib Resistance and a Novel Therapeutic Target in Melanoma*," Cancer Discov. pii: CD-14-0295. EphA2 does not appear to be merely a marker for cancer, but rather appears to be persistently overexpressed and functionally changed in numerous human cancers (Chen, P. et al. (2014) "*EphA2 Enhances The Proliferation And Invasion Ability Of LnCap Prostate Cancer Cells*," Oncol. Lett. 8(1):41-46). The epitope-binding site of any anti-EphA2 antibody may be used in accordance with the present invention. Presented below are several exemplary murine anti-EphA2 antibodies, humanized derivatives of such antibodies are particularly preferred.

(a) EphA2 MAB-1

Antibody EphA2 MAB-1 is a murine anti-EphA2 monoclonal antibody. The amino acid sequence of the VH Domain of EphA2 MAB-1 is (SEQ ID NO:128) (CDR residues are shown underlined):

```
QVQLKESGPG LVAPSQSLSI TCTVSGFSLS RYSVHWVRQP

PGKGLEWLGM IWGGGSTDYN SALKSRLSIS KDNSKSQVFL

KMNSLQTDDT AMYYCARKHG NYYTMDYWGQ GTSVTVSS
```

The amino acid sequence of the VL Domain of EphA2 MAB-1 is (SEQ ID NO:129) (CDR residues are shown underlined):

```
DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIK
```

(b) EphA2 MAB-2

Antibody EphA2 MAB-2 is a murine anti-EphA2 monoclonal antibody. The amino acid sequence of the VH Domain of EphA2 MAB-2 is (SEQ ID NO:130) (CDR residues are shown underlined):

```
QIQLVQSGPE LKKPGETVKI SCKASGFTFT NYGMNWVKQA

PGKGLKWMGW INTYIGEPTY ADDFKGRFVF SLETSASTAY

LQINNLKNED MATYFCAREL GPYYFDYWGQ GTTLTVSS
```

The amino acid sequence of the VL Domain of EphA2 MAB-2 is (SEQ ID NO:131) (CDR residues are shown underlined):

```
DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI K
```

(c) EphA2 MAB-3

Antibody EphA2 MAB-3 is a murine anti-EphA2 monoclonal antibody. The amino acid sequence of the VH Domain of EphA2 MAB-3 is (SEQ ID NO:132) (CDR residues are shown underlined):

```
EVQLVESGGG SVKPGGSLKL SCAASGFTFT DHYMYWVRQT

PEKRLEWVAT ISDGGSFTSY PDSVKGRFTI SRDIAKNNLY

LQMSSLKSED TAMYYCTRDE SDRPFPYWGQ GTLVTVSS
```

The amino acid sequence of the VL Domain of EphA2 MAB-3 is (SEQ ID NO:133) (CDR residues are shown underlined):

```
DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIK
```

(d) Other EphA2 Antibodies

In addition to the above-identified anti-EphA2 antibodies, the invention contemplates the use of any of the following anti-EphA2 antibodies: SPL1, LUCA19, SG5, or LUCA40 (see, PCT Patent Publication WO 2006/084226); B13 (see, U.S. Pat. No. 7,101,976); D7 (see, U.S. Pat. No. 7,192,698); B-233, and EA2 (see, PCT Patent Publication WO 2003/094859).

The present invention specifically includes and encompasses CD137×EphA2 Binding Molecules that comprise the VL and/or VH Domain, and/or 1, 2 or all 3 of the CDRLs of the VL Region and/or 1, 2 or all 3 of the CDRHs of the VH Domain of anti-EphA2 monoclonal antibodies EphA2 MAB-1, EphA2 MAB-2 and EphA2 MAB-3.

3. Antibodies that Bind to 5T4

The oncofetal protein, 5T4, is a tumor-associated protein displayed on the cell membrane of many carcinomas, including kidney, colon, prostate, lung, carcinoma and in acute lymphoblastic leukemia (see, Boghaert, E. R. et al. (2008) "*The Oncofetal Protein, 5T4, Is A Suitable Target For Antibody-Guided Anti-Cancer Chemotherapy With Calicheamicin,*" Int. J. Oncol. 32(1):221-234; Eisen, T. et al. (2014) "*Naptumomab Estafenatox: Targeted Immunotherapy with a Novel Immunotoxin,*" Curr. Oncol. Rep. 16:370, pp. 1-6). The epitope-binding site of any anti-5T4 antibody may be used in accordance with the present invention. Presented below are two exemplary anti-5T4 antibodies, "5T4 MAB-1," and "5T4 MAB-2". Additional ant-5T4 antibodies are described in the art (see, e.g., U.S. Pat. Nos. 8,084,249; 8,409,577; 8,759,495; 8,409,577; PCT Publication Nos: WO 2013/041687; WO 2014/137931; WO 2016/022939)

(a) 5T4 MAB-1

The amino acid sequence of the VH Domain of 5T4 MAB-1 is (SEQ ID NO:134) (CDR residues are shown underlined):

```
QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSS
```

The amino acid sequence of the VL Domain of 5T4 MAB-1 is (SEQ ID NO:135) (CDR residues are shown underlined):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIK
```

(b) 5T4 MAB-2

The amino acid sequence of the VH Domain of 5T4 MAB-2 is (SEQ ID NO:136) (CDR residues are shown underlined):

```
QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN SYAMDYWGQG

TSVTVSS
```

The amino acid sequence of the VL Domain of 5T4 MAB-2 is (SEQ ID NO:137) (CDR residues are shown underlined):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IK
```

The present invention specifically includes and encompasses CD137×5T4 Binding Molecules that comprise the VL and/or VH Domain, and/or 1, 2 or all 3 of the CDRLs of the VL Region and/or 1, 2 or all 3 of the CDRHs of the VH Domain of the anti-5T4 monoclonal antibodies 5T4 MAB-1 or 5T4 MAB-2, or of any of the anti-5T4 antibodies provided in WO 2007/106744; WO 2013/041687 or WO 2015/184203.

4. Antibodies that Bind to B7-H3

B7-H3 is a Tumor Antigen that is over-expressed on a wide variety of solid tumor types and is a member of the B7 family of molecules that are involved in immune regulation (see, U.S. Pat. No. 8,802,091; US 2014/0328750; US 2013/0149236; Loo, D. et al. (2012) "Development Of An Fc-Enhanced Anti-B7-H3 Monoclonal Antibody With Potent Antitumor Activity," Clin. Cancer Res. 18(14):3834-3845). In particular, several independent studies have shown that human malignant tumor cells (e.g., tumor cells of neuroblastomas and gastric, ovarian and non-small cell lung cancers) exhibit a marked increase in expression of B7-H3 protein and that this increased expression was associated with increased disease severity (Zang, X. et al. (2007) "*The B7 Family And Cancer Therapy: Costimulation And Coinhibition,*" Clin. Cancer Res. 13:5271-5279), suggesting that B7-H3 is exploited by tumors as an immune evasion pathway (Hofmeyer, K. et al. (2008) "*The Contrasting Role Of B7-H3,*" Proc. Natl. Acad. Sci. (U.S.A.) 105(30):10277-10278).

The epitope-binding site of any anti-B7-H3 antibody may be used in accordance with the present invention. One exemplary antibody that bind human B7-H3 is "Enoblituzumab." Enoblituzumab (also known as MGA271; CAS Reg No. 1353485-38-7; see for example, U.S. Pat. No. 8,802,091) is an Fc-optimized monoclonal antibody that binds to B7-H3 and mediates enhanced ADCC activity. Additional exemplary anti-B7-H3 antibodies are also presented.

(a) Enoblituzumab

The amino acid sequence of the VH Domain of Enoblituzumab is (SEQ ID NO:138) (CDR$_H$ residues are shown underlined):

```
EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCGRGR ENIYYGSRLD YWGQGTTVTV

SS
```

The amino acid sequence of the VL Domain of Enoblituzumab is (SEQ ID NO:139) (CDR$_L$ residues are shown underlined):

```
DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIK
```

(b) BRCA69D

Antibody BRCA69D is a murine anti-B7-H3 monoclonal antibody. The amino acid sequence of the VH Domain of BRCA69D (SEQ ID NO:140) is shown below (CDR$_H$ residues are shown underlined).

```
QVQLQQSGAE LARPGASVKL SCKASGYTFT SYWMQWVKQR

PGQGLEWIGT IYPGDGDTRY TQKFKGKATL TADKSSSTAY

MQLSSLASED SAVYYCARRG IPRLWYFDVW GAGTTVTVSS
```

The amino acid sequence of the VL Domain of BRCA69D (SEQ ID NO:141) is shown below (CDR$_L$ residues are shown underlined).

```
DIQMTQTTSS LSASLGDRVT ISCRASQDIS NYLNWYQQKP

DGTVKLLIYY TSRLHSGVPS RFSGSGSGTD YSLTIDNLEQ

EDIATYFCQQ GNTLPPTFGG GTKLEIK
```

(c) Humanized BRCA69D

Antibody BRCA69D was humanized yielding two variant VH Domains, hBRCA69D VH1 and hBRCA69D VH2; and two variant VL Domains hBRCA69D VL1 and hBRCA69D VL2, which may be used in any combination of VH/VL to yield a functional humanized binding domain. The amino sequences of such humanized variants are provided below.

The amino acid sequence of the VH Domain of hBRCA69D VH1 is (SEQ ID NO:142) (CDR$_H$ residues are shown underlined):

```
QVQLVQSGAE VKKPGASVKV SCKASGYTFT SYWMQWVRQA

PGQGLEWMGT IYPGDGDTRY TQKFKGRVTI TADKSTSTAY

MELSSLRSED TAVYYCARRG IPRLWYFDVW GQGTTVTVSS
```

The amino acid sequence of the VH Domain of hBRCA69D VH2 is (SEQ ID NO:143) (CDR$_H$ residues are shown underlined):

```
QVQLVQSGAE VKKPGASVKV SCKASGYTFT SYWMQWVRQA

PGQGLEWMGT IYPGGGDTRY TQKFQGRVTI TADKSTSTAY

MELSSLRSED TAVYYCARRG IPRLWYFDVW GQGTTVTVSS
```

The amino acid sequence of the VL Domain of hBRCA69D VL1 is (SEQ ID NO:144) (CDR$_L$ residues are shown underlined).

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIK
```

The amino acid sequence of the VL Domain of hBRCA69D VL2 is (SEQ ID NO:145) (CDR$_L$ residues are shown underlined).

```
DIQMTQSPSS LSASVGDRVT ITCRASQSIS SYLNWYQQKP

GKAPKLLIYY TSRLQSGVPS RFSGSGSGTD FTLTISSLQP

EDIATYYCQQ GNTLPPTFGG GTKLEIK
```

PRCA157

Antibody PRCA157 is a murine anti-B7-H3 monoclonal antibody. The amino acid sequence of the VH Domain of PRCA157 is (SEQ ID NO:146) (CDR$_H$ residues are shown underlined).

```
EVQQVESGGD LVKPGGSLKL SCAASGFTFS SYGMSWVRQT

PDKRLEWVAT INSGGSNTYY PDSLKGRFTI SRDNAKNTLY

LQMRSLKSED TAMYYCARHD GGAMDYWGQG TSVTVSS
```

The amino acid sequence of the VL Domain of PRCA157 is (SEQ ID NO:147) (CDR$_H$ residues are shown underlined).

```
DIQMTQSPAS LSVSVGETVT ITCRASESIY SYLAWYQQKQ

GKSPQLLVYN TKTLPEGVPS RFSGSGSGTQ FSLKINSLQP

EDFGRYYCQH HYGTPPWTFG GGTNLEIK
```

(e) Humanized PRCA157

Antibody PRCA157 was humanized yielding one humanized VH Domain, hPRCA157 VH1 and one humanized VL Domains hPRCA157 VL1, to yield a functional humanized binding domain. The amino sequences of humanized PRCA157 are provided below.

The amino acid sequence of the VH Domain of hPRCA157 VH1 is (SEQ ID NO:202) (CDR$_H$ residues are shown underlined):

```
EVQLVESGGG LVKPGGSLRL SCAASGFTFS SYGMSWVRQA

PGKGLEWVAT INSGGSNTYY PDSLKGRFTI SRDNAKNSLY

LQMNSLRAED TAVYYCARHD GGAMDYWGQG TTVTVSS
```

The amino acid sequence of the VL Domain of hPRCA157 VL1 is (SEQ ID NO:203) (CDR$_L$ residues are shown underlined):

```
DIQMTQSPSS LSASVGDRVT ITCRASESIY SYLAWYQQKP
```

-continued

```
GKAPKLLVYN TKTLPEGVPS RFSGSGSGTD FTLTISSLQP

EDFATYYCQH HYGTPPWTFG QGTRLEIK
```

(f) Other Anti-B7-H3 Antibodies

In addition to the above-identified preferred anti-B7-H3 Binding Molecules, the invention contemplates the use of any of the following anti-B7-H3 Binding Molecules: LUCA1; BLA8; PA20; or SKN2 (see, U.S. Pat. Nos. 7,527,969; 8,779,098 and PCT Patent Publication WO 2004/001381); M30; cM30; M30-H1-L1; M30-H1-L2; M30-H1-L3; M30-H1-L4; M30-H1-L5; M30-H1-L6; M30-H1-L7; M30-H4-L1; M30-H4-L2; M30-H4-L3; and M30-H4-L4 (see, US Patent Publication 2013/0078234 and PCT Patent Publication WO 2012/147713; and 8H9 (see U.S. Pat. Nos. 7,666,424; 7,737,258; 7,740,845; 8,148,154; 8,414,892; 8,501,471; 9,062,110; US Patent Publication 2010/0143245 and PCT Patent Publication WO 2008/116219).

The present invention specifically includes and encompasses CD137×B7-H3 Binding Molecules that comprise the VL and/or VH Domain, and/or 1, 2 or all 3 of the $CDR_L$s of the VL Region and/or 1, 2 or all 3 of the $CDR_H$s of the VH Domain of any of, BRCA69D, humanized BRCA69D, PRCA157, humanized PRCA157, or Enoblituzumab, or any of the other anti-B7-H3 antibodies provided herein; and more preferably possess 1, 2 or all 3 of the $CDR_L$s of the VL Region and/or 1, 2 or all 3 of the $CDR_H$s of the VH Domain of such anti-B7-H3 monoclonal antibodies.

5. Antibodies that Bind to GpA33

The 43 kD transmembrane glycoprotein A33 (gpA33) is expressed in >95% of all colorectal carcinomas (Heath, J. K. et al. (1997) "*The Human A33 Antigen Is A Transmembrane Glycoprotein And A Novel Member Of The Immunoglobulin Superfamily*," Proc. Natl. Acad. Sci. (U.S.A.) 94(2):469-474; Ritter, G. et al. (1997) "*Characterization Of Posttranslational Modifications Of Human A33Antigen, A Novel Palmitoylated Surface Glycoprotein Of Human Gastrointestinal Epithelium*," Biochem. Biophys. Res. Commun. 236 (3):682-686; Wong, N. A. et al. (2006) "*EpCAM and gpA33 Are Markers Of Barrett's Metaplasia*," J. Clin. Pathol. 59(3):260-263). The epitope-binding site of any anti-gpA33 antibody may be used in accordance with the present invention. An exemplary anti-gpA33 antibody ("gpA33 MAB-1") is presented below.

The amino acid sequence of the VH Domain of gpA33 MAB-1 is (SEQ ID NO:148) (CDR residues are shown underlined):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSS
```

The amino acid sequence of the VL Domain of gpA33 MAB-1 is (SEQ ID NO:149) (CDR residues are shown underlined):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIK
```

The present invention specifically includes and encompasses CD137×gpA33 Binding Molecules that comprise the VL and/or VH Domain, and/or 1, 2 or all 3 of the CDRLs of the VL Region and/or 1, 2 or all 3 of the CDRHs of the VH Domain of anti-gpA33 monoclonal antibodies gpA33 MAB-1, or of any of the anti-gpA33 monoclonal antibodies provided in WO 2015/026894.

6. Antibodies that Bind to CEACAM5 and CEACAM6

Carcinoembryonic Antigen-Related Cell Adhesion Molecules 5 (CEACAM5) and 6 (CEACAM6) have been found to be associated with various types of cancers including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Publication No. WO 2011/034660), and particularly colorectal, gastrointestinal, pancreatic, non-small cell lung cancer (NSCL), breast, thyroid, stomach, ovarian and uterine carcinomas (Zheng, C. et al. (2011) "*A Novel Anti-CEACAM5 Monoclonal Antibody, CC4, Suppresses Colorectal Tumor Growth and Enhances NK Cells-Mediated Tumor Immunity*," PLoS One 6(6):e21146, pp. 1-11). CEACAM5 has been found to be overexpressed in 90% of gastrointestinal, colorectal and pancreatic cancers, 70% of non-small cell lung cancer cells and 50% of breast cancers (Thompson, J. A. et al. (1991) "*Carcinoembryonic Antigen Gene Family: Molecular Biology And Clinical Perspectives*," J. Clin. Lab. Anal. 5:344-366). Overexpressed carcinoembryonic antigen-related cellular adhesion molecule 6 (CEACAM6) plays important roles in the invasion and metastasis of a variety of human cancers, including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Publication No. WO 2011/034660; Deng, X., et al. (2014) "*Expression Profiling Of CEACAM6 Associated With The Tumorigenesis And Progression In Gastric Adenocarcinoma*," Genet. Mol. Res. 13(3):7686-7697; Cameron, S. et al. (2012) "*Focal Overexpression Of CEACAM6 Contributes To Enhanced Tumourigenesis In Head And Neck Cancer Via Suppression Of Apoptosis*," Mol. Cancer 11:74, pp. 1-11; Chapin, C. et al. (2012) "*Distribution And Surfactant Association Of Carcinoembryonic Cell Adhesion Molecule 6 In Human Lung*," Amer. J. Physiol. Lung Cell. Mol. Physiol. 302(2):L216-L25; Riley, C. J. et al. (2009) "*Design And Activity Of A Murine And Humanized Anti-CEACAM6 Single-Chain Variable Fragment In The Treatment Of Pancreatic Cancer*," Cancer Res. 69(5):1933-1940; Lewis-Wambi, J. S. et al. (2008) "*Overexpression Of CEACAM6 Promotes Migration And Invasion Of Oestrogen-Deprived Breast Cancer Cells*," Eur. J. Cancer 44(12):1770-1779; Blumenthal, R. D. et al. (2007) "*Expression Patterns Of CEACAM5 And CEACAM6 In Primary And Metastatic Cancers*," BMC Cancer. 7:2, pp. 1-15). The epitope-binding site of any anti-CEACAM5/CEACAM6 antibody may be used in accordance with the present invention. Exemplary anti-CEACAM5/CEACAM6 antibodies are provided below.

(a) 16C3

The amino acid sequence of the VH Domain of the humanized anti-CEACAM5/CEACAM6 antibody 16C3 (EP 2585476) is (SEQ ID NO:150) (CDR residues are shown underlined):

```
QVQLQQSGPE VVRPGVSVKI SCKGSGYTFT DYAMHWVKQS
```

-continued

```
HAKSLEWIGL ISTYSGDTKY NQNFKGKATM TVDKSASTAY

MELSSLRSED TAVYYCARGD YSGSRYWFAY WGQGTLVTVS

S
```

The amino acid sequence of the VL Domain of the humanized anti-CEACAM5/CEACAM6 antibody 16C3 (EP 2585476) is (SEQ ID NO:151) (CDR residues are shown underlined):

```
DIQMTQSPSS LSASVGDRVT ITCGASENIY GALNWYQRKP

GKSPKLLIWG ASNLADGMPS RFSGSGSGRQ YTLTISSLQP

EDVATYYCQN VLSSPYTFGG GTKLEIK
``` b) hMN15

The amino acid sequence of the VH Domain of the humanized anti-CEACAM5/CEACAM6 antibody hMN15 (WO 2011/034660) is (SEQ ID NO:152) (CDR residues are shown underlined):

```
QVQLVESGGG VVQPGRSLRL SCSSSGFALT DYYMSWVRQA

PGKGLEWLGF IANKANGHTT DYSPSVKGRF TISRDNSKNT

LFLQMDSLRP EDTGVYFCAR DMGIRWNFDV WGQGTPVTVS

S
```

The amino acid sequence of the VL Domain of the humanized anti-CEACAM5/CEACAM6 antibody hMN15 (WO 2011/034660) is (SEQ ID NO:153) (CDR residues are shown underlined):

```
DIQLTQSPSS LSASVGDRVT MTCSASSRVS YIHWYQQKPG

KAPKRWIYGT STLASGVPAR FSGSGSGTDF TFTISSLQPE

DIATYYCQQW SYNPPTFGQG TKVEIKR
```

The present invention specifically includes and encompasses CD137×CEACAM5/CEACAM6 Binding Molecules that comprise the VL and/or VH Domain, and/or 1, 2 or all 3 of the CDR$_L$S of the VL Region and/or 1, 2 or all 3 of the CDR$_H$s of the VH Domain of the anti-CEACAM5/CEACAM6 monoclonal antibodies 16C3 or hMN15.

7. Antibodies that Bind to CD19

CD19 (B lymphocyte surface antigen B4, Genbank accession number M28170) is a component of the B cell-receptor (BCR) complex, and is a positive regulator of B cell signaling that modulates the threshold for B cell activation and humoral immunity. CD19 is one of the most ubiquitously expressed antigens in the B cell lineage and is expressed on >95% of B cell malignancies, including acute lymphoblastic leukemia (ALL), chronic lymphocytic leukemia (CLL), and non-Hodgkin's Lymphoma (NHL). Notably, CD19 expression is maintained on B cell lymphomas that become resistant to anti-CD20 therapy (Davis et al. (1999) "*Therapy of B-cell Lymphoma With Anti-CD20 Antibodies Can Result In The Loss Of CD20Antigen Expression.*" Clin Cancer Res, 5:611-615, 1999). CD19 has also been suggested as a target to treat autoimmune diseases (Tedder (2009) "*CD19: A Promising B Cell Target For Rheumatoid Arthritis,*" Nat. Rev. Rheumatol. 5:572-577).

An exemplary antibody that binds to human CD19, and that may be employed in the present invention, is the anti-CD19 antibody disclosed in WO 2016/048938 (referred to herein as "CD19 MAB-1").

The amino acid sequence of the VH Domain of CD19 MAB-1 (SEQ ID NO:204) is shown below (CDR$_H$ residues are shown underlined):

```
QVTLRESGPA LVKPTQTLTL TCTFSGFSLS TSGMGVGWIR

QPPGKALEWL AHIWWDDDKR YNPALKSRLT ISKDTSKNQV

FLTMTNMDPV DTATYYCARM ELWSYYFDYW GQGTTVTVSS
```

The amino acid sequence of the VL Domain of CD19 MAB-1 (SEQ ID NO:205) is shown below (CDR$_L$ residues are shown underlined):

```
ENVLTQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIK
```

The present invention specifically includes and encompasses CD137×CD19 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CD19 monoclonal antibody CD19 MAB-1, or any of the anti-CD19 antibodies disclosed in U.S. Pat. No. 7,112,324, or present in blinatumomab (BLINCYTO®; amino acid sequence found in WHO Drug Information, 2009, Recommended INN: List 62, 23(3):240-241) and duvortuxizumab (aka MGD011; amino acid sequence found in WHO Drug Information, 2016, Proposed INN: List 116, 30(4):627-629).

8. Antibodies that Bind to CD123

CD123 (interleukin 3 receptor alpha, IL-3Ra) is a 40 kDa molecule and is part of the interleukin 3 receptor complex (Stomski, F. C. et al. (1996) "*Human Interleukin-3 (IL-3) Induces Disulfide-Linked IL-3 Receptor Alpha-And Beta-Chain Heterodimerization, Which Is Required For Receptor Activation But Not High-Affinity Binding,*" Mol. Cell. Biol. 16(6):3035-3046). Interleukin 3 (IL-3) drives early differentiation of multipotent stem cells into cells of the erythroid, myeloid and lymphoid progenitors. CD123 has been reported to be overexpressed on malignant cells in a wide range of hematologic malignancies including acute myeloid leukemia (AML) and myelodysplastic syndrome (MDS) (Muñoz, L. et al. (2001) "*Interleukin-3 Receptor Alpha Chain (CD123) Is Widely Expressed In Hematologic Malignancies,*" Haematologica 86(12):1261-1269). Overexpression of CD123 is associated with poorer prognosis in AML (Tettamanti, M. S. et al. (2013) "*Targeting Of Acute Myeloid Leukaemia By Cytokine-Induced Killer Cells Redirected With A Novel CD123-Specific Chimeric Antigen Receptor,*" Br. J. Haematol. 161:389-401).

An exemplary antibody that binds to human CD123, and that may be employed in the present invention, is "CD123 MAB-1" (see, e.g., PCT Patent Publication WO 2015/026892).

The amino acid sequence of the VH Domain of CD123 MAB-1 (SEQ ID NO:206) is shown below (CDR$_H$ residues are shown underlined):

```
EVQLVQSGAE LKKPGASVKV SCKASGYTFT DYYMKWVRQA

PGQGLEWIGD IIPSNGATFY NQKFKGRVTI TVDKSTSTAY

MELSSLRSED TAVYYCARSH LLRASWFAYW GQGTLVTVSS
```

The amino acid sequence of the VL Domain of CD123 MAB-1 (SEQ ID NO:207) is shown below (CDR$_L$ residues are shown underlined):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIK
```

The present invention specifically includes and encompasses CD137×CD123 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CD123 monoclonal antibody CD123 MAB-1, or any of the anti-CD123 antibodies disclosed in US 2017/081424 and WO 2016/036937, or present in JNJ-63709178 (Johnson & Johnson, also see, WO 2016/036937) and XmAb14045 (Xencor, also see, US 2017/081424).

G. Preferred CD137 Variable Domains

The epitope-binding site of any anti-CD137 antibody may be used in accordance with the present invention. Exemplary antibodies that bind human CD137 include "urelumab," and "utomilumab" currently being evaluated in human clinical trials. Urelumab (also known as BMS-663513, designated "CD137 MAB-1" herein) is a fully human monoclonal antibody having IgG4/kappa constant regions (see, U.S. Pat. No. 8,137,667). Utomilumab (also known as PF-05082566, designated "CD137 MAB-2" herein) is a fully human monoclonal antibody having IgG2/lambda constant regions (see, U.S. Pat. No. 8,337,850). Additional exemplary antibodies that are immunospecific for human CD137 (designated "CD137 MAB-3," "CD137 MAB-4" and "CD137 MAB-5") are provided below.

1. CD137 MAB-1

The amino acid sequence of the VH Domain of CD137 MAB-1 (CD137 MAB-1 VH) is (SEQ ID NO:70) (CDR$_H$ residues are shown underlined):

```
QVQLQQWGAG LLKPSETLSL TCAVYGGSFS GYYWSWIRQS

PEKGLEWIGE INHGGYVTYN PSLESRVTIS VDTSKNQFSL

KLSSVTAADT AVYYCARDYG PGNYDWYFDL WGRGTLVTVS

S
```

The amino acid sequence of the VL Domain of CD137 MAB-1 (CD137 MAB-1 VL) is (SEQ ID NO:71) (CDR$_L$ residues are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RSNWPPALTF GGGTKVEIK
```

2. CD137 MAB-2

The amino acid sequence of the VH Domain of CD137 MAB-2 (CD137 MAB-2 VH) is (SEQ ID NO:72) (CDR$_H$ residues are shown underlined):

```
EVQLVQSGAE VKKPGESLRI SCKGSGYSFS TYWISWVRQM

PGKGLEWMGK IYPGDSYTNY SPSFQGQVTI SADKSISTAY

LQWSSLKASD TAMYYCARGY GIFDYWGQGT LVTVSS
```

The amino acid sequence of the VL Domain of CD137 MAB-2 (CD137 MAB-2 VL) is (SEQ ID NO:73) (CDR$_L$ residues are shown underlined):

```
SYELTQPPSV SVSPGQTASI TCSGDNIGDQ YAHWYQQKPG

QSPVLVIYQD KNRPSGIPER FSGSNSGNTA TLTISGTQAM

DEADYYCATY TGFGSLAVFG GGTKLTVL
```

3. CD137 MAB-3

CD137 MAB-3 is a novel murine monoclonal antibody. The amino acid sequence of the VH Domain of CD137 MAB-3 (CD137 MAB-3 VH) is (SEQ ID NO:74) (CDR$_H$ residues are shown underlined):

```
QVQLQQPGAE LVRPGASVKL SCKASGYTFT SYWINWVKQR

PGQGLEWIGN IYPSDSYTNY NQKFKDKATL TVDKSSSTAY

MQLSSPTSED SAVYYCTRDY GSSYSFDYWG QGTTLTVSS
```

The amino acid sequences of the CDR$_H$s of CD137 MAB-3 VH are:

```
    CDR_H1 (SEQ ID NO: 154):
    SYWIN

CDR_H2 (SEQ ID NO: 155):
    NIYPSDSYTNYNQKFKD

CDR_H3 (SEQ ID NO: 156):
    DYGSSYSFDY
```

The amino acid sequence of the VL Domain of CD137 MAB-3 (CD137 MAB-3 VL) is (SEQ ID NO:75) (CDR$_L$ residues are shown underlined):

```
DIQMTQTTSS LSASLGDRVT ISCRPSQDIS NYLNWYQQKP

DGTVKLLIYY TSRLRSGVPS RFSGSGSGTD YSLTISNLEQ

EDIATYFCQQ GDTLPYTFGG GTKLEIK
```

The amino acid sequences of the CDR$_L$S of CD137 MAB-3 VL are:

```
    CDR_L1 (SEQ ID NO: 157):
    RPSQDISNYLN

CDR_L2 (SEQ ID NO: 158):
    YTSRLRS

CDR_L3 (SEQ ID NO: 159):
    QQGDTLPYT
```

4. hCD137 MAB-3

Antibody CD137 MAB-3 was humanized to form antibody hCD137 MAB-3. The amino acid sequence of the VH Domain of such humanized antibody (hCD137 MAB-3 VH1) is (SEQ ID NO:76) (CDR$_H$ residues are shown underlined):

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSSYSFDYWG QGTTVTVSS
```

The VH Domain of humanized antibody hCD137 MAB-3 (hCD137 MAB-3 VH1) was optimized to yield a VH Domain having the amino acid sequence of SEQ ID NO:77:

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSX10X11X12X13X14X15WG

QGTTVTVSS wherein: X10X11X12X13X14X15 are:
(1A; SEQ ID NO: 78)
AYSFHP,
or (1B; SEQ ID NO: 79)
AYSMST,
or (1C; SEQ ID NO: 80)
AYSYSL,
or (1D; SEQ ID NO: 81)
SYSYNV.
```

As indicated above, the corresponding parental sequence (present in SEQ ID NO:74) is SYSFDY (SEQ ID NO:160).

The VL Domain of humanized antibody hCD137 MAB-3 (hCD137 MAB-3 VL) was optimized to yield a VL Domain having the amino acid sequence of SEQ ID NO:82:

```
DIQMTQSPSS LSASVGDRVT ITCRPSQDIS NYLNWYQQKP

X7X8TVKLLIYY TSRLRSGVPS RFSGSGSGTD FTFTISSLQP

EDIATYFCQQ GDTLPYTFGQ GTKLEIK wherein: X7 is D or G; X8 is G or K.
```

Four variant hCD137 MAB-3 VH1 Domains were isolated: hCD137 MAB-3 VH1A, hCD137 MAB-3 VH1B, hCD137 MAB-3 VH1C and hCD137 MAB-3 VH1D. The amino acid sequences of such variant hCD137 MAB-3 VH1 Domains are presented below.

The amino acid sequence of hCD137 MAB-3 VH1A is (SEQ ID NO:83) (CDR$_H$ residues are shown underlined; note that residues 5-10 of CDR$_3$H are AYSFHP (SEQ ID NO:78):

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSAYSFHPWG QGTTVTVSS
```

The amino acid sequence of hCD137 MAB-3 VH1B is (SEQ ID NO:84) (CDR$_H$ residues are shown underlined; note that residues 5-10 of CDR$_3$H are AYSMST (SEQ ID NO:79):

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSAYSMSTWG QGTTVTVSS
```

The amino acid sequence of hCD137 MAB-3 VH1C is (SEQ ID NO:85) (CDR$_H$ residues are shown underlined; note that residues 5-10 of CDR$_3$H are AYSYSL (SEQ ID NO:80):

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSAYSYSLWG QGTTVTVSS
```

The amino acid sequence of hCD137 MAB-3 VH1D is (SEQ ID NO:86) (CDR$_H$ residues are shown underlined; note that residues 5-10 of CDR$_3$H are SYSYNV (1D; SEQ ID NO:81):

```
QVQLVQSGAE VKKPGASVKV SCKASGYTFT SYWINWVKQA

PGQGLEWIGN IYPSDSYTNY NQKFKDKATI TADKSTSTAY

MELSSLRSED TAVYYCTRDY GSSYSYNVWG QGTTVTVSS
```

Thus, the amino acid sequence of CDR$_H$1 of hCD137 MAB-3 VH1A, hCD137 MAB-3 VH1B, hCD137 MAB-3 VH1C, and hCD137 MAB-3 VH1D are the same (SEQ ID NO:154) and the amino acid sequence of CDR$_H$2 of hCD137 MAB-3 VH1A, hCD137 MAB-3 VH1B, hCD137 MAB-3 VH1C, and hCD137 MAB-3 VH1D are the same (SEQ ID NO:155). However, the amino acid sequences of CDR$_H$3 of hCD137 MAB-3 VH1A, hCD137 MAB-3 VH1B, hCD137 MAB-3 VH1C, and hCD137 MAB-3 VH1D differ:

```
hCD137 MAB-3 VH1A CDR_H3 (SEQ ID NO: 161):
DYGSAYSFHP hCD137 MAB-3 VH1B CDR_H3 (SEQ ID NO: 162):
DYGSAYSMST hCD137 MAB-3 VH1C CDR_H3 (SEQ ID NO: 163):
DYGSAYSYSL hCD137 MAB-3 VH1D CDR_H3 (SEQ ID NO: 164):
DYGSSYSYNV
```

Three variant hCD137 MAB-3 VL Domains were isolated: hCD137 MAB-3 VL1, hCD137 MAB-3 VL2 and hCD137 MAB-3 VL3. The amino acid sequences of such variant hCD137 MAB-3 VL Domains are presented below.

The amino acid sequence of hCD137 MAB-3 VL1 is (SEQ ID NO:87) (CDR$_L$ residues are shown underlined; note that residues 41 and 42 are D and G, respectively):

```
DIQMTQSPSS LSASVGDRVT ITCRPSQDIS NYLNWYQQKP

DGTVKLLIYY TSRLRSGVPS RFSGSGSGTD FTFTISSLQP

EDIATYFCQQ GDTLPYTFGQ GTKLEIK
```

The amino acid sequence of hCD137 MAB-3 VL2 is (SEQ ID NO:88) (CDR$_L$ residues are shown underlined; note that that residues 41 and 42 are both G):

```
DIQMTQSPSS LSASVGDRVT ITCRPSQDIS NYLNWYQQKP

GGTVKLLIYY TSRLRSGVPS RFSGSGSGTD FTFTISSLQP

EDIATYFCQQ GDTLPYTFGQ GTKLEIK
```

The amino acid sequence of hCD137 MAB-3 VL3 is (SEQ ID NO:89) (CDR$_L$ residues are shown underlined; note that that residues 41 and 42 are D and K, respectively):

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIK
```

The VH Domain hCD137 MAB-3 VH1B was deimmunized as described in the Examples below. The amino acid sequences of three of the resulting deimmunized VH Domains designated hCD137 MAB-3 VH1E, hCD137 MAB-3 VH1F, and hCD137 MAB-3 VH1G, having an amino acid substitution at Kabat residue 38 and/or 48 are provided below. It is specifically contemplated that the identified substitutions, R38K and/or I48A may be incorporated into any of the disclosed hCD137 MAB-3 VH Domains. In a specific embodiment, the K38R amino acid substitution is incorporated into SEQ ID NO:76, SEQ ID NO:77, SEQ ID NO:83, SEQ ID NO:84, SEQ ID NO:85, or SEQ ID NO:86.

The amino acid sequence of hCD137 MAB-3 VH1E comprising K38R is (SEQ ID NO:208) (CDR$_H$ residues are shown underlined; substitution is doubled underlined):

```
QVQLVQSGAE VKKPGASVKV SCKASGYTFT SYWINWVRQA

PGQGLEWIGN IYPSDSYTNY NQKFKDKATI TADKSTSTAY

MELSSLRSED TAVYYCTRDY GSAYSMSTWGQGTTVTVSS
```

The amino acid sequence of hCD137 MAB-3 VH1F comprising I48A is (SEQ ID NO:209) (CDR$_H$ residues are shown underlined; substitutions are doubled underlined)):

```
QVQLVQSGAE VKKPGASVKV SCKASGYTFT SYWINWVKQA

PGQGLEWAGN IYPSDSYTNY NQKFKDKATI TADKSTSTAY

MELSSLRSED TAVYYCTRDY GSAYSMSTWGQGTTVTVSS
```

The amino acid sequence of hCD137 MAB-3 VH1G comprising K38R/I48A (SEQ ID NO:210) (CDR$_H$ residues are shown underlined; substitutions are doubled underlined)):

```
QVQLVQSGAE VKKPGASVKV SCKASGYTFT SYWINWVRQA

PGQGLEWAGN IYPSDSYTNY NQKFKDKATI TADKSTSTAY

MELSSLRSED TAVYYCTRDY GSAYSMSTWGQGTTVTVSS
```

The VL Domain hCD137 MAB-3 VL3 was deimmunized as described in the Examples below. The amino acid sequences of twelve of the resulting deimmunized VL Domains designated hCD137 MAB-3 VL4-VL15, having an amino acid substitution at Kabat residue 24, 25, 44, 48, 52, and/or 54 are provided below. It is specifically contemplated that the identified substitutions, R24Q, P25A, V44A, I48A, S52T, S52G, and/or L54A may be incorporated into any of the disclosed hCD137 MAB-3 VL Domains provided above to yield a deimmunized VL Domain. In a specific embodiment, R24Q, P25A, I48A, S52G, and L54A amino acid substitutions are incorporated into SEQ ID NO: 82, SEQ ID NO: 87, SEQ ID NO: 88 or SEQ ID NO: 89. In another specific embodiment, R24Q, P25A, I48A, S52T, and L54A amino acid substitutions are incorporated into SEQ ID NO: 82, SEQ ID NO: 87, SEQ ID NO: 88 or SEQ ID NO: 89.

The amino acid sequence of hCD137 MAB-3 VL4 comprising R24Q/P25A is (SEQ ID NO:211) (CDR$_H$ residues are shown underlined; substitutions are (doubled underlined):

```
DIQMTQSPSS LSASVGDRVT ITCQASQDIS NYLNWYQQKP

DKTVKLLIYY TSRLRSGVPS RFSGSGSGTD FTFTISSLQP

EDIATYFCQQ GDTLPYTFGQ GTKLEIK
```

The amino acid sequence of hCD137 MAB-3 VL5 comprising V44A is (SEQ ID NO:212) (CDR$_H$ residues are shown underlined; substitution is doubled underlined):

```
DIQMTQSPSS LSASVGDRVT ITCRPSQDIS NYLNWYQQKP

DKTAKLLIYY TSRLRSGVPS RFSGSGSGTD FTFTISSLQP

EDIATYFCQQ GDTLPYTFGQ GTKLEIK
```

The amino acid sequence of hCD137 MAB-3 VL6 comprising L54A is (SEQ ID NO:213) (CDR$_H$ residues are shown underlined; substitution is doubled underlined):

```
DIQMTQSPSS LSASVGDRVT ITCRPSQDIS NYLNWYQQKP

DKTVKLLIYY TSRARSGVPS RFSGSGSGTD FTFTISSLQP

EDIATYFCQQ GDTLPYTFGQ GTKLEIK
```

The amino acid sequence of hCD137 MAB-3 VL7 comprising R24Q/P25A/V44A is (SEQ ID NO:214) (CDR$_H$ residues are shown underlined; substitutions are doubled underlined):

```
DIQMTQSPSS LSASVGDRVT ITCQASQDIS NYLNWYQQKP

DKTAKLLIYY TSRLRSGVPS RFSGSGSGTD FTFTISSLQP

EDIATYFCQQ GDTLPYTFGQ GTKLEIK
```

The amino acid sequence of hCD137 MAB-3 VL8 comprising R24Q/P25A/V44A/L54A is (SEQ ID NO:215) (CDR$_H$ residues are shown underlined; substitutions are doubled underlined):

```
DIQMTQSPSS LSASVGDRVT ITCQASQDIS NYLNWYQQKP

DKTAKLLIYY TSRARSGVPS RFSGSGSGTD FTFTISSLQP

EDIATYFCQQ GDTLPYTFGQ GTKLEIK
```

The amino acid sequence of hCD137 MAB-3 VL9 comprising R24Q/P25A/L54A is (SEQ ID NO:216) (CDR$_H$ residues are shown underlined; substitutions are doubled underlined):

```
DIQMTQSPSS LSASVGDRVT ITCQASQDIS NYLNWYQQKP

DKTVKLLIYY TSRARSGVPS RFSGSGSGTD FTFTISSLQP

EDIATYFCQQ GDTLPYTFGQ GTKLEIK
```

The amino acid sequence of hCD137 MAB-3 VL10 comprising S52T is (SEQ ID NO:217) (CDR$_H$ residues are shown underlined; substitution is doubled underlined):

```
DIQMTQSPSS LSASVGDRVT ITCRPSQDIS NYLNWYQQKP

DKTVKLLIYY TTRLRSGVPS RFSGSGSGTD FTFTISSLQP

EDIATYFCQQ GDTLPYTFGQ GTKLEIK
```

The amino acid sequence of hCD137 MAB-3 VL11 comprising S52G is (SEQ ID NO:218) (CDR$_H$ residues are shown underlined; substitution is doubled underlined):

```
DIQMTQSPSS LSASVGDRVT ITCRPSQDIS NYLNWYQQKP

DKTVKLLIYY TGRLRSGVPS RFSGSGSGTD FTFTISSLQP

EDIATYFCQQ GDTLPYTFGQ GTKLEIK
```

The amino acid sequence of hCD137 MAB-3 VL12 comprising I48A/S52T is (SEQ ID NO:219) (CDR$_H$ residues are shown underlined; substitutions are doubled underlined):

```
DIQMTQSPSS LSASVGDRVT ITCRPSQDIS NYLNWYQQKP

DKTVKLLAYY TTRLRSGVPS RFSGSGSGTD FTFTISSLQP

EDIATYFCQQ GDTLPYTFGQ GTKLEIK
```

The amino acid sequence of hCD137 MAB-3 VL13 comprising I48A/S52G is (SEQ ID NO:220) (CDR$_H$ residues are shown underlined; substitutions are doubled underlined):

```
DIQMTQSPSS LSASVGDRVT ITCRPSQDIS NYLNWYQQKP

DKTVKLLAYY TGRLRSGVPS RFSGSGSGTD FTFTISSLQP

EDIATYFCQQ GDTLPYTFGQ GTKLEIK
```

The amino acid sequence of hCD137 MAB-3 VL14 comprising R24Q/P25A/S52T/L54A is (SEQ ID NO:221) (CDR$_H$ residues are shown underlined; substitutions are doubled underlined):

```
DIQMTQSPSS LSASVGDRVT ITCQASQDIS NYLNWYQQKP

DKTVKLLIYY TTRARSGVPS RFSGSGSGTD FTFTISSLQP

EDIATYFCQQ GDTLPYTFGQ GTKLEIK
```

The amino acid sequence of hCD137 MAB-3 VL15 comprising R24Q/P25A/S52G/L54A is (SEQ ID NO:222) (CDR$_H$ residues are shown underlined; substitutions are doubled underlined):

```
DIQMTQSPSS LSASVGDRVT ITCQASQDIS NYLNWYQQKP

DKTVKLLIYY TGRARSGVPS RFSGSGSGTD FTFTISSLQP

EDIATYFCQQ GDTLPYTFGQ GTKLEIK
```

Thus, the amino acid sequence of CDR$_L$3 of hCD137 MAB-3 VL3-VL15 are the same (QQGDTLPYT; SEQ ID NO:159). However, the amino acid sequences of CDR$_L$1 and/or CDR$_L$2 of hCD137 MAB-3 VL4, and hCD137 MAB-3 VL6-VL15 differ:

```
hCD137 MAB-3 VL4, VL7, VL8, VL9, VL14, and VL15
CDR_L1 (SEQ ID NO: 223):
QASQDISNYLN hCD137 MAB-3 VL6, VL8, and VL9 CDR_L2
(SEQ ID NO: 224):
YTSRARS hCD137 MAB-3 VL10, and VL12 CDR_L2
(SEQ ID NO: 225):
YTTRLRS hCD137 MAB-3 VL11, and VL13 CDR_L2
(SEQ ID NO: 226):
YTGRLRS hCD137 MAB-3 VL14 CDR_L2 (SEQ ID NO: 227):
YTTRARS hCD137 MAB-3 VL15 CDR_L2 (SEQ ID NO: 228):
YTGRARS
```

The CDRs, VL Domain, and/or VH Domain of any of such humanized, optimized, and/or deimmunized VH and VL hCD137 MAB-3 Domains, including any embraced within the generic sequence(s) of the hCD137 MAB-3 VH and/or VL Domains presented above may be used to form an antibody, diabody or binding molecule capable of binding CD137.

5. CD137 MAB-4

CD137 MAB-4 is a novel murine monoclonal antibody. The amino acid sequence of the VH Domain of CD137 MAB-4 (CD137 MAB-4 VH) is (SEQ ID NO:90) (CDR$_H$ residues are shown underlined):

```
QVQLQQPGAE LVRPGASVKL SCKASGYTFT SYWINWVKQR

PGQGLEWIGN IYPSDSYTNY DQKFKDKATL TVDKSSSTAY

MQLSSPTSED SAVYYCTKSG EYGKIGYYAM DYWGQGTSVT

VSS
```

The amino acid sequences of the CDR$_H$S of CD137 MAB-4 VH are:

```
CDR_H1 (SEQ ID NO: 165):
SYWIN

CDR_H2 (SEQ ID NO: 166):
NIYPSDSYTNYDQKFKD

CDR_H3 (SEQ ID NO: 167):
SGEYGKIGYYAMDY
```

The amino acid sequence of the VL Domain of CD137 MAB-4 (CD137 MAB-4 VL) is (SEQ ID NO:91) (CDR$_L$ residues are shown underlined):

```
DIQMTQTTSS LSASLGDRVT ISCRASQDIS NYLNWYQQKP

DGTVKLLIYY TSRLHSGVPS RFSGSGSGTD YSLTISNLEQ

EDIATYFCQQ GNTLPYTFGG GTKLEIK
```

The amino acid sequences of the CDR$_L$S of CD137 MAB-4 VL are:

```
CDR_L1 (SEQ ID NO: 168):
RASQDISNYLN

CDR_L2 (SEQ ID NO: 169):
YTSRLHS

CDR_L3 (SEQ ID NO: 170):
QQGNTLPYT
```

6. hCD137 MAB-4

Antibody CD137 MAB-4 was humanized to form antibody hCD137 MAB-4. The amino acid sequence of the VH Domain of humanized antibody hCD137 MAB-4 (hCD137 MAB-4 VH1) is (SEQ ID NO:92) (CDR$_H$ residues are shown underlined):

```
QVQLVQSGAE VKKPGASVKV SCKASGYTFT SYWINWVRQA

PGQGLEWMGN IYPSDSYTNY DQKFKDRVTM TRDTSTSTVY

MELSSLRSED TAVYYCTKSG EYGKIGYYAM DYWGQGTTVT

VSS
```

The VL Domain of humanized antibody hCD137 MAB-4 was humanized and optimized to yield a VL Domain (hCD137 MAB-3 VL) having the amino acid sequence of SEQ ID NO:93 (CDR$_L$ residues are shown underlined):

```
DIQMTQSPSS LSASVGDRVT ITCRASQDIS NYLNWYQQKP

DKTVKLLIYY TSRLHSGVPS RFSGSGSGTD YTLTISSLQP

EDIATYX_9CQQ GNTLPYTFGQ GTKLEIK
``` wherein X$_9$ is F or Y wherein X$_9$ is F or Y

Two variant hCD137 MAB-4 VL Domains were isolated: hCD137 MAB-4 VL1 and hCD137 MAB-4 VL2. The amino acid sequences of such variant hCD137 MAB-4 VL Domains are presented below.

The amino acid sequence of hCD137 MAB-4 VL1 is (SEQ ID NO:94) (CDR$_L$ residues are shown underlined; note that residue 87 is F):

```
DIQMTQSPSS LSASVGDRVT ITCRASQDIS NYLNWYQQKP

DKTVKLLIYY TSRLHSGVPS RFSGSGSGTD YTLTISSLQP

EDIATYFCQQ GNTLPYTFGQ GTKLEIK
```

The amino acid sequence of hCD137 MAB-4 VL2 is (SEQ ID NO:95) (CDR$_L$ residues are shown underlined; note that residue 87 is Y):

```
DIQMTQSPSS LSASVGDRVT ITCRASQDIS NYLNWYQQKP

DKTVKLLIYY TSRLHSGVPS RFSGSGSGTD YTLTISSLQP

EDIATYYCQQ GNTLPYTFGQ GTKLEIK
```

7. CD137 MAB-5

CD137 MAB-5 is a novel murine monoclonal antibody. The amino acid sequence of the VH Domain of CD137 MAB-5 (CD137 MAB-5 VH) is (SEQ ID NO:96) (CDR$_H$ residues are shown underlined):

```
QVQLKESGPG LVAPSQSLSI TCTVSGFSLT SYDISWIRQP

PGKGLEWLGV VWTGGGTNYN SAFMSRLSIS KDNSKSQVFL

KMNSLQTDDT AIYYCERVDY WGQGTSVTVS S
```

The amino acid sequences of the CDR$_H$s of CD137 MAB-5 VH are:

```
CDR_H1 (SEQ ID NO: 171):
SYDIS

CDR_H2 (SEQ ID NO: 172):
VVWTGGGTNYNSAFMS

CDR_H3 (SEQ ID NO: 173):
VDY
```

The amino acid sequence of the VL Domain of CD137 MAB-5 (CD137 MAB-5 VL) is (SEQ ID NO:97) (CDR$_L$ residues are shown underlined):

```
DVVMTQTPLS LPVSLGDQAS ISCRSSQSLV HSNGNTYLHW

YLQKPGQSPK LLIYKVSNRF SGVPDRFSGS GSGTDFTLKI

SRVEAEDLGV YFCSQSTHVP WTFGGGTKLE IK
```

The amino acid sequences of the CDR$_L$s of CD137 MAB-5 VL are:

```
CDR_L1 (SEQ ID NO: 174):
RSSQSLVHSNGNTYLH

CDR_L2 (SEQ ID NO: 175):
KVSNRFS

CDR_L3 (SEQ ID NO: 176):
SQSTHVPWT
```

III. CD137×TA Binding Molecules of the Present Invention

The present invention is particularly directed to Trivalent CD137×TA Binding Molecules that comprise an Fc Domain, Fc-bearing CD137×TA DART® diabodies capable of simultaneous binding to CD137 and a TA, and other Fc-bearing CD137×TA Binding Molecules capable of simultaneous binding to CD137 and a TA. The present invention is further directed to the use of such molecules in the treatment of cancer and other diseases and conditions. Although non-optimized CD137×TA Binding Molecules are fully functional, analogous to the improvements obtained in gene expression through codon optimization (see, e.g., Grosjean, H. et al. (1982) *"Preferential Codon Usage In Prokaryotic Genes: The Optimal Codon-Anticodon Interaction Energy And The Selective Codon Usage In Efficiently Expressed Genes"* Gene 18(3):199-209), it is possible to further enhance the stability and/or function of the CD137×TA Binding Molecules of the present invention by modifying or refining their sequences.

A. CD137×TA Fc-Bearing DART® Diabodies

The present invention particularly encompasses a wide variety of Fc-bearing DART® diabodies capable of simultaneous binding to CD137 and a TA. Exemplary CD137×TA Fc-bearing DART® Diabodies are described below.

Figure 2:
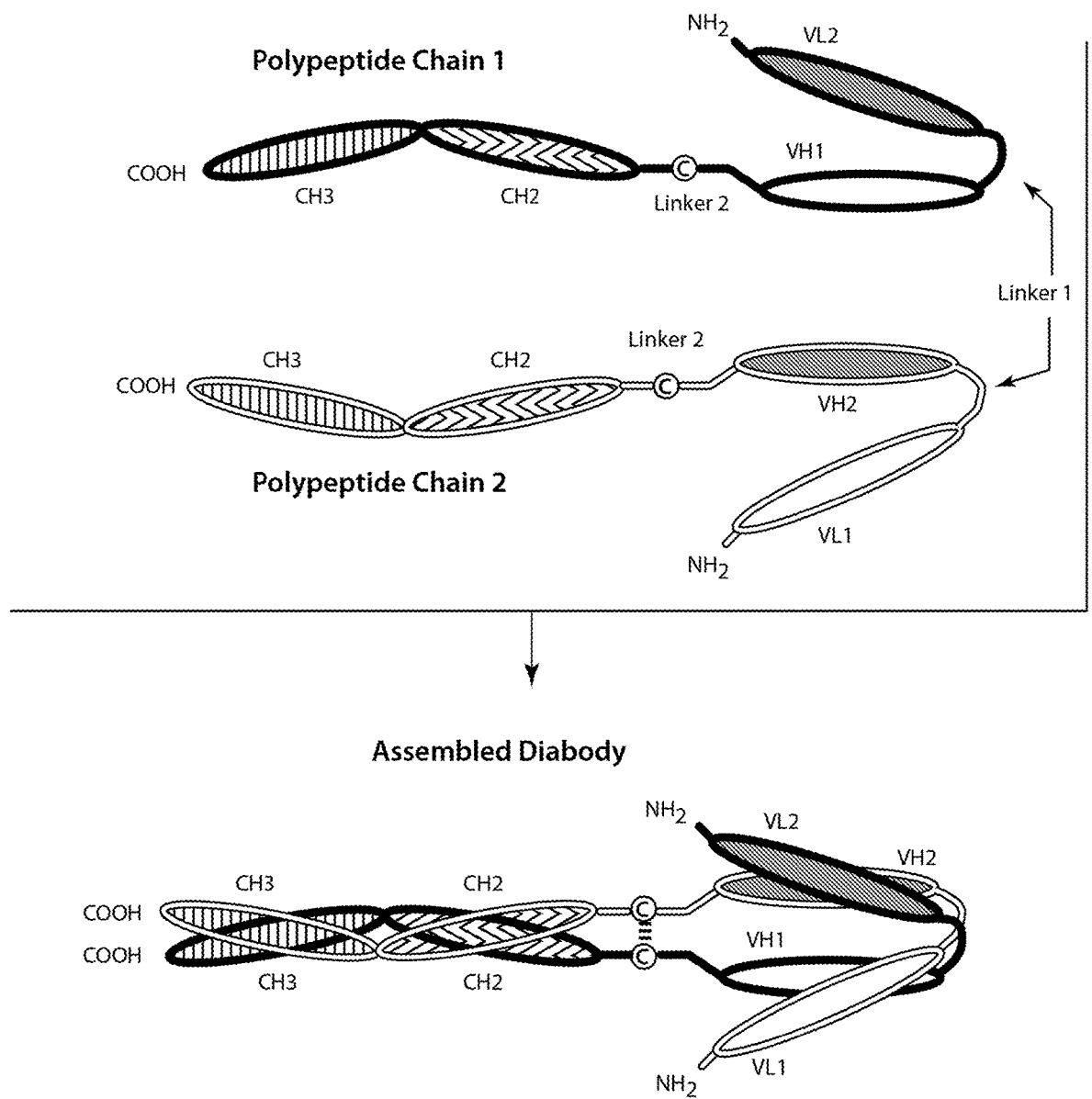
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

In one embodiment, such Fc-bearing diabodies will comprise two polypeptide chains. As shown in FIG. 2, the first of such polypeptide chains may contain, in the N-terminal to C-terminal direction, an N-terminus, a Light Chain Variable Domain (VL) capable of binding to an epitope of a "first" antigen (VL1) (either CD137 or TA), a Heavy Chain Variable Domain (VH) capable of binding to an epitope of a "second" antigen (VH2) (TA, if VL1 was selected to bind to an epitope of CD137; CD137 if VL1 was selected to bind to an epitope of TA), a cysteine-containing linker, a CH2-CH3 Domain, and a C-terminus. The second of such polypeptide chains may contain, in the N-terminal to C-terminal direction, an N-terminus, a Light Chain Variable Domain (VL) capable of binding to an epitope of the "second" antigen (VL2) (TA, if the first antigen was CD137; CD137, if the first antigen was TA)), a Heavy Chain Variable Domain (VH) capable of binding to an epitope of the "second" antigen (VH2) (TA, if VL2 was selected to bind to an epitope of CD137; CD137 if VL2 was selected to bind to an epitope of TA, a cysteine-containing linker, a CH2-CH3 Domain, and a C-terminus. An intervening linker peptide (Linker 1) separates the Light Chain Variable Domain (VL1 or VL2) from the Heavy Chain Variable Domain (VH1 or VH2).

Figure 4A:
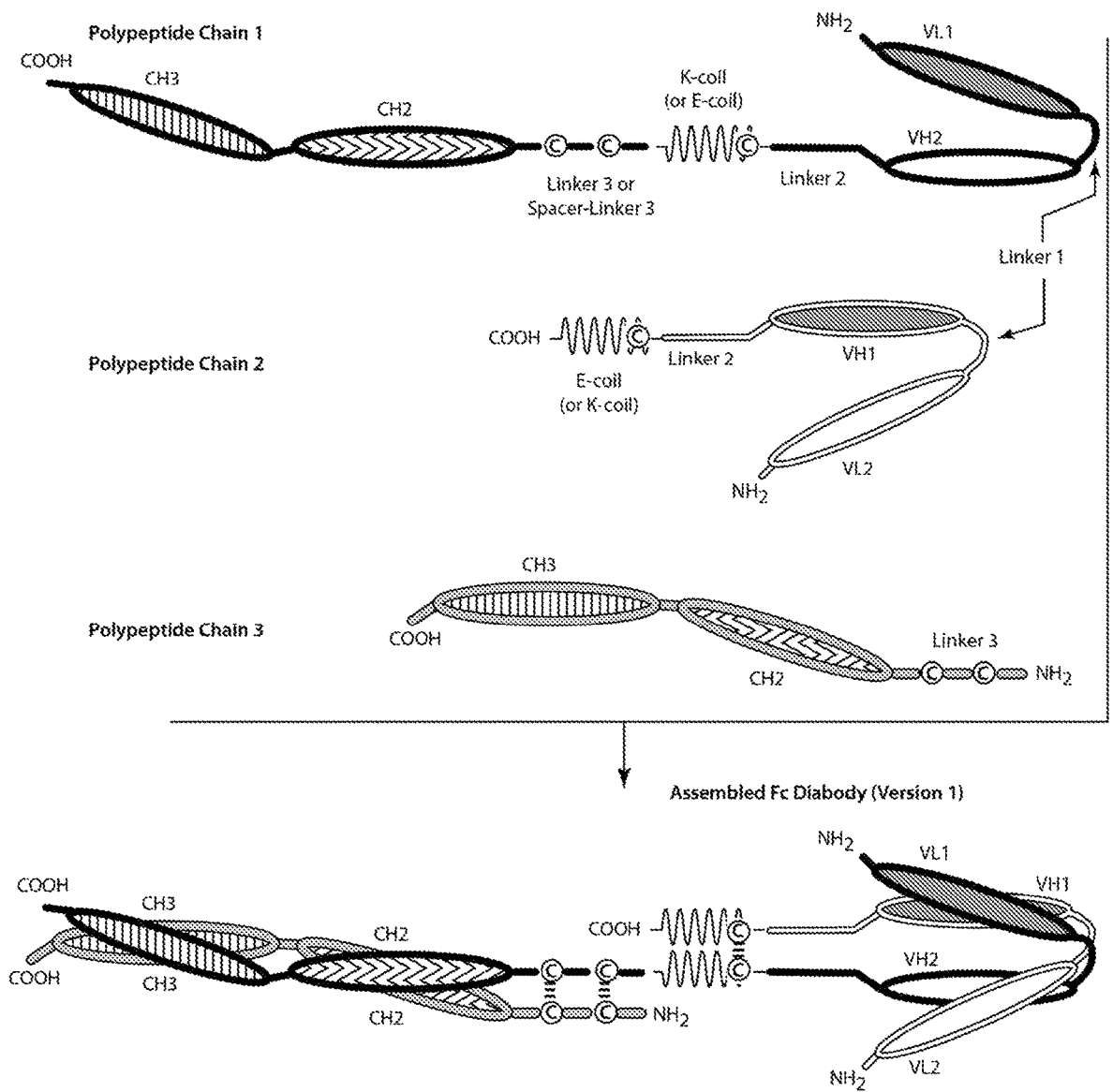
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
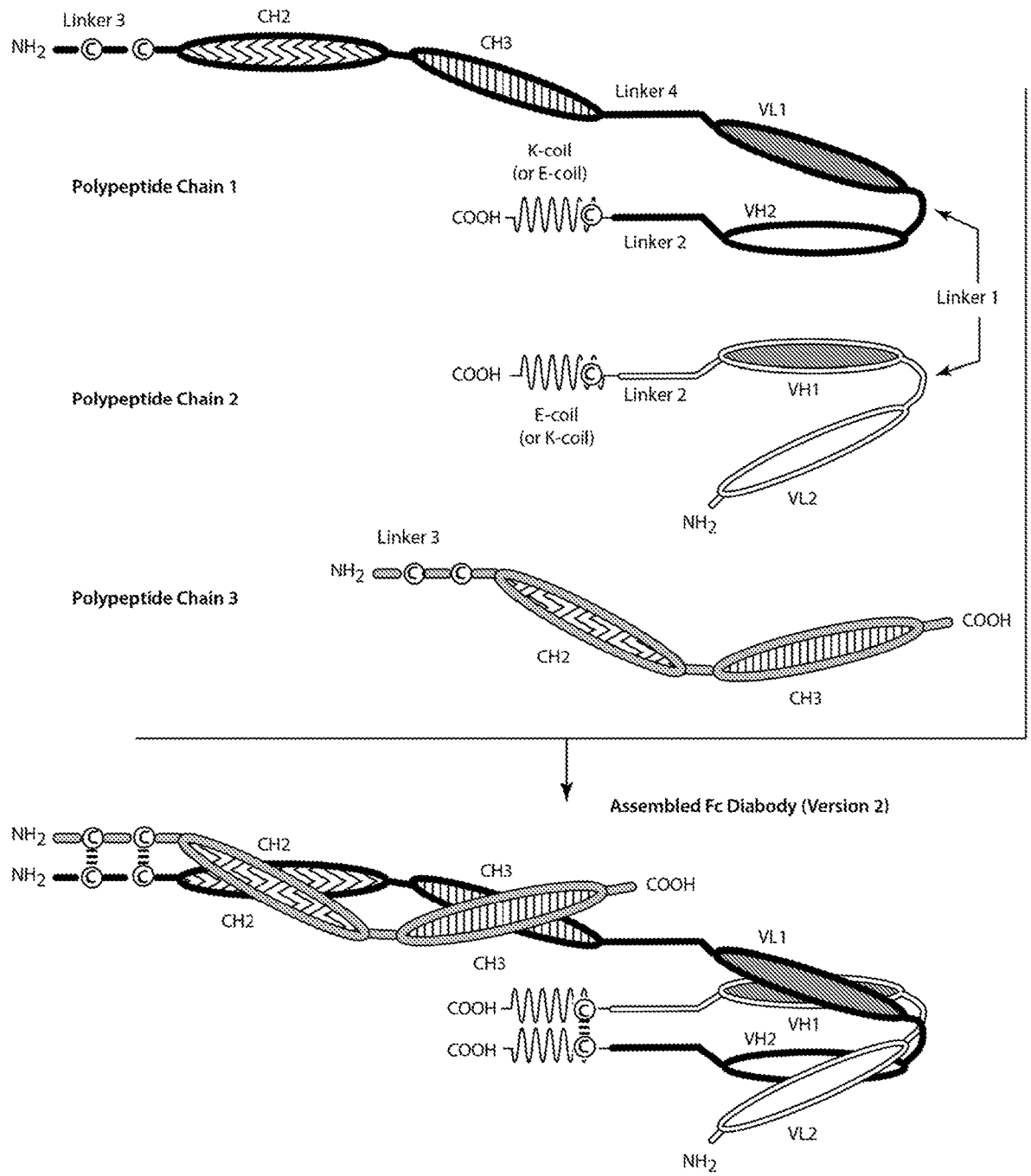

In another embodiment, Fc-bearing diabodies of the present invention comprise three polypeptide chains, and are depicted in FIGS. 4A-4B. The first polypeptide chain of such a diabody contains four Domains: (i) a VL1-containing Domain, (ii) a VH2-containing Domain, (iii) a Domain that promotes heterodimerization (a "Heterodimer-Promoting Domain") and covalent bonding with the diabody's second polypeptide chain, and (iv) a Domain containing a CH2-CH3 sequence. The second polypeptide chain of such Fc-bearing diabodies contains: (i) a VL2-containing Domain, (ii) a VH1-containing Domain and (iii) a Domain that promotes heterodimerization (a "Heterodimer-Promoting Domain") and covalent bonding with the diabody's first polypeptide chain. The third polypeptide chain of such Fc-bearing diabodies comprises a CH2-CH3 sequence. Thus, the first and second polypeptide chains of such Fc-bearing diabodies associate together to form a VL1/VH1 binding site that is capable of binding to a first epitope (1), as well as a VL2/VH2 binding site that is capable of binding to a second epitope (2). The preferred Fc-bearing diabodies of the present invention are CD137×TA bispecific diabodies that are capable of binding to the "first epitope," which may be either CD137 or TA, and the "second epitope," which is TA when the first epitope is CD137, and is CD137 when the first epitope is TA. The first and second polypeptides are bonded to one another through one or more disulfide bonds involving cysteine residues in their respective linkers and/or third Domains. Notably, the first and third polypeptide chains complex with one another to form an Fc Domain that is stabilized via a disulfide bond. Such diabodies have enhanced potency. Preferred Fc-bearing diabodies of the present invention may have either of two orientations (Table 2):

TABLE 2

| First Orientation | 3rd Chain | NH₂-©-CH2—CH3—COOH |
|---|---|---|
| | 1st Chain | NH₂-VL2-VH1-©-HPD-©-CH2—CH3—COOH |
| | 2nd Chain | NH₂-VL1-VH2-©-HPD-COOH |
| Second Orientation | 3rd Chain | NH₂-©-CH2—CH3—COOH |
| | 1st Chain | NH₂-©-CH2—CH3-VL2-VH1-©-HPD-COOH |
| | 2nd Chain | NH₂-VL1-VH2-©-HPD-COOH |

(—©—denotes a cysteine-containing polypeptide domain that possesses one, two, or more than two cysteine residues. The representation is intended to be illustrative and non-limiting. Cysteine residues may be present in additional or alternative domains, such as within the Heterodimer-Promoting Domain (HPD))

As shown in FIG. 4A, in a first embodiment, the first of such three polypeptide chains may contain, in the N-terminal to C-terminal direction, an N-terminus, a Light Chain Variable Domain (VL) capable of binding to an epitope of a "first" antigen (VL1) (either CD137 or TA), a Heavy Chain Variable Domain (VH) capable of binding to an epitope of a "second" antigen (VH2) (TA, as the first antigen if the second antigen was CD137; CD137, as the first antigen if the second antigen was TA), a cysteine-containing domain, a Heterodimer-Promoting Domain, a second cysteine-containing domain, a CH2-CH3 domain and a C-terminus. An intervening linker peptide (Linker 1) separates the Light Chain Variable Domain (VL1) from the Heavy Chain Variable Domain (VH2). Preferably, the Heavy Chain Variable Domain (VH1) is linked to a Heterodimer-Promoting Domain by an intervening linker peptide (Linker 2). In a preferred CD137×TA bispecific Fc-bearing diabody embodiment, the C-terminus of the Heterodimer-Promoting Domain is linked to CH2-CH3 domains of an Fc Region ("Fc Domain") by an intervening linker peptide (Linker 3) or by an intervening spacer peptide (Linker 3). Most preferably, the first of the three polypeptide chains will thus contain, in the N-terminal to C-terminal direction: VL1-Linker 1-VH2-Linker 2-Heterodimer-Promoting Domain-Linker 3-Fc Domain.

The second of such three polypeptide chains will contain, in the N-terminal to C-terminal direction, an N-terminus, a Light Chain Variable Domain (VL) capable of binding to the epitope of the "second" antigen (VL2), a Heavy Chain Variable Domain (VH) capable of binding to the epitope of the "first" antigen (VH1), a cysteine-containing domain, a Heterodimer-Promoting Domain and a C-terminus. An intervening linker peptide (Linker 1) separates the Light Chain Variable Domain (VL2) from the Heavy Chain Variable Domain (VH1). Preferably, the Heavy Chain Variable Domain (VH1) is linked to the Heterodimer-Promoting Domain by an intervening linker peptide (Linker 2). Most preferably, the second of the three polypeptide chains will thus contain, in the N-terminal to C-terminal direction: VL2-Linker 1-VH1-Linker 2-Heterodimer-Promoting Domain.

The third of such three polypeptide chains will contain, in the N-terminal to C-terminal direction, a cysteine-containing peptide (such as Linker 3), and the CH2-CH3 domains of an Fc region ("Fc Domain"). As the third polypeptide chain does not comprise a VL Domain or a VH Domain the third polypeptide chain may be identical between two or more different CD137×TA bispecific Fc diabodies of the present invention.

Alternatively, as shown in FIG. 4B, in a second embodiment, the first of such three polypeptide chains will contain, in the N-terminal to C-terminal direction, an N-terminus, a cysteine-containing peptide (such as Linker 3), the CH2-CH3 domains of an Fc Region ("Fc Domain"), an intervening spacer peptide (Linker 4), a Light Chain Variable Domain (VL) capable of binding to an epitope of the "first" antigen (VL1) (either CD137 or TA), a Heavy Chain Variable Domain (VH) capable of binding to an epitope of the "second" antigen (VH2) (TA, if the first antigen was CD137; CD137, if the first antigen was TA), a cysteine-containing linker, a Heterodimer-Promoting Domain, and a C-terminus. An intervening linker peptide (Linker 1) separates the Light Chain Variable Domain (VL1) from the Heavy Chain Variable Domain (VH2). Preferably, the Heavy Chain Variable Domain (VH1) is linked to a Heterodimer-Promoting Domain by an intervening linker peptide (Linker 2). Most preferably, in such alternative orientation, the first of the three polypeptide chains will thus contain, in the N-terminal to C-terminal direction: Linker 3-Fc Domain-Linker 4-VL1-Linker 1-VH2-Linker 2-Heterodimer-Promoting Domain. The second and third polypeptide chains of such alternative diabody may be the same as the second and third polypeptide chains of the first embodiment.

In each of the above embodiments, the Light Chain Variable Domain of the first polypeptide chain (VL1) is coordinately selected so as to permit it to interact with the Heavy Chain Variable Domain of the second polypeptide chain (VH1) to thereby form a functional epitope-binding site that is capable of immunospecifically binding an epitope of the first antigen (i.e., either TA or CD137). Likewise, the Light Chain Variable Domain of the second polypeptide chain (VL2) is coordinately selected so as to permit it to interact with the Heavy Chain Variable Domain of the first polypeptide chain (VH2) to thereby form a functional epitope-binding site that is capable of immunospecifically binding an epitope of the second antigen (i.e., either a TA or CD137). Thus, the selection of the Light Chain Variable Domains and the Heavy Chain Variable Domains are coordinated, such that the two polypeptide chains collectively comprise epitope-binding sites capable of binding to CD137 and a TA.

Figure 3A:
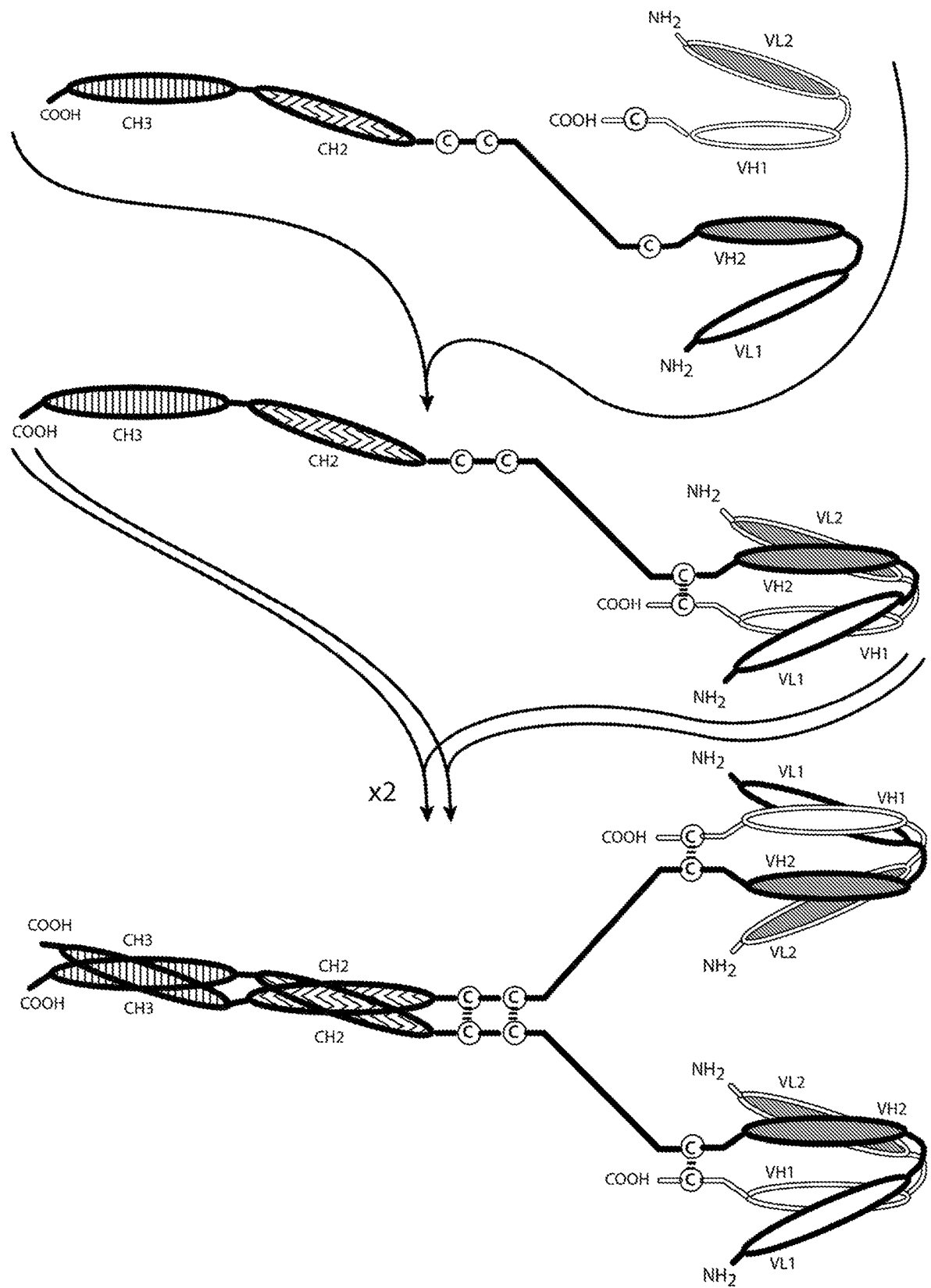
FIGS. 3A-3E provide schematics showing representative covalently bonded tetravalent diabodies having four epitope-binding sites composed of two pairs of polypeptide chains (i.e., four polypeptide chains in all). One polypeptide chain of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments, wherein the two pairs of polypeptide chains are the same and the VL and VH Domains recognize different epitopes (as shown in FIGS. 3A-3B), the resulting molecule possesses four epitope-binding sites and is bispecific and bivalent with respect to each bound epitope. In such embodiments, wherein the VL and VH Domains recognize the same epitope (e.g., the same VL Domain CDRs and the same VH Domain CDRs are used on both chains) the resulting molecule possesses four epitope-binding sites and is monospecific and tetravalent with respect to a single epitope. Alternatively, the two pairs of polypeptides may be different. In such embodiments, wherein the two pairs of polypeptide chains are different and the VL and VH Domains of each pair of polypeptides recognize different epitopes (as shown by the different shading and patterns in FIG. 3C), the resulting molecule possesses four epitope-binding sites and is tetraspecific and monovalent with respect to each bound epitope.
Figure 3B:
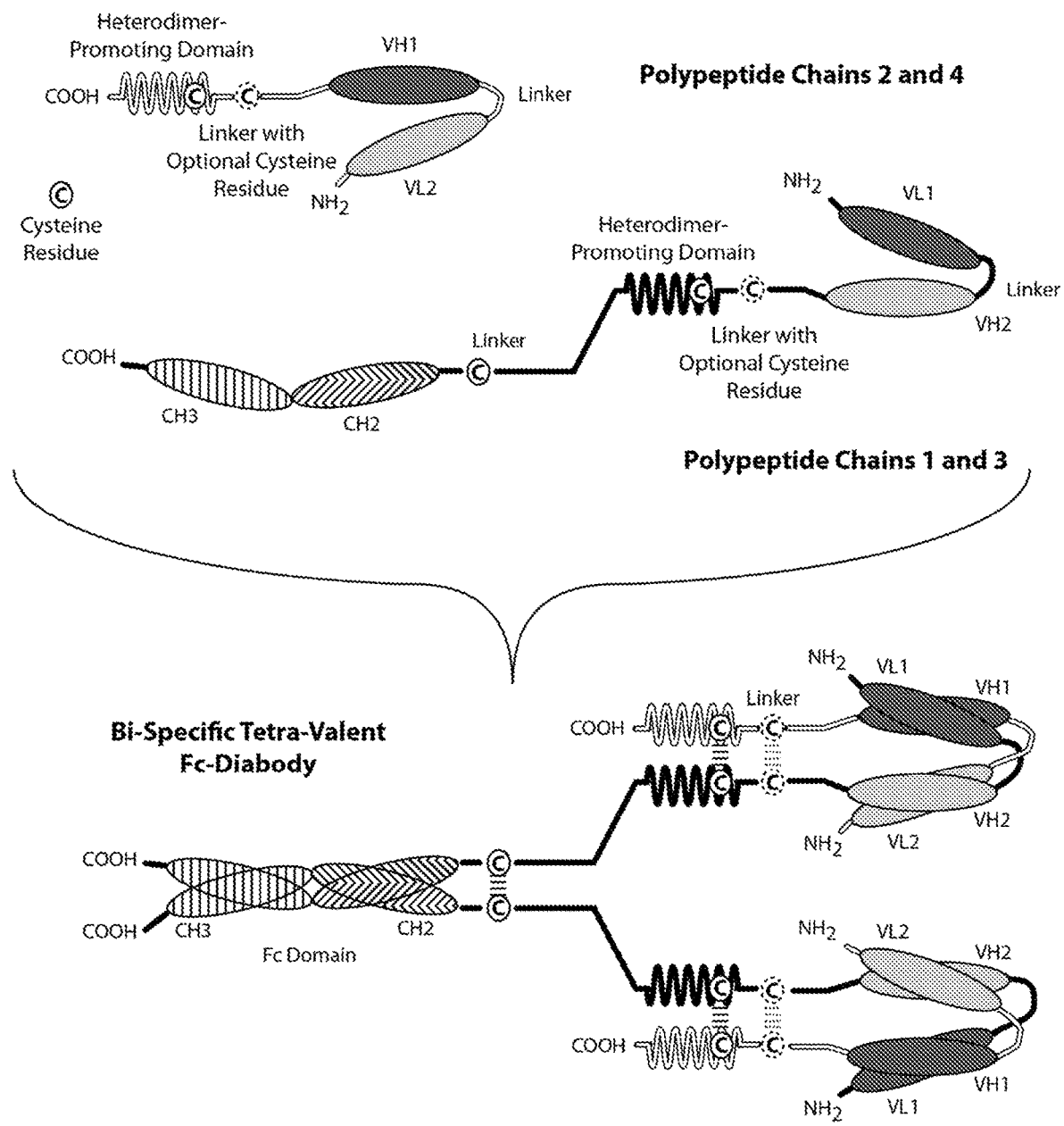
Figure 3C:
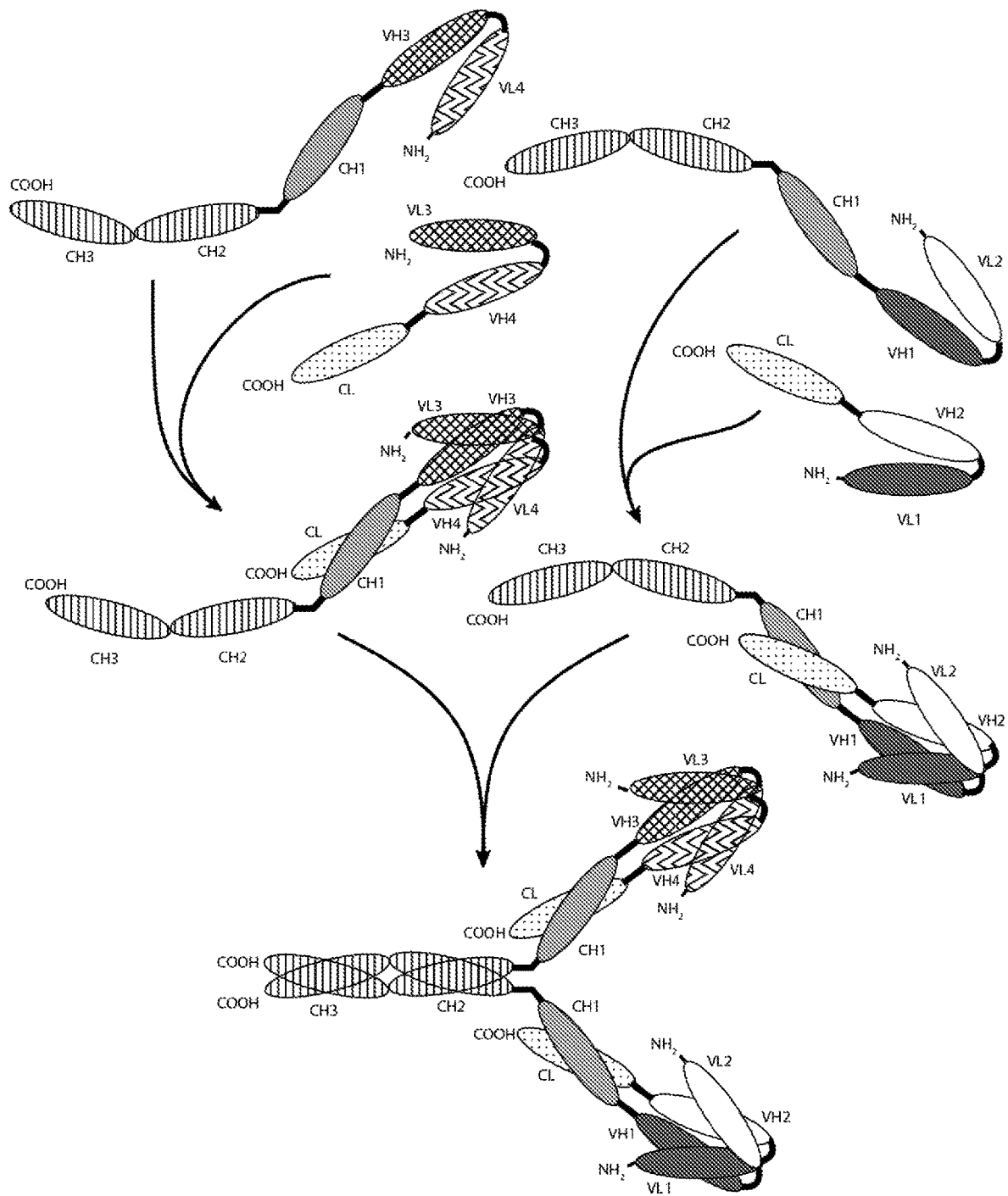

Preferred Fc-bearing diabodies of the present invention are covalently bonded tetravalent diabodies having four epitope-binding sites that comprise four polypeptide chains, and are depicted in FIGS. 3A-3C. The first and third polypeptide chains of such a diabody contain: (i) a VL1-containing Domain, (ii) a VH2-containing Domain, (iii) Heterodimer-Promoting Domain and (iv) a Domain containing a CH2-CH3 sequence. The second and fourth polypeptide chains contain: (i) a VL2-containing Domain, (ii) a VH1-containing Domain and (iii) a Heterodimer-Promoting Domain, where the Heterodimer-Promoting Domains promote the dimerization and covalent bonding of the first/third polypeptide chains with the second/fourth polypeptide chains. Preferably, the VH Domains are linked to the Heterodimer-Promoting Domains by intervening linker peptides (Linker 2). In a preferred CD137×TA bispecific Fc-bearing diabody embodiment, the C-terminus of the Heterodimer-Promoting Domain of the first polypeptide chain is linked to CH2-CH3 domains by an intervening linker peptide (Linker 3) or by an intervening spacer peptide (Linker 3). The VL and/or VH Domains of the third and fourth polypeptide chains, and VL and/or VH Domains of the first and second polypeptide chains may be the same or different so as to permit tetravalent binding that is either monospecific, bispecific or tetraspecific. The notations "VL3" and "VH3" denote, respectively, the Light Chain Variable Domain and Variable Heavy Chain Domain that bind a "third" epitope of such diabody. Similarly, the notations "VL4" and "VH4" denote, respectively, the Light Chain Variable Domain and Variable Heavy Chain Domain that bind a "fourth" epitope of such diabody. The general structure of the polypeptide chains of a representative four-chain bispecific Fc Region-containing diabodies of invention is provided in Table 3:

TABLE 3

| | | |
|---|---|---|
| Bi-specific | 2$^{nd}$ Chain | NH$_2$-VL2-VH1-©-HPD-COOH |
| | 1$^{st}$ Chain | NH$_2$-VL1-VH2-©-HPD-©-CH2—CH3—COOH |
| | 1$^{st}$ Chain | NH$_2$-VL1-VH2-©-HPD-©-CH2—CH3—COOH |
| | 2$^{nd}$ Chain | NH$_2$-VL2-VH1-©-HPD-COOH |
| Tetra-specific | 2$^{nd}$ Chain | NH$_2$-VL2-VH1-©-HPD-COOH |
| | 1$^{st}$ Chain | NH$_2$-VL1-VH2-©-HPD-©-CH2—CH3—COOH |
| | 3$^{rd}$ Chain | NH$_2$-VL3-VH4-©-HPD-©-CH2—CH3—COOH |
| | 4$^{th}$ Chain | NH$_2$-VL4-VH3-©-HPD-COOH |

(—©—denotes a cysteine-containing polypeptide domain that possesses one, two, or more than two cysteine residues. The representation is intended to be illustrative and non-limiting. Cysteine residues may be present in additional or alternative domains, such as within the Heterodimer-Promoting Domain (HPD))

In preferred embodiments, CD137×TA Binding Molecules of the present invention are bispecific, tetravalent (i.e., possess four epitope-binding sites), Fc-bearing diabodies that are composed of four total polypeptide chains (FIGS. 3A-3C). The CD137×TA Binding Molecules of the invention are bispecific, tetravalent, Fc-bearing diabodies that comprise two epitope-binding sites immunospecific for CD137 (which may be capable of binding to the same epitope of CD137 or to different epitopes of CD137), and two epitope-binding sites immunospecific for a tumor antigen (which may be capable of binding to the same epitope of a TA or to different epitopes of a TA or different epitopes of different TAs).

Additional preferred Fc-bearing diabodies of the present invention comprise five polypeptide chains, and are depicted in FIGS. 5A-5D. The first polypeptide chain of such a diabody contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such a diabody contain: (i) a VL1-containing domain, and (ii) a CL-containing domain. The second and/or fifth polypeptide chains of such a diabody may be light chains of an antibody that contains a VL1 complementary to the VH1 of the first/third polypeptide chain. The first, second and/or fifth polypeptide chains may be isolated from a naturally occurring antibody. Alternatively, they may be constructed recombinantly. In a preferred embodiment, the second and fifth polypeptide chains have the same amino acid sequence. The third polypeptide chain of such a diabody contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain. Preferably, the C-terminus of the VH3- and VH2-containing domains of the third and fourth polypeptide chains are linked to a Heterodimer-Promoting Domain by an intervening linker peptide (Linker 2), and the C-terminus of the CH2-CH3 domains of the third polypeptide chain is linked to the VL2-containing Domain by an intervening linker peptide (Linker 4).

Thus, the first and second, and the third and fifth, polypeptide chains of such diabodies associate together to form two VL1/VH1 binding sites capable of binding a first epitope. The third and fourth polypeptide chains of such diabodies associate together to form a VL2/VH2 binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such bispecific diabodies have enhanced potency. FIGS. 5A-5D illustrate the structure of such diabodies. It will be understood that the VL1/VH1, VL2/VH2, and VL3/VH3 Domains may be the same or different so as to permit binding that is monospecific, bispecific or trispecific. However, as provided herein, these domains are preferably selected so as to bind CD137 and a TA.

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains may be selected such that a bispecific diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIGS. 5A-5D). The general structure of the polypeptide chains of representative five-chain Fc Region-containing diabodies of invention is provided in Table 4:

epitopes of a TA or different epitopes of different TAs). In another embodiment, the CD137×TA Binding Molecules of the invention are bispecific, tetravalent, Fc-bearing diabodies that comprise three epitope-binding sites immunospecific for CD137 (which may be capable of binding to the same epitope of CD137 or to two or three different epitopes of CD137), and one epitope-binding site specific for a TA.

B. Trivalent CD137×TA Binding Molecules

In one embodiment, the CD137×TA Binding Molecules of the present invention are trivalent and will comprise a first epitope-binding site (e.g., a VL1 and VH1), a second epitope-binding site (e.g., a VL2 and VH2), and a third epitope-binding site (e.g., a VL3 and VH3), and will thus be able to bind to an epitope of TA, an epitope of CD137, and a third epitope, which third epitope may be:

(a) the same or a different epitope of the TA;
(b) the same or a different epitope of CD137; or
(c) an epitope of a different TA.

Preferably, such "Trivalent CD137×TA Binding Molecules" of the present invention will comprise two epitope-binding sites for an epitope of CD137 (which epitopes may be the same or different), and one epitope-binding site for an epitope of a TA.

In general, such Trivalent CD137×TA Binding Molecules of the present invention are composed of three, four, five or more than five polypeptide chains that, by virtue of one or more disulfide bonds between pairs of such polypeptides, form a covalently bonded molecular complex that comprises a "Diabody-Type Binding Domain" and a "Non-Diabody-Type Binding Domain."

A "Diabody-Type Binding Domain" is the Epitope-Binding Domain of a diabody, and especially, a DART® diabody. The terms "diabody" and "DART® diabody" have been discussed above. A "Non-Diabody-Type" Binding Domain is intended to denote a Binding Domain that does not have the structure of a Diabody-Type Binding Domain. Preferably, a Non-Diabody-Type Binding Domain is a Fab-Type Binding Domain or an ScFv-Type Binding Domain. As used herein, the term "Fab-Type Binding Domain" refers to an

TABLE 4

| | | |
|---|---|---|
| Bispecific (2 × 2) | 2$^{nd}$ Chain | NH$_2$-VL1-CL-ⓒ-COOH |
| | 1$^{st}$ Chain | NH$_2$-VH1-CH1-ⓒ-ⓒ-CH2—CH3—COOH |
| | 3$^{rd}$ Chain | NH$_2$-VH1-CH1-ⓒ-ⓒ-CH2—CH3-VL2-VH2-ⓒ-HPD-COOH |
| | 5$^{nd}$ Chain | NH$_2$-VL1-CL-ⓒ-COOH |
| | 4$^{th}$ Chain | NH$_2$-VL2-VH2-ⓒ-HPD-COOH |
| Bispecific (3 × 1) | 2$^{nd}$ Chain | NH$_2$-VL1-CL-ⓒ-COOH |
| | 1$^{st}$ Chain | NH$_2$-VH1-CH1-ⓒ-ⓒ-CH2—CH3—COOH |
| | 3$^{rd}$ Chain | NH$_2$-VH1-CH1-ⓒ-ⓒ-CH2—CH3-VL1-VH2-ⓒ-HPD-COOH |
| | 5$^{nd}$ Chain | NH$_2$-VL1-CL-ⓒ-COOH |
| | 4$^{th}$ Chain | NH$_2$-VL2-VH1-ⓒ-HPD-COOH |
| Trispecific (2 × 1 × 1) | 2$^{nd}$ Chain | NH$_2$-VL1-CL-ⓒ-COOH |
| | 1$^{st}$ Chain | NH$_2$-VH1-CH1-ⓒ-ⓒ-CH2—CH3—COOH |
| | 3$^{rd}$ Chain | NH$_2$-VH1-CH1-ⓒ-ⓒ-CH2—CH3-VL2-VH3-ⓒ-HPD-COOH |
| | 5$^{nd}$ Chain | NH$_2$-VL1-CL-ⓒ-COOH |
| | 4$^{th}$ Chain | NH$_2$-VL3-VH2-ⓒ-HPD-COOH |

(—ⓒ—denotes a cysteine-containing polypeptide domain that possesses one, two, or more than two cysteine residues. The representation is intended to be illustrative and non-limiting. Cysteine residues may be present in additional or alternative domains, such as within the Heterodimer-Promoting Domain (HPD))

In a preferred embodiment, CD137×TA Binding Molecules of the present invention are bispecific, tetravalent (i.e., possess four epitope-binding sites), Fc-bearing diabodies that are composed of five total polypeptide chains having two epitope-binding sites immunospecific for CD137 (which may be capable of binding to the same epitope of CD137 or to different epitopes of CD137), and two epitope-binding sites immunospecific for a TA (which may be capable of binding to the same epitope of a TA or to different Epitope-Binding Domain that is formed by the interaction of the VL Domain of an immunoglobulin Light Chain and a complementing VH Domain of an immunoglobulin heavy chain. Fab-Type Binding Domains differ from Diabody-Type Binding Domain in that the two polypeptide chains that form a Fab-Type Binding Domain comprise only a single Epitope-Binding Domain, whereas the two polypeptide chains that form a Diabody-Type Binding Domain comprise at least two Epitope-Binding Domains. ScFv-Type Binding Domains differ from Diabody-Type Binding Domain in that VL and VH Domains of the same polypeptide chain interact to form an Epitope-Binding Domain. Thus, as used herein, Fab-Type Binding Domains and ScFv-Type Binding Domains are distinct from Diabody-Type Binding Domain.

Thus, the Trivalent CD137×TA Binding Molecules of the present invention preferably comprise:
(I) a "first" Epitope-Binding Domain that is capable of immunospecifically binding to a "first" epitope;
(II) a "second" Epitope-Binding Domain that is capable of immunospecifically binding to a "second" epitope;
(III) a "third" Epitope-Binding Domain that is capable of immunospecifically binding to a "third" epitope; and
(IV) an Fc Domain that is formed by the association of two CH2-CH3 Domains to one another;
wherein:
(A) the "first" Epitope-Binding Domain and the "second" Epitope-Binding Domain are both "Diabody-Type Binding Domains;
(B) the "third" Epitope-Binding Domain is a Non-Diabody-Type Binding Domain; and
(C) one of such "first," "second," or "third" Epitope-Binding Domains binds an epitope of TA, and another of such "first," "second," or "third" Epitope-Binding Domains binds an epitope of CD137;

The epitope that is bound by the remaining Epitope-Binding Domain may be any desired epitope, preferably an epitope of CD137. Such epitope which may be the same or different from the CD137 epitope that is bound by other Epitope-Binding Domains of the molecule.

FIGS. 6A-6H provide a diagrammatic representation of the Domains of preferred Trivalent CD137×TA Binding Molecules. FIGS. 6A-6D illustrate schematically the Domains of preferred Trivalent CD137×TA Binding Molecules that are composed from the covalent complexing of four polypeptide chains and possess one Non-Diabody-Type Binding Site (VL3/VH3 and thus being monovalent for such epitope), and two Diabody-Type Binding Sites (VL1/VH1 and VL2/VH2, and thus being monovalent for each of such epitopes). FIGS. 6E-6H illustrate schematically the Domains of preferred Trivalent CD137×TA Binding Molecules that are composed from the covalent complexing of three polypeptide chains and possess one Non-Diabody-Type Binding Site (VL3/VH3 and thus being monovalent for such epitope), and two Diabody-Type Binding Sites (VL1/VH1 and VL2/VH2, and thus being monovalent for each of such epitopes). The Non-Diabody-Type Binding Site shown in FIGS. 6A-6H is a Fab-Type Binding Domain in FIGS. 6A-6D and is an scFv-Type Binding Domain in FIGS. 6E-6H. As provided below, VL/VH binding sites formed by the association of the polypeptide chains may be the same or different so as to permit trivalent binding that is monospecific, bispecific, or trispecific.

IV. Exemplary CD137×TA Binding Molecules

The invention provides CD137×TA Binding Molecule that are bispecific tetravalent Fc diabodies capable of simultaneously and specifically binding to CD137 and to a TA. As indicated above, the CD137×TA Binding Molecules of the present invention may comprise four or five polypeptide chains. The polypeptide chains of seven exemplary CD137× TA Binding Molecules capable of binding to CD137 and to the TA, HER2/neu are provided below (designated "DART-A," "DART-B," "DART-C," "DART-D," "DART-E," "DART-F," "DART-G," "DART-G1," "DART-G2," "DART-G3," and "DART-G4," respectively). The invention further provides CD137×TA Binding Molecule that are bispecific trivalent binding molecules capable of simultaneously and specifically binding to CD137 and to a TA. As indicated above, the Trivalent CD137×TA Binding Molecules of the present invention may comprise four polypeptide chains. The polypeptide chains of an exemplary CD137×TA Trispecific Binding Molecule capable of binding to CD137 and to the TA, HER2/neu, and optimized variants of the same are provided below (designated "TRIDENT-A," "TRIDENT-A1," "TRIDENT-A2," "TRIDENT-A3," "TRIDENT-A5," "TRIDENT-B," "TRIDENT-B2," and "TRIDENT-B5" respectively).

A. DART-A

DART-A is composed of four polypeptide chains, in which the first and third polypeptide chains are the same and the second and fourth polypeptide chains are the same (see FIG. 3B).

The first and third polypeptide chains of DART-A comprise, in the N-terminal to C-terminal direction, an N-terminus, a VL domain of a monoclonal antibody capable of binding to HER2/neu ($VL_{HER2/neu}$) (hHER2 MAB-1 VL2 (SEQ ID NO:68)), an intervening linker peptide (Linker 1; GGGSGGGG (SEQ ID NO:16)), a VH domain of a monoclonal antibody capable of binding to CD137 ($VH_{CD137}$) (hCD137 MAB-3 VH1 (SEQ ID NO:76)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:38)), a linker (LEPKSADKTHTCPPCP (SEQ ID NO:30)), the CH2-CH3 Domain of an exemplary human IgG1 that substantially lacks effector function (SEQ ID NO:40), and a C-terminus:

The amino acid sequence of the first and third polypeptide chains of DART-A is (SEQ ID NO:98):

```
DIQMTQSPSS LSASVGDRVT ITCKASQDIN TYLSWFQQKP

GKAPKTLIYR ANRLVEGVPS RFSGSGSGTD FTLTISSLQP

EDFATYYCLQ HDEFPWTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS FDYWGQGTTV TVSSGGCGGG

EVAACEKEVA ALEKEVAALE KEVAALEKLE PKSADKTHTC

PPCPAPEAAG GPSVFLFPPK PKDTLMISRT PEVTCVVVDV

SHEDPEVKFN WYVDGVEVHN AKTKPREEQY NSTYRVVSVL

TVLHQDWLNG KEYKCKVSNK ALPAPIEKTI SKAKGQPREP

QVYTLPPSRE EMTKNQVSLT CLVKGFYPSD IAVEWESNGQ

PENNYKTTPP VLDSDGSFFL YSKLTVDKSR WQQGNVFSCS

VMHEALHNHY TQKSLSLSPG
```

Thus, the first and third polypeptide chain of DART-A is composed of: SEQ ID NO:68-SEQ ID NO:16-SEQ ID NO:76-SEQ ID NO:18-SEQ ID NO:38-SEQ ID NO:30-SEQ ID NO:40.

The second and fourth polypeptide chain of DART-A comprise, in the N-terminal to C-terminal direction, an N-terminus, a VL domain of a monoclonal antibody capable of binding to CD137 ($VL_{CD137}$ (hCD137 MAB-3 VL1 (SEQ ID NO:87)), an intervening linker peptide (Linker 1; GGGSGGGG (SEQ ID NO:16)), a VH domain of a monoclonal antibody capable of binding to HER2/neu ($VH_{HER2/neu}$ (hHER2 MAB-1 VH1, SEQ ID NO:64)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:39), and a C-terminus.

Thus, the second and fourth polypeptide chain of DART-A is composed of: SEQ ID NO:87-SEQ ID NO:16-SEQ ID NO:64-SEQ ID NO:18-SEQ ID NO:39.

The amino acid sequence of the second and fourth polypeptide chain of DART-A is (SEQ ID NO:99):

```
DIQMTQSPSS LSASVGDRVT ITCRPSQDIS NYLNWYQQKP

DGTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTNYGMN WVRQAPGQGL

EWMGWINTNI GEPTYTEEFK GRVTMTRDTS ISTAYMELSR

LRSDDTAVYY CARDDGYGNR VSYWGQGTLV TVSSGGCGGG

KVAACKEKVA ALKEKVAALK EKVAALKE
```

B. DART-B

DART-B is composed of four polypeptide chains, in which the first and third polypeptide chains are the same and the second and fourth polypeptide chains are the same (see FIG. 3B).

The first and third polypeptide chain of DART-B comprise, in the N-terminal to C-terminal direction, an N-terminus, a VL domain of a monoclonal antibody capable of binding to HER2/neu (VL$_{HER2/neu}$) (hHER2 MAB-1 VL3 (SEQ ID NO:69)), an intervening linker peptide (Linker 1; GGGSGGGG (SEQ ID NO:16)), a VH domain of a monoclonal antibody capable of binding to CD137 (VH$_{CD137}$) (hCD137 MAB-3 VH1 (SEQ ID NO:76)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:38)), a linker (LEPKSADKTHTCPPCP (SEQ ID NO:30)), the CH2-CH3 Domain of an exemplary human IgG1 that substantially lacks effector function (SEQ ID NO:40), and a C-terminus.

Thus, the first and third polypeptide chain of DART-B is composed of: SEQ ID NO:69-SEQ ID NO:16-SEQ ID NO:76-SEQ ID NO:18-SEQ ID NO:38-SEQ ID NO:30-SEQ ID NO:40.

The amino acid sequence of the first and third polypeptide chains of DART-B is (SEQ ID NO:100):

```
DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS FDYWGQGTTV TVSSGGCGGG

EVAACEKEVA ALEKEVAALE KEVAALEKLE PKSADKTHTC

PPCPAPEAAG GPSVFLFPPK PKDTLMISRT PEVTCVVVDV

SHEDPEVKFN WYVDGVEVHN AKTKPREEQY NSTYRVVSVL

TVLHQDWLNG KEYKCKVSNK ALPAPIEKTI SKAKGQPREP

QVYTLPPSRE EMTKNQVSLT CLVKGFYPSD IAVEWESNGQ

PENNYKTTPP VLDSDGSFFL YSKLTVDKSR WQQGNVFSCS

VMHEALHNHY TQKSLSLSPG
```

The second and fourth polypeptide chain of DART-B comprise, in the N-terminal to C-terminal direction, an N-terminus, a VL domain of a monoclonal antibody capable of binding to CD137 (VL$_{CD137}$ (hCD137 MAB-3 VL3 (SEQ ID NO:89)), an intervening linker peptide (Linker 1; GGGSGGGG (SEQ ID NO:16)), a VH domain of a monoclonal antibody capable of binding to HER2/neu (VH$_{HER2/neu}$ (hHER2 MAB-1 VH1, SEQ ID NO:64)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:39), and a C-terminus.

Thus, the second and fourth polypeptide chain of DART-B is composed of: SEQ ID NO:89-SEQ ID NO:16-SEQ ID NO:64-SEQ ID NO:18-SEQ ID NO:39.

The amino acid sequence of the second and fourth polypeptide chain of DART-B is (SEQ ID NO:101):

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTNYGMN WVRQAPGQGL

EWMGWINTNI GEPTYTEEFK GRVTMTRDTS ISTAYMELSR

LRSDDTAVYY CARDDGYGNR VSYWGQGTLV TVSSGGCGGG

KVAACKEKVA ALKEKVAALK EKVAALKE
```

C. DART-C

DART-C is composed of four polypeptide chains, in which the first and third polypeptide chains are the same and the second and fourth polypeptide chains are the same (see FIG. 3B).

The first and third polypeptide chain of DART-C comprise, in the N-terminal to C-terminal direction, an N-terminus, a VL domain of a monoclonal antibody capable of binding to CD137 (VL$_{CD137}$ (hCD137 MAB-3 VL3 (SEQ ID NO:89)), an intervening linker peptide (Linker 1; GGGSGGGG (SEQ ID NO:16)), a VH domain of a monoclonal antibody capable of binding to HER2/neu (VH$_{HER2/neu}$) (hHER2 MAB-1 VH1 (SEQ ID NO:64)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:38)), a linker (LEPKSADKTHTCPPCP (SEQ ID NO:30)), the CH2-CH3 Domain of an exemplary human IgG1 that substantially lacks effector function (SEQ ID NO:40), and a C-terminus.

Thus, the first and third polypeptide chain of DART-C is composed of: SEQ ID NO:89-SEQ ID NO:16-SEQ ID NO:64-SEQ ID NO:18-SEQ ID NO:38-SEQ ID NO:30-SEQ ID NO:40.

The amino acid sequence of the first and third polypeptide chains of DART-C is (SEQ ID NO:102):

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTNYGMN WVRQAPGQGL

EWMGWINTNI GEPTYTEEFK GRVTMTRDTS ISTAYMELSR
```

```
LRSDDTAVYY CARDDGYGNR VSYWGQGTLV TVSSGGCGGG

EVAACEKEVA ALEKEVAALE KEVAALEKLE PKSADKTHTC

PPCPAPEAAG GPSVFLFPPK PKDTLMISRT PEVTCVVVDV

SHEDPEVKFN WYVDGVEVHN AKTKPREEQY NSTYRVVSVL

TVLHQDWLNG KEYKCKVSNK ALPAPIEKTI SKAKGQPREP

QVYTLPPSRE EMTKNQVSLT CLVKGFYPSD IAVEWESNGQ

PENNYKTTPP VLDSDGSFFL YSKLTVDKSR WQQGNVFSCS

VMHEALHNHY TQKSLSLSPG
```

The second and fourth polypeptide chain of DART-C comprises, in the N-terminal to C-terminal direction, an N-terminus, a VL domain of a monoclonal antibody capable of binding to HER2/neu ($VL_{HER2/neu}$ (hHER2 MAB-1 VL3, SEQ ID NO:69)), an intervening linker peptide (Linker 1; GGGSGGGG (SEQ ID NO:16)), a VH domain of a monoclonal antibody capable of binding CD137 ($VH_{CD137}$ (hCD137 MAB-3 VH1 (SEQ ID NO:76)), an intervening linker peptide (Linker 2; GGCGGG (SEQ ID NO:18)), a Heterodimer-Promoting (K-coil) Domain (<u>K</u>VAAC<u>K</u>E-<u>K</u>VAAL<u>K</u>E-<u>K</u>VAAL<u>K</u>E-<u>K</u>VAAL<u>K</u>E (SEQ ID NO:39), and a C-terminus.

Thus, the second and fourth polypeptide chain of DART-C is composed of: SEQ ID NO:69-SEQ ID NO:16-SEQ ID NO:76-SEQ ID NO:18-SEQ ID NO:39.

The amino acid sequence of the second and fourth polypeptide chain of DART-C is (SEQ ID NO:103):

```
DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS FDYWGQGTTV TVSSGGCGGG

KVAACKEKVA ALKEKVAALK EKVAALKE
```

D. DART-D

Figure 5A:
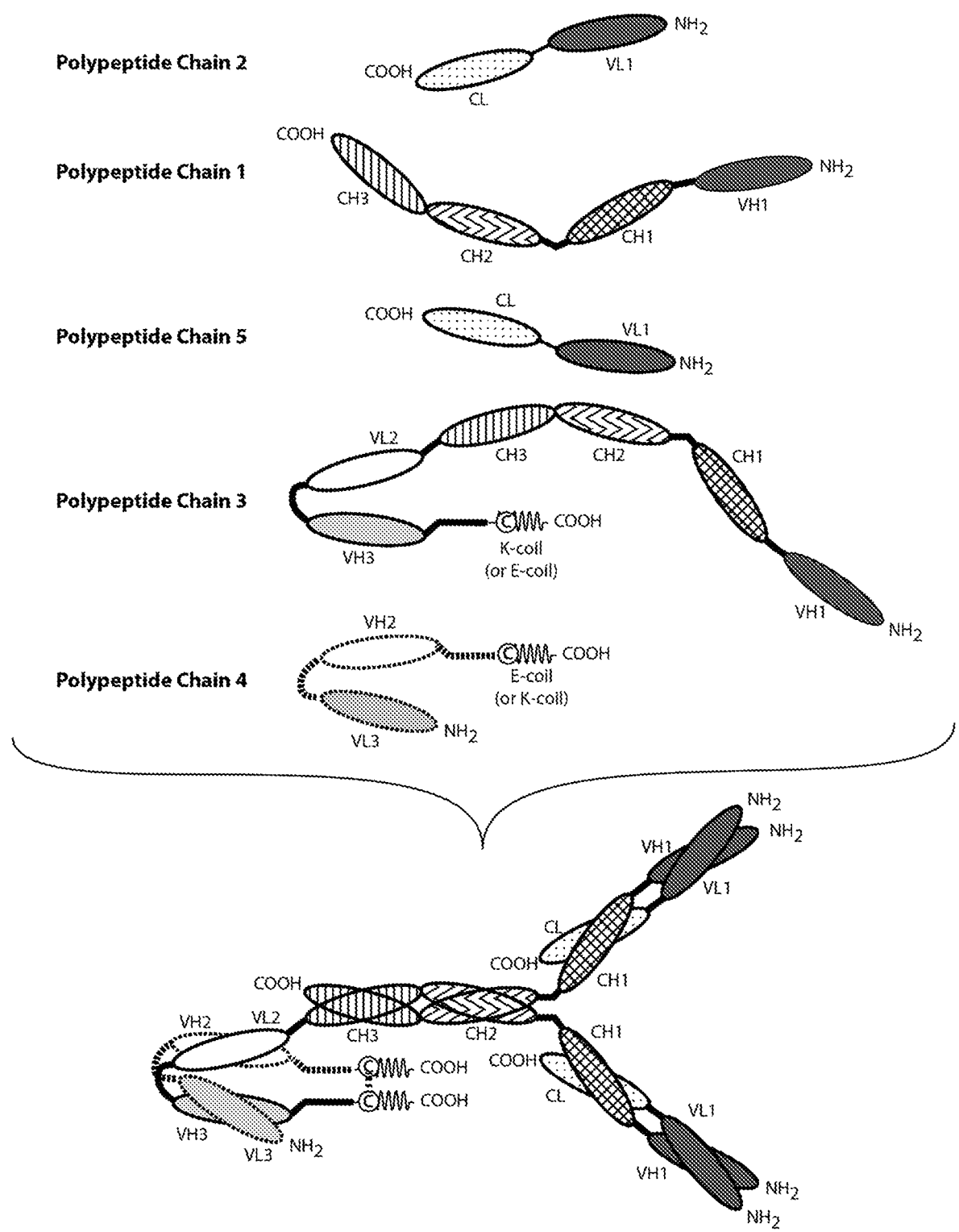
FIGS. 5A-5D provide schematics of a representative covalently bonded Binding Molecule having four epitope-binding sites composed of five polypeptide chains.
Figure 5B:
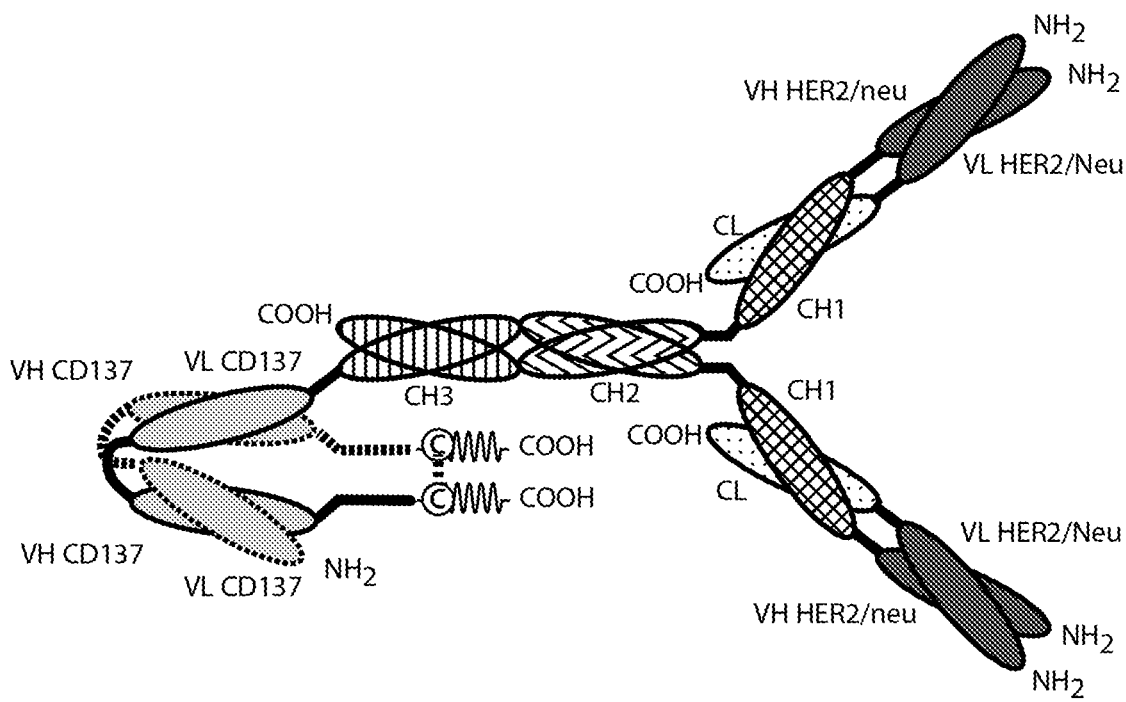

DART-D is composed of five polypeptide chains, of which the second and fifth are identical (see, FIG. 5A, wherein VL2/VH2 are the same as VL3/VH3, and FIG. 5B).

The first polypeptide chain of DART-D comprises, in the N-terminal to C-terminal direction, an N-terminus, a VH domain of a monoclonal antibody capable of binding to HER2/neu ($VH_{HER2/neu}$ (hHER2 MAB-1 VH1 (SEQ ID NO:64)), a human IgG1 CH1 Domain (SEQ ID NO:3), a human IgG1 Hinge Region (SEQ ID NO:7), and a "hole-bearing" CH2 and CH3 Domain (SEQ ID NO:47).

Thus, the first polypeptide chain of DART-D is composed of: SEQ ID NO:64-SEQ ID NO:3-SEQ ID NO:7-SEQ ID NO:47.

The amino acid sequence of the first polypeptide chain of DART-D is (SEQ ID NO:104):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

The second and fifth polypeptide chains of DART-D comprise, in the N-terminal to C-terminal direction, an N-terminus, a VL domain of a monoclonal antibody capable of binding to HER2/neu ($VL_{HER2/neu}$) (hHER2 MAB-1 VL3 (SEQ ID NO:69)), a human IgG CL Kappa Domain (SEQ ID NO:1), and a C-terminus.

Thus, the second and fifth polypeptide chains of DART-D are composed of: SEQ ID NO:69-SEQ ID NO:1.

The amino acid sequence of the second and fifth polypeptide chains of DART-D is (SEQ ID NO:105):

```
DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The third polypeptide chain of DART-D comprises, in the N-terminal to C-terminal direction, an N-terminus, a VH domain of a monoclonal antibody capable of binding to HER2/neu ($VH_{HER2/neu}$) (hHER2 MAB-1 VH1, SEQ ID NO:64)), a human IgG1 CH1 Domain (SEQ ID NO:3), a human IgG1 Hinge Region (SEQ ID NO:7), a "knob-bearing CH2 and CH3 Domain (SEQ ID NO:44), an intervening linker peptide (GGGSGGGSGGG (SEQ ID NO:24)), a VL domain of a monoclonal antibody capable of binding CD137 ($VL_{CD137}$) (CD137 MAB-3 VL (SEQ ID NO:75)), an intervening linker peptide (Linker 1; GGGS GGGG (SEQ ID NO:16)), a VH domain of a monoclonal antibody capable of binding CD137 ($VH_{CD137}$) (CD137 MAB-3 VH (SEQ ID NO:74)), an intervening linker peptide (Linker 2; GGCGGG (SEQ ID NO:18)), a Heterodimer-Promoting (E-coil) Domain (<u>E</u>VAAL<u>E</u>K-<u>E</u>VAAL<u>E</u>K-<u>E</u>VAAL<u>E</u>K-<u>E</u>VAAL<u>E</u>K (SEQ ID NO:36), and a C-terminus.

Thus, the third polypeptide chain of DART-D is composed of: SEQ ID NO:64-SEQ ID NO:3-SEQ ID NO:7-SEQ ID NO:44-SEQ ID NO:24-SEQ ID NO:75-SEQ ID NO:16-SEQ ID NO:74-SEQ ID NO:18-SEQ ID NO:36.

The amino acid sequence of the third polypeptide chains of DART-D is (SEQ ID NO:106):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSSA
```

```
STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLWCL VKGFYPSDIA VEWESNGQPE NNYKTTPPVL

DSDGSFFLYS KLTVDKSRWQ QGNVFSCSVM HEALHNHYTQ

KSLSLSPGGG GSGGGSGGGD IQMTQTTSSL SASLGDRVTI

SCRPSQDISN YLNWYQQKPD GTVKLLIYYT SRLRSGVPSR

FSGSGSGTDY SLTISNLEQE DIATYFCQQG DTLPYTFGGG

TKLEIKGGGS GGGGQVQLQQ PGAELVRPGA SVKLSCKASG

YTFTSYWINW VKQRPGQGLE WIGNIYPSDS YTNYNQKFKD

KATLTVDKSS STAYMQLSSP TSEDSAVYYC TRDYGSSYSF

DYWGQGTTLT VSSGGCGGGE VAALEKEVAA LEKEVAALEK

EVAALEK
```

The fourth polypeptide chain of DART-D comprises, in the N-terminal to C-terminal direction, an N-terminus, a VL domain of a monoclonal antibody capable of binding CD137 ($VL_{CD137}$) (CD137 MAB-3 VL (SEQ ID NO:75)), an intervening linker peptide (Linker 1; GGGSGGGG (SEQ ID NO:16)), a VH domain of a monoclonal antibody capable of binding CD137 ($VH_{CD137}$) (CD137 MAB-3 VH (SEQ ID NO:74)), an intervening linker peptide (Linker 2; GGCGGG (SEQ ID NO:18)), a Heterodimer-Promoting (K-coil) Domain (KVAALKE-KVAALKE-KVAALKE-KVAALKE) (SEQ ID NO:37) and a C-terminus.

Thus, the fourth polypeptide chain of DART-D is composed of: SEQ ID NO:75-SEQ ID NO:16-SEQ ID NO:74-SEQ ID NO:18-SEQ ID NO:37.

The amino acid sequence of the fourth polypeptide chain of DART-D is (SEQ ID NO:107):

```
DIQMTQTTSS LSASLGDRVT ISCRPSQDIS NYLNWYQQKP

DGTVKLLIYY TSRLRSGVPS RFSGSGSGTD YSLTISNLEQ

EDIATYFCQQ GDTLPYTFGG GTKLEIKGGG SGGGGQVQLQ

QPGAELVRPG ASVKLSCKAS GYTFTSYWIN WVKQRPGQGL

EWIGNIYPSD SYTNYNQKFK DKATLTVDKS SSTAYMQLSS

PTSEDSAVYY CTRDYGSSYS FDYWGQGTTL TVSSGGCGGG

KVAALKEKVA ALKEKVAALK EKVAALKE
```

E. DART-E

Figure 5C:
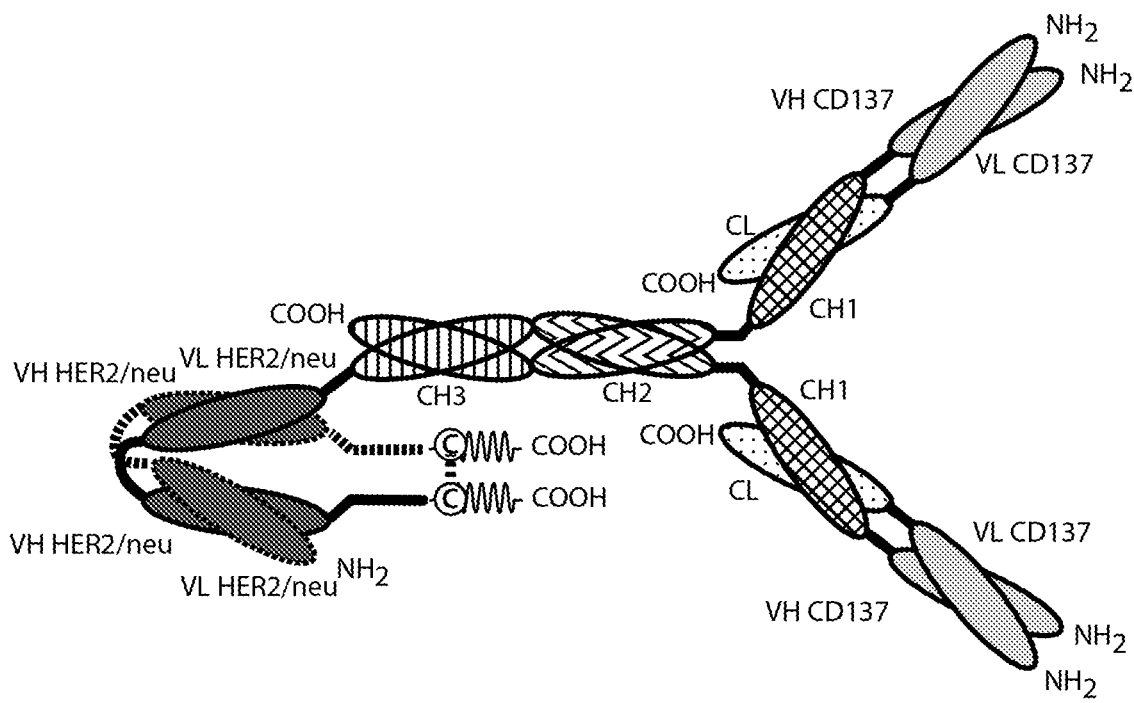
Figure 5D:
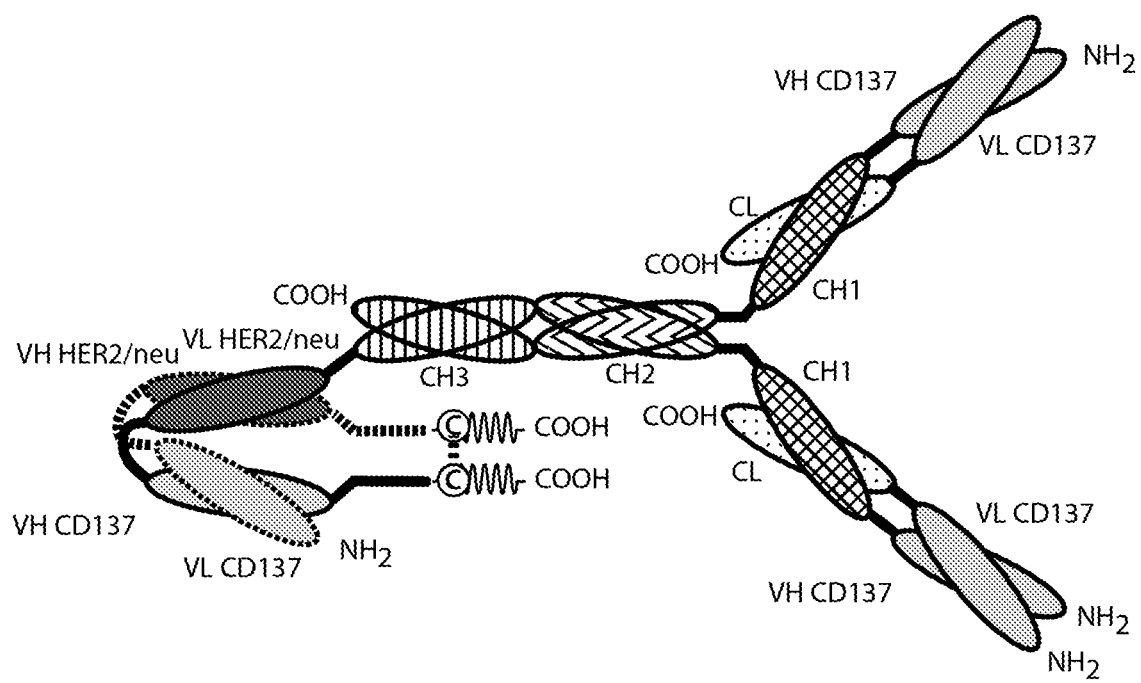
Figure 6A:
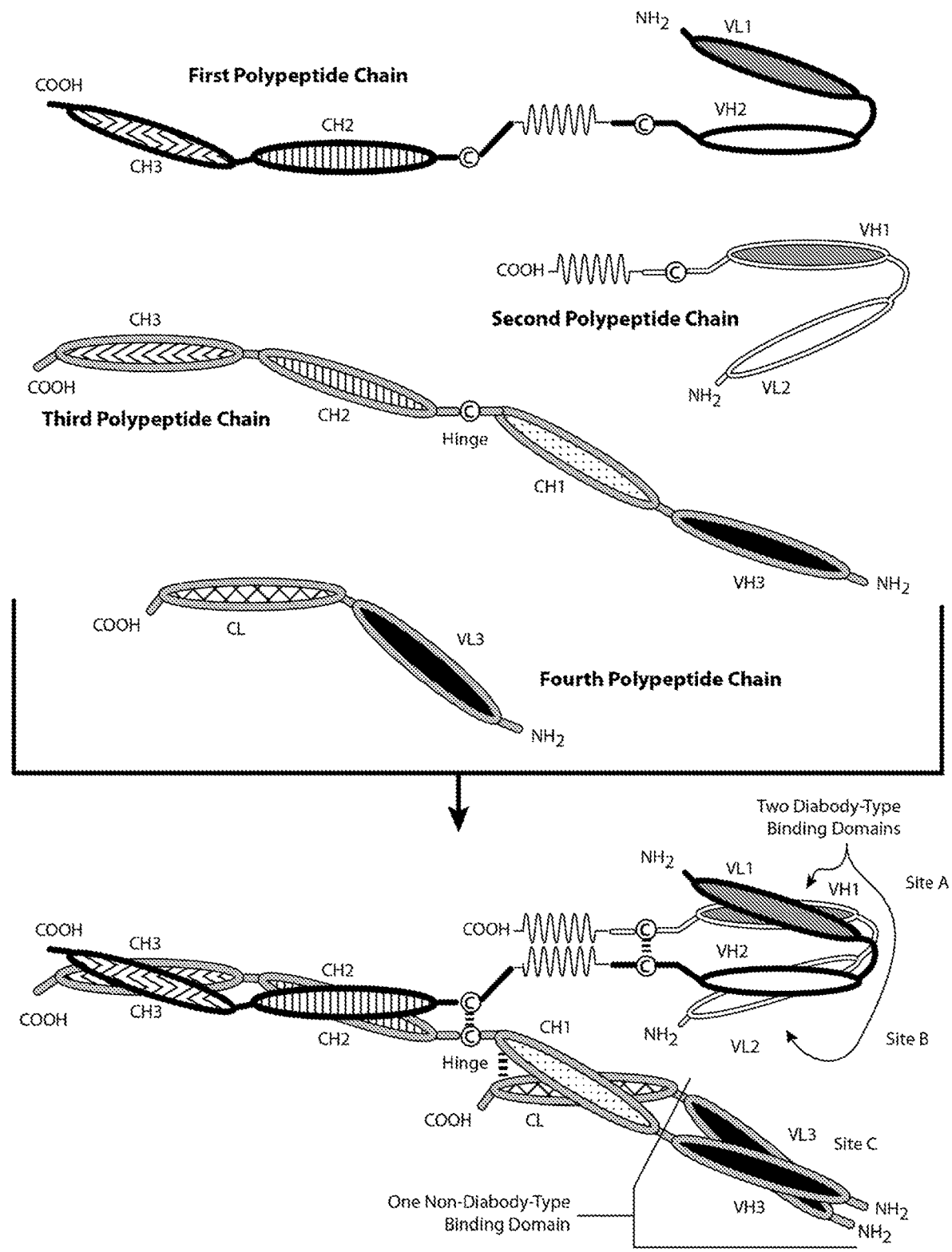
FIGS. 6A-6F provide schematics of representative Fc Region-containing trivalent binding molecules having three epitope-binding sites.
Figure 6B:
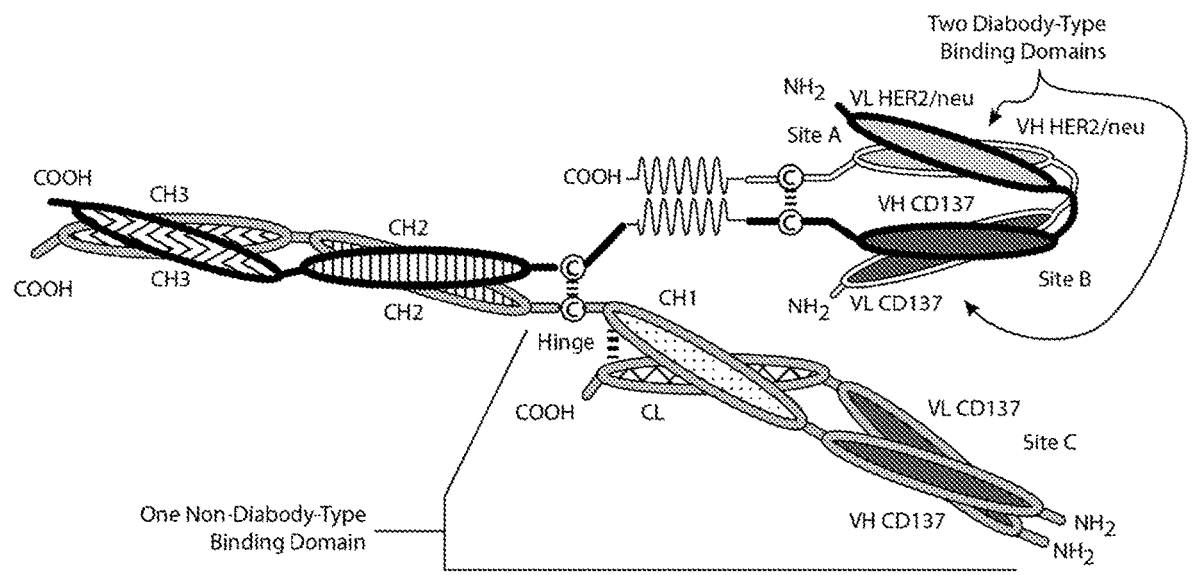
Figure 6C:
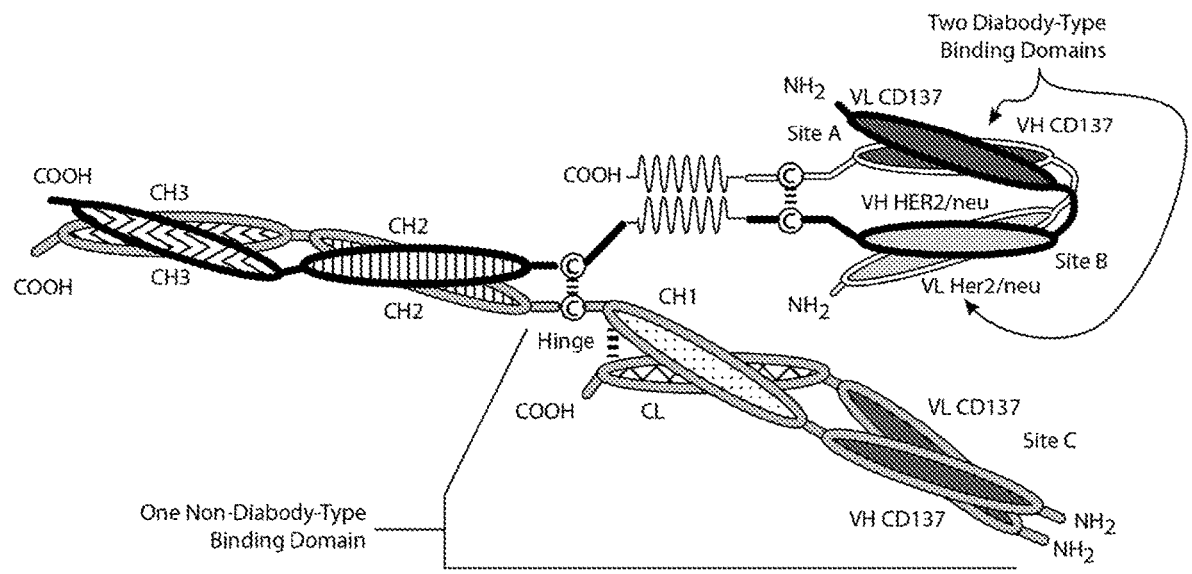
Figure 6D:
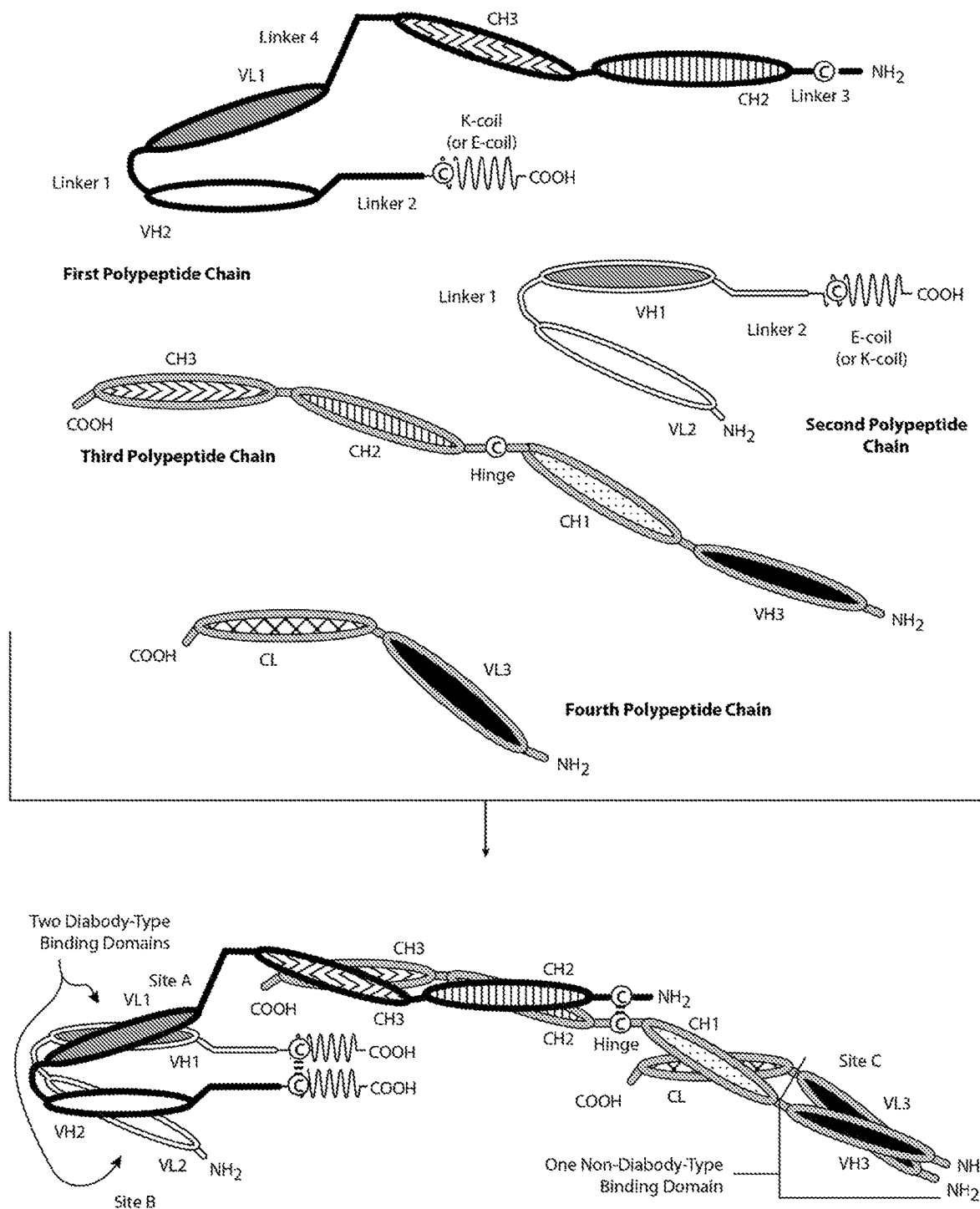
Figure 6E:
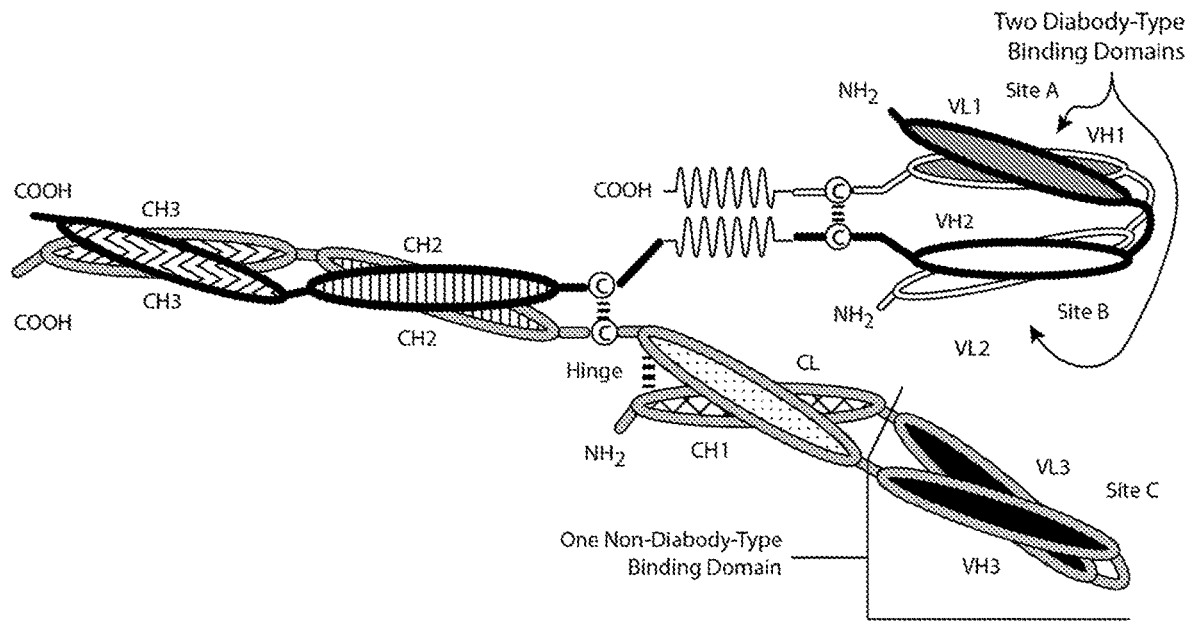
Figure 6F:
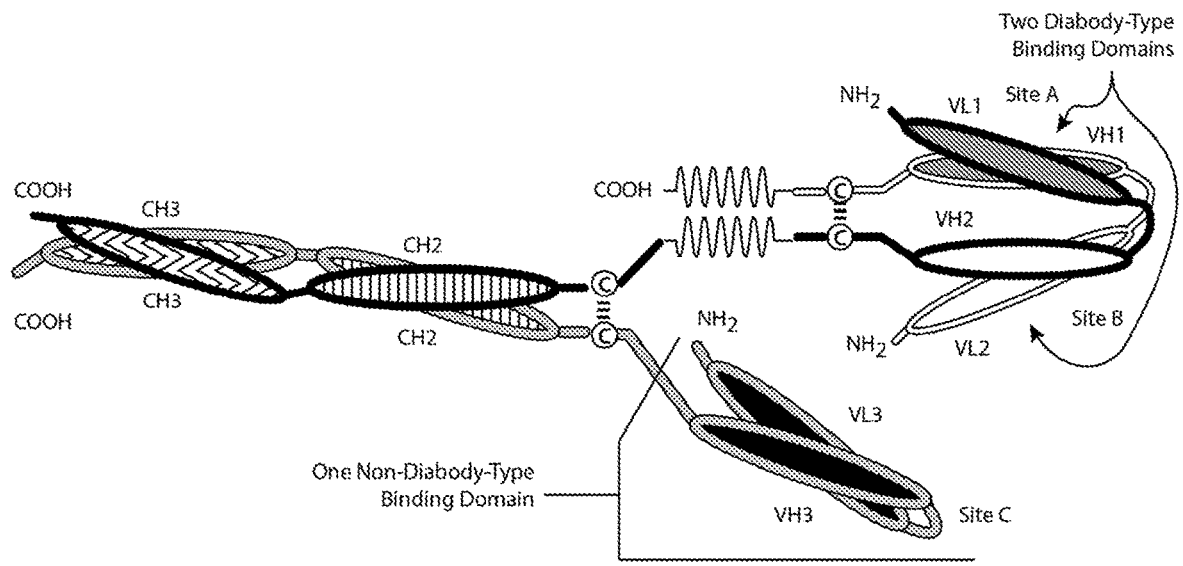
Figure 6G:
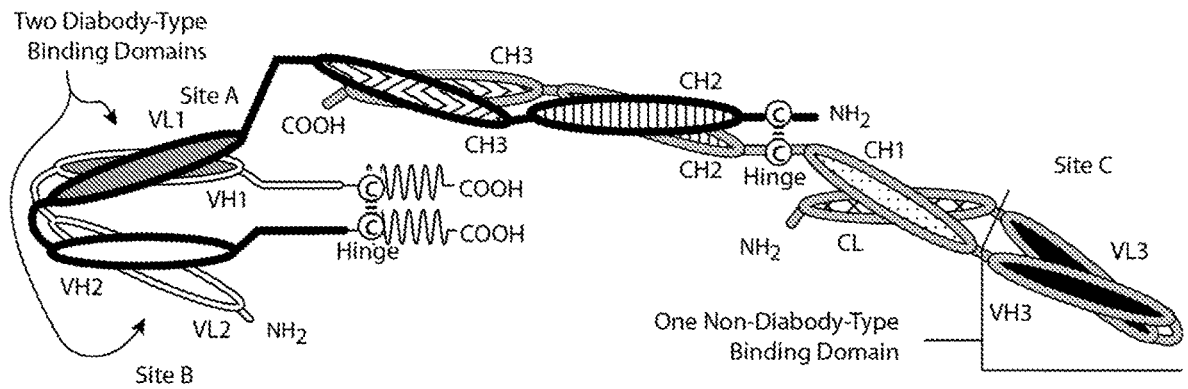
Figure 6H:
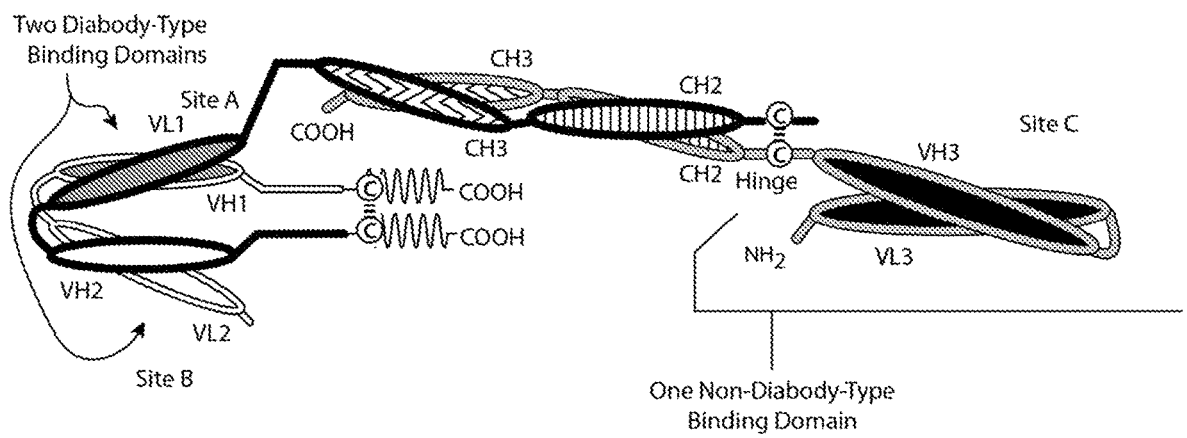

DART-E is composed of five polypeptide chains, of which the second and fifth are identical (see, FIG. 5A, wherein VL2/VH2 are the same as VL3/VH3, and FIG. 5C).

The first polypeptide chain of DART-E comprises, in the N-terminal to C-terminal direction, an N-terminus, a VH domain of a monoclonal antibody capable of binding to CD137 ($VH_{CD137}$) (CD137 MAB-3 VH (SEQ ID NO:74)), an IgG1 CH1 Domain (SEQ ID NO:3), an IgG1 Hinge Domain (SEQ ID NO:7), a "hole-bearing CH2 and CH3 Domain (SEQ ID NO:47), and a C-terminus.

Thus, the first polypeptide chain of DART-E is composed of: SEQ ID NO:74-SEQ ID NO:3-SEQ ID NO:7-SEQ ID NO:47.

The amino acid sequence of the first polypeptide chain of DART-E is (SEQ ID NO:108):

```
QVQLQQPGAE LVRPGASVKL SCKASGYTFT SYWINWVKQR

PGQGLEWIGN IYPSDSYTNY NQKFKDKATL TVDKSSSTAY

MQLSSPTSED SAVYYCTRDY GSSYSFDYWG QGTTLTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL

DSDGSFFLVS KLTVDKSRWQ QGNVFSCSVM HEALHNRYTQ

KSLSLSPGK
```

The second and fifth polypeptide chains of DART-E comprise, in the N-terminal to C-terminal direction, an N-terminus, a VL domain of a monoclonal antibody capable of binding to CD137 ($VL_{CD137u}$) (CD137 MAB-3 VL (SEQ ID NO:75)), a human IgG CL Kappa Domain (SEQ ID NO:1), and a C-terminus.

Thus, the second and fifth polypeptide chains of DART-E are composed of SEQ ID NO:75-SEQ ID NO:1.

The amino acid sequence of the second and fifth polypeptide chains of DART-E is (SEQ ID NO:109):

```
DIQMTQTTSS LSASLGDRVT ISCRPSQDIS NYLNWYQQKP

DGTVKLLIYY TSRLRSGVPS RFSGSGSGTD YSLTISNLEQ

EDIATYFCQQ GDTLPYTFGG GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The third polypeptide chain of DART-E comprises, in the N-terminal to C-terminal direction, an N-terminus, a VH domain of a monoclonal antibody capable of binding to CD137 ($VH_{CD137}$) (CD137 MAB-3 VH, SEQ ID NO:74)), a human IgG1 CH1 Domain (SEQ ID NO:3), a human IgG1 Hinge Region (SEQ ID NO:7), a "knob-bearing CH2 and CH3 Domain (SEQ ID NO:44), an intervening linker peptide (GGGSGGGSGGG (SEQ ID NO:24)), a VL domain of a monoclonal antibody capable of binding HER2/neu ($VL_{HER2/neu}$) (hHER2 MAB-1 VL3 (SEQ ID NO:69)), an intervening linker peptide (Linker 1; GGGSGGGG (SEQ ID NO:16)), a VH domain of a monoclonal antibody capable of binding HER2/neu ($VH_{HER2/neu}$) (hHER2 MAB-1 VH1 (SEQ ID NO:64)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:36), and a C-terminus.

Thus, the third polypeptide chain of DART-E is composed of: SEQ ID NO:74-SEQ ID NO:3-SEQ ID NO:7-SEQ ID NO:44-SEQ ID NO:24-SEQ ID NO:69-SEQ ID NO:16-SEQ ID NO:64-SEQ ID NO:18-SEQ ID NO:36.

The amino acid sequence of the third polypeptide chains of DART-E is (SEQ ID NO:110):

```
QVQLQQPGAE LVRPGASVKL SCKASGYTFT SYWINWVKQR

PGQGLEWIGN IYPSDSYTNY NQKFKDKATL TVDKSSSTAY

MQLSSPTSED SAVYYCTRDY GSSYSFDYWG QGTTLTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLWCL VKGFYPSDIA VEWESNGQPE NNYKTTPPVL

DSDGSFFLYS KLTVDKSRWQ QGNVFSCSVM HEALHNHYTQ

KSLSLSPGGG GSGGGSGGGD IQMTQSPSSL SASVGDRVTI

TCKASQDISN YLSWFQQKPG KAPKTLIYRA NRLQSGVPSR

FSGSGSGTDF TLTISSLQPE DFATYYCLQH DEFPWTFGQG

TKLEIKGGGS GGGGQVQLVQ SGAEVKKPGA SVKVSCKASG

YTFTNYGMNW VRQAPGQGLE WMGWINTNIG EPTYTEEFKG

RVTMTRDTSI STAYMELSRL RSDDTAVYYC ARDDGYGNRV

SYWGQGTLVT VSSGGCGGGE VAALEKEVAA LEKEVAALEK

EVAALEK
```

The fourth polypeptide chain of DART-E comprises, in the N-terminal to C-terminal direction, an N-terminus, a VL domain of a monoclonal antibody capable of binding HER2/neu ($VL_{HER2/neu}$) (hHER2 MAB-1 VL3 (SEQ ID NO:69)), an intervening linker peptide (Linker 1; GGGSGGGG (SEQ ID NO:16)), a VH domain of a monoclonal antibody capable of binding HER2/neu ($VH_{HER2/neu}$) (hHER2 MAB-1 VH1 (SEQ ID NO:64)), an intervening linker peptide (Linker 2; GGCGGG (SEQ ID NO:18)), a Heterodimer-Promoting (K-coil) Domain (KVAALKE-KVAALKE-KVAALKE-KVAALKE) (SEQ ID NO:37) and a C-terminus.

Thus, the fourth polypeptide chain of DART-E is composed of: SEQ ID NO:69-SEQ ID NO:16-SEQ ID NO:64-SEQ ID NO:18-SEQ ID NO:37.

The amino acid sequence of the fourth polypeptide chain of DART-E is (SEQ ID NO:111):

```
DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIKGGG SGGGGQVQLV

QSGAEVKKPG ASVKVSCKAS GYTFTNYGMN WVRQAPGQGL

EWMGWINTNI GEPTYTEEFK GRVTMTRDTS ISTAYMELSR

LRSDDTAVYY CARDDGYGNR VSYWGQGTLV TVSSGGCGGG

KVAALKEKVA ALKEKVAALK EKVAALKE
```

F. DART-F

DART-F is composed of five polypeptide chains, of which the second and fifth are identical (see, FIG. 5A, wherein VL2/VH2 are the same as VL3/VH3, and FIG. 5B).

The first polypeptide chain of DART-F is the same as the first polypeptide chain of DART-D (SEQ ID NO:104).

The second and fifth polypeptide chains of DART-F are the same as the second and fifth polypeptide chains of DART-D (SEQ ID NO:105).

The third polypeptide chain of DART-F comprises, in the N-terminal to C-terminal direction, an N-terminus, a VH domain of a monoclonal antibody capable of binding to HER2/neu ($VH_{HER2/neu}$) (hHER2 MAB-1 VH1 (SEQ ID NO:64)), an IgG1 CH1 Domain (SEQ ID NO:3), an IgG1 Hinge Domain (SEQ ID NO:7), a "knob-bearing CH2 and CH3 Domain (SEQ ID NO:44), an intervening linker peptide (GGGSGGGSGGG (SEQ ID NO:24)), a VL domain of a monoclonal antibody capable of binding CD137 ($VL_{CD137}$) (CD137 MAB-4 VL (SEQ ID NO:91)), an intervening linker peptide (Linker 1; GGGSGGGG (SEQ ID NO:16)), a VH domain of a monoclonal antibody capable of binding CD137 ($VH_{CD137}$) (CD137 MAB-4 VH (SEQ ID NO:90)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:36), and a C-terminus.

Thus, the third polypeptide chain of DART-F is composed of: SEQ ID NO:64-SEQ ID NO:3-SEQ ID NO:7-SEQ ID NO:44-SEQ ID NO:24-SEQ ID NO:91-SEQ ID NO:16-SEQ ID NO:90-SEQ ID NO:18-SEQ ID NO:36.

The amino acid sequence of the third polypeptide chain of DART-F is (SEQ ID NO:112):

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLWCL VKGFYPSDIA VEWESNGQPE NNYKTTPPVL

DSDGSFFLYS KLTVDKSRWQ QGNVFSCSVM HEALHNHYTQ

KSLSLSPGGG GSGGGSGGGD IQMTQTTSSL SASLGDRVTI

SCRASQDISN YLNWYQQKPD GTVKLLIYYT SRLHSGVPSR

FSGSGSGTDY SLTISNLEQE DIATYFCQQG NTLPYTFGGG

TKLEIKGGGS GGGGQVQLQQ PGAELVRPGA SVKLSCKASG

YTFTSYWINW VKQRPGQGLE WIGNIYPSDS YTNYDQKFKD

KATLTVDKSS STAYMQLSSP TSEDSAVYYC TKSGEYGKIG

YYAMDYWGQG TSVTVSSGGC GGGEVAALEK EVAALEKEVA

ALEKEVAALE K
```

The fourth polypeptide chain of DART-F comprises, in the N-terminal to C-terminal direction, an N-terminus, a VL domain of a monoclonal antibody capable of binding CD137 (VL$_{CD137}$) (CD137 MAB-4 VL (SEQ ID NO:91)), an intervening linker peptide (Linker 1; GGGSGGGG (SEQ ID NO:16)), a VH domain of a monoclonal antibody capable of binding CD137 (VH$_{CD137}$) (CD137 MAB-4 VH (SEQ ID NO:90)), an intervening linker peptide (Linker 2; GGCGGG (SEQ ID NO:18)), a Heterodimer-Promoting (K-coil) Domain (KVAALKE-KVAALKE-KVAALKE-KVAALKE) (SEQ ID NO:37) and a C-terminus.

Thus, the fourth polypeptide chain of DART-F is composed of: SEQ ID NO:91-SEQ ID NO:16-SEQ ID NO:90-SEQ ID NO:18-SEQ ID NO:37.

The amino acid sequence of the fourth polypeptide chain of DART-F is (SEQ ID NO:113):

```
DIQMTQTTSS LSASLGDRVT ISCRASQDIS NYLNWYQQKP
DGTVKLLIYY TSRLHSGVPS RFSGSGSGTD YSLTISNLEQ
EDIATYFCQQ GNTLPYTFGG GTKLEIKGGG SGGGGQVQLQ
QPGAELVRPG ASVKLSCKAS GYTFTSYWIN WVKQRPGQGL
EWIGNIYPSD SYTNYDQKFK DKATLTVDKS SSTAYMQLSS
PTSEDSAVYY CTKSGEYGKI GYYAMDYWGQ GTSVTVSSGG
CGGGKVAALK EKVAALKEKV AALKEKVAAL KE
```

G. DART-G

DART-G is composed of five polypeptide chains, of which the second and fifth are identical (see, FIG. 5A, wherein VL2/VH2 are the same as VL3/VH3, and FIG. 5B).

The first polypeptide chain of DART-G is the same as the first polypeptide chain of DART-D (SEQ ID NO:104).

The second and fifth polypeptide chains of DART-G are the same as the second and fifth polypeptide chains of DART-D (SEQ ID NO:105).

The third polypeptide chain of DART-G comprises, in the N-terminal to C-terminal direction, an N-terminus, a VH domain of a monoclonal antibody capable of binding to HER2/neu (VH$_{HER2/neu}$) (hHER2 MAB-1 VH1 (SEQ ID NO:64)), an IgG1 CH1 Domain (SEQ ID NO:3), an IgG1 Hinge Domain (SEQ ID NO:7), a "knob-bearing CH2 and CH3 Domain (SEQ ID NO:44), an intervening linker peptide (GGGSGGGSGGG (SEQ ID NO:24)), a VL domain of a monoclonal antibody capable of binding CD137 (VL$_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 (VH$_{CD137}$) (hCD137 MAB-3 VH1 (SEQ ID NO:76)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:36), and a C-terminus.

Thus, the third polypeptide chain of DART-G is composed of: SEQ ID NO:64-SEQ ID NO:3-SEQ ID NO:7-SEQ ID NO:44-SEQ ID NO:24-SEQ ID NO:89-SEQ ID NO:16-SEQ ID NO:76-SEQ ID NO:18-SEQ ID NO:36.

The amino acid sequence of the third polypeptide chain of DART-G is (SEQ ID NO:114):

```
QVQLVQSGAE VKKPGASVKV SCKASGYTFT NYGMNWVRQA
PGQGLEWMGW INTNIGEPTY TEEFKGRVTM TRDTSISTAY
MELSRLRSDD TAVYYCARDD GYGNRVSYWG QGTLVTVSSA
```

-continued
```
STKGPSVFPL APSSKSTSGG TAALGCLVKD YFPEPVTVSW
NSGALTSGVH TFPAVLQSSG LYSLSSVVTV PSSSLGTQTY
ICNVNHKPSN TKVDKRVEPK SCDKTHTCPP CPAPEAAGGP
SVFLFPPKPK DTLMISRTPE VTCVVVDVSH EDPEVKFNWY
VDGVEVHNAK TKPREEQYNS TYRVVSVLTV LHQDWLNGKE
YKCKVSNKAL PAPIEKTISK AKGQPREPQV YTLPPSREEM
TKNQVSLWCL VKGFYPSDIA VEWESNGQPE NNYKTTPPVL
DSDGSFFLYS KLTVDKSRWQ QGNVFSCSVM HEALHNHYTQ
KSLSLSPGGG GSGGGSGGGD IQMTQSPSSL SASVGDRVTI
TCRPSQDISN YLNWYQQKPD KTVKLLIYYT SRLRSGVPSR
FSGSGSGTDF TFTISSLQPE DIATYFCQQG DTLPYTFGQG
TKLEIKGGGS GGGGQVQLVQ SGAEVKKPGA SVKVSCKASG
YTFTSYWINW VKQAPGQGLE WIGNIYPSDS YTNYNQKFKD
KATITADKST STAYMELSSL RSEDTAVYYC TRDYGSSYSF
DYWGQGTTVT VSSGGCGGGE VAALEKEVAA LEKEVAALEK
EVAALEK
```

Alternative DART-G third polypeptide chains may be employed in which the amino acid residues of SEQ ID NO:76 (the VH domain of a monoclonal antibody capable of binding CD137 (VH$_{CD137}$)) are replaced with the amino acid residues of SEQ ID NO:83 (hCD137 MAB-3 VH1A), SEQ ID NO:84 (hCD137 MAB-3 VH1B), SEQ ID NO:85 (hCD137 MAB-3 VH1C), or SEQ ID NO:86 (hCD137 MAB-3 VH1D). Optimized molecules comprising such polypeptide chains are described below.

The fourth polypeptide chain of DART-G comprises, in the N-terminal to C-terminal direction, an N-terminus, a VL domain of a monoclonal antibody capable of binding CD137 (VL$_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 (VH$_{CD137}$) (hCD137 MAB-3 VH1 (SEQ ID NO:76)), an intervening linker peptide (Linker 2; GGCGGG (SEQ ID NO:18)), a Heterodimer-Promoting (K-coil) Domain (KVAALKE-KVAALKE-KVAALKE-KVAALKE) (SEQ ID NO:37) and a C-terminus.

Thus, the fourth polypeptide chain of DART-G is composed of: SEQ ID NO:89-SEQ ID NO:16-SEQ ID NO:76-SEQ ID NO:18-SEQ ID NO:37.

The amino acid sequence of the fourth polypeptide chain of DART-G is (SEQ ID NO:119):

```
DIQMTQSPSS LSASVGDRVT ITCRPSQDIS NYLNWYQQKP
DKTVKLLIYY TSRLRSGVPS RFSGSGSGTD FTFTISSLQP
EDIATYFCQQ GDTLPYTFGQ GTKLEIKGGG SGGGGQVQLV
QSGAEVKKPG ASVKVSCKAS GYTFTSYWIN WVKQAPGQGL
EWIGNIYPSD SYTNYNQKFK DKATITADKS TSTAYMELSS
LRSEDTAVYY CTRDYGSSYS FDYWGQGTTV TVSSGGCGGG
KVAALKEKVA ALKEKVAALK EKVAALKE
```

Alternative DART-G fourth polypeptide chains may be employed in which the amino acid residues of SEQ ID NO:76 (the VH domain of a monoclonal antibody capable of binding CD137 (VH$_{CD137}$)) are replaced with the amino acid residues of SEQ ID NO:83 (hCD137 MAB-3 VH1A), SEQ ID NO:84 (hCD137 MAB-3 VH1B), SEQ ID NO:85 (hCD137 MAB-3 VH1C), or SEQ ID NO:86 (hCD137 MAB-3 VH1D). Optimized molecules comprising such polypeptide chains are described below.

H. Optimized DART-G

Optimized variants of DART-G designated "DART-G1," "DART-G2," "DART-G3," and "DART-G4" are composed of five polypeptide chains, and contain the HER2/neu binding domains of antibody hHER2 MAB-1 (1.3) and the CD137 binding domains of any of antibody hCD137 MAB-3 (1A.3)-(1D.3).

The first polypeptide chain of such optimized variants of DART-G have the same amino acid sequence as the first polypeptide chain of DART-G (SEQ ID NO:104).

The second and fifth polypeptide chains of such optimized variants of DART-G have the same amino acid sequence as the second and fifth polypeptide chains of DART-G (SEQ ID NO:105).

The third and fourth polypeptide chains of such optimized variants of DART-G have the amino acid sequences of SEQ ID NO:115 and SEQ ID NO:120 (DART-G1); of SEQ ID NO:116 and SEQ ID NO:121 (DART-G2); of SEQ ID NO:117 and SEQ ID NO:122 (DART-G3); or of SEQ ID NO:118 and SEQ ID NO:123 (DART-G4), as provided below.

The amino acid sequence of the third polypeptide chain of optimized DART-G1, comprising SEQ ID NO:83 (hCD137 MAB-3 VH1A), is SEQ ID NO:115:

```
QVQLVQSGAE VKKPGASVKV SCKASGYTFT NYGMNWVRQA
PGQGLEWMGW INTNIGEPTY TEEFKGRVTM TRDTSISTAY
MELSRLRSDD TAVYYCARDD GYGNRVSYWG QGTLVTVSSA
STKGPSVFPL APSSKSTSGG TAALGCLVKD YFPEPVTVSW
NSGALTSGVH TFPAVLQSSG LYSLSSVVTV PSSSLGTQTY
ICNVNHKPSN TKVDKRVEPK SCDKTHTCPP CPAPEAAGGP
SVFLFPPKPK DTLMISRTPE VTCVVVDVSH EDPEVKFNWY
VDGVEVHNAK TKPREEQYNS TYRVVSVLTV LHQDWLNGKE
YKCKVSNKAL PAPIEKTISK AKGQPREPQV YTLPPSREEM
TKNQVSLWCL VKGFYPSDIA VEWESNGQPE NNYKTTPPVL
DSDGSFFLYS KLTVDKSRWQ QGNVFSCSVM HEALHNHYTQ
KSLSLSPGGG GSGGGSGGGD IQMTQSPSSL SASVGDRVTI
TCRPSQDISN YLNWYQQKPD KTVKLLIYYT SRLRSGVPSR
FSGSGSGTDF TFTISSLQPE DIATYFCQQG DTLPYTFGQG
TKLEIKGGGS GGGGQVQVQL VQSGAEVKKP GASVKVSCKA
SGYTFTSYWI NWVKQAPGQG LEWIGNIYPS DSYTNYNQKF
KDKATITADK STSTAYMELS SLRSEDTAVY YCTRDYGSAY
SFHPWGQGTT VTVSSGGCGG GEVAALEKEV AALEKEVAAL
EKEVAALEK
```

The amino acid sequence of the third polypeptide chain of optimized DART-G2, comprising SEQ ID NO:84 (hCD137 MAB-3 VH1B), is SEQ ID NO:116:

```
QVQLVQSGAE VKKPGASVKV SCKASGYTFT NYGMNWVRQA
PGQGLEWMGW INTNIGEPTY TEEFKGRVTM TRDTSISTAY
MELSRLRSDD TAVYYCARDD GYGNRVSYWG QGTLVTVSSA
STKGPSVFPL APSSKSTSGG TAALGCLVKD YFPEPVTVSW
NSGALTSGVH TFPAVLQSSG LYSLSSVVTV PSSSLGTQTY
ICNVNHKPSN TKVDKRVEPK SCDKTHTCPP CPAPEAAGGP
SVFLFPPKPK DTLMISRTPE VTCVVVDVSH EDPEVKFNWY
VDGVEVHNAK TKPREEQYNS TYRVVSVLTV LHQDWLNGKE
YKCKVSNKAL PAPIEKTISK AKGQPREPQV YTLPPSREEM
TKNQVSLWCL VKGFYPSDIA VEWESNGQPE NNYKTTPPVL
DSDGSFFLYS KLTVDKSRWQ QGNVFSCSVM HEALHNHYTQ
KSLSLSPGGG GSGGGSGGGD IQMTQSPSSL SASVGDRVTI
TCRPSQDISN YLNWYQQKPD KTVKLLIYYT SRLRSGVPSR
FSGSGSGTDF TFTISSLQPE DIATYFCQQG DTLPYTFGQG
TKLEIKGGGS GGGGQVQVQL VQSGAEVKKP GASVKVSCKA
SGYTFTSYWI NWVKQAPGQG LEWIGNIYPS DSYTNYNQKF
KDKATITADK STSTAYMELS SLRSEDTAVY YCTRDYGSAY
SMSTWGQGTT VTVSSGGCGG GEVAALEKEV AALEKEVAAL
EKEVAALEK
```

The amino acid sequence of the third polypeptide chain of optimized DART-G3, comprising SEQ ID NO:85 (hCD137 MAB-3 VH1C), is SEQ ID NO:117:

```
QVQLVQSGAE VKKPGASVKV SCKASGYTFT NYGMNWVRQA
PGQGLEWMGW INTNIGEPTY TEEFKGRVTM TRDTSISTAY
MELSRLRSDD TAVYYCARDD GYGNRVSYWG QGTLVTVSSA
STKGPSVFPL APSSKSTSGG TAALGCLVKD YFPEPVTVSW
NSGALTSGVH TFPAVLQSSG LYSLSSVVTV PSSSLGTQTY
ICNVNHKPSN TKVDKRVEPK SCDKTHTCPP CPAPEAAGGP
SVFLFPPKPK DTLMISRTPE VTCVVVDVSH EDPEVKFNWY
VDGVEVHNAK TKPREEQYNS TYRVVSVLTV LHQDWLNGKE
YKCKVSNKAL PAPIEKTISK AKGQPREPQV YTLPPSREEM
TKNQVSLWCL VKGFYPSDIA VEWESNGQPE NNYKTTPPVL
DSDGSFFLYS KLTVDKSRWQ QGNVFSCSVM HEALHNHYTQ
KSLSLSPGGG GSGGGSGGGD IQMTQSPSSL SASVGDRVTI
TCRPSQDISN YLNWYQQKPD KTVKLLIYYT SRLRSGVPSR
FSGSGSGTDF TFTISSLQPE DIATYFCQQG DTLPYTFGQG
TKLEIKGGGS GGGGQVQVQL VQSGAEVKKP GASVKVSCKA
SGYTFTSYWI NWVKQAPGQG LEWIGNIYPS DSYTNYNQKF
```

```
KDKATITADK STSTAYMELS SLRSEDTAVY YCTRDYGSAY

SYSLWGQGTT VTVSSGGCGG GEVAALEKEV AALEKEVAAL

EKEVAALEK
```

The amino acid sequence of the third polypeptide chain of optimized DART-G4, comprising SEQ ID NO:86 (hCD137 MAB-3 VH1D), is SEQ ID NO:118:

```
QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLWCL VKGFYPSDIA VEWESNGQPE NNYKTTPPVL

DSDGSFFLYS KLTVDKSRWQ QGNVFSCSVM HEALHNHYTQ

KSLSLSPGGG GSGGGSGGGD IQMTQSPSSL SASVGDRVTI

TCRPSQDISN YLNWYQQKPD KTVKLLIYYT SRLRSGVPSR

FSGSGSGTDF TFTISSLQPE DIATYFCQQG DTLPYTFGQG

TKLEIKGGGS GGGGQVQVQL VQSGAEVKKP GASVKVSCKA

SGYTFTSYWI NWVKQAPGQG LEWIGNIYPS DSYTNYNQKF

KDKATITADK STSTAYMELS SLRSEDTAVY YCTRDYGSSY

SYNVWGQGTT VTVSSGGCGG GEVAALEKEV AALEKEVAAL

EKEVAALEK
```

The amino acid sequence of the fourth polypeptide chain of optimized DART-G1, comprising SEQ ID NO:83 (hCD137 MAB-3 VH1A), is SEQ ID NO:120:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS FHPWGQGTTV TVSSGGCGGG

KVAALKEKVA ALKEKVAALK EKVAALKE
```

The amino acid sequence of the fourth polypeptide chain of optimized DART-G2, comprising SEQ ID NO:84 (hCD137 MAB-3 VH1B), is SEQ ID NO:121:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS MSTWGQGTTV TVSSGGCGGG

KVAALKEKVA ALKEKVAALK EKVAALKE
```

The amino acid sequence of the fourth polypeptide chain of optimized DART-G3, comprising SEQ ID NO:85 (hCD137 MAB-3 VH1C), SEQ ID NO:122:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS YSLWGQGTTV TVSSGGCGGG

KVAALKEKVA ALKEKVAALK EKVAALKE
```

The amino acid sequence of the fourth polypeptide chain of optimized DART-G4, comprising SEQ ID NO:86 (hCD137 MAB-3 VH1D), is SEQ ID NO:123:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS YNVWGQGTTV TVSSGGCGGG

KVAALKEKVA ALKEKVAALK EKVAALKE
```

I. TRIDENT-A

TRIDENT-A is a Trivalent CD137×CD137×TA Binding Molecule having two CD137 binding sites and one binding site for the exemplary TA, HER2/neu. TRIDENT-A is composed of four polypeptide chains (see, FIG. 6A, wherein VL1/VH1 (Site A) are the same as VL2/VH2 (Site B) and bind CD137, and VL3/VH3 (Site C) bind HER2/neu).

The first polypeptide chain of TRIDENT-A comprises, in the N-terminal to C-terminal direction, an N-terminus, a VL domain of a monoclonal antibody capable of binding CD137 ($VL_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 ($VH_{CD137}$) (hCD137 MAB-3 VH1 (SEQ ID NO:76)), an intervening linker peptide (Linker 2; ASTKG (SEQ ID NO:19)), a cysteine containing Heterodimer-Promoting (E-coil) Domain (EVAACEK-EVAALEK-EVAAL EK-EVAALEK (SEQ ID NO:38)), an intervening linker peptide (GGGDKTHTCPPCP (SEQ ID NO:21)), a "knob-bearing CH2 and CH3 Domain (SEQ ID NO:44), and a C-terminus.

Thus, the first polypeptide chain of TRIDENT-A is composed of: SEQ ID NO:89-SEQ ID NO:16-SEQ ID NO:76-SEQ ID NO:19-SEQ ID NO:38-SEQ ID NO:21-SEQ ID NO:44.

The amino acid sequence of the first polypeptide chain of TRIDENT-A is (SEQ ID NO:192):

```
DIQMTQSPSS LSASVGDRVT ITCRPSQDIS NYLNWYQQKP
DKTVKLLIYY TSRLRSGVPS RFSGSGSGTD FTFTISSLQP
EDIATYFCQQ GDTLPYTFGQ GTKLEIKGGG SGGGGQVQLV
QSGAEVKKPG ASVKVSCKAS GYTFTSYWIN WVKQAPGQGL
EWIGNIYPSD SYTNYNQKFK DKATITADKS TSTAYMELSS
LRSEDTAVYY CTRDYGSSYS FDYWGQGTTV TVSSASTKGE
VAACEKEVAA LEKEVAALEK EVAALEKGGG DKTHTCPPCP
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLWCLVK GFYPSDIAVE WESNGQPENN
YKTTPPVLDS DGSFFLYSKL TVDKSRWQQG NVFSCSVMHE
ALHNHYTQKS LSLSPGK
```

The second polypeptide chain of TRIDENT-A comprises, in the N-terminal to C-terminal direction, an N-terminus, a VL domain of a monoclonal antibody capable of binding CD137 (VL$_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 (VH$_{CD137}$) (hCD137 MAB-3 VH1 (SEQ ID NO:76)), an intervening linker peptide (Linker 2; ASTKG (SEQ ID NO:19)), a cysteine containing Heterodimer-Promoting (K-coil) Domain (KVAACKE-KVAALKE-KVAALKE-KVAALKE (SEQ ID NO:39)), and a C-terminus.

Thus, the second polypeptide chain of TRIDENT-A is composed of: SEQ ID NO:89-SEQ ID NO:16-SEQ ID NO:76-SEQ ID NO:19-SEQ ID NO:39.

The amino acid sequence of the second polypeptide chain of TRIDENT-A is (SEQ ID NO:197):

```
DIQMTQSPSS LSASVGDRVT ITCRPSQDIS NYLNWYQQKP
DKTVKLLIYY TSRLRSGVPS RFSGSGSGTD FTFTISSLQP
EDIATYFCQQ GDTLPYTFGQ GTKLEIKGGG SGGGGQVQLV
QSGAEVKKPG ASVKVSCKAS GYTFTSYWIN WVKQAPGQGL
EWIGNIYPSD SYTNYNQKFK DKATITADKS TSTAYMELSS
LRSEDTAVYY CTRDYGSSYS FDYWGQGTTV TVSSASTKGK
VAACKEKVAA LKEKVAALKE KVAALKE
```

Alternative TRIDENT-A first and second polypeptide chains may be employed in which the amino acid residues of SEQ ID NO:76 (the VH domain of a monoclonal antibody capable of binding CD137 (VH$_{CD137}$)) are replaced with the amino acid residues of SEQ ID NO:83 (hCD137 MAB-3 VH1A), SEQ ID NO:84 (hCD137 MAB-3 VH1B), SEQ ID NO:85 (hCD137 MAB-3 VH1C), SEQ ID NO:86 (hCD137 MAB-3 VH1D), SEQ ID NO:208 (hCD137 MAB-3 VH1E), SEQ ID NO:209 (hCD137 MAB-3 VH1F), or SEQ ID NO:210 (hCD137 MAB-3 VH1G) and/or the amino acid residues of SEQ ID NO:89 (the VL domain of a monoclonal antibody capable of binding CD137 (VH$_{CD137}$)) are replaced with the amino acid residues of SEQ ID NO:211 (hCD137 MAB-3 VL4), SEQ ID NO:212 (hCD137 MAB-3 VL5), SEQ ID NO:213 (hCD137 MAB-3 VL6), SEQ ID NO:214 (hCD137 MAB-3 VL7), SEQ ID NO:215 (hCD137 MAB-3 VL8), SEQ ID NO:216 (hCD137 MAB-3 VL9), SEQ ID NO:217 (hCD137 MAB-3 VL10), SEQ ID NO:218 (hCD137 MAB-3 VL11), SEQ ID NO:219 (hCD137 MAB-3 VL12), SEQ ID NO:220 (hCD137 MAB-3 VL13), SEQ ID NO:221 (hCD137 MAB-3 VL14), or SEQ ID NO:222 (hCD137 MAB-3 VL15). Optimized/deimmunized molecules comprising many of such polypeptide chains are described below.

The third polypeptide chain of TRIDENT-A comprises, in the N-terminal to C-terminal direction, an N-terminus, a VH domain of a monoclonal antibody capable of binding to HER2/neu (VH$_{HER2/neu}$) (hHER2 MAB-1 VH1 (SEQ ID NO:64)), a human IgG1 CH1 Domain (SEQ ID NO:3), a human IgG1 Hinge Region (SEQ ID NO:7), and a "hole-bearing" CH2 and CH3 Domain (SEQ ID NO:47). Thus, the third polypeptide chain of TRIDENT-A is composed of: SEQ ID NO:64-SEQ ID NO:3-SEQ ID NO:7-SEQ ID NO:47, and has the same amino acid sequence as the first polypeptide chain of DART-D (SEQ ID NO:104) provided above.

The fourth polypeptide chain of TRIDENT-A comprises, in the N-terminal to C-terminal direction, an N-terminus, a VL domain of a monoclonal antibody capable of binding to HER2/neu (VL$_{HER2/neu}$) (hHER2 MAB-1 VL3 (SEQ ID NO:69)), a human IgG CL Kappa Domain (SEQ ID NO:1), and a C-terminus. Thus, the fourth polypeptide chain of TRIDENT-A is composed of: SEQ ID NO:69-SEQ ID NO:1, and has the same amino acid sequence as the second and fifth polypeptide chains of DART-D (SEQ ID NO: 105) provided above.

1. Optimized Variants of TRIDENT-A

Optimized variants of TRIDENT-A designated "TRIDENT-A1," "TRIDENT-A2," "TRIDENT-A3," and "TRIDENT-A4" are composed of four polypeptide chains, and contain the HER2/neu binding domains of antibody hHER2 MAB-1 (1.3) and the CD137 binding domains of any of antibody hCD137 MAB-3 (1A.3)-(1D.3).

The third polypeptide chain of such optimized TRIDENT-A have the same amino acid sequence as the third polypeptide chain of TRIDENT-A, which as noted above is the same as the first polypeptide chain of DART-D (SEQ ID NO:104).

The fourth polypeptide chain of such optimized TRIDENT-A have the same amino acid sequence as the fourth polypeptide chains of TRIDENT-A, which as noted above is the same as the second and fifth polypeptide chains of DART-D (SEQ ID NO:105).

The first and second polypeptide chains of such optimized variants of TRIDENT-A have the amino acid sequence of SEQ ID NO:193 and SEQ ID NO:198 (TRIDENT-A1); of SEQ ID NO:194 and SEQ ID NO:199 (TRIDENT-A2); of SEQ ID NO:195 and SEQ ID NO:200 (TRIDENT-A3); or of SEQ ID NO:196 and SEQ ID NO:201 (TRIDENT-A4), as provided below.

The amino acid sequence of the first polypeptide chain of TRIDENT-A1, comprising SEQ ID NO:83 (hCD137 MAB-3 VH1A), is SEQ ID NO:193:

```
DIQMTQSPSS LSASVGDRVT ITCRPSQDIS NYLNWYQQKP
DKTVKLLIYY TSRLRSGVPS RFSGSGSGTD FTFTISSLQP
```

```
EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS FHPWGQGTTV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

The amino acid sequence of the first polypeptide chain of TRIDENT-A2, comprising SEQ ID NO:84 (hCD137 MAB-3 VH1B), is SEQ ID NO:194:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS MSTWGQGTTV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

The amino acid sequence of the first polypeptide chain of TRIDENT-A3, comprising SEQ ID NO:85 (hCD137 MAB-3 VH1C), is SEQ ID NO:195:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS YSLWGQGTTV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

The amino acid sequence of the first polypeptide chain of TRIDENT-A4, comprising SEQ ID NO:86 (hCD137 MAB-3 VH1D), is SEQ ID NO:196:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS YNVWGQGTTV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

The amino acid sequence of the second polypeptide chain of TRIDENT-A1, comprising SEQ ID NO:83 (hCD137 MAB-3 VH1A), is SEQ ID NO:198:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS FHPWGQGTTV TVSSASTKGK

VAACEKEVAA LKEKVAALKE KVAALKE
```

The amino acid sequence of the second polypeptide chain of TRIDENT-A2, comprising SEQ ID NO:84 (hCD137 MAB-3 VH1B), is SEQ ID NO:199:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS MSTWGQGTTV TVSSASTKGK

VAACEKEVAA LKEKVAALKE KVAALKE
```

The amino acid sequence of the second polypeptide chain of TRIDENT-A3, comprising SEQ ID NO:85 (hCD137 MAB-3 VH1C), is SEQ ID NO:200:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSAYS YSLWGQGTTV TVSSASTKGK

VAACKEKVAA LKEKVAALKE KVAALKE
```

The amino acid sequence of the second polypeptide chain of TRIDENT-A4, comprising SEQ ID NO:86 (hCD137 MAB-3 VH1D), is SEQ ID NO:201:

```
DIQMTQSPSS LSASVGDRVT ITCRPSQDIS NYLNWYQQKP

DKTVKLLIYY TSRLRSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVKQAPGQGL

EWIGNIYPSD SYTNYNQKFK DKATITADKS TSTAYMELSS

LRSEDTAVYY CTRDYGSSYS YNVWGQGTTV TVSSASTKGK

VAACKEKVAA LKEKVAALKE KVAALKE
```

2. Deimmunized Variants of TRIDENT-A

Deimmunized variants of TRIDENT-A are composed of four polypeptide chains, and contain the HER2/neu binding domains of antibody hHER2 MAB-1 (1.3) and the CD137 VH Domain of any of hCD137 MAB-3 VH1E-VH1G and the CD137 VL Domain of any of hCD137 MAB-3 VL4-VL15.

An exemplary deimmunized variant of TRIDENT-A designated "TRIDENT-A5," is composed of four polypeptide chains, and contains the HER2/neu binding domains of antibody hHER2 MAB-1 (1.3) and the CD137 binding domains of any of antibody hCD137 MAB-3 (1E.15).

The amino acid sequence of the first polypeptide chain of TRIDENT-A5 (comprising hCD137 MAB-3 VH1E and hCD137 MAB-3 VL15), is (SEQ ID NO:229):

```
DIQMTQSPSS LSASVGDRVT ITCQASQDIS NYLNWYQQKP

DKTVKLLIYY TGRARSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVRQAPGQGL

EWIGNIYPSD SYTNYNQKFK DKATITADKS TSTAYMELSS

LRSEDTAVYY CTRDYGSAYS MSTWGQGTTV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

The amino acid sequence of the second polypeptide chain of TRIDENT-A5, (comprising hCD137 MAB-3 VH1E and hCD137 MAB-3 VL15), is SEQ ID NO:230:

```
DIQMTQSPSS LSASVGDRVT ITCQASQDIS NYLNWYQQKP

DKTVKLLIYY TGRARSGVPS RFSGSGSGTD FTFTISSLQP

EDIATYFCQQ GDTLPYTFGQ GTKLEIKGGG SGGGGQVQLV

QSGAEVKKPG ASVKVSCKAS GYTFTSYWIN WVRQAPGQGL

EWIGNIYPSD SYTNYNQKFK DKATITADKS TSTAYMELSS

LRSEDTAVYY CTRDYGSAYS MSTWGQGTTV TVSSASTKGK

VAACKEKVAA LKEKVAALKE KVAALKE
```

The third polypeptide chain of such deimmunized TRIDENT-A5 have the same amino acid sequence as the third polypeptide chain of TRIDENT-A, which as noted above is the same as the first polypeptide chain of DART-D (SEQ ID NO:104).

The fourth polypeptide chain of such deimmunized TRIDENT-A5 have the same amino acid sequence as the fourth polypeptide chains of TRIDENT-A, which as noted above is the same as the second and fifth polypeptide chains of DART-D (SEQ ID NO:105).

J. TRIDENT-B

TRIDENT-B is a Trivalent CD137×CD137×TA Binding Molecule having two CD137 binding sites and one binding site for the exemplary TA, 5T4. TRIDENT-B is composed of four polypeptide chains (see, FIG. 6A, wherein VL1/VH1 (Site A) are the same as VL2/VH2 (Site B) and bind CD137, and VL3/VH3 (Site C) bind 5T4).

The first polypeptide chain of TRIDENT-B comprises, in the N-terminal to C-terminal direction, an N-terminus, a VL domain of a monoclonal antibody capable of binding CD137 (VL$_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 (VH$_{CD137}$) (hCD137 MAB-3 VH1 (SEQ ID NO:76)), an intervening linker peptide (Linker 2; ASTKG (SEQ ID NO:19)), a cysteine containing Heterodimer-Promoting (E-coil) Domain (EVAACEK-EVAALEK-EVAAL EK-EVAALEK (SEQ ID NO:38)), an intervening linker peptide (GGGDKTHTCPPCP (SEQ ID NO:21)), a "knob-bearing CH2 and CH3 Domain (SEQ ID NO:44), and a C-terminus. Thus, the first polypeptide chain of TRIDENT-B is composed of: SEQ ID NO:89-SEQ ID NO:16-SEQ ID NO:76-SEQ ID NO:19-SEQ ID NO:38-SEQ ID NO:21-SEQ ID NO:44, and has the same amino acid sequence as the first polypeptide chain of TRIDENT-A (SEQ ID NO: 192) provided above The second polypeptide chain of TRIDENT-B comprises, in the N-terminal to C-terminal direction, an N-terminus, a VL domain of a monoclonal antibody capable of binding CD137 (VL$_{CD137}$) (hCD137 MAB-3 VL3 (SEQ ID NO:89)), an intervening linker peptide (Linker 1; GGGSGGGG (SEQ ID NO:16)), a VH domain of a monoclonal antibody capable of binding CD137 (VH$_{CD137}$) (hCD137 MAB-3 VH1 (SEQ ID NO:76)), an intervening linker peptide (Linker 2; ASTKG (SEQ ID NO:19)), a cysteine containing Heterodimer-Promoting (K-coil) Domain (KVAACKE-KVAALKE-KVAALKE-KVAALKE (SEQ ID NO:39)), and a C-terminus. Thus, the second polypeptide chain of TRIDENT-B is composed of: SEQ ID NO:89-SEQ ID NO:16-SEQ ID NO:76-SEQ ID NO:19-

SEQ ID NO:39, and has the same amino acid sequence as the second polypeptide chain of TRIDENT-A (SEQ ID NO: 197) provided above.

Alternative TRIDENT-B first and second polypeptide chains may be employed in which the amino acid residues of SEQ ID NO:76 (the VH domain of a monoclonal antibody capable of binding CD137 (VH$_{CD137}$)) are replaced with the amino acid residues of SEQ ID NO:83 (hCD137 MAB-3 VH1A), SEQ ID NO:84 (hCD137 MAB-3 VH1B), SEQ ID NO:85 (hCD137 MAB-3 VH1C), SEQ ID NO:86 (hCD137 MAB-3 VH1D), SEQ ID NO:208 (hCD137 MAB-3 VH1E), SEQ ID NO:209 (hCD137 MAB-3 VH1F), or SEQ ID NO:210 (hCD137 MAB-3 VH1G) and/or the amino acid residues of SEQ ID NO:89 (the VL domain of a monoclonal antibody capable of binding CD137 (VH$_{CD137}$)) are replaced with the amino acid residues of SEQ ID NO:211 (hCD137 MAB-3 VL4), SEQ ID NO:212 (hCD137 MAB-3 VL5), SEQ ID NO:213 (hCD137 MAB-3 VL6), SEQ ID NO:214 (hCD137 MAB-3 VL7), SEQ ID NO:215 (hCD137 MAB-3 VL8), SEQ ID NO:216 (hCD137 MAB-3 VL9), SEQ ID NO:217 (hCD137 MAB-3 VL10), SEQ ID NO:218 (hCD137 MAB-3 VL11), SEQ ID NO:219 (hCD137 MAB-3 VL12), SEQ ID NO:220 (hCD137 MAB-3 VL13), SEQ ID NO:221 (hCD137 MAB-3 VL14), or SEQ ID NO:222 (hCD137 MAB-3 VL15). Optimized/deimmunized molecules comprising many of such polypeptide chains are described herein and have the same amino acid sequences as the first and second polypeptide chains of optimized/deimmunized TRIDENT-A molecules (e.g., TRIDENT-A1-TRIDENT-A5)

The third polypeptide chain of TRIDENT-B comprises, in the N-terminal to C-terminal direction, an N-terminus, a VH domain of a monoclonal antibody capable of binding to 5T4 (VH$_{5T4}$) (h5T4 MAB-1 VH1 (SEQ ID NO:134)), a human IgG1 CH1 Domain (SEQ ID NO:3), a human IgG1 Hinge Region (SEQ ID NO:7), and a "hole-bearing" CH2 and CH3 Domain (SEQ ID NO:47). Thus, the first polypeptide chain of TRIDENT-B is composed of: SEQ ID NO:134-SEQ ID NO:3-SEQ ID NO:7-SEQ ID NO:47.

The amino acid sequence of the third polypeptide chain of TRIDENT-B is (SEQ ID NO:231):

```
QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The fourth polypeptide chain of TRIDENT-B comprises, in the N-terminal to C-terminal direction, an N-terminus, a VL domain of a monoclonal antibody capable of binding to 5T4 (VL$_{5T4}$) (h5T4 MAB-1 VL1 (SEQ ID NO:135)), a human IgG CL Kappa Domain (SEQ ID NO:1), and a C-terminus. Thus, the fourth polypeptide chain of TRIDENT-B is composed of SEQ ID NO:135-SEQ ID NO:1.

The amino acid sequence of the fourth polypeptide chains of TRIDENT-B is (SEQ ID NO:232):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

1. Optimized and Deimmunized Variants TRIDENT-B

Optimized and deimmunized variants of TRIDENT-B are composed of four polypeptide chains, and contain the 5T4 binding domains of antibody h5T4 MAB-1 and the CD137 VH Domain of any of hCD137 MAB-3 VH1A-VH1G and the CD137 VL Domain of any of hCD137 MAB-3 VL3-VL15.

Exemplary optimized and deimmunized variants of TRIDENT-B designated "TRIDENT-B2," and "TRIDENT-B5" are composed of four polypeptide chains, and contain the 5T4 binding domains of antibody h5T4 MAB-1 and the CD137 binding domains of antibody hCD137 MAB-3 (1B.3), and hCD137 MAB-3 (1E.15), respectively.

The first polypeptide chain of TRIDENT-B2 has the same amino acid sequence as the first polypeptide chain of TRIDENT-A2 (SEQ ID NO:194), as provided above.

The second polypeptide chain of TRIDENT-B2 has the same amino acid sequence as the second polypeptide chain of TRIDENT-A2 (SEQ ID NO:199), as provided above.

The first polypeptide chain of TRIDENT-B5 has the same amino acid sequence as the first polypeptide chain of TRIDENT-A5 (SEQ ID NO:229), as provided above.

The second polypeptide chain of TRIDENT-B5 has the same amino acid sequence as the second polypeptide of TRIDENT-A5 (SEQ ID NO:230), as provided above.

The third polypeptide chains of both exemplary optimized and deimmunized variants of TRIDENT-B have the same amino acid sequence as the third polypeptide chain of TRIDENT-B (SEQ ID NO:231).

The fourth polypeptide chain of both exemplary optimized and deimmunized variants of TRIDENT-B have the same amino acid sequence as the fourth polypeptide chains of TRIDENT-B (SEQ ID NO:232).

K. Alternative CD137×TA Binding Molecules

As will be recognized in view of the instant disclosure, additional CD137×TA binding molecules having the general structure of any of the above exemplary molecules and comprising a binding site for an alternative Tumor Antigen and/or having an optimized/deimmunized CD137 binding site may be constructed by employing the VL and VH domains of alternative Tumor Antigen antibodies in lieu of the VL and VH domains of the anti-HER2/neu or anti-5T4 antibodies, and/or the VL and VH domains of any of the optimized/deimmunized CD137 antibodies disclosed herein. Similarly, as provided herein, alternative CD137×TA binding molecules may likewise be constructed incorporating alternative linkers and/or heterodimer promoting domains.

V. Control Molecules

In order to more meaningfully demonstrate the properties of the CD137×TA Binding Molecules of the present invention, control antibodies, whose VL and VH domains may be used to produce control Fc-bearing diabodies and other control binding molecules, are presented below.

The anti-fluorescein antibody 4-4-20 (Gruber, M. et al. (1994) "*Efficient Tumor Cell Lysis Mediated By A Bispecific Single Chain Antibody Expressed In Escherichia coli*," J. Immunol. 152(11):5368-5374; Bedzyk, W. D. et al. (1989) "*Comparison Of Variable Region Primary Structures Within An Anti-Fluorescein Idiotype Family*," J. Biol. Chem. 264 (3): 1565-1569) is a suitable control antibody, diabodies. The amino acid sequences of the variable light and variable heavy Domains of anti-fluorescein antibody 4-4-20 are as follows:

The amino acid sequence of the VH Domain of anti-fluorescein antibody 4-4-20 (SEQ ID NO:124) is shown below (CDR$_H$ residues are shown underlined):

```
EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSS
```

The amino acid sequence of the VL Domain of anti-fluorescein antibody 4-4-20 (SEQ ID NO:125) is shown below (CDR$_L$ residues are shown underlined):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IK
```

Palivizumab (see, e.g., Protein Data Bank (PDB) ID No. 2HWZ) is a humanized monoclonal antibody (IgG) directed against an epitope in the A antigenic site of the F protein of RSV, and is a suitable control antibody, whose VL and VH domains may be used to produce control diabodies and other control binding molecules. Alternative anti-RSV glycoprotein F antibodies include motavizumab (see, e.g., PDB ID No. 3IXT) and a variant of palivizumab engineered to remove a cysteine residues from CDR 1 of the light chain. The variant of palivizumab was used for generation of the control molecules below The amino acid sequence of the VH Domain of the variant of palivizumab (SEQ ID NO:126) is shown below (CDR$_H$ residues are shown underlined):

```
QVTLRESGPA LVKPTQTLTL TCTFSGFSLS TSGMSVGWIR

QPPGKALEWL ADIWWDDKKD YNPSLKSRLT ISKDTSKNQV

VLKVTNMDPA DTATYYCARS MITNWYFDVW GAGTTVTVSS
```

The amino acid sequence of the VL Domain of the variant of palivizumab (SEQ ID NO:127) is shown below (CDR$_L$ residues are shown underlined):

```
DIQMTQSPST LSASVGDRVT ITCRASQSVG YMHWYQQKPG

KAPKLLIYDT SKLASGVPSR FSGSGSGTEF TLTISSLQPD

DFATYYCFQG SGYPFTFGGG TKLEIK
```

VI. Summary of CD137×TA Binding and Control Molecules

Table 5 summarizes the domain attributes of DART-A— DART-G, TRIDENT-A-A5

TABLE 5

| Name (No. of Chains) | Parental mAbs | Fc Domain | Chain No. | SEQ ID NOs. | Other Components |
|---|---|---|---|---|---|
| DART-A (4 Chains) | hHER2 MAB-1 (1.2) hCD137 MAB-3 (1.1) | IgG1 (AA) | 1 2 3 4 | 98 99 98 99 | E/K Coils |
| DART-B (4 Chains) | hHER2 MAB-1 (1.3) hCD137 MAB-3 (1.3) | IgG1 (AA) | 1 2 3 4 | 100 101 100 101 | E/K Coils |
| DART-C (4 Chains) | hCD137 MAB-3 (1.3) hHER2 MAB-1 (1.3) | IgG1 (AA) | 1 2 3 4 | 102 103 102 103 | E/K Coils |
| DART-D (5 Chains) | hHER2 MAB-1 (1.3) CD137 MAB-3 | IgG1 (AA) (knob/hole) | 1 2 3 4 5 | 104 105 106 107 105 | CL/CH1 and E/K Coils |
| DART-E (5 Chains) | CD137 MAB-3 hHER2 MAB-1 (1.3) | IgG1 (AA) (knob/hole) | 1 2 3 4 5 | 108 109 110 111 109 | CL/CH1 and E/K Coils |
| DART-F (5 Chains) | hHER2 MAB-1 (1.3) CD137 MAB-4 | IgG1 (AA) (knob/hole) | 1 2 3 4 5 | 104 105 112 113 105 | CL/CH1 and E/K Coils |
| DART-G (5 Chains) | hHER2 MAB-1 (1.3) hCD137 MAB-3 (1.3) | IgG1 (AA) (knob/hole) | 1 2 3 4 5 | 104 105 114 119 105 | CL/CH1 and E/K Coils |

TABLE 5-continued

| Name (No. of Chains) | Parental mAbs | Fc Domain | Chain No. | SEQ ID NOs. | Other Components |
|---|---|---|---|---|---|
| Optimized DART-G1-G4 (5 Chains) | hHER2 MAB-1 (1.3) hCD137 MAB-3 (1A.3)-(1D.3) | IgG1 (AA) (knob/hole) | 1<br>2<br>3/4<br>3/4<br>3/4<br>3/4<br>5 | 104<br>105<br>115/120<br>116/121<br>117/122<br>118/123<br>105 | CL/CH1 and E/K Coils |
| TRIDENT-A (4 Chains) | hHER2 MAB-1 (1.3) hCD137 MAB-3 (1.3) | IgG1 (AA) (knob/hole) | 1<br>2<br>3<br>4 | 192<br>197<br>104<br>105 | CL/CH1 and E/K Coils |
| Optimized TRIDENT-A1-A4 (4 Chains) | hHER2 MAB-1 (1.3) hCD137 MAB-3 (1A.3)-(1D.3) | IgG1 (AA) (knob/hole) | 1/2<br>1/2<br>1/2<br>1/2<br>3<br>4 | 193/198<br>194/199<br>195/200<br>196/201<br>104<br>105 | CL/CH1 and E/K Coils |
| Deimmunized TRIDENT A5 (4 chains) | hHER2 MAB-1 (1.3) hCD137 MAB-3 (1E.15) | IgG1 (AA) (knob/hole) | 1<br>2<br>3<br>4 | 229<br>230<br>104<br>105 | CL/CH1 and E/K Coils |
| TRIDENT-B | h5T4 MAB-1 hCD137 MAB-3 (1.3) | IgG1 (AA) (knob/hole) | 1<br>2<br>3<br>4 | 192<br>197<br>231<br>232 | CL/CH1 and E/K Coils |
| Optimized TRIDENT-B2 | h5T4 MAB-1 hCD137 MAB-3 (1B.3) | IgG1 (AA) (knob/hole) | 1<br>2<br>3<br>4 | 194<br>199<br>231<br>232 | CL/CH1 and E/K Coils |
| Deimmunized TRIDENT-B5 | h5T4 MAB-1 hCD137 MAB-3 (1E.15) | IgG1 (AA) (knob/hole) | 1<br>2<br>3<br>4 | 229<br>230<br>231<br>232 | CL/CH1 and E/K Coils |

Table 6 shows the attributes of additional DART and TRIDENT molecules that were prepared:

TABLE 6

| Name (No. of Chains) | Parental mAbs | Fc Domain | Other Components |
|---|---|---|---|
| DART-1 (4 Chains) | hHER2 MAB-1 (1.2) CD137 MAB-1 | IgG1 (AA) | Same as DART-A except comprising VH/VL of CD137 MAB-1 in place of the VH/VL of hCD137 MAB-3(1.1) |
| DART-2 (4 Chains) | hHER2 MAB-1 (1.2) CD137 MAB-2 | IgG1 (AA) | Same as DART-A except comprising VH/VL of CD137 MAB-2 in place of the VH/VL of hCD137 MAB-3(1.1) |
| DART-3 (4 Chains) | hHER2 MAB-1 (1.2) variant palivizumab | IgG1 (AA) | Same as DART-A except comprising VH/VL of variant palivizumab in place of the VH/VL of hCD137 MAB-3(1.1) |
| DART-4 (5 Chains) | hHER2 MAB-1 (1.3) CD137 MAB-1 | IgG1 (AA) (knob/hole) | Same as DART-D except comprising VH/VL of CD137 MAB-1 in place of the VH/VL of CD137 MAB-3 |
| DART-5 (5 Chains) | hHER2 MAB-1 (1.3) CD137 MAB-2 | IgG1 (AA) (knob/hole) | Same as DART-D except comprising VH/VL of CD137 MAB-2 in place of the VH/VL of CD137 MAB-3 |
| DART-6 (5 Chains) | variant palivizumab CD137 MAB-3 | IgG1 (AA) (knob/hole) | Same as DART-D except comprising VH/VL of variant palivizumab in place of the VH/VL of hHER2 MAB-1 (1.3) |
| DART-7 (4 Chains) | Humanized EphA2 MAB-3 CD137 MAB-1 | IgG1 (AA) | Same as DART-1 except comprising VH/VL of a humanized variant of EphA2 MAB-3 in place of hHER2 MAB-1 (1.2) |
| DART-8 (4 Chains) | Humanized EphA2 MAB-3 variant palivizumab | IgG1 (AA) | Same as DART-3 except comprising VH/VL of a humanized variant of EphA2 MAB-3 in place of hHER2 MAB-1 (1.2) |
| TRIDENT-1 (4 Chains) | variant palivizumab CD137 MAB-3 (1B.3) | IgG1 (AA) (knob/hole) | Same as TRIDENT A2 except comprising VH/VL of variant palivizumab in place of the VH/VL of hHER2 MAB-1 (1.3) |

TABLE 6-continued

| Name (No. of Chains) | Parental mAbs | Fc Domain | Other Components |
|---|---|---|---|
| TRIDENT-2 (4 Chains) | hHER2 MAB-1 (1.3) 4-4-20 variant palivizumab | IgG1 (AA) (knob/hole) | Same as TRIDENT-A except the CD137 MAB-3 (1.3) VH and VL Domains are replaced with the VH/VL of variant palivizumab, and the VH/VL of 4-4-20 |
| TRIDENT-3 (4 Chains) | 5T4 MAB-1 4-4-20 Palivizumab | IgG1 (AA) (knob/hole) | Same as TRIDENT-2 except the hHER2 MAB-1 (1.3) VH and VL Domains are replaced with the VH/VL of 5T4 MAB-1 |
| TRIDENT-4 (4 Chains) | Palivizumab CD137 MAB-3 (1E.15) | IgG1 (AA) (knob/hole) | Same as TRIDENT A5 except comprising VH/VL of variant palivizumab in place of the VH/VL of hHER2 MAB-1 (1.3) |

VII. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a CD137×TA Binding Molecule of the present invention, or a combination of such agents and a pharmaceutically acceptable carrier. Preferably, compositions of the invention comprise a prophylactically or therapeutically effective amount of the CD137×TA bispecific Fc-bearing diabody of the invention and a pharmaceutically acceptable carrier.

The invention also encompasses pharmaceutical compositions comprising a CD137×TA Binding Molecules of the invention and one or more additional molecules that are effective in stimulating an immune response (e.g., an immune checkpoint inhibitor) and/or in combination with one or more additional molecules that specifically bind a tumor antigen (e.g., a tumor-specific monoclonal antibody or diabody) that is specific for at least one particular tumor antigen (TA, as described above), and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids. Aqueous carriers, such as saline solutions, aqueous dextrose and glycerol solutions are preferred when the pharmaceutical composition is administered intravenously.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers containing a CD137×TA Binding Molecule of the present invention alone or with other agents, preferably with a pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

A kit can comprise a CD137×TA Binding Molecule of the invention. The kit can further comprise one or more other prophylactic and/or therapeutic agents useful for the treatment of cancer, in one or more containers; and/or the kit can further comprise one or more cytotoxic antibodies that bind one or more tumor antigens (TAs). In certain embodiments, the other prophylactic or therapeutic agent is a chemotherapeutic. In other embodiments, the prophylactic or therapeutic agent is a biological or hormonal therapeutic.

VIII. Methods of Administration

The compositions of the present invention may be provided for the treatment, prophylaxis, and amelioration of one or more symptoms associated with cancer or other disease, or disorder by administering to a subject an effective amount of a molecule of the invention, or a pharmaceutical composition comprising a molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the molecules and compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262:4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the CD137×TA Binding Molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The invention also provides that the CD137×TA Binding Molecules of the invention are packaged in a hermetically sealed container such as an ampoule or sachette indicating the quantity of the molecule. In one embodiment, the CD137×TA Binding Molecules of the invention are supplied as a dry sterilized lyophilized powder or water free concentrate in a hermetically sealed container and can be reconstituted, e.g., with water or saline to the appropriate concentration for administration to a subject. Preferably, the CD137×TA Binding Molecules of the invention are supplied as a dry sterile lyophilized powder in a hermetically sealed container.

The lyophilized CD137×TA Binding Molecules of the present invention should be stored at between 2 and 8° C. in their original container and the molecules should be administered within 12 hours, preferably within 6 hours, within 5 hours, within 3 hours, or within 1 hour after being reconstituted. In an alternative embodiment, CD137×TA Binding Molecules of the invention are supplied in liquid form in a hermetically sealed container indicating the quantity and concentration of the molecule, fusion protein, or conjugated molecule. Preferably, the liquid form of the CD137×TA Binding Molecules of the invention are supplied in a hermetically sealed container.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition, in one embodiment, is an amount sufficient to effect beneficial or desired results including, without limitation, clinical results such as decreasing symptoms resulting from the disease attenuating a symptom of disease (e.g., the proliferation of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

Such effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the disease (e.g., cancer) either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the CD137×TA Binding Molecules encompassed by the invention, the dosage administered to a patient is preferably determined based upon the body weight (kg) of the recipient subject. The dosage administered is typically from about 0.01 µg/kg to about 150 mg/kg, or more, of the subject's body weight.

The dosage and frequency of administration of the CD137×TA Binding Molecules of the present invention may be reduced or altered by enhancing uptake and tissue penetration of the CD137×TA Binding Molecules by modifications such as, for example, lipidation.

The dosage of the CD137×TA Binding Molecules of the invention administered to a patient may be calculated for use as a single agent therapy. Alternatively, the CD137×TA Binding Molecules of the invention are used in combination with other therapeutic compositions such that the dosage administered to a patient is lower than when said molecules are used as a single agent therapy.

Treatment of a subject with a therapeutically or prophylactically effective amount of a CD137×TA Binding Molecules of the invention can include a single treatment or, preferably, can include a series of treatments. In a preferred example, a subject is treated with such a diabody one time per week, one time bi-weekly (i.e., once every other week), or one time every three weeks, for between about 1 to 52 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

IX. Uses of the Compositions of the Invention

The CD137×TA Binding Molecules of the present invention have the ability to bind T cells (APCs) (for example, by binding to CD137 expressed on the surfaces of such T cells) and the ability to bind TA-expressing tumor cells (for example, by binding to a TA expressed on the surfaces of such tumor cells). Thus, the CD137×TA Binding Molecules of the present invention have the ability to co-localize T cells to TA-expressing tumor cells, and thus may be used to treat any disease or condition associated with or characterized by the expression of a TA. Thus, without limitation, pharmaceutical compositions comprising such molecules may be employed in the diagnosis or treatment of cancers that express a TA, including such cancers characterized by the presence of a cancer cell, including but not limited to a cancer cell, of an acute myeloid leukemia, an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, a glioblastoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a malignant mesothelioma, a multiple endocrine neoplasia, a multiple myeloma, a myelodysplastic syndrome, a neuroblastoma, a neuroendocrine tumors, a non-small cell lung cancer, an ovarian cancer, a pancreatic cancer, a pharyngeal cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal cell carcinoma, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

In particular, CD137×TA Binding Molecules of the present invention are useful for the treatment of squamous cell cancers of the head and neck (SCCHN), bladder cancers, breast cancers, colorectal cancers, gastric cancers, glioblastomas, kidney cancers, lung cancers including non-small cell lung cancers (NSCLC), melanomas, ovarian cancers, pancreatic cancers, pharyngeal cancers, prostate cancers, renal cell carcinomas, and small round blue cell tumors of childhood including neuroblastomas and rhabdomyosarcomas, each of which highly express TAs.

The CD137×TA Binding Molecules of the present invention may additionally be used in the manufacture of medicaments for the treatment of the above-described conditions.

As demonstrated herein, the CD137×TA Binding Molecules of the present invention enhance the activity of tumor targeting agents. According, the CD137×TA Binding Molecules of the present invention may additionally be used in combination with other a tumor targeting agents, including but not limited to an antibody, an antigen binding fragment of an antibody (e.g., an scFv, a Fab, a F(ab)2, etc.), a TandAb, etc.), a multispecific binding molecule (e.g., a diabody, a bispecific antibody, a trivalent binding molecule, etc.), capable of binding a desired TA. It is specifically contemplated that the tumor targeting agent may bind the same or a different TA as the CD137×TA Binding Molecule used in such combinations. In particular embodiments, the tumor targeting agent is a multispecific molecule that binds to a TA and to an epitope expressed on T-cells including, for example, CD3, and/or CD8. Exemplary tumor targeting agents include, but are not limited to, molecules that bind to a TA and CD3 ("TA×CD3"). Exemplary TA×CD3 binding molecules (e.g., bispecific antibodies, DART® molecules, BiTe® molecules, TandAbs, etc.), and methods for making the same, which may be used in such combinations are well known in the art. (see for e.g., WO2013026835, WO2013158856, WO2014047231; WO2014110601; WO2014131711; WO 2015/026894; WO2015026892; WO 2015/184203; WO 2016/036937; WO2016182751; WO2017091656; WO2017/142928; WO2017118675).

As provided herein, the use of CD137×TA Binding Molecules of the present invention in combination with a tumor targeting agent (e.g., a TA×CD3 binding molecule) can lead to up-regulation of the inhibitory immune modulator Programmed Death-1 ("PD-1," also known as "CD279"). PD-1 mediates its inhibition of the immune system by binding PD-L1 and PD-L2 (also known as B7-H1 and B7-DC) (Flies, D. B. et al. (2007) "*The New B7s: Playing a Pivotal Role in Tumor Immunity*," J. Immunother. 30(3):251-260; U.S. Pat. Nos. 6,803,192; 7,794,710; United States Patent Application Publication Nos. 2005/0059051; 2009/0055944; 2009/0274666; 2009/0313687; PCT Publication Nos. WO 01/39722; WO 02/086083). However, as demonstrated herein, the further addition of an agent that inhibits the inhibitory activity of PD-1 ("PD-1/PD-L1 Checkpoint Inhibitor") down regulates the expression of PD-1 and further enhances the activity of the CD137×TA and tumor targeting agents such as TA×CD3 Binding Molecules. The invention particularly encompasses PD-1/PD-L1 Checkpoint Inhibitors comprising an epitope-binding site of an antibody that binds PD-1.

Accordingly, the CD137×TA Binding Molecules of the present invention may additionally be used in combination with other tumor targeting agents, in further combination with a PD-1/PD-L1 checkpoint inhibitor. PD-1/PD-L1 Checkpoint Inhibitors include, but not limited to, an antibody, an antigen binding fragment of an antibody (e.g., an scFv, a Fab, a F(ab)2, etc.), a TandAb, etc.), a multispecific binding molecule (e.g., a diabody, a bispecific antibody, a trivalent binding molecule, etc.), capable of binding to PD-1 and/or PD-L1. Exemplary PD-1/PD-L1 Checkpoint Inhibitors and methods for making the same, which may be used in such combinations are well known in the art. (see for e.g., U.S. Pat. Nos. 9,617,338; 9,273,135, 9,062,112, 8,981,063, 8,779,108, 8,609,089; 8,552,154; 8,460,927; 8,008,449; US Patent Publication Nos: 2015/0197571; 2016/0075782; 2016/0159905; 2016/0319019; 2017/0044259; PCT Patent Publication Nos. WO 2004/056875; WO 2006/121168; WO 2008/156712; WO 2012/135408; WO 2012/145549; WO 2013/014668; WO 2014/055897; WO 2013/079174; WO 2014/179664; WO 2014/194302; WO 2015/109124; WO 2015/112800; WO 2015/112805; WO 2016/000619; WO 2016007235; WO 2016/061142; WO 2016/111645; WO 2016/210262; WO 2016/014688; WO 2016/077397; WO 2017/019846; WO 2017/079112; WO 2017/087547; and WO 2017/106656).

Where such combinations are employed, it is specifically contemplated that, one or more of the molecules may be administered to a subject "concurrently" (e.g., a CD137×TA Binding Molecule may be administered at the same time as a TA×CD3 binding molecule and/or a PD-1/PD-L1 Checkpoint Inhibitor is administered) and/or that one or more of the molecules may be administered "sequentially" (e.g., a CD137×TA Binding Molecule is administered and, at a later time, a TA×CD3 binding molecule and/or a PD-1/PD-L1 Checkpoint Inhibitor is administered, or vice versa).

X. Particular Embodiments of the Invention

Having now generally described the invention, the same will be more readily understood through reference to the following numbered Embodiments ("E"), which are provided by way of illustration and are not intended to be limiting of the present invention unless specified:

E1. A CD137×TA Binding Molecule, wherein such Binding Molecule is capable of specific binding to an epitope of CD137 and an epitope of a tumor antigen (TA), and wherein such CD137×TA Binding Molecule comprises a first Light Chain Variable Domain that comprises a $CDR_L1$, $CDR_L2$ and $CDR_L3$, and a first Heavy Chain Variable Domain that comprises a $CDR_H1$, $CDR_H2$ and $CDR_H3$; and wherein, (A) (1) said first Light Chain Variable Domain CDR$_L$1, CDR$_L$2, and CDR$_L$3 are the Light Chain CDRs of CD137 MAB-3 VL15 (SEQ ID NO:222); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(B) (1) said first Light Chain Variable Domain CDR$_L$1, CDR$_L$2, and CDR$_L$3 are the Light Chain CDRs of CD137 MAB-3 VL14 (SEQ ID NO:221); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(C) (1) said first Light Chain Variable Domain CDR$_L$1, CDR$_L$2, and CDR$_L$3 are the Light Chain CDRs of CD137 MAB-3 VL11 (SEQ ID NO:218); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(D) (1) said first Light Chain Variable Domain CDR$_L$1, CDR$_L$2, and CDR$_L$3 are the Light Chain CDRs of CD137 MAB-3 VL10 (SEQ ID NO:217); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(E) (1) said first Light Chain Variable Domain CDR$_L$1, CDR$_L$2, and CDR$_L$3 are the Light Chain CDRs of CD137 MAB-3 VL6 (SEQ ID NO:213); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(F) (1) said first Light Chain Variable Domain CDR$_L$1, CDR$_L$2, and CDR$_L$3 are the Light Chain CDRs of CD137 MAB-3 VL4 (SEQ ID NO:211); and
(2) said first Heavy Chain Variable Domain CDR$_H$1, CDR$_H$2, and CDR$_H$3 are the Heavy Chain CDRs of CD137 MAB-3 VH1B (SEQ ID NO:84);
(G) (1) the first Light Chain Variable Domain CDR$_L$1, CDR$_L$2, and CDR$_L$3 are the Light Chain CDRs of CD137 MAB-3 VL (SEQ ID NO:75); and
(2) the first Heavy Chain Variable Domain CDR$_H$1, CDR$_H$2, and CDR$_H$3 are the Heavy Chain CDRs of CD137 MAB-3 VH (SEQ ID NO:74);
(H) (1) the first Light Chain Variable Domain CDR$_L$1, CDR$_L$2, and CDR$_L$3 are the Light Chain CDRs of CD137 MAB-4 VL (SEQ ID NO:91); and
(2) the first Heavy Chain Variable Domain CDR$_H$1, CDR$_H$2, and CDR$_H$3 are the Heavy Chain CDRs of CD137 MAB-4 VH (SEQ ID NO:90);
(I) (1) the first Light Chain Variable Domain CDR$_L$1, CDR$_L$2, and CDR$_L$3 are the Light Chain CDRs of CD137 MAB-5 VL (SEQ ID NO:97); and
(2) the first Heavy Chain Variable Domain CDR$_H$1, CDR$_H$2, and CDR$_H$3 are the Heavy Chain CDRs of CD137 MAB-5 VH (SEQ ID NO:96);
(J) (1) the first Light Chain Variable Domain CDR$_L$1, CDR$_L$2, and CDR$_L$3 are the Light Chain CDRs of CD137 MAB-3 VL (SEQ ID NO:75); and
(2) the first Heavy Chain Variable Domain CDR$_H$1, CDR$_H$2, and CDR$_H$3 are the Heavy Chain CDRs of CD137 MAB-3 VH1A (SEQ ID NO:83);
(K) (1) the first Light Chain Variable Domain CDR$_L$1, CDR$_L$2, and CDR$_L$3 are the Light Chain CDRs of CD137 MAB-3 VL (SEQ ID NO:75); and
(2) the first Heavy Chain Variable Domain CDR$_H$1, CDR$_H$2, and CDR$_H$3 are the Heavy Chain CDRs of CD137 MAB-3 VH1B (SEQ ID NO:84);
(L) (1) the first Light Chain Variable Domain CDR$_L$1, CDR$_L$2, and CDR$_L$3 are the Light Chain CDRs of CD137 MAB-3 VL (SEQ ID NO:75); and
(2) the first Heavy Chain Variable Domain CDR$_H$1, CDR$_H$2, and CDR$_H$3 are the Heavy Chain CDRs of CD137 MAB-3 VH1C (SEQ ID NO:85);
or
(M) (1) the first Light Chain Variable Domain CDR$_L$1, CDR$_L$2, and CDR$_L$3 are the Light Chain CDRs of CD137 MAB-3 VL (SEQ ID NO:75); and
(2) the first Heavy Chain Variable Domain CDR$_H$1, CDR$_H$2, and CDR$_H$3 are the Heavy Chain CDRs of CD137 MAB-3 VH1D (SEQ ID NO:86).

E2. The CD137×TA Binding Molecule of E1, wherein the first Heavy Chain Variable Domain comprises the amino acid sequence of:
(A) hCD137 MAB-3 (SEQ ID NO:77); or
(B) hCD137 MAB-4 (SEQ ID NO:92).

E3. The CD137×TA Binding Molecule of E1 or E2, wherein the first Light Chain Variable Domain comprises the amino acid sequence of:
(A) hCD137 MAB-3 (SEQ ID NO:82); or
(B) hCD137 MAB-4 (SEQ ID NO:93).

E4. The CD137×TA Binding Molecule of any one of E1-E3, wherein the first Heavy Chain Variable Domain comprises the amino acid sequence of:
(A) hCD137 MAB-3 VH1E (SEQ ID NO:208);
(B) hCD137 MAB-3 VH1B (SEQ ID NO:84);
(C) hCD137 MAB-3 VH1A (SEQ ID NO:83);
(D) hCD137 MAB-3 VH1 (SEQ ID NO:76);
(E) hCD137 MAB-3 VH1C (SEQ ID NO:85);
(F) hCD137 MAB-3 VH1D (SEQ ID NO:86);
(G) hCD137 MAB-3 VH1F (SEQ ID NO:209);
(H) hCD137 MAB-3 VH1G (SEQ ID NO:210); or
(I) hCD137 MAB-4 VH1 (SEQ ID NO:92).

E5. The CD137×TA Binding Molecule of any one of E1-E4, wherein the first Light Chain Variable Domain comprises the amino acid sequence of:
(A) hCD137 MAB-3 VL15 (SEQ ID NO:222);
(B) hCD137 MAB-3 VL14 (SEQ ID NO:221);
(C) hCD137 MAB-3 VL1 (SEQ ID NO:87);
(D) hCD137 MAB-3 VL2 (SEQ ID NO:88);
(E) hCD137 MAB-3 VL3 (SEQ ID NO:89);
(F) hCD137 MAB-3 VL4 (SEQ ID NO:211);
(G) hCD137 MAB-3 VL5 (SEQ ID NO:212);
(H) hCD137 MAB-3 VL6 (SEQ ID NO:213);
(I) hCD137 MAB-3 VL7 (SEQ ID NO:214);
(J) hCD137 MAB-3 VL8 (SEQ ID NO:215);
(K) hCD137 MAB-3 VL9 (SEQ ID NO:216);
(L) hCD137 MAB-3 VL10 (SEQ ID NO:217);
(M) hCD137 MAB-3 VL11 (SEQ ID NO:218);
(N) hCD137 MAB-3 VL12 (SEQ ID NO:219);
(O) hCD137 MAB-3 VL13 (SEQ ID NO:220);
(P) hCD137 MAB-4 VL1 (SEQ ID NO:94); or
(Q) hCD137 MAB-4 VL2 (SEQ ID NO:95).

E6. The CD137×TA Binding Molecule of any one of E1-E5, wherein the tumor antigen (TA) is selected from the group of tumor antigens consisting of: 19.9; oncofetal protein 5T4; antigen 4.2; A33; AFP; ALCAM; BAGE; beta-catenin; CA125; Carboxypeptidase M; B1; CD5; CD19; CD20; CD22; CD23; CD25; CD27; CD30; CD33; CD36; CD46; CD52; CD79a/CD79b; CD123; CD317; CEA; CEACAM5; CEACAM6; CO-43; CO-514; CTLA-1; CTLA-4; Cytokeratin 8; E1 series; EGF-R; an Ephrin receptor; Erb; F3; FC10.2; a GAGE GD2; GD3; GD49; GM2; GM3; GICA 19-9; gp37; gp75; gp100; HER-2/neu; human B-lymphoma antigen-CD20; human milk fat globule antigen; human papillomavirus-E6/human papillomavirus-E7; HMW-MAA; I antigen; ITGB6; IL13Rα2; JAM-3; KID3; KID31; KS 1/4 pan-carcinoma antigen; KS 1/4; KSA; L6; L20; LEA; LUCA-2; M1:22:25:8; M18; M39; a MAGE; MART; Myl; MUC-1; MUM-1; N-acetylglucosaminyltransferase; neoglycoprotein; NS-10; OFA-1; OFA-2; Oncostatin M; p15; PSA; PSMA; PEMA; PIPA; prostatic acid phosphate; R24; ROR1; SSEA-1; SSEA-3; SSEA-4; sTn; T cell receptor derived peptide; TAG-72; TL5; TNF-α receptor; TNF-β receptor; TNF-γ receptor; TRA-1-85; Transferrin Receptor; TSTA; and VEGF-R.

E7. The CD137×TA Binding Molecule of any one of E1-E5, wherein the tumor antigen (TA) is selected from the tumor antigens of Table 1.

E8. The CD137×TA Binding Molecule of any one of E1-E7, wherein the tumor antigen (TA) is: HER2/neu, EphA2 or 5T4.

E9. The CD137×TA Binding Molecule of E8, wherein the tumor antigen (TA) is HER2/neu and wherein the CD137×TA Binding Molecule comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$; and wherein:
(A) the second Light Chain Variable Domain $CDR_L1$, $CDR_L2$, and $CDR_L3$ are the Light Chain CDRs of HER2 MAB-1 VL (SEQ ID NO:63); and
(B) the second Heavy Chain Variable Domain $CDR_H1$, $CDR_H2$, and $CDR_H3$ are the Heavy Chain CDRs of HER2 MAB-1 VH (SEQ ID NO:62).

E10. The CD137×TA Binding Molecule of E9, wherein:
(A) (1) the second Light Chain Variable Domain $CDR_L1$, $CDR_L2$, and $CDR_L3$ are the Light Chain CDRs of hHER2 MAB-1 VL1 (SEQ ID NO:67);
(2) the second Light Chain Variable Domain $CDR_L1$, $CDR_L2$, and $CDR_L3$ are the Light Chain CDRs of hHER2 MAB-1 VL2 (SEQ ID NO:68); or
(3) the second Light Chain Variable Domain $CDR_L1$, $CDR_L2$, and $CDR_L3$ are the Light Chain CDRs of hHER2 MAB-1 VL3 (SEQ ID NO:69);
and
(B) (1) the second Heavy Chain Variable Domain $CDR_H1$, $CDR_H2$, and $CDR_H3$ are the Heavy Chain CDRs of hHER2 MAB-1 VH1 (SEQ ID NO:64);
(2) the second Heavy Chain Variable Domain $CDR_H1$, $CDR_H2$, and $CDR_H3$ are the Heavy Chain CDRs of hHER2 MAB-1 VH2 (SEQ ID NO:65); or
(3) the second Heavy Chain Variable Domain $CDR_H1$, $CDR_H2$, and $CDR_H3$ are the Heavy Chain CDRs of hHER2 MAB-1 VH3 (SEQ ID NO:66).

E11. The CD137×TA Binding Molecule of E10, wherein the second Heavy Chain Variable Domain comprises the amino acid sequence of:
(A) hHER2 MAB-1 VH1 (SEQ ID NO:64);
(B) hHER2 MAB-1 VH2 (SEQ ID NO:65); or
(C) hHER2 MAB-1 VH3 (SEQ ID NO:66).

E12. The CD137×TA Binding Molecule of E10 or E11, wherein the second Light Chain Variable Domain comprises the amino acid sequence of:
(A) hHER2 MAB-1 VL1 (SEQ ID NO:67);
(B) hHER2 MAB-1 VL2 (SEQ ID NO:68); or
(C) hHER2 MAB-1 VL3 (SEQ ID NO:69).

E13. The CD137×TA Binding Molecule of E8, wherein the tumor antigen (TA) is 5T4 and wherein the CD137×TA Binding Molecule comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$; and wherein:
(I) (A) the second Light Chain Variable Domain $CDR_L1$, $CDR_L2$, and $CDR_L3$ are the Light Chain CDRs of 5T4 MAB-1 VL (SEQ ID NO:135); and
(B) the second Heavy Chain Variable Domain $CDR_H1$, $CDR_H2$, and $CDR_H3$ are the Heavy Chain CDRs of 5T4 MAB-1 VH (SEQ ID NO:134); or
(II) (A) the second Light Chain Variable Domain $CDR_L1$, $CDR_L2$, and $CDR_L3$ are the Light Chain CDRs of 5T4 MAB-2 VL (SEQ ID NO:137); and
(B) the second Heavy Chain Variable Domain $CDR_H1$, $CDR_H2$, and $CDR_H3$ are the Heavy Chain CDRs of 5T4 MAB-2 VH (SEQ ID NO:136).

E14. The CD137×TA Binding Molecule of E13, wherein the second Heavy Chain Variable Domain comprises the amino acid sequence of: MAB-1 VH1 (SEQ ID NO:135).

E15. The CD137×TA Binding Molecule of E13 or E14, wherein the second Light Chain Variable Domain comprises the amino acid sequence of: MAB-1 VH1 (SEQ ID NO:136).

E16. The CD137×TA Binding Molecule of any one of E1-E15, wherein the molecule is a bispecific tetravalent Fc-bearing diabody comprising a first, a second, a third, and a fourth polypeptide chain, wherein the polypeptide chains form a covalently bonded complex.

E17. The CD137×TA Binding Molecule of E16, wherein the tumor antigen (TA) is HER2/neu and wherein:
(I) (A) the first and the third polypeptide chain have the amino acid sequence of SEQ ID NO:100; and
(B) the second and the fourth polypeptide chain have the amino acid sequence of SEQ ID NO:101;
or
(II) (A) the first and the third polypeptide chain have the amino acid sequence of SEQ ID NO:102; and
(B) the second and the fourth polypeptide chain have the amino acid sequence of SEQ ID NO:103.

E18. The CD137×TA Binding Molecule of any one of E1-E15, wherein the molecule is bispecific and tetravalent, and comprises a first, a second, a third, a fourth, and a fifth polypeptide chain, wherein the polypeptide chains form a covalently bonded complex.

E19. The CD137×TA Binding Molecule of E15, wherein the tumor antigen (TA) is HER2/neu and wherein:
(I) (A) the first polypeptide chain has the amino acid sequence of SEQ ID NO:104;
(B) the second and the fifth polypeptide chain have the amino acid sequence of SEQ ID NO:105;
(C) the third polypeptide chain has the amino acid sequence of SEQ ID NO:106; and
(D) the fourth polypeptide chain has the amino acid sequence of SEQ ID NO:107;
or
(II) (A) the first polypeptide chain has the amino acid sequence of SEQ ID NO:104;
(B) the second and the fifth polypeptide chain have the amino acid sequence of SEQ ID NO:105;
(C) the third polypeptide chain has the amino acid sequence of SEQ ID NO:114, SEQ ID NO:115, SEQ ID NO:116, SEQ ID NO:117, or SEQ ID NO:118; and
(D) the fourth polypeptide chain has the amino acid sequence of SEQ ID NO:119, SEQ ID NO:120, SEQ ID NO:121, SEQ ID NO:122, or SEQ ID NO:123.

E20. The CD137×TA Binding Molecule of any one of E1-15, wherein said molecule is bispecific and trivalent, and comprises a first, a second, a third, and a fourth, polypeptide chain, wherein said polypeptide chains form a covalently bonded complex.

E21. The CD137×TA Binding Molecule of E20, wherein said tumor antigen (TA) is HER2/neu and wherein:
(A) said first polypeptide chain has the amino acid sequence of SEQ ID NO:192, SEQ ID NO:193, SEQ ID NO:194, SEQ ID NO:195, SEQ ID NO:196, or SEQ ID NO:229;
(B) said second polypeptide chain has the amino acid sequence of SEQ ID NO:197, SEQ ID NO:198, SEQ ID NO:199, SEQ ID NO:200, SEQ ID NO:201, or SEQ ID NO:230;
(C) said third polypeptide chain has the amino acid sequence of SEQ ID NO:104; and
(D) said fourth polypeptide chain has the amino acid sequence of SEQ ID NO:105.

E23. The CD137×TA Binding Molecule of E20, wherein said tumor antigen (TA) is 5T4 and wherein:
(A) said first polypeptide chain has the amino acid sequence of SEQ ID NO:192, SEQ ID NO:193, SEQ ID NO:194, SEQ ID NO:195, SEQ ID NO:196, or SEQ ID NO:229;
(B) said second polypeptide chain has the amino acid sequence of SEQ ID NO:197, SEQ ID NO:198, SEQ ID NO:199, SEQ ID NO:200, SEQ ID NO:201, or SEQ ID NO:230;
(C) said third polypeptide chain has the amino acid sequence of SEQ ID NO:231; and
(D) said fourth polypeptide chain has the amino acid sequence of SEQ ID NO:232.

E24. A pharmaceutical composition comprising the CD137× TA Binding Molecule of and one E1-E23, and a physiologically acceptable carrier.

E25. Use of the CD137×TA Binding Molecule of any one of E1-E23, or the pharmaceutical composition of E24, in the treatment of a disease or condition associated with or characterized by the expression of the tumor antigen (TA).

E26. The use of E25, wherein the disease or condition associated with or characterized by the expression of the tumor antigen (TA) is cancer.

E27. A CD137 binding molecule that comprises a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:
(A) (1) said first Light Chain Variable Domain $CDR_L1$, $CDR_L2$, and $CDR_L3$ are the Light Chain CDRs of CD137 MAB-3 VL15 (SEQ ID NO:222); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(B) (1) said first Light Chain Variable Domain $CDR_L1$, $CDR_L2$, and $CDR_L3$ are the Light Chain CDRs of CD137 MAB-3 VL14 (SEQ ID NO:221); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(C) (1) said first Light Chain Variable Domain $CDR_L1$, $CDR_L2$, and $CDR_L3$ are the Light Chain CDRs of CD137 MAB-3 VL11 (SEQ ID NO:218); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(D) (1) said first Light Chain Variable Domain $CDR_L1$, $CDR_L2$, and $CDR_L3$ are the Light Chain CDRs of CD137 MAB-3 VL10 (SEQ ID NO:217); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(E) (1) said first Light Chain Variable Domain $CDR_L1$, $CDR_L2$, and $CDR_L3$ are the Light Chain CDRs of CD137 MAB-3 VL6 (SEQ ID NO:213); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(F) (1) said first Light Chain Variable Domain $CDR_L1$, $CDR_L2$, and $CDR_L3$ are the Light Chain CDRs of CD137 MAB-3 VL4 (SEQ ID NO:211); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(G) (1) the Light Chain Variable Domain $CDR_L1$, $CDR_L2$, and $CDR_L3$ are the Light Chain CDRs of CD137 MAB-3 VL (SEQ ID NO:75); and
(2) the Heavy Chain Variable Domain $CDR_H1$, $CDR_H2$, and $CDR_H3$ are the Heavy Chain CDRs of CD137 MAB-3 VH (SEQ ID NO:74);
(H) (1) the Light Chain Variable Domain $CDR_L1$, $CDR_L2$, and $CDR_L3$ are the Light Chain CDRs of CD137 MAB-4 VL (SEQ ID NO:91); and
(2) the Heavy Chain Variable Domain $CDR_H1$, $CDR_H2$, and $CDR_H3$ are the Heavy Chain CDRs of CD137 MAB-4 VH (SEQ ID NO:90);
(I) (1) the Light Chain Variable Domain $CDR_L1$, $CDR_L2$, and $CDR_L3$ are the Light Chain CDRs of CD137 MAB-5 VL (SEQ ID NO:97); and
(2) the Heavy Chain Variable Domain $CDR_H1$, $CDR_H2$, and $CDR_H3$ are the Heavy Chain CDRs of CD137 MAB-5 VH (SEQ ID NO:96);
(J) (1) the Light Chain Variable Domain $CDR_L1$, $CDR_L2$, and $CDR_L3$ are the Light Chain CDRs of CD137 MAB-3 VL (SEQ ID NO:75); and
(2) the Heavy Chain Variable Domain $CDR_H1$, $CDR_H2$, and $CDR_H3$ are the Heavy Chain CDRs of CD137 MAB-3 VH1A (SEQ ID NO:83);
(K) (1) the first Light Chain Variable Domain $CDR_L1$, $CDR_L2$, and $CDR_L3$ are the Light Chain CDRs of CD137 MAB-3 VL (SEQ ID NO:75); and
(2) the first Heavy Chain Variable Domain $CDR_H1$, $CDR_H2$, and $CDR_H3$ are the Heavy Chain CDRs of CD137 MAB-3 VH1B (SEQ ID NO:84);
(L) (1) the first Light Chain Variable Domain $CDR_L1$, $CDR_L2$, and $CDR_L3$ are the Light Chain CDRs of CD137 MAB-3 VL (SEQ ID NO:75); and
(2) the first Heavy Chain Variable Domain $CDR_H1$, $CDR_H2$, and $CDR_H3$ are the Heavy Chain CDRs of CD137 MAB-3 VH1C (SEQ ID NO:85);
or
(M) (1) the first Light Chain Variable Domain $CDR_L1$, $CDR_L2$, and $CDR_L3$ are the Light Chain CDRs of CD137 MAB-3 VL (SEQ ID NO:75); and
(2) the first Heavy Chain Variable Domain $CDR_H1$, $CDR_H2$, and $CDR_H3$ are the Heavy Chain CDRs of CD137 MAB-3 VH1D (SEQ ID NO:86).

E28. The CD137 Binding Molecule of E27, wherein the Heavy Chain Variable Domain comprises the amino acid sequence of:
(A) hCD137 MAB-3 (SEQ ID NO:77); or
(B) hCD137 MAB-4 (SEQ ID NO:92).

E29. The CD137 Binding Molecule of E27 or E28, wherein the Light Chain Variable Domain comprises the amino acid sequence of:
(A) hCD137 MAB-3 (SEQ ID NO:82); or
(B) hCD137 MAB-4 (SEQ ID NO:93).

E30. The CD137 Binding Molecule of any one of E27-E29, wherein the Heavy Chain Variable Domain comprises the amino acid sequence of:
(A) hCD137 MAB-3 VH1 (SEQ ID NO:76);
(B) hCD137 MAB-3 VH1A (SEQ ID NO:83);
(C) hCD137 MAB-3 VH1B (SEQ ID NO:84);
(D) hCD137 MAB-3 VH1C (SEQ ID NO:85);
(E) hCD137 MAB-3 VH1D (SEQ ID NO:86);
(F) hCD137 MAB-3 VH1E (SEQ ID NO:208);
(G) hCD137 MAB-3 VH1F (SEQ ID NO:209);
(H) hCD137 MAB-3 VH1G (SEQ ID NO:210); or
(I) hCD137 MAB-4 VH1 (SEQ ID NO:92).

E31. The CD137 Binding Molecule of any one of E27-E30, wherein the Light Chain Variable Domain comprises the amino acid sequence of:
(A) hCD137 MAB-3 VL15 (SEQ ID NO:222);
(B) hCD137 MAB-3 VL14 (SEQ ID NO:221);
(C) hCD137 MAB-3 VL1 (SEQ ID NO:87);
(D) hCD137 MAB-3 VL2 (SEQ ID NO:88);
(E) hCD137 MAB-3 VL3 (SEQ ID NO:89);
(F) hCD137 MAB-3 VL4 (SEQ ID NO:211);
(G) hCD137 MAB-3 VL5 (SEQ ID NO:212);
(H) hCD137 MAB-3 VL6 (SEQ ID NO:213);
(I) hCD137 MAB-3 VL7 (SEQ ID NO:214);
(J) hCD137 MAB-3 VL8 (SEQ ID NO:215);
(K) hCD137 MAB-3 VL9 (SEQ ID NO:216);
(L) hCD137 MAB-3 VL10 (SEQ ID NO:217);
(M) hCD137 MAB-3 VL11 (SEQ ID NO:218);
(N) hCD137 MAB-3 VL12 (SEQ ID NO:219);
(O) hCD137 MAB-3 VL13 (SEQ ID NO:220);
(P) hCD137 MAB-4 VL1 (SEQ ID NO:94); or
(Q) hCD137 MAB-4 VL2 (SEQ ID NO:95).

E32. The CD137 Binding Molecule of and one E27-31, wherein the molecule is an antibody or an antigen binding fragment thereof.

E33. A pharmaceutical composition comprising the CD137 Binding Molecule of any one E27-E32, and a physiologically acceptable carrier.

E34. Use of the CD137 Binding Molecule of any one of E27-E31, or the pharmaceutical composition of E33, in the treatment of a disease or condition associated with a suppressed immune system or characterized by the expression of a tumor antigen (TA).

E35. The use of E34, wherein the condition associated with a suppressed immune system or characterized by the expression of the tumor antigen (TA) is cancer.

E36. An anti-HER2/neu Binding Molecule that comprises a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:
(A) the Light Chain Variable Domain $CDR_L1$, $CDR_L2$, and $CDR_L3$ are the Light Chain CDRs of HER2 MAB-1 VL (SEQ ID NO:63); and
(B) the Heavy Chain Variable Domain $CDR_H1$, $CDR_H2$, and $CDR_H3$ are the Heavy Chain CDRs of HER2 MAB-1 VH (SEQ ID NO:62).

E37. The anti-HER2/neu Binding Molecule of E36, wherein:
(A) (1) the Light Chain Variable Domain $CDR_L1$, $CDR_L2$, and $CDR_L3$ are the Light Chain CDRs of hHER2 MAB-1 VL1 (SEQ ID NO:67);
(2) the Light Chain Variable Domain $CDR_L1$, $CDR_L2$, and $CDR_L3$ are the Light Chain CDRs of hHER2 MAB-1 VL2 (SEQ ID NO:68); or
(3) the Light Chain Variable Domain $CDR_L1$, $CDR_L2$, and $CDR_L3$ are the Light Chain CDRs of hHER2 MAB-1 VL3 (SEQ ID NO:69);
and
(B) (1) the Heavy Chain Variable Domain $CDR_H1$, $CDR_H2$, and $CDR_H3$ are the Heavy Chain CDRs of hHER2 MAB-1 VH1 (SEQ ID NO:64);
(2) the Heavy Chain Variable Domain $CDR_H1$, $CDR_H2$, and $CDR_H3$ are the Heavy Chain CDRs of hHER2 MAB-1 VH2 (SEQ ID NO:65); or
(3) the Heavy Chain Variable Domain $CDR_H1$, $CDR_H2$, and $CDR_H3$ are the Heavy Chain CDRs of hHER2 MAB-1 VH3 (SEQ ID NO:66).

E38. The anti-HER2/neu Binding Molecule of E337, wherein the Heavy Chain Variable Domain comprises the amino acid sequence of:
(A) hHER2 MAB-1 VH1 (SEQ ID NO:64);
(B) hHER2 MAB-1 VH2 (SEQ ID NO:65); or
(C) hHER2 MAB-1 VH3 (SEQ ID NO:66).

E39. The anti-HER2/neu Binding Molecule of E37-E38, wherein the Light Chain Variable Domain comprises the amino acid sequence of:
(A) hHER2 MAB-1 VL1 (SEQ ID NO:67);
(B) hHER2 MAB-1 VL2 (SEQ ID NO:68); or
(C) hHER2 MAB-1 VL3 (SEQ ID NO:69).

E40. The anti-HER2/neu Binding Molecule of and one E36-E39, wherein the molecule is an antibody or an antigen binding fragment thereof.

E41. A pharmaceutical composition comprising the anti-HER2/neu Binding Molecule of any one E36-E40 and a physiologically acceptable carrier.

E42. Use of the anti-HER2/neu Binding Molecule of any one of E33-E37, or the pharmaceutical composition of E41, in the treatment of a disease or condition associated with or characterized by the expression of HER2/neu.

E43. The use of E42, wherein the condition associated with or characterized by the expression of HER2/neu is cancer.

E44. A method of enhancing the activity of a tumor targeting agent comprising administering said tumor targeting agent in combination with the CD137×TA Binding Molecule of any one of E1-E23, or the pharmaceutical composition of embodiment E24.

E45. A method of treating a disease or condition associated with a suppressed immune system or characterized by the expression of a tumor antigen (TA) comprising administering to a subject in need thereof the CD137×TA Binding Molecule of any one of E1-E23, or the pharmaceutical composition of E24.

E46. The method of E45, wherein the condition associated with a suppressed immune system or characterized by the expression of the tumor antigen (TA) is cancer.

E47. The method of E45 or E46, further comprising administering a tumor targeting agent.

E48. The method of any one of E44-E47, further comprising administering a PD-1/PD-L1 checkpoint inhibitor.

E49. The method of E44 or E47, wherein said tumor targeting agent is an antibody, an epitope binding fragment of an antibody, or an agent that mediates T-cell redirected killing of a target cell.

E50. The method of E48 or E49, wherein said PD-1/PD-L1 checkpoint inhibitor is an anti-PD-1 antibody or an anti-PD-L1 antibody.

E51. The method of any one of E48-E50, wherein said PD-1/PD-L1 checkpoint inhibitor comprises the VH and VL Domains of an antibody selected from those listed in Table 7:

TABLE 7

| PD-1 and PD-L1 Antibodies | Reference/Source |
| --- | --- |
| nivolumab | CAS Reg. No.: 946414-94-4; WHO Drug Information, 2013, Recommended INN: List 69, 27(1): 68-69 |
| pembrolizumab | CAS Reg. No.: 1374853-91-4; WHO Drug Information, 2014, Recommended INN: List 75, 28(3): 407 |
| PD1-17; PD1-28; PD1-33; PD1-35; and PD1-F2 | U.S. Pat. Nos. 7,488,802; 7,521,051 and 8,088,905; PCT Patent Publication WO 2004/056875 |
| 17D8; 2D3; 4H1; 5C4; 4A11; 7D3; and 5F4 | U.S. Pat. Nos. 8,008,449; 8,779,105 and 9,084,776; PCT Patent Publication WO 2006/121168 |
| hPD-1.08A; hPD-1.09A; 109A; K09A; 409A; h409A11; h409A16; h409A17; Codon optimized 109A; and Codon optimized 409A | U.S. Pat. Nos. 8,354,509; 8,900,587 and 5,952,136; PCT Patent Publication WO 2008/156712 |
| 1E3; 1E8; and 1H3 | U.S. Pat. Publication 2014/0044738; PCT Patent Publication WO 2012/145493 |
| 9A2; 10B11; 6E9; APE1922; APE1923; APE1924; APE1950; APE1963; and APE2058 | PCT Patent Publication WO 2014/179664 |
| GA1; GA2; GB1; GB6; GH1; A2; C7; H7; SH-A4; SH-A9; RG1H10; RG1H11; RG2H7; RG2H10; RG3E12; RG4A6; RG5D9; RG1H10-H2A-22-1S; RG1H10-H2A-27-25; RG1H10-3C; RG1H10-16C; RG1H10-17C; RG1H10-19C; RG1H10-21C; and RG1H10-23C2 | U.S. Pat. Publication 2014/0356363; PCT Patent Publication WO 2014/194302 |
| H1M7789N; H1M7799N; H1M7800N; H2M7780N; H2M7788N; H2M7790N; H2M7791N; H2M7794N; H2M7795N; H2M7796N; H2M7798N; H4H9019P; H4xH9034P2; H4xH9035P2; H4xH9037P2; H4xH9045P2; H4xH9048P2; H4H9057P2; H4H9068P2; H4xH9119P2; H4xH9120P2; H4Xh9128p2; H4Xh9135p2; H4Xh9145p2; H4Xh8992p; H4Xh8999p; and H4Xh9008p; | U.S. Pat. Publication 2015/0203579; PCT Patent Publication WO 2015/112800 |
| mAb1; mAb2; mAb3; mAb4; mAb7; mAb8; mAb9; mAb10; mAb11; mAb12; mAb13; mAb14; mAb15; and mAb16 | U.S. Pat. Publication 2016/0159905 |
| 246A10; 244C8; 413D2; 393C5; 388D4; 413E1; 244C8-1; 244C8-2; 244C8-3; 388D4-1; 388D4-2; and 388D4-3 | U.S. Pat. Publication 2016/0319019 |
| 22A5; 6El; lODl, 4C1; 7D3; 13Fl; 14A6; 15H5; 5A8; 7A4; and humanized versions of the same | PCT Publication No. WO 2016/014688 |
| 1E9; hlE9-1; hlE9-2; hlE9-4; hlE9-5; 4B10; h4B10-1; h4B10-2; h4B10-3; 1B10; 10B4; A09; C07; F09; G08; G10; H08; and H09 | PCT Publication No. WO 2016/077397 |
| M136-M13-MHC723; m136-M14-MHC724; m136-M19-MHC725; m245-M3-MHC728; m245-M5-MHC729; A1.0; A1.6; Ba2; Bb2/C1.1; and D4 | U.S. Pat. Publication 2017/0044259 |
| PD-1 mAb 1; PD-1 mAb 2; hPD-1 mAb 2; PD-1 mAb 3; hPD-1 mAb 4; PD-1 mAb 5; PD-1 mAb 6; PD-1 mAb 7; hPD-1 mAb 7; PD-1 mAb 8; PD-1 mAb 9; hPD-1 mAb 9; PD-1 mAb 10; PD-1 mAb 11; hPD-1 mAb 12; PD-1 mAb 13; PD-1 mAb 14; PD-1 mAb 15; hPD-1 mAb 15; and humanized versions of the same; particularly anti-PD-1 mAb (hPD-1 mAb 7(1.2) IgG4 (P) | PCT Publication No. WO 2017/019846 (particularly SEQ ID NOs: 264 and 266) |
| atezolizumab | CAS Reg No. 1380723-44-3; (WHO Drug Information, 2015, Recommended INN: List 74, 29(3): 387 |
| durvalumab | CAS Reg No. 1428935-60-7; WHO Drug Information, 2015, Recommended INN: List 74, 29(3): 393-394 |
| avelumab, MDX1105 | CAS Reg No. 1537032-82-8; WHO Drug Information, 2016, Recommended INN: List 74, 30(1): 100-101 |
| A09-188-1, and affinity matured and optimized variants: A09-204-1, A09-211-1, A09-212-1, A09-213-1, A09-214-1, A09-215-1, A09-216-1 A09-219-1, A09-220-1, A09-221-1, A09-222-1 A09-223-1, A09-202-1, A09-248-2, A09-239-2, A09-240-2, A09-241-2, A09-242-2, A09-243-2, A09-244-2, A09-245-2, A09-246-2, and A09-247-2 | PCT Patent Publication WO 2013/079174 |
| 1B9.2E11.2, 4H1.G10.15, 1A8, 1E4, 8G2, 1D11, 3A2, 3B11, 3F4, 3H6, 4C1, 4E1, 5A6, 9C12, 1B4, 1B11, 1F6, 1H8, 1H12, 2D5, 2H11, 3D12, 4C8, 4C9, 5E10, 5H4, 5H5, 8A1, 9G9, 10A7, and 10H6 | U.S. Pat. Publication U.S.2015/0197571 |
| 1D05, 84G09, 411B08, 411C04, 411D07, 386H03, 386A03, 385F01, 413D08, 413G05, 413F09, 414B06 | U.S. Pat. No. 9,617,338 |
| 3G10,12A4, 10A5, 5F8, 10H10, 1B12, 7H1, 11E6, 12B7, and 13G4 | U.S. Publication 2016/0075782 |
| A1, C2, C4, H12, and H12-GL | U.S. Publication 2017/0319690; PCT Patent Publication WO 2016/111645 |
| Ab-14, Ab-16, Ab-22, Ab-30, Ab-31, Ab-32, Ab-38, Ab-42, Ab-46, Ab-50, Ab-52, Ab-55, Ab-56, and Ab-65. | PCT Patent Publication WO 2014/055897 |
| R2κA3, R2κA4, R2κA6, R2κF4, R2κH5, R2κH6, R2κH3, sR3κA8, sR3κA9, sR3κB2, sR3κB5, tccR3KA8, tccR3KAl1, tccR3KB7, tccR3KD9, tccKF10, tctR3KA4, tctR3KF8, R2λA7, R2λB12, R2λ12, sR3λD7, sR3λE1, tccAF8, tccAD7, tctR3λH4, and others | PCT Patent Publication WO 2015/109124 |
| H2M8306N, H2M8307N, H2M8309N, H2M8310N, H2M8312N, H2M8314N, H2M8316N, H2M8317N, H2M8321N, H2M8323N, H2M8718N, H2M8718N2, and H2M8719N, H1H9323P, H1 H9327P, H1 H9329P, H1H9336P, H1H9344P2, 1H9345P2, H1H9351P2, H1H9354P2, H1H9364P2, H1H9373P2, H1H9382P2, H1H9387P2, and H1H9396P2 | PCT Patent Publication WO 2015/112805 |
| Mu333, Mu277, and humanized variants thereof including: hu333-2B, hu333-3A2, hu333-3C2 and hu333-3H2 | PCT Patent Publication WO 2016/000619 |
| BAP058 and humanized variants thereof including: BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, and BAP058-hum17 | PCT Patent Publication WO 2016/061142 |
| 332M1 and humanized variants there of including: 332M7, 332M72, and 332M8 | PCT Patent Publication WO 2017/087547 |

E52. The use of E26, E35, E42 or the method of any one of E46-E51, wherein the cancer is selected from the group consisting of: an acute myeloid leukemia, an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, a glioblastoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a malignant mesothelioma, a multiple endocrine neoplasia, a multiple myeloma, a myelodysplastic syndrome, a neuroblastoma, a neuroendocrine tumors, a non-small cell lung cancer, an ovarian cancer, a pancreatic cancer, a pharyngeal cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal cell carcinoma, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

E53. The use of E26, E35, E42 or the method of any one of E46-E51, wherein the cancer is selected from the group consisting: bladder cancer, breast cancer, colorectal cancer, gastric cancer, glioblastoma, kidney cancer, lung cancer, melanoma, neuroblastoma, ovarian cancer, pancreatic cancer, pharyngeal cancer, prostate cancer, renal cell carcinoma, rhabdomyosarcoma, and squamous cell cancer of the head and neck (SCCHN).

EXAMPLES

The following examples illustrate various methods for compositions in the diagnostic or treatment methods of the invention. The examples are intended to illustrate, but in no way limit, the scope of the invention.

Example 1

The Humanization of HER2 MAB-1

PCT Publication WO 2001/036005 discloses an anti-HER2/neu antibody, designated therein as "8H11," however, the sequences of the VL and VH Domains provided therein are inaccurate. The 8H11 antibody binds a HER2/neu epitope that is distinct from the epitope bound by trastuzumab, margetuximab, and pertuzumab.

The correct sequences for the VH and VL Domains of anti-HER2/neu antibody 8H11 were deduced (to thereby provide HER2-MAB-1 VH (SEQ ID NO:60) and HER2-MAB-1 VL (SEQ ID NO:61)), and multiple rounds of humanization were then undertaken in order to obtain the above-described humanized VH Domain "hHER2 MAB-1 VH1" (SEQ ID NO:64) and humanized VL Domain "hHER2 MAB-1 VL1" (SEQ ID NO:67). In the course of such efforts, several potential sequence liabilities were identified in the hHER2 MAB-1 VH1 and hHER2 MAB-1 VL1 Domains, and substitutions were made that removed these liabilities while maintaining binding affinity. Specifically:

(1) an aspartic acid isomerization site was identified at Kabat position 96 of the hHER2 MAB-1 VH1 Domain, and was corrected either by the substitution D96E or by the substitution G97I, as in hHER2 MAB-1 VH2 (SEQ ID NO:65) and hHER2 MAB-1 VH3 (SEQ ID NO:66), respectively;

(2) a potential asparagine deamidation site was identified at Kabat position 30 of the hHER2 MAB-1 VL1 Domain and was corrected either by the substitution N30S or by the substitution S31T, as in hHER2 MAB-1 VL3 (SEQ ID NO:69) and hHER2 MAB-1 VL2 (SEQ ID NO:68), respectively;

(3) potential aspartic acid isomerization site was identified at Kabat position D56 of the hHER2 MAB-1 VL1 Domain and was corrected by a substitution: V55Q, D56E, or D56S, as in hHER2 MAB-1 VL3 (SEQ ID NO:69), and hHER2 MAB-1 VL2 (SEQ ID NO:68).

The humanized heavy and light chain variable domains of hHER2 MAB-1 may be used in any combination and particular combinations of humanized chains are referred to by reference to the specific VH/VL Domains. For example, a humanized antibody comprising hHER2 MAB-1 VH1 and hHER2 MAB-1 VL3 is referred to herein as "hHER2 MAB-1 (1.3)."

The humanized variants were selected to have improved binding affinity as compared to the parental murine antibody and as described may be further engineered to eliminate sequence liabilities (e.g., isomerization, deamidation sites) as described above. The binding affinity of several combinations of humanized VH and VL domains was examined by BIACORE®. Thus, an extracellular portion of human HER2 fused to a histidine-containing peptide ("huHER2") was passed over a surface coated with immobilized antibody. Briefly, each test molecule was captured onto an F(ab)$_2$ goat-anti-human Fc-coated surface and then incubated in the presence of different concentrations (6.25 nM-50 nM) of huHER2. The kinetics of binding were determined via BIACORE® analysis binding (normalized 1:1 Langmuir binding model). The calculated $k_a$, $k_d$ and $K_D$ from these studies are presented in Table 8.

TABLE 8

| Antibody | VH | VL | $k_a$ (M$^{-1}$s$^{-1}$) | $k_d$ (s$^{-1}$) | $K_D$ (nM) |
|---|---|---|---|---|---|
| HER2 MAB-1 | murine | murine | 5.1 × 10$^5$ | 6.54 × 10$^{-4}$ | 1.27 |
| hHER2 MAB-1 (1.2) | 1 | 2 | 6.2 × 10$^5$ | 2.80 × 10$^{-4}$ | 0.45 |
| hHER2 MAB-1 (1.3) | 1 | 3 | 6.18 × 10$^5$ | 2.23 × 10$^{-4}$ | 0.36 |

In a separate study, the binding kinetics of the CD137×TA bispecific diabody, DART-B (described above), were determined for binding to human HER2 and cynomolgus monkey HER2, essentially as described above. The calculated $k_a$, $k_d$ and $K_D$ from these studies are presented in Table 9.

TABLE 9

| HER2/neu | $k_a$ (M$^{-1}$s$^{-1}$) | $k_d$ (s$^{-1}$) | $K_D$ (nM) |
|---|---|---|---|
| Human | 4.8 × 10$^5$ | 1.82 × 10$^{-4}$ | 0.38 |
| Cynomolgus Monkey | 4.44 × 10$^5$ | 2.94 × 10$^{-4}$ | 0.66 |

Example 2

The Isolation and Characterization of Murine Anti-CD137 mAbs

A panel of murine monoclonal antibodies specific for human CD137 were screened for antibodies exhibiting high affinity binding. Three antibodies were selected for further study. For such evaluations, purified pan T-cells (see above) were stimulated with anti-CD3/CD28 beads (cells:beads=1:1) for 72 hours in the presence of IL-2 (100 U/mL). 100 μL of activated T cells ($1.0 \times 10^6$ cells/mL) and 100 μL of serially diluted (5- or 10-fold dilutions) test article (antibody or bispecific diabody) was added to each well of microtiter assay plate(s), mixed and incubated at RT for 45 min. The cells were washed with FACS Buffer and secondary antibody (anti-human-Fc region-APC) was then added to each well; mixed and incubated at RT for 30 min. Cells were then washed FACS Buffer and T cell surface marker antibodies (anti-CD4 labeled with V510, and anti-CD8 labeled with FITC) were then added to each well; mixed and incubated at RT for 30 min. Cells were washed and resuspended in 100 μL FACS Buffer and analyzed by flow cytometry (BD LSR Fortessa or FACSCanto 11) for cell event collection. Data analysis were performed via FloJo v10.

Two of such selected antibodies, CD137 MAB-3 and CD137 MAB-4, were found to exhibit strong binding to human CD137 and were able to block binding between CD137 and its natural ligands. The third of such selected antibodies, CD137 MAB-5, exhibited lower binding to human CD137 and was not capable of blocking binding between CD137 and its natural ligands.

Figure 7:
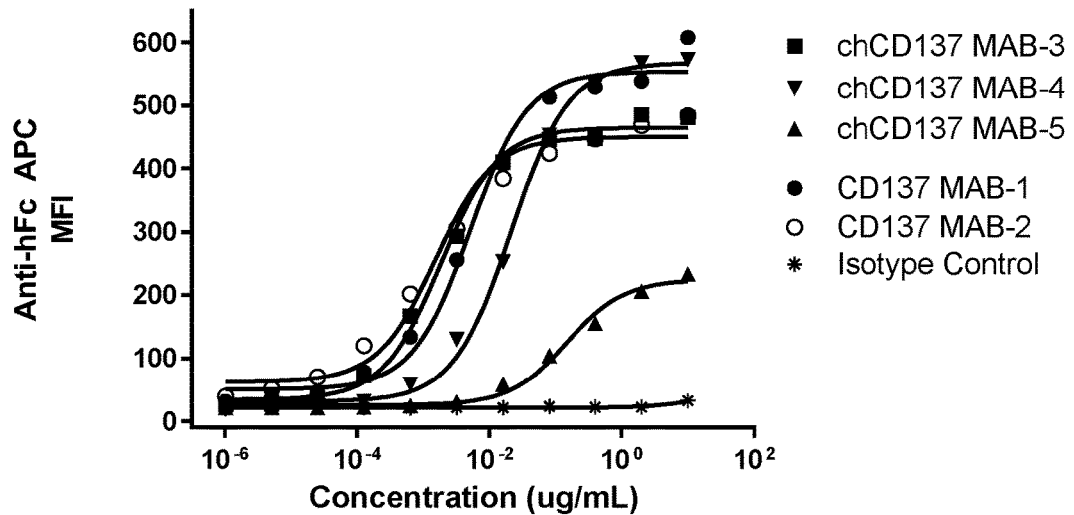
FIG. 7 shows the binding curves of the anti-CD137 antibodies urelumab and utomilumab (CD137 MAB-1 and CD137 MAB-2, respectively) and several novel chimeric CD137 mAbs (chCD137 MAB-3; chCD137 MAB-4 and chCD137 MAB-5) to activated $CD8^+$ T cells.

Chimeric antibodies having human IgG1 Fc regions and murine VH/VL domains were generated (designated: chCD137 MAB-1, chCD137 MAB-2, chCD137 MAB-3, chCD137 MAB-4 and chCD137 MAB-5, respectively), and were tested for their ability to bind to activated CD8⁺ T cells. As shown in FIG. 7, the selected antibodies exhibited a range of binding affinities.

Epitope binning was performed by cross-competition studies. The results of these and ligand binding competition studies indicate that:

(1) CD137 MAB-2, CD137 MAB-3 and CD137 MAB-4 compete with CD137L for binding to CD137, but that CD137 MAB-2 recognizes an epitope of CD137 that is distinct from the epitope recognized by CD137 MAB-1, CD137 MAB-3, CD137 MAB-4 and CD137 MAB-5;

(2) CD137 MAB-1 and CD137 MAB-5 do not compete with CD137L for binding to CD137;

(3) CD137 MAB-3 and CD137 MAB-4 exhibit competition with CD137 MAB-1, but bind a distinct epitope as demonstrated by their ability to compete for ligand binding;

(4) CD137 MAB-5 recognizes an epitope that is distinct from the epitopes recognized by CD137 MAB-1, CD137 MAB-2, CD137 MAB-3 or CD137 MAB-4.

The chimeric antibodies were also tested for their ability to induce cytokine (e.g., IFN-γ, TNF-α) release from T cells (i.e., their agonist activity) in the absence of ligand. For such evaluations, purified pan T cells (see above) were resuspended in assay media and placed in a tissue culture incubator overnight. Tumor target cells (including JIMT-1, N87) were obtained from culture. After washing, the cell pellets were resuspended in culture media at cell density of $1.0 \times 10^5$ cells/mL. $10^4$ cells were then added to each well of white flat-bottom assay plate placed in a tissue culture incubator overnight. The next day, rested human pan T cells were measured for density and viability by trypan blue exclusion using a Beckman Coulter Vi-Cell counter and adjusted to a density of $2 \times 10^6$ cells/mL. Tumor target cells pre-seeded on plate were washed once with assay media.

For the cytokine release assays: 50 μL of serially diluted test article (antibodies (+/− cross-linking with anti-human Fc (Fab)'₂), diabodies, trivalent molecules, etc.), 50 μL of prewashed Dynabead αCD3 (REF 11151D; Invitrogen by Thermo Fisher Scientific) at $2 \times 10^6$ beads/mL, 50 μL/well of human pan T cells at $2 \times 10^6$ cells/mL, and 50 μL of assay media alone or containing 1.6 μg/mL αCD28 (Cat: 555725; BD Pharmigen) were added to each well of the assay plate. The final volume of each well on the plate was 200 μL. For those control wells that did not contain test article or αCD3 beads, assay media was added to bring up the total volume to 200 μL and the plates were incubated for 72 hours in a tissue culture incubator. The supernatants were then collected from each well and the released cytokines of IFN-γ, TNF-α and IL-2R were measured using a Cytokine ELISA Kit from R&D System (Human IL-2 DuoSet ELISA (Cat: DY202), Human IFN-gamma DuoSet ELISA (Cat: DY285) and Human TNF-alpha DuoSet ELISA (Cat: DY210) or similar commercial reagents. The ELISA methods were provided with the kits. Microsoft Excel and SoftMax Pro were used for data analysis to extrapolate cytokine levels, which were plotted with Prism.

Figure 8:
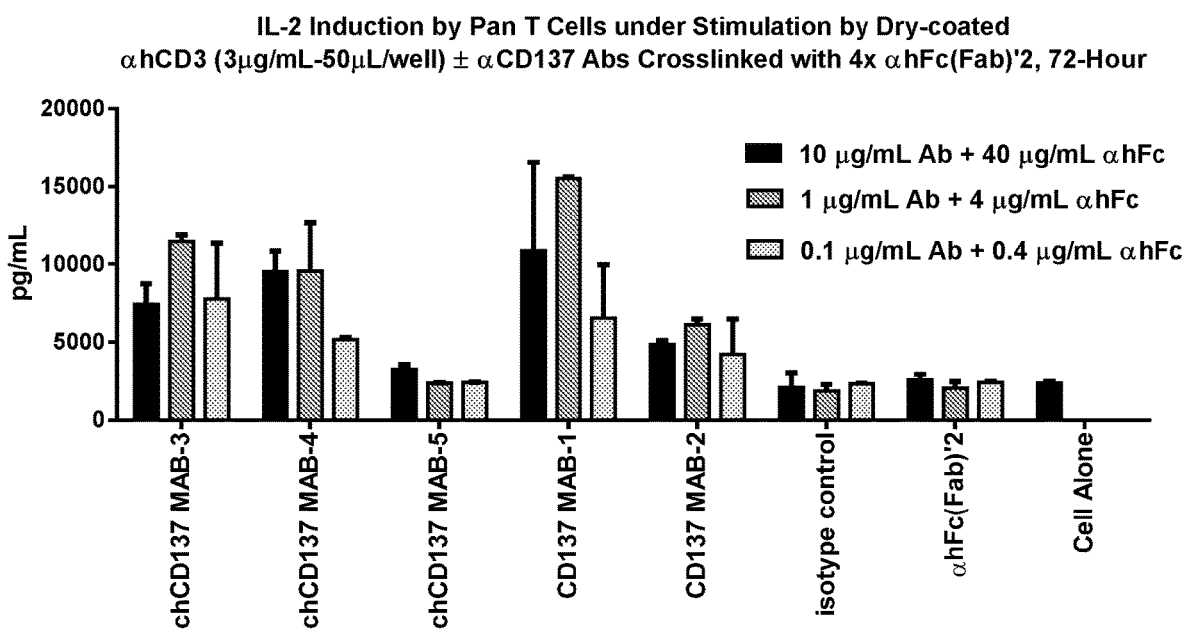
FIG. 8 shows the induction after 72 hours of IL-2 secretion by pan T cells upon stimulation with dry-coated anti-CD3 antibody (3 µg/mL-50 µg/mL) in the presence of the anti-CD137 antibodies urelumab or utomilumab (CD137 MAB-1 or CD137 MAB-2, respectively) or the novel chimeric anti-CD137 antibodies (chCD137 MAB-3, chCD137 MAB-4 or chCD137 MAB-5) that had been crosslinked with 4×hFc F(ab)'$_2$. The cross-linked antibodies (Ab+αhFc) were used at 0.1, 1.0 or 10 µg/mL. The following controls are also plotted: stimulated pan T cells treated with isotype control antibody, hFc F(ab)'$_2$ alone, or untreated cells.

As shown in FIG. 8, CD137 MAB-1, chCD137 MAB-3 and chCD137 MAB-4 each exhibited strong agonist activity, CD137 MAB-2 exhibited less agonist activity and CD137 MAB-5 exhibited no agonist activity in the absence of ligand.

Figure 9:
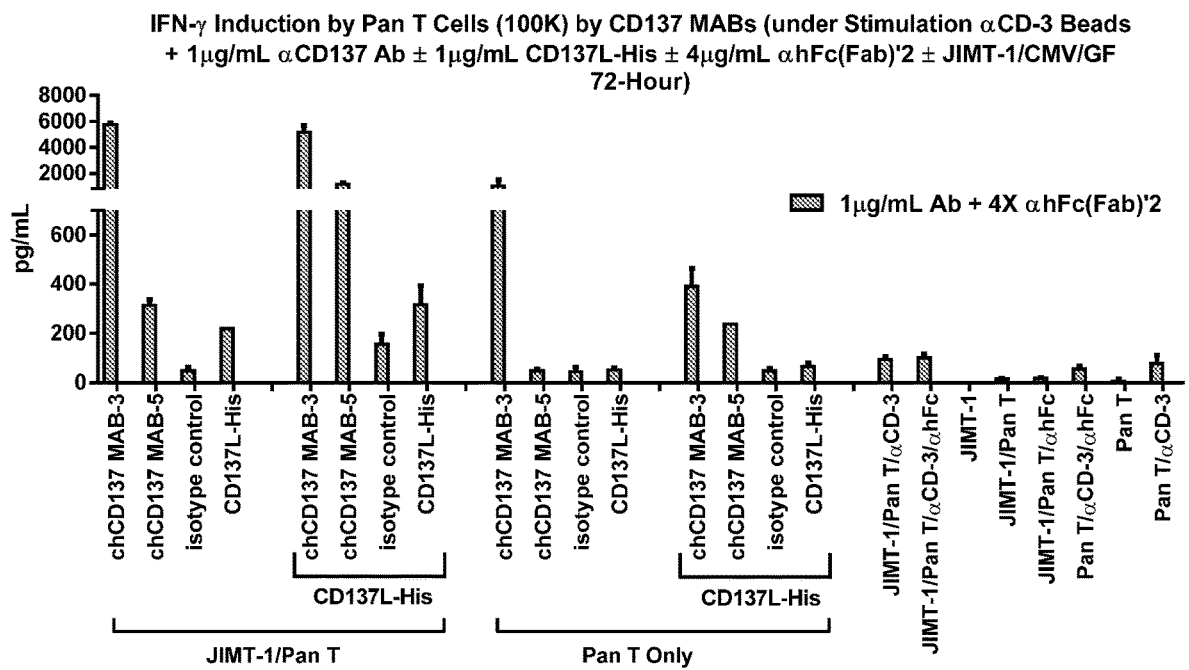
FIG. 9 shows the induction after 72 hours of IFN-γ secretion by pan T cells upon stimulation with anti-CD3 beads in the presence of cross-linked chimeric anti-CD137 antibodies (chCD137 MAB-3 or chCD137 MAB-5) (1 μg/mL CD-137 antibody+4 μg/mL hFc F(ab)'$_2$)±JIMT-1 (HER2/neu$^{++}$) target cells, in the presence or absence of ligand (1 μg/mL CD-137L-His). The following control samples are also plotted: stimulated pan T cells JIMT-1 cells, ±hFc F(ab)'$_2$, and untreated/unstimulated pan T cells and JIMT-1 cells.

Chimeric antibodies chCD137 MAB-3 and chCD137 MAB-4 were also tested for their ability to induce cytokine (e.g., IFN-γ, TNF-α) release from pan T cells in the absence and presence of ligand and/or target cells. Human pan T cells were purified from donor PBMC using Dynabeads Untouched Human T Cells Kit (Invitrogen Cat #11344D) per manufacture's protocol. The results for IFN-γ release are on shown in FIG. 9. FIG. 9 shows the induction of IFN-γ by pan T cells 72 hours after stimulation with CD3 coated beads in the presence or absence of 1 μg/mL chimeric anti-CD137 antibodies (chCD137 MAB-3 or chCD137 MAB-5), and in the presence or absence of 1 μg/mL CD-137L-His and 4 μg/mL hFc F(ab)'₂. The figure shows that IFN-γ was induced in the presence or absence of CD137-His, and that greater induction was observed with JIMT-1/pan T cells relative to that observed with pan T cells alone. Similar results were seen for TNF-α.

In the presence of both T-cells and Target cells, or T-cells alone, chCD137 MAB-3 exhibited strong agonist activity which was similar in the presence or absence of ligand. In contrast, chCD137 MAB-5 exhibited minimal agonist activity in the absence of ligand and a greatly enhanced agonist activity in the presence of ligand.

Example 3

The Humanization of Murine Anti-CD137 mAbs

Antibodies CD137 MAB-3 and CD137 MAB-4 were selected for humanization. Four rounds of humanization were undertaken for CD137 MAB-3, which yielded one humanized VH domain, designated as "hCD137 MAB-3 VH1" (SEQ ID NO:76), and three humanized VL domains, designated as "hCD137 MAB-3 VL1" (SEQ ID NO:87), "hCD137 MAB-3 VL2" (SEQ ID NO:88) and "hCD137 MAB-3 VL3" (SEQ ID NO:89).

Three rounds of humanization were undertaken for CD137 MAB-4, which yielded one humanized VH domain, designated as "hCD137 MAB-4 VH1" (SEQ ID NO:92), and two humanized VL domains, designated as "hCD137 MAB-4 VL1" (SEQ ID NO:94) and "hCD137 MAB-4 VL2" (SEQ ID NO:95).

The humanized heavy and light chain variable domains of a particular anti-CD137 antibody (e.g., CD137 MAB-3) may be used in any combination and particular combinations of humanized chains are referred to by reference to the specific VH/VL Domains, for example a humanized antibody comprising hCD137 MAB-3 VH1 and hCD137 MAB-3 VL3 is referred to herein as "hCD137 MAB-3 (1.3)."

The binding affinities of the chimeric antibodies having the murine variable domains and fully humanized antibodies were examined by Biacore.

Thus, an extracellular portion of human CD137 fused to a histidine-containing peptide ("huCD137") was passed over a surface coated with immobilized antibody. Briefly, each test molecule was captured onto an F(ab)$_2$ goat-anti-human Fc-coated surface and then incubated in the presence of different concentrations (25 nM and 100 nM) of huCD137. The kinetics of binding were determined via BIACORE® analysis binding (normalized 1:1 Langmuir binding model). The calculated $k_a$, $k_d$ and $K_D$ from these studies are presented in Table 10 and show that the humanized mAbs exhibited about a 2-fold decrease in binding affinity relative to the murine antibodies.

TABLE 10

| Antibody | VH | VL | $k_a$ (M$^{-1}$s$^{-1}$) | $k_d$ (s$^{-1}$) | $K_D$ (nM) |
|---|---|---|---|---|---|
| chCD137 MAB-3 | murine | murine | 8.9 × 10$^5$ | 0.020 | 23 |
| chCD137 MAB-3 (1.1) | 1 | 1 | 6.7 × 10$^5$ | 0.031 | 46 |
| chCD137 MAB-3 (1.2) | 1 | 2 | 6.1 × 10$^5$ | 0.030 | 49 |
| chCD137 MAB-3 (1.3 | 1 | 3 | 6.6 × 10$^5$ | 0.033 | 50 |
| chCD137 MAB-4 | murine | murine | 1.5 × 10$^5$ | 9.2 × 10$^{-4}$ | 6.1 |
| chCD137 MAB-4 (1.1) | 1 | 1 | 1.3 × 10$^5$ | 2.1 × 10$^{-3}$ | 16.2 |
| chCD137 MAB-4 (1.2) | 1 | 2 | 1.4 × 10$^5$ | 1.9 × 10$^{-3}$ | 13.6 |

Example 4

Characterization of CD137×TA Binding Molecules

Figure 3D:
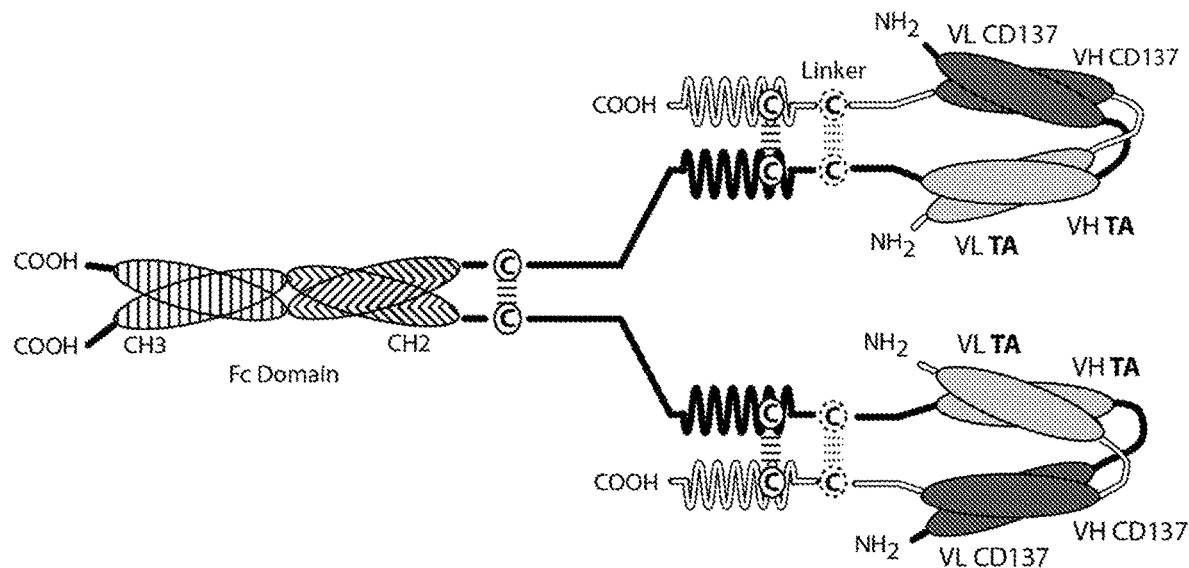
Figure 3E:
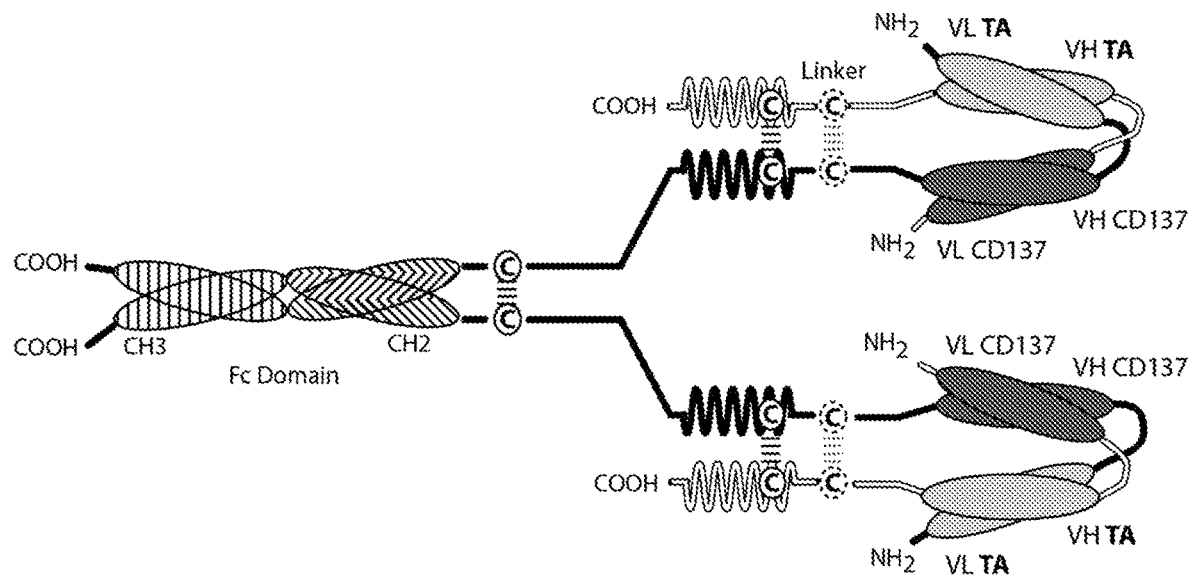

As described above a number of exemplary CD137×TA Binding Molecules capable of binding to CD137 and to the exemplary TA, HER2/neu, were generated. In particular, six bispecific diabodies (designated "DART-A," "DART-B," and "DART-C," "DART-D," "DART-E," and "DART-G") comprising CD137 MAB-3 or hCD137 MAB-3 domains, one bispecific diabody (designated "DART-F") comprising CD137 MAB-4 domains, two bispecific diabodies (designated "DART-1," and "DART-4") comprising CD137 MAB-1 domains, and two bispecific diabodies (designated "DART-2," and "DART-5") comprising CD137 MAB-2 domains, were generated, each comprising hHER2 MAB-1 domains. DART-A, DART-B, DART-C, DART-1, and DART-2 have the general structure shown in FIG. 3B (DART-A, DART-B, DART-1 and DART-2 have the structure shown in FIG. 3E; DART-C has the structure shown in FIG. 3D). DART-D, DART-E, DART-F, DART-G, DART-4, and DART-5 have the general structure shown in FIG. 5A (DART-D, DART-F, DART-G, DART-4, and DART-5 have the structure shown in FIG. 5B; DART-E has the structure shown in FIG. 5C).

Another exemplary CD137×TA Binding Molecule capable of binding to CD137 and to the exemplary TA, EphA2 (designated "DART-7") was generated. DART-7 is a bispecific diabody having the structure presented in FIG. 3B, comprising CD137 MAB-1 humanized EphA2 MAB-3 domains.

In addition, three control molecules, "DART-3," comprising hHER2 MAB-1 and variant palivizumab domains (HER2×RSV), "DART-6," comprising variant palivizumab and CD137 MAB-3 domains (RSV×CD137), and "DART-8," comprising humanized EphA2 MAB-3 and variant palivizumab domains (EphA2×RSV), were generated.

Figure 10A:
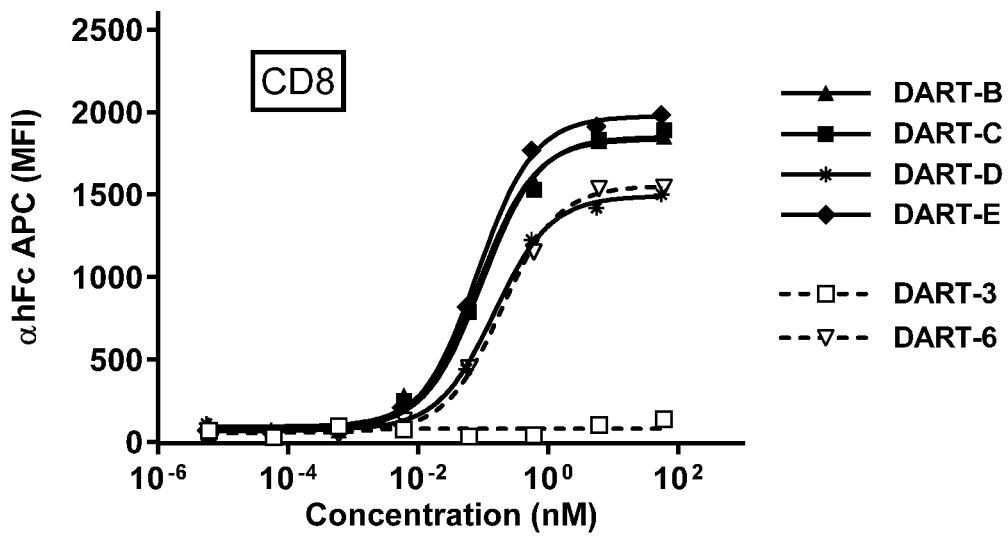
FIGS. 10A-10B show the ability of CD137×TA Binding Molecules to bind to CD137 of activated CD8$^+$ T cells as measured by FACS using FITC-labeled CD8 and αhFc APC.
Figure 10B:
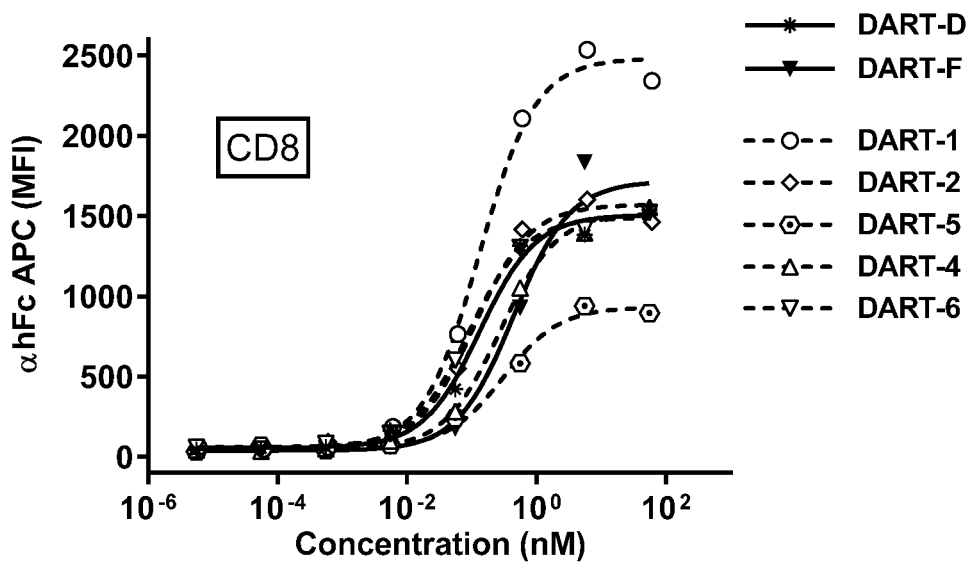

CD137×TA Binding Molecules having two binding sites for CD137 and 2 binding sites for HER2/neu, and the CD137×RSV control molecule (DART-6) bound to CD137 present on the surface of activated T cells. In contrast, the HER2/neu×RSV control molecule (DART-3) did not exhibit any binding. DART-1 exhibited the highest binding and DART-5 exhibited the lowest binding in this assay, with the remaining molecules tested (DART-B, DART-C, DART-D, DART-E, DART-F, DART-2, DART-4 and DART-6) exhibiting comparable binding (FIG. 10). The relative positions of the HER2/neu and CD137 binding domains had minimal to no impact on CD137 binding in this assay for molecules having the structure presented in FIG. 3B (compare DART-B/DART-C) or the structure presented in FIGS. 5B-5C (compare DART-D/DART-E).

Figure 11A:
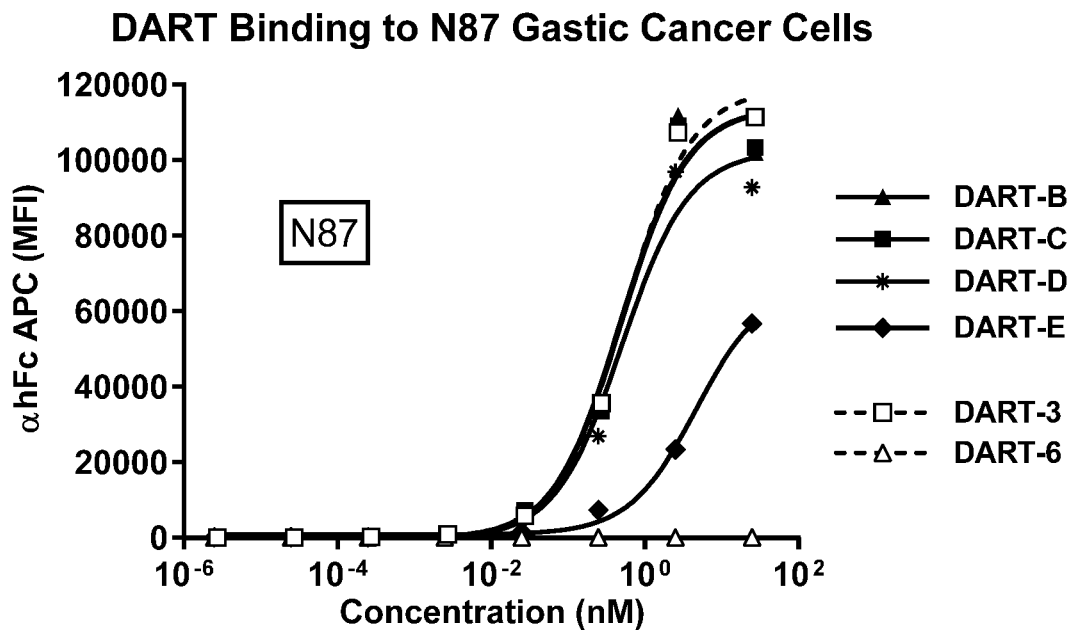
FIGS. 11A-11B show the ability of CD137×TA Binding Molecules to bind to an illustrative TA, HER2/neu, on the surface of target N87 (HER2$^{+++}$) gastric cancer cells as measured by mean fluorescence intensity (MFI).
Figure 11B:
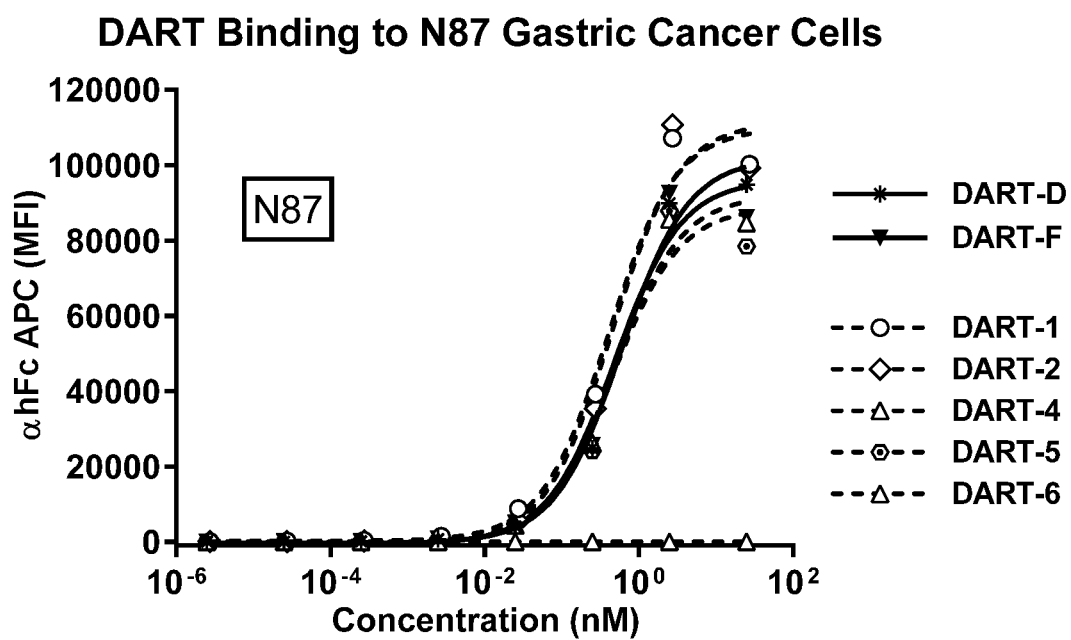

Similarly, the CD137×TA Binding Molecules were evaluated for their ability to bind to HER2/neu present on the surface of target N87 gastric cancer cells (FIGS. 11A-11B). The RSV×CD137 control molecule (DART-6) did not exhibit any binding. The relative positions of the HER2/neu and CD137 binding domains had minimal to no impact on HER2/neu binding in this assay for molecules having the structure presented in FIG. 3B (compare DART-B/DART-C). In contrast, DART-E exhibited reduced HER2/neu binding as compared to DART-D, suggesting that there may be a positional effect on HER2/neu binding for molecules having the structure presented in FIGS. 5B-5C, or that the binding mediated by the HER2/neu binding domains of hHER2 MAB-1 (1.3) in particular, exhibits a positional effect.

Figure 12A:
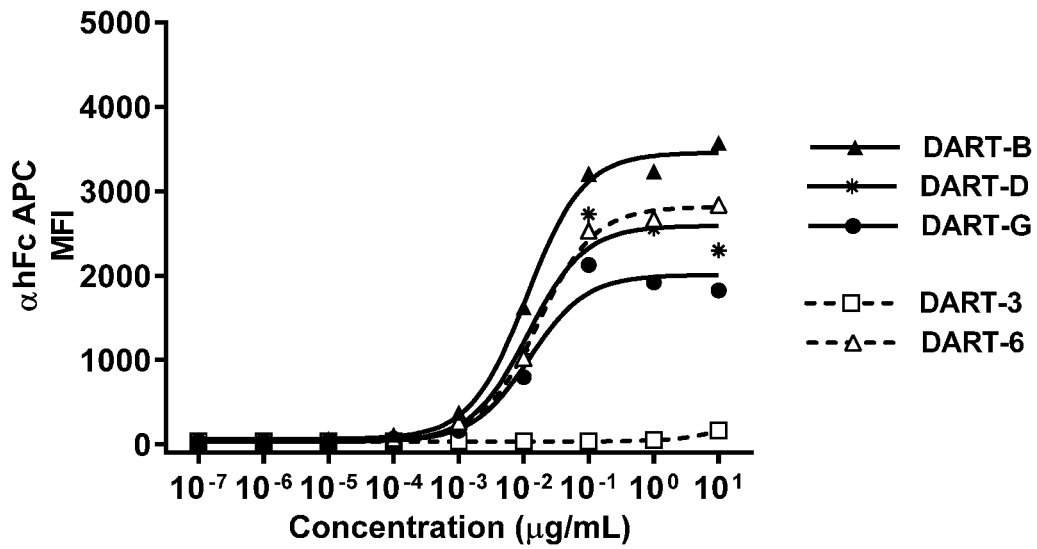
FIGS. 12A-12B show the ability of CD137×TA Binding Molecules DART-B, DART-D, and DART-G, and the control molecules DART-3, and DART-6 to bind to CD137 expressed by engineered CHO cells (FIG. 12A) and CD137 expressed by activated CD8$^+$ T cells (FIG. 12B).
Figure 12B:
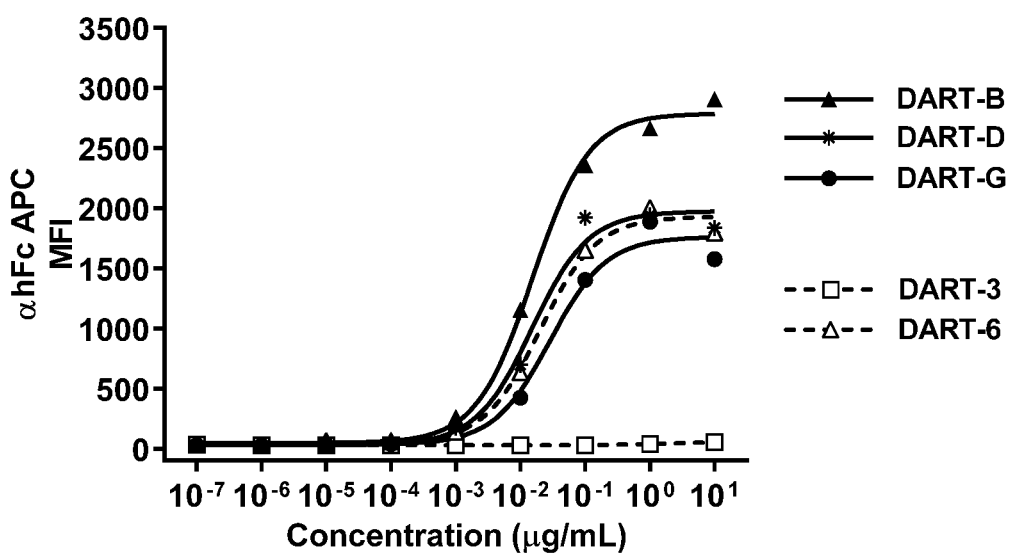

CD137×TA Binding Molecules, DART-B, DART-D, DART-G and the control molecules DART-3 and DART-6 were additionally evaluated for their ability to bind to CD137 expressed by CHO cells (FIG. 12A) and activated T cells (FIG. 12B).

Figure 13A:
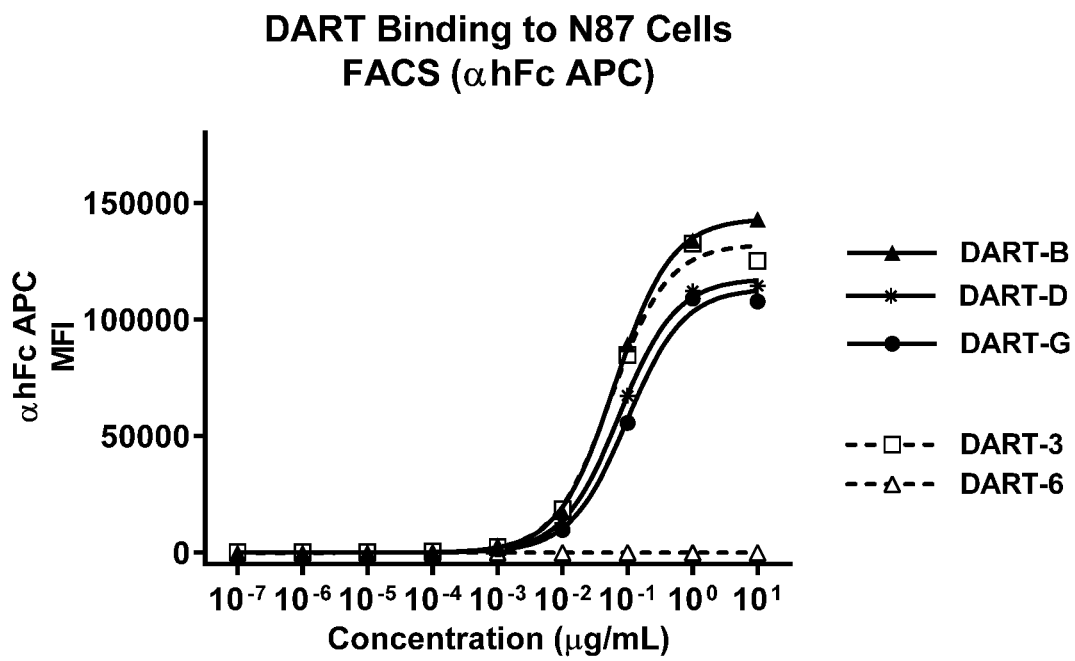
FIGS. 13A-13B show the ability of CD137×TA Binding Molecules DART-B, DART-D, and DART-G, and the control molecules DART-3, and DART-6 to bind to an illustrative TA, HER2/neu, expressed by target N87 (HER2$^{+++}$) gastric cancer cells (FIG. 13A) and target JIMT-1 (HER2$^{++}$) cells (FIG. 13B).
Figure 13B:
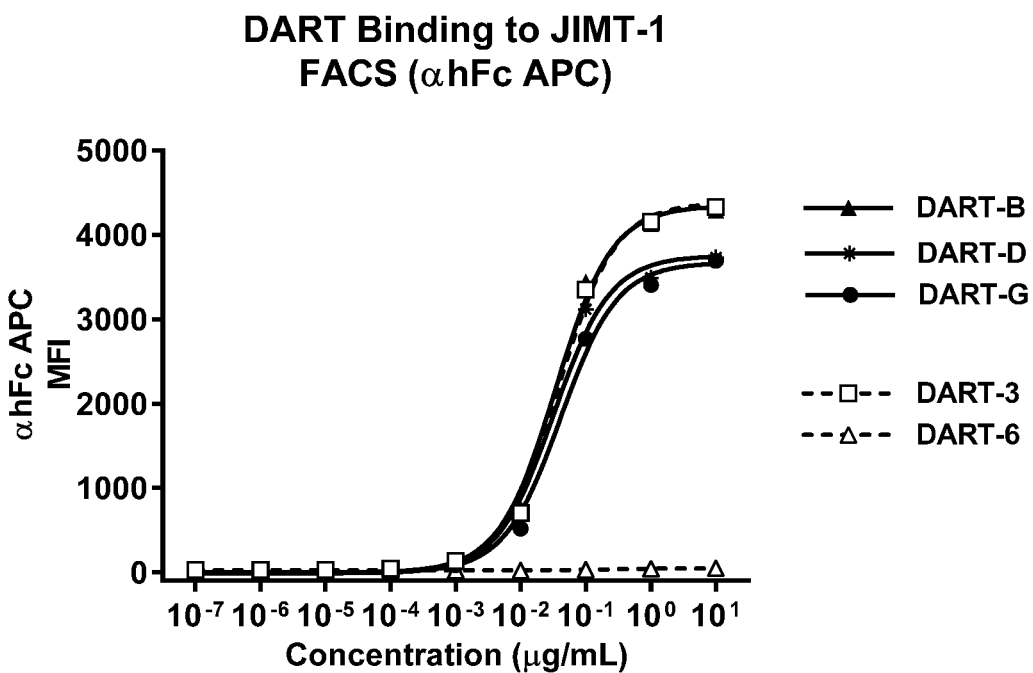

CD137×TA Binding Molecules, DART-B, DART-D, DART-G and the control molecules DART-3 and DART-6 were additionally evaluated for their ability to bind to HER2/neu expressed on N87 cells (FIG. 13A) and JIMT-1 cells (FIG. 13B). For such evaluation, 100 µL of HER2/neu expressing target cells (1.0×10$^6$ cells/mL) and 100 µL of serially diluted (5- or 10-fold dilutions) test article (bispecific diabody) were added to each well of microtiter assay plate(s), mixed and incubated at RT for 45 min. The cells were washed with FACS Buffer and secondary antibody (anti-human-Fc region-APC) was then added to each well; mixed and incubated at RT for 30 min. Cells were washed and resuspended in 100 µL FACS Buffer and analyzed by flow cytometry (BD LSR Fortessa or FACSCanto 11) for cell event collection. Data analysis were performed via FloJo v10. The HER2×CD137 Binding Molecules having the structure presented in FIG. 3B exhibited slightly better binding to HER2/neu than those having the structure presented in FIGS. 5A-5C (compare DART-B/DART-D). The RSV×CD137 control molecule (DART-6) did not exhibit any binding. CD137×TA bispecific diabodies having a murine or humanized CD137 binding site exhibited similar binding to HER2/neu (compare DART-D/DART-G).

Figure 14A:
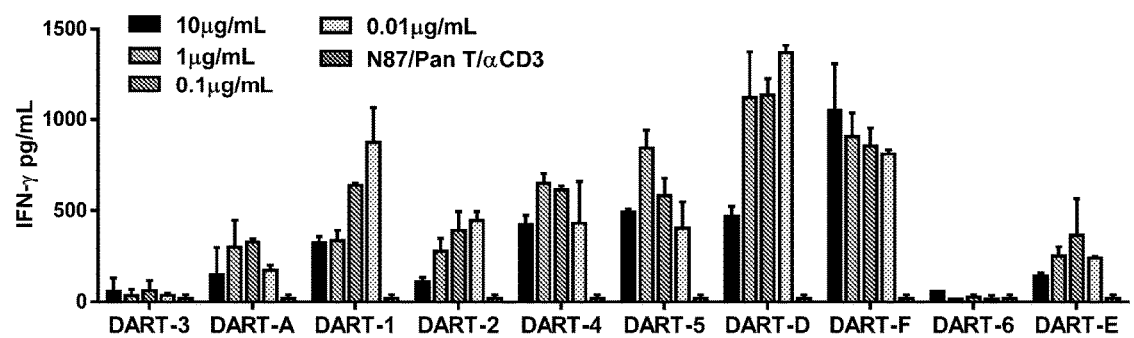
FIGS. 14A-14B provide the results of a first representative assay of the ability of CD137×TA Binding Molecules to mediate a co-stimulatory activity in a T cell cytokine release assay (exemplified by release of IFN-γ). The Figures show results for DART-1, DART-2, DART-4, DART-5, DART-A, DART-D, DART-E and DART-F, and the control molecules, DART-3 and DART-6, tested in the presence of HER2/neu-expressing N87 (HER2$^{+++}$) (FIG. 14A) or JIMT-1 (HER2$^{++}$) target cells (FIG. 14B), no co-stimulatory activity was seen using HER2/neu-negative Hs700T target cells, or no target cells.
Figure 14B:
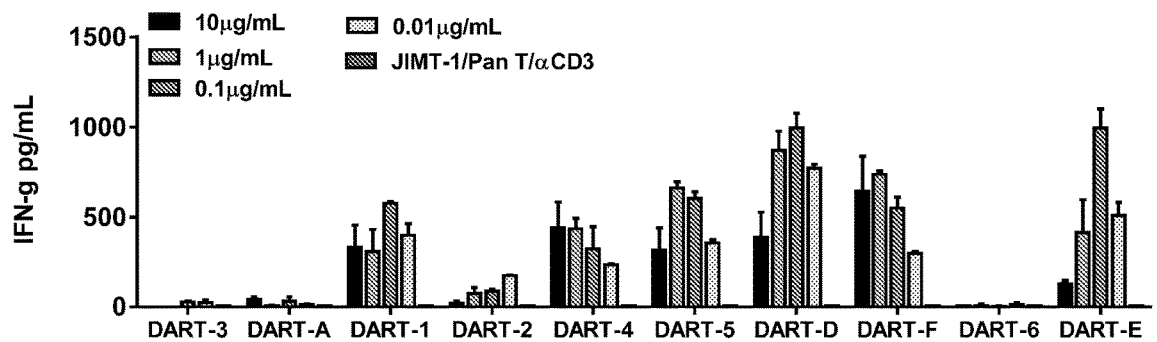

FIGS. 14A-14B provide the results of a first representative assay of the ability of CD137×TA Binding Molecules to mediate a co-stimulatory activity in a T cell cytokine release assay (performed essentially as described in Example 2 above, and exemplified by release of IFN-γ) in the presence or absence of target cells expressing the exemplary TA, HER2/neu. The Figures show results for DART-1, DART-2, DART-3, DART-4, DART-5, DART-6, DART-A, DART-D, DART-E and DART-F, tested (using the above-described protocols) in the presence of HER2/neu-expressing N87 (3$^+$) (FIG. 14A) or JIMT-1 (2$^+$) target cells (FIG. 14B), HER2/neu-negative Hs700T target cells, or no target cells. The results show that the control molecules, DART-3 and DART-6 exhibited no co-stimulatory activity. The CD137×TA Binding Molecules did not exhibit any observable co-stimulatory activity in the absence of target cells or with HER2/neu-negative target cells. DART-D and DART-F, comprising novel anti-CD137 antibodies (CD137 MAB-3 and MAB-4, respectively) exhibited the highest co-stimulatory activity in the presence of either target cell line. DART-E (comprising swapped HER2/neu and CD137 domains) exhibited lower co-stimulatory activity, particularly in presence of N87 target cells. Similar patterns were seen with IL-2 and TNF-α.

Figure 15A:
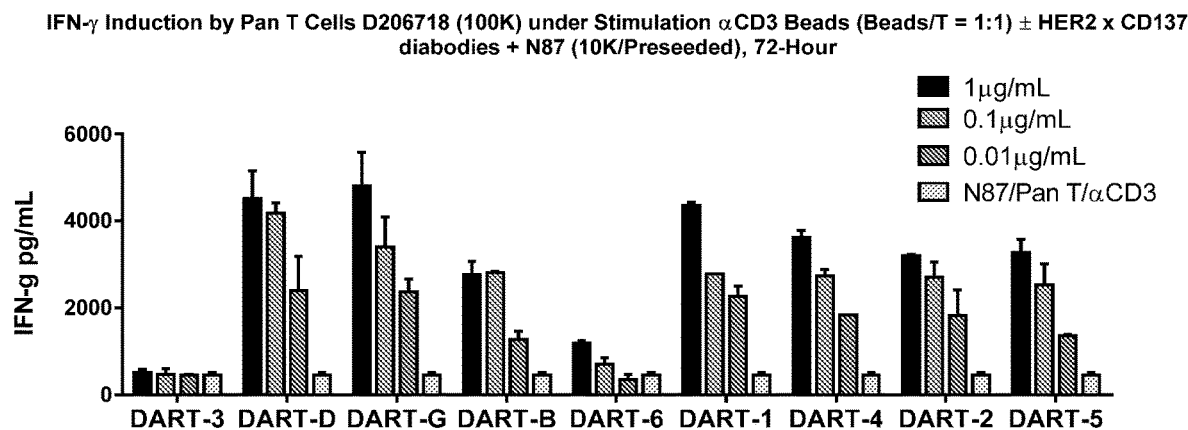
FIGS. 15A-15B provide the results of a second representative assay of the ability of CD137×TA Binding Molecules to mediate a co-stimulatory activity in a T cell cytokine release assay (exemplified by the release of IFN-γ). The Figures show results for DART-1, DART-2, DART-4, DART-5, DART-B, DART-D and DART-G, and the control molecules DART-3 and DART-6, tested in the presence of HER2/neu-expressing N87 (HER2$^{+++}$) (FIG. 15A) or JIMT-1 (HER2$^{++}$) target cells (FIG. 15B), no co-stimulatory activity was seen using HER2/neu-negative Hs700T target cells, or in the absence of target cells.
Figure 15B:
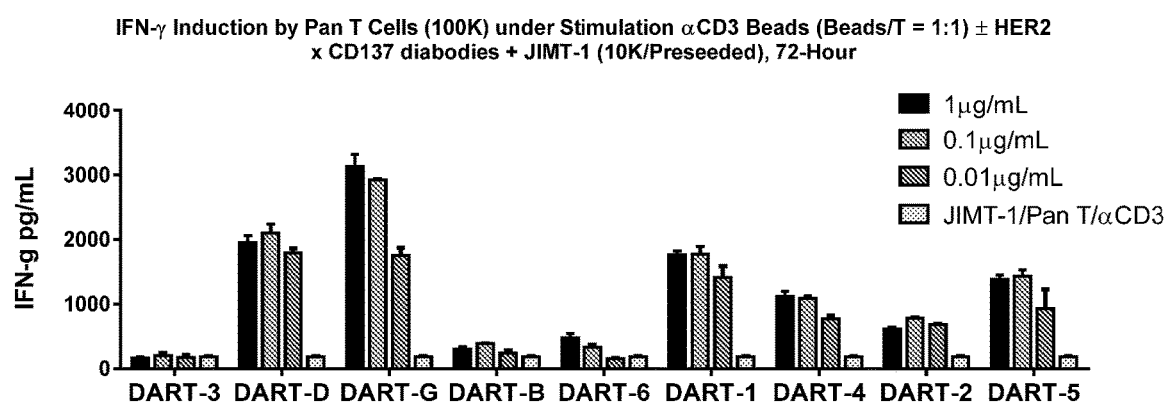

FIGS. 15A-15B provide the results of a second representative assay of the ability of CD137×TA Binding Molecules to mediate a co-stimulatory activity in a T cell cytokine release assay (performed essentially as described in Example 2 above, and exemplified by release of IFN-γ). The Figures show results for DART-1, DART-2, DART-3, DART-4, DART-5, DART-6, DART-B, DART-D and DART-G, tested (using the above-described protocols) in the presence of HER2/neu-expressing N87 (FIG. 15A) or JIMT-1 target cells (FIG. 15B), HER2/neu-negative Hs700T target cells, or no target cells.

The results show that the control molecules, DART-3 and DART-6 exhibited no co-stimulatory activity. The CD137×TA Binding Molecules did not exhibit any observable co-stimulatory activity in the absence of target cells or with HER2/neu-negative target cells. DART-D and DART-G, comprising the novel anti-CD137 antibody, CD137 MAB-3 (murine and humanized, respectively) exhibited the highest co-stimulatory activity in the presence of either target cell line. DART-G exhibited the highest co-stimulatory activity despite exhibiting slightly lower binding to cell surface expressed CD137. As detailed above, DART-B and DART-G comprise the same HER2 and CD137 binding sites but have the structures shown in FIG. 3B and FIG. 5B, respectively. DART-G exhibited higher co-stimulatory activity than DART-B in the presence of either target cell line.

Figure 16A:
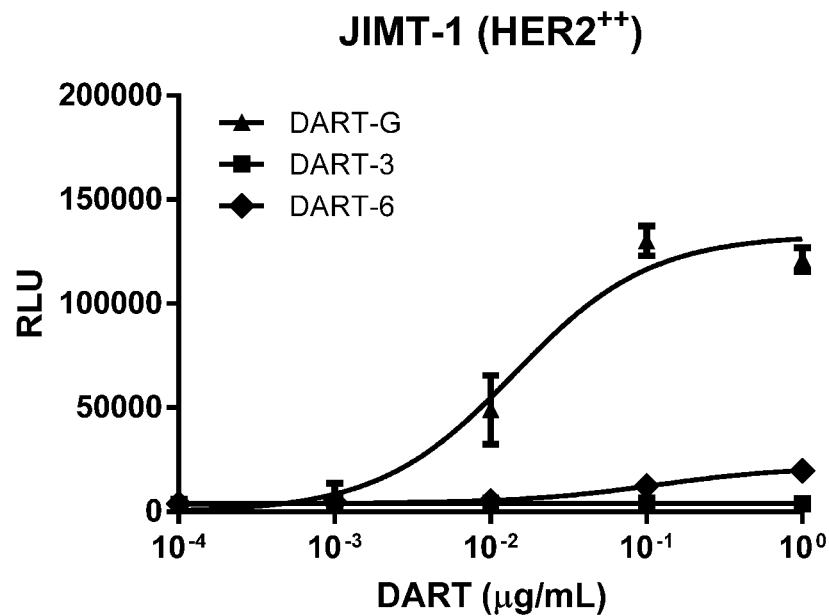
FIGS. 16A and 16B show the ability of CD137×TA Binding Molecules to mediate dose and target dependent signal transduction of NF/kB pathway in CD137 expressing reporter cell line (Jurkat-NF-κB-Luc) as demonstrated by increased luciferase expression. The Figures show results for DART-G, and the control binding molecules DART-3 and DART-6 on CD137 expressing Jurkat-NF-κB-Luc cells co-cultured with either HER2/neu expressing JIMT-1 cells (FIG. 16A) or HER2/neu-negative KG-1 cells (FIG. 16B).
Figure 16B:
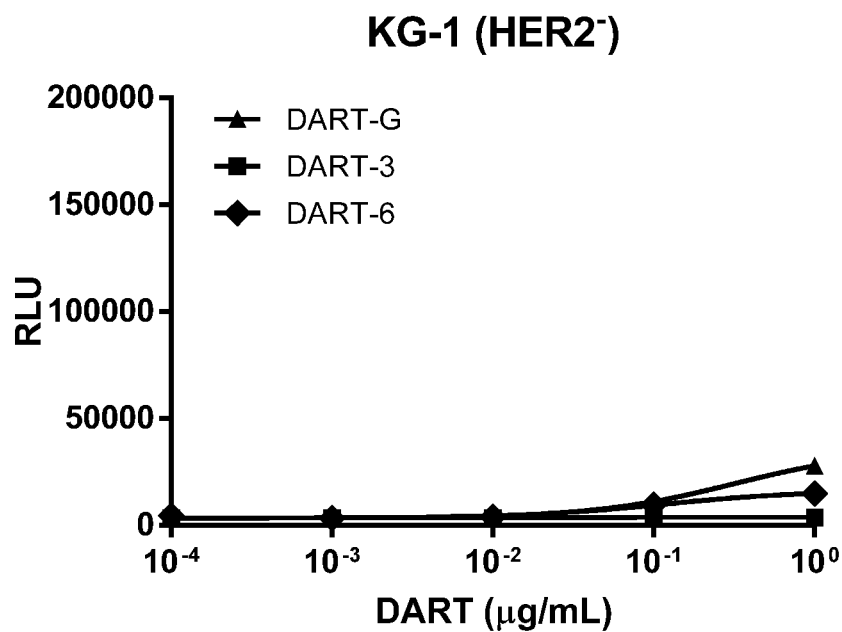

The CD137×TA Binding Molecule, DART-G and the control molecules, DART-3 and DART-6, were additionally evaluated for their ability to mediate dose dependent T-cell signal transduction of the NF/κB pathway in a CD137 expressing reporter cell line (Jurkat-NF-κB-Luc) in the presence of target cells positive or negative for the exemplary TA, HER2/neu. Briefly, Jurkat-NF-κB-Luc reporter cells overexpressing CD137 were co-cultured with HER2/neu expressing JIMT-1 cells (FIG. 16A) or HER2/neu-negative KG-1 cells (FIG. 16B) in the presence of increasing concentrations of DART-G, DART-3, or DART-6. After incubation, signal transduction was measured by luminescence with luminescence relative light unit (RLU) as the read-out. The results show that CD137×TA Binding Molecules such as DART-G, mediate dose dependent T-cell signal transduction that is dependent on the presence of TA-expressing target cells.

The CD137×TA Binding Molecule, DART-A and the control molecules, DART-3 and DART-6, were additionally evaluated for their ability to mediate enhanced T-cell proliferation in the presence of cells expressing different levels of the exemplary TA, HER2/neu. Briefly, CFSE-labeled human T cells ±sub-optimal αCD3/αCD28 stimulation were co-cultured with HER2/neu-high N87 target cells (FIG. 17, Panels A-C and J-K), HER2/neu-low MCF-7 target cells (FIG. 17, Panels D-F and L-M), or were cultured alone (FIG. 17, Panels G-I and N-O) in the presence of DART-A (FIG. 17, Panels A, D and G), DART-3 (FIG. 17, B, E and H), DART-6 (FIG. 17, Panels C, F and I), or no molecule (FIG. 17, Panels J, L and N) and monitored for T cell proliferation. The results show that CD137×TA Binding Molecules, such as DART-A, enhance T-cell signal proliferation. Such enhanced T cell proliferations is TA-expression dependent and correlates with TA expression levels.

Figure 18A:
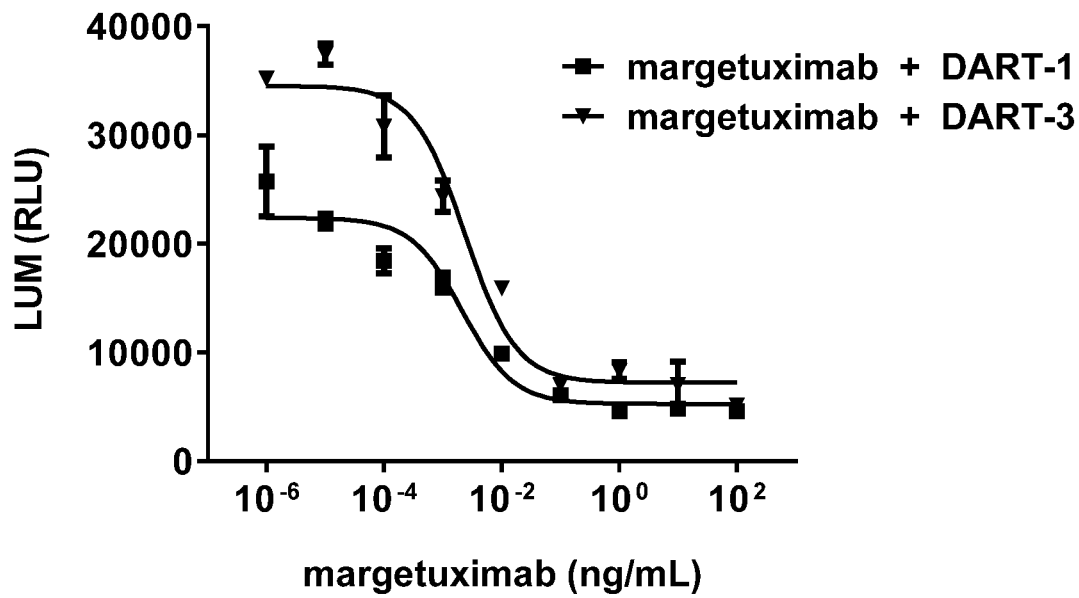
FIGS. 18A-18B show the ability of CD137×TA Binding Molecule DART-1 to enhance the anti-TA antibody margetuximab-mediated ADCC killing of N87 target cells as measured by cell-associated luciferase activity (FIG. 18A) and to enhance margituximab-mediated NK cell activation as measured by CD69 expression (FIG. 18B).
Figure 18B:
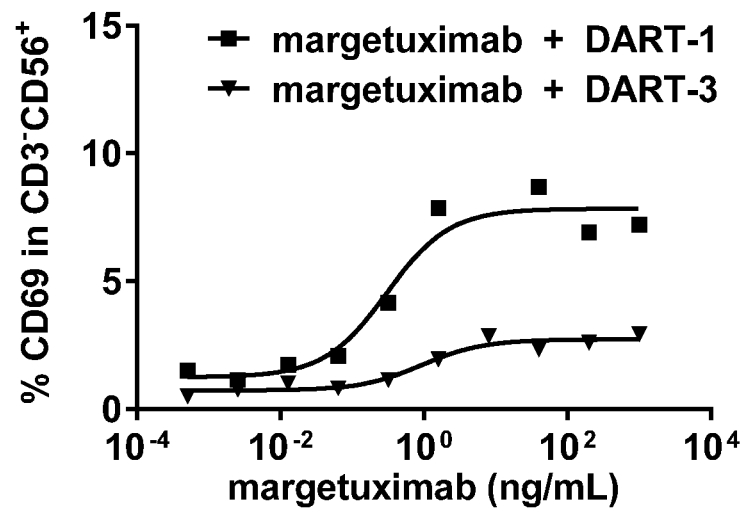

Margetuximab is an Fc-optimized anti-HER2/neu monoclonal antibody that can induce enhanced antibody dependent cell-mediated cytotoxicity after binding target tumor cell. As noted above, HER2 MAB-1 binds to a HER2/neu epitope that is distinct from that bound by margetuximab. The target cell killing activity of the anti-TA antibody margetuximab was examined in combination with the CD137×TA Binding Molecule DART-1 or the control molecule DART-3 (HER2×RSV). Briefly, target N87 cells that had been engineered to express the luciferase (luc) reporter gene (N87/GFP/Luc cells) were incubated with purified NK effector cells (at an effector:target (E:T) ratio of 2:1, increasing concentrations of margetuximab in combination with a fixed concentration (0.1 μg/mL) of DART-1 or DART-3 for 72 hours, and cytotoxicity was determined by luminescence (LUM) assay measuring cellular luciferase activity of the target cells with luminescence relative light unit (RLU) as the read-out (FIG. 18A). In addition, NK cells (CD3$^-$/CD56$^+$) from this assay were evaluated for expression of the activation marker, CD69 (FIG. 18B). The results of this study demonstrate that the CD137×TA Binding Molecule DART-1 enhanced both margituximab-mediated ADCC activity against N87/Luc target cells, and margituximab-mediated CD69 upregulation on NK cells as compared to the control molecule having just HER2/neu binding.

Figure 19A:
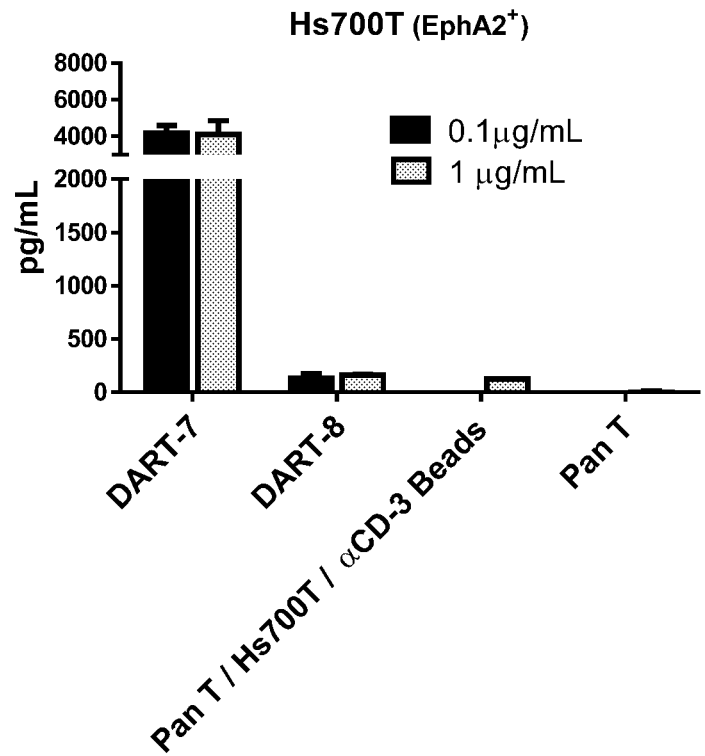
FIGS. 19A-19B show the results of a representative assay of the ability of the CD137×TA Binding Molecule DART-7, and the control molecule DART-8 to mediate co-stimulatory activity in a T cell cytokine release assay (exemplified by the release of IFN-γ). Cytokine release was measured in the presence of EphA2-expressing Hs700T target cells (FIG. 19A), or EphA2-negative Hs700T (EphA2.KO) target cells (FIG. 19B), or with no target cells present. The following control samples are also plotted: stimulated pan T cells+ target cells, and untreated/unstimulated pan T cells.
Figure 19B:
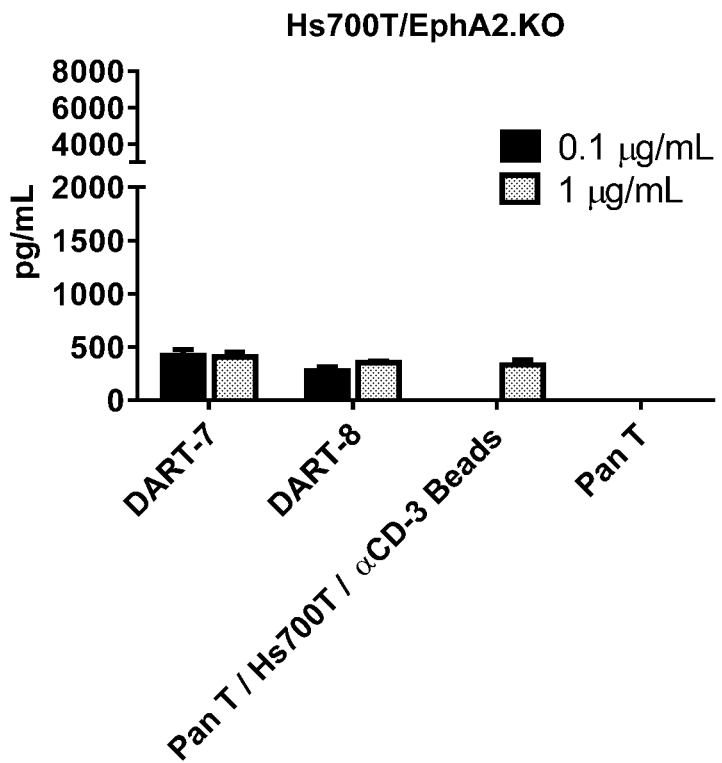

The ability of a CD137×TA Binding Molecule designated "DART-7," which binds the illustrative TA EphA2, to mediate a co-stimulatory activity in a T cell cytokine release assay (performed essentially as described in Example 2 above, and exemplified by release of IFN-γ) was examined. The CD137×TA Binding Molecule DART-7 and the control molecule DART-8, were tested (using the above-described protocols) in the presence of EphA2-expressing Hs700T target cells (FIG. 19A) or EphA2-negative Hs700T (EphA2.KO) target cells (FIG. 19B), or no target cells. The results show that the CD137×TA Binding Molecule DART-7 exhibited co-stimulatory activity in the presence of EphA2-expressing cells but did not exhibit any observable co-stimulatory activity in the absence of target cells or with EphA2-negative target cells. The control molecule, DART-8 exhibited no co-stimulatory activity.

The co-stimulatory activity of CD137×TA Binding Molecules on T cell populations was examined by evaluating the fraction of Central Memory T cells (Tcm) and Effector Memory T Cells (Tem). Briefly, human T cells were co-cultured with EphA2 positive colon adenocarcinoma Colo205 target cells for 5 days under sub-optimal stimulation conditions in the presence of the CD137×TA Binding Molecule DART-7 or the control molecules DART-8 or DART-6. Following co-culture, the percentage of Tcm (CCR7⁺CD45RA⁻) and Tem (CCR7⁻CD45RA⁻) cells was determined in gated CD4⁺ and gated CD8⁺ subsets. The results, summarized in Table 11, show that there is a substantial increase in the fraction of CD8⁺ Tcm and Tem cell types and that this increase requires the binding of both CD137 and the TA (e.g., EphA2). These results indicate that CD137×TA Binding Molecules induce a substantial increase in the fraction of CD8⁺ Tcm and Tem cells in the presence of the proper tumor antigen expressing cells. The targeted T-cell agonism exhibited by CD137×TA Binding Molecules may offer an opportunity to induce tumor-cell anchored CD137 activation, limiting systemic immune-cell activation and related side effects.

TABLE 11

| Treatment | Gated CD4⁺ | | Gated CD8⁺ | |
|---|---|---|---|---|
| | Tcm (%) (CCR7⁺CD45RA⁻) | Tem (%) (CCR7⁻CD45RA⁻) | Tcm (%) (CCR7⁺CD45RA⁻) | Tem (%) (CCR7⁻CD45RA⁻) |
| DART-7 | 50.1 | 17.7 | 20.5 | 38.6 |
| DART-8 | 44.8 | 10.4 | 6.10 | 23.5 |
| DART-6 | 44.4 | 9.95 | 6.67 | 25.2 |

In addition, CD137×TA Binding Molecules having one binding site for CD137 and one or more binding sites for HER2/neu (see, e.g., FIGS. 4A, 5A, and 6A) were constructed and tested. Such molecules are monovalent for CD137, and exhibited reduced binding to activated T cells as expected in view of their reduced avidity. Such molecules exhibited a range of binding to target N87 cells. However, none of the molecules monovalent for CD137 exhibited any co-stimulatory activity in T cell cytokine release assays. This observation suggests that at least two CD137 binding sites may be required for co-stimulatory activity in these assays.

Example 5

Optimization of Humanized CD137 MAB-3

As noted above humanization of CD137 MAB-3 resulted in approximately a 2-fold loss in binding affinity (see, e.g., Table 9 above). Optimization was used to identify humanized CD137 MAB-3 clones having similar or better binding affinity than the parental murine antibody. Briefly, random mutagenesis was used to introduce substitutions within the Heavy Chain CDR$_H$3 (Kabat positions 99-102) domains of hCD137 MAB-3 (1.3). Three rounds of selection screening using increasing stringency were used to identify clones having enhanced binding to CD137. 48 clones were selected from rounds 2 and 3, and were evaluated as diabodies (having the structure shown in FIG. 5B) for affinity. Table 12 provides an alignment of the amino acid sequence of CDR$_H$3 Kabat residues 99-102 from four clones selected for enhanced binding to hCD137.

TABLE 12

| Clone ID | Clone SEQ ID NO. | CDR$_H$3 (Kabat 99-102) | CDR$_H$3 SEQ ID NO. |
|---|---|---|---|
| hCD137 MAB-3 VH1 | 76 | SYSFDY | 160 |
| hCD137 MAB-3 VH1A | 83 | AYSFHP | 78 |
| hCD137 MAB-3 VH1B | 84 | AYSMST | 79 |

TABLE 12-continued

| Clone ID | Clone SEQ ID NO. | CDR$_H$3 (Kabat 99-102) | CDR$_H$3 SEQ ID NO. |
|---|---|---|---|
| hCD137 MAB-3 VH1C | 85 | AYSYSL | 80 |
| hCD137 MAB-3 VH1D | 86 | SYSYNV | 81 |

The amino acid sequences of these clones were incorporated into the 5 chain diabody DART-G to yield optimized DART-G molecules (designated as DART-G1, DART-G2; DART-G3, and DART-G4). The binding affinity of DART-G2, DART-G3, and DART-G4 were evaluated via BIAcore (Table 11). For such evaluation, His-tagged soluble human CD137 (huCD137) or cynomolgus monkey CD137 (cynoCD137) (containing an extracellular portion of human or cynomolgus monkey CD137 fused to a histidine-containing peptide) was passed over a surface coated with immobilized antibody. Briefly, each test molecule was captured onto an F(ab)₂ goat-anti-human Fc-coated surface and then incubated in the presence of different concentrations (6.25-100 nM) of huCD137 or cynoCD137. The kinetics of binding were determined via BIACORE® analysis binding (normalized 1:1 Langmuir binding model). The calculated $k_a$, $k_d$ and $K_D$ from these studies are presented in Table 13.

TABLE 13

| hCD137 | | huCD137 | | | cynoCD137 | | |
|---|---|---|---|---|---|---|---|
| Molecule | MAB-3 VH Domain | $k_a$ (×10⁵) (M⁻¹s⁻¹) | $k_d$ (×10⁻³) (s⁻¹) | KD (nM) | $k_a$ (×10⁵) (M⁻¹s⁻¹) | $k_d$ (×10⁻⁴) (s⁻¹) | KD (nM) |
| DART-D | murine | 4.7 | 25 | 53 | 4.6 | 31 | 67 |
| DART-G | VH1 | 3.7 | 42 | 114 | 3.9 | 45 | 115 |
| DART-G2 | VH1B | 3.5 | 21 | 60 | 3.9 | 25 | 64 |
| DART-G3 | VH1C | 2.2 | 14 | 64 | 2.3 | 18 | 78 |
| DART-G4 | VH1D | 3.1 | 8.7 | 28 | 3.5 | 14 | 40 |

Figure 20A:
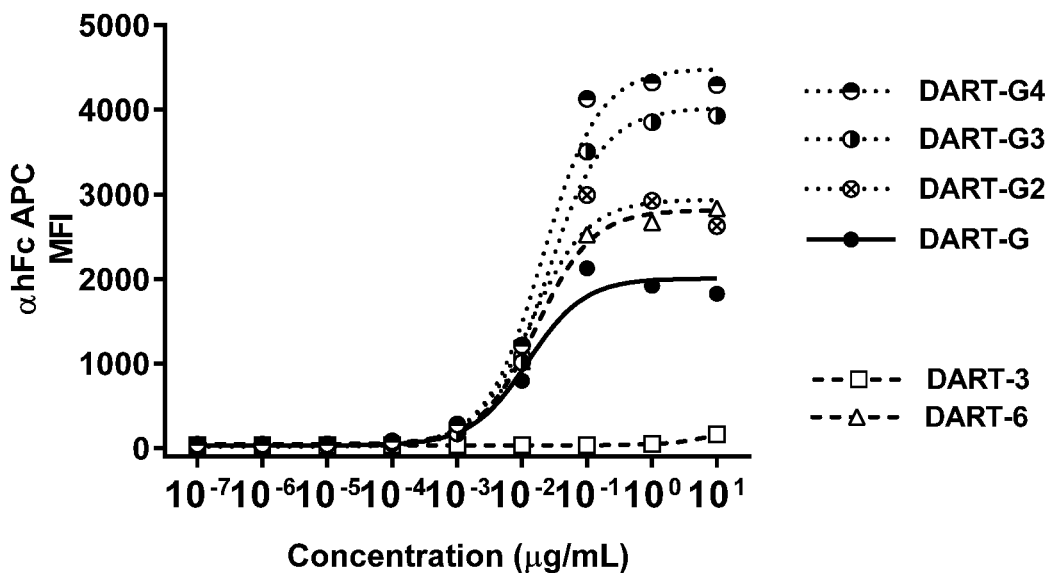
FIGS. 20A-20B show the ability of DART-G derivatives having optimized CDR$_H$3s to bind to CD137 expressed on the surface of engineered CHO cells (FIG. 20A) or CD8$^+$ T cells (FIG. 20B).
Figure 20B:
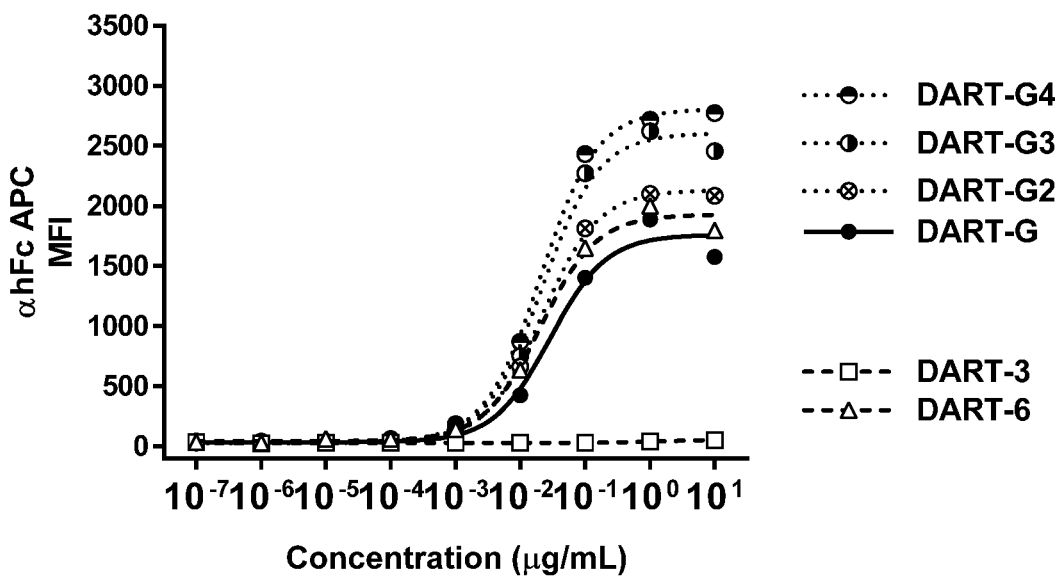

The diabodies were evaluated for their ability to bind CD137 in the same manner as described above. The results of this study are shown in FIGS. 20A-20B. As noted above DART-G, having hCD137 MAB-3 (1.3) binding sites for CD137 exhibited slightly lower binding as compared to constructs having the same structure but comprising the CD137 binding sites of murine CD137 MAB-3 (DART-6). HER2×CD137 diabodies comprising the optimized hCD137 MAB-3 VH domains exhibited higher binding, the relative binding activity of the molecules to human CD137 was: DART-G4>DART-G3>DART-G2≈DART-6>DART-G.

DART-G and the optimized variants all exhibited nearly identical binding to HER2 on the surface of multiple target cell types including: N87, JIMT-1 and MDA-MB231 cells.

Figure 21A:
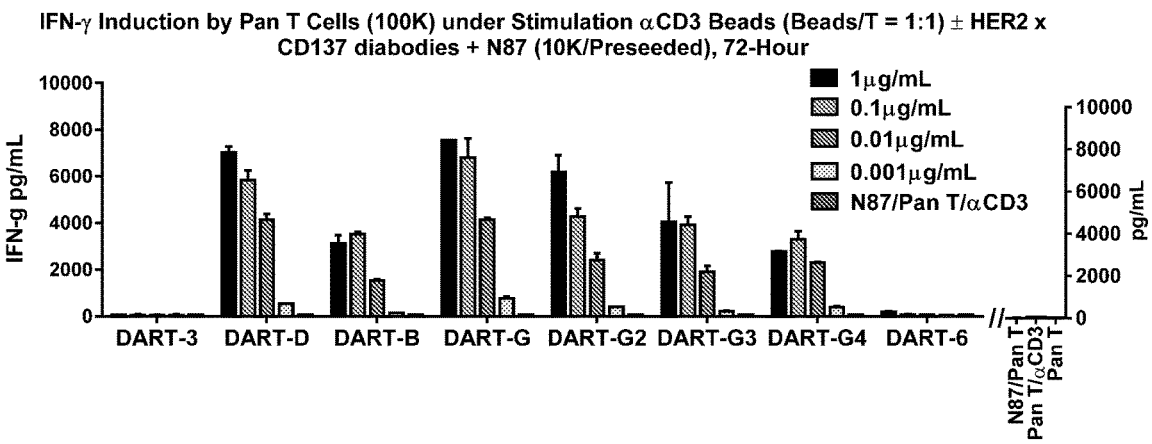
FIGS. 21A-21C show the results of a representative assay of the ability of CD137×TA Binding Molecules DART-B, DART-D, DART-G, DART-G2, DART-G3 and DART-G4, and the control molecules DART-3, DART-6, to mediate co-stimulatory activity in a T cell cytokine release assay (exemplified by the release of IFN-γ). Cytokine release was measured in the presence of HER2/neu-expressing N87 target cells (FIG. 21A), JIMT-1 target cells (FIG. 21B), or MDA-231 (FIG. 21C) target cells, or with no target cells present.
Figure 21B:
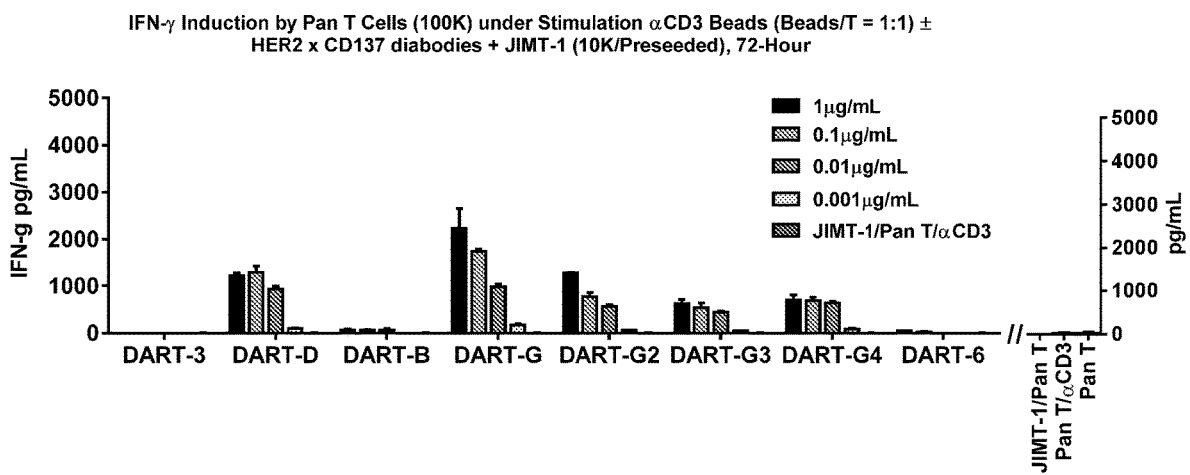
Figure 21C:
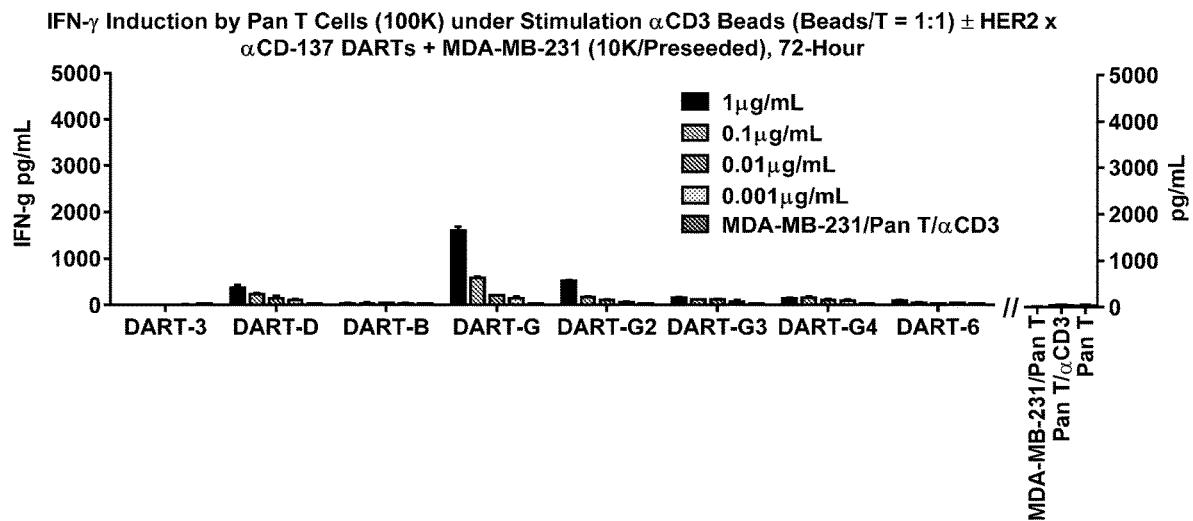

FIGS. 21A-21C show the results of a representative assay of the ability of DART-3, DART-6, DART-B, DART-D, DART-G, DART-G2, DART-G3 and DART-G4 to mediate co-stimulatory activity in a T cell cytokine release assay (performed essentially as described in Example 2 above, and exemplified by the release of IFN-γ). Cytokine release was measured as described above in the presence of HER2/neu-expressing N87 target cells (FIG. 21A), JIMT-1 target cells (FIG. 21B), or MDA-231 (FIG. 21C) target cells, or with no target cells present.

The results show that the control diabodies, DART-3 and DART-6 exhibited no co-stimulatory activity. The CD137×TA Binding Molecules did not exhibit any observable co-stimulatory activity in the absence of target cells or with HER2/neu-negative target cells. DART-G, comprising the novel anti-CD137 humanized antibody, hCD137 MAB-3, exhibited the highest co-stimulatory activity in the presence of either target cell line. TNF-α and IL-2 show similar release patterns.

The co-stimulatory activity of the optimized variants DART-G2, DART-G3 and DART-G4 was found to be inversely related to the increased binding to cell surface expressed CD137, indicating that higher binding affinity does not appear to directly correlate with co-stimulatory activity in this assay. However, as shown below, the optimized variants perform comparably in other functional assays. These attributes make the affinity optimized variants particularly useful for detection of CD137 expression and for diagnostic assays that measure the expression of CD137 in addition to their use as co-stimulatory agents.

Figure 22:
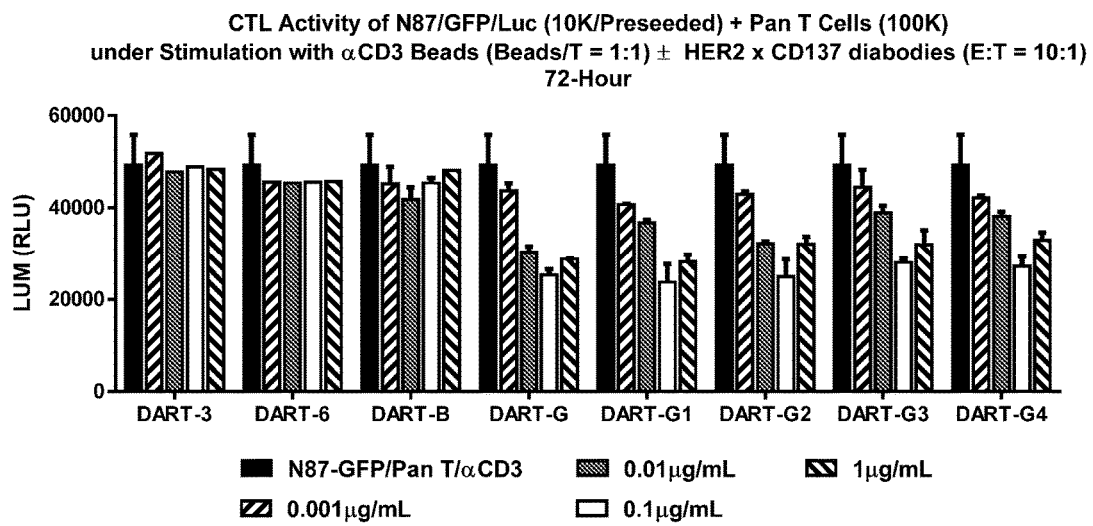
FIG. 22 shows the results of a representative assay of the ability of CD137×TA Binding Molecules DART-B, DART-G, DART-G1, DART-G2, DART-G3 and DART-G4, and the control molecules DART-3, DART-6, to mediate redirected cell killing of N87 (HER2$^{+++}$) target cells as measured by cell-associated luciferase activity.

The ability of the CD137×TA Binding Molecules to mediate redirected cell killing of tumor target cells was examined. Briefly, N87/GFP/Luc target cells (engineered to express the luciferase (luc) reporter gene) were incubated with pan T cells under sub-optimal stimulation conditions for 72 hours in the absence or presence of DART-B, DART-G, DART-G1, DART-G2, DART-G3, DART-G4 or the control molecules DART-3 or DART-6 (each at 0.001, 0.01, 0.1, and 1 µg/mL), essentially as described above for the co-stimulation assays. At the end of the incubation cytotoxicity was determined by luminescence (LUM) assay measuring cellular luciferase activity of the target cells with luminescence relative light unit (RLU) as the read-out (FIG. 22). Each of the CD137×TA Binding Molecules examined exhibited some redirected cell killing activity with DART-G exhibiting the highest activity and DART-B, exhibiting the lowest activity. In contrast, the control molecules exhibited no detectable redirected cell killing activity. The results of this study demonstrate that the CD137×TA Binding Molecules are able to mediate redirected cell killing of tumor cells.

Example 6

Characterization of Trivalent CD137×TA Binding Molecules

Figure 23A:
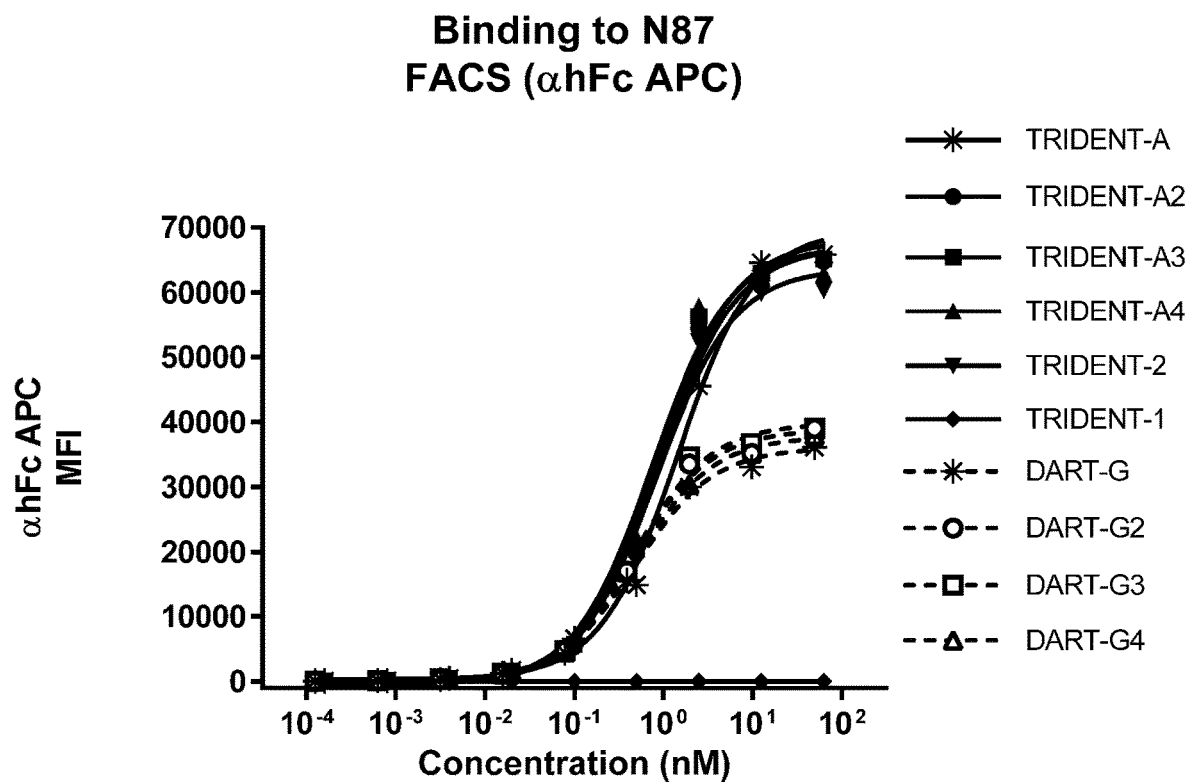
FIGS. 23A-23C show the ability of CD137×TA Binding Molecules to bind different cells expressing the illustrative TA, HER2/neu, as measured by mean fluorescence intensity (MFI).
Figure 23B:
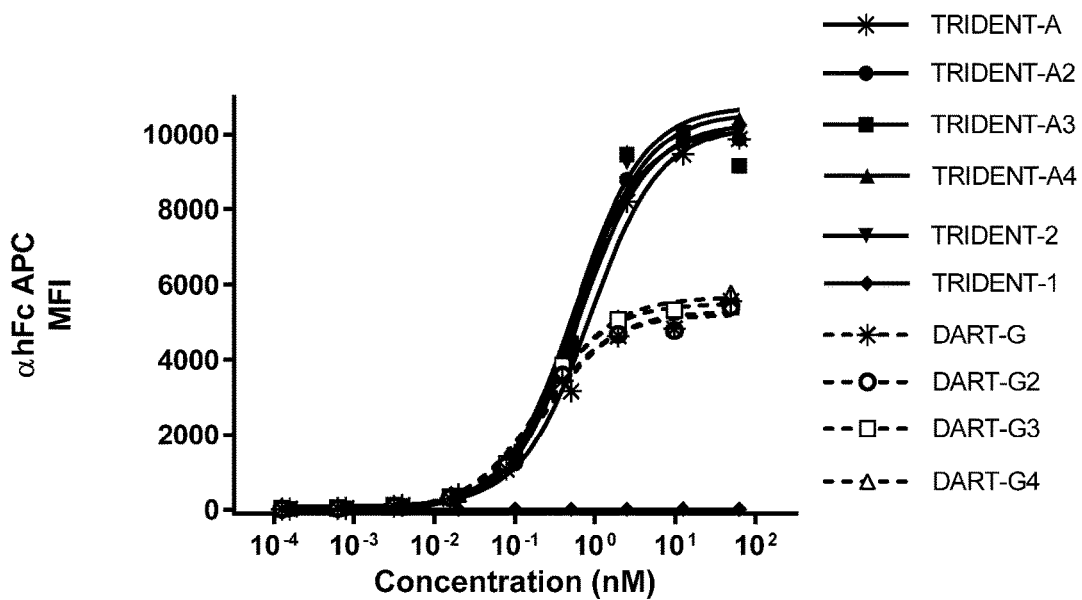
Figure 23C:
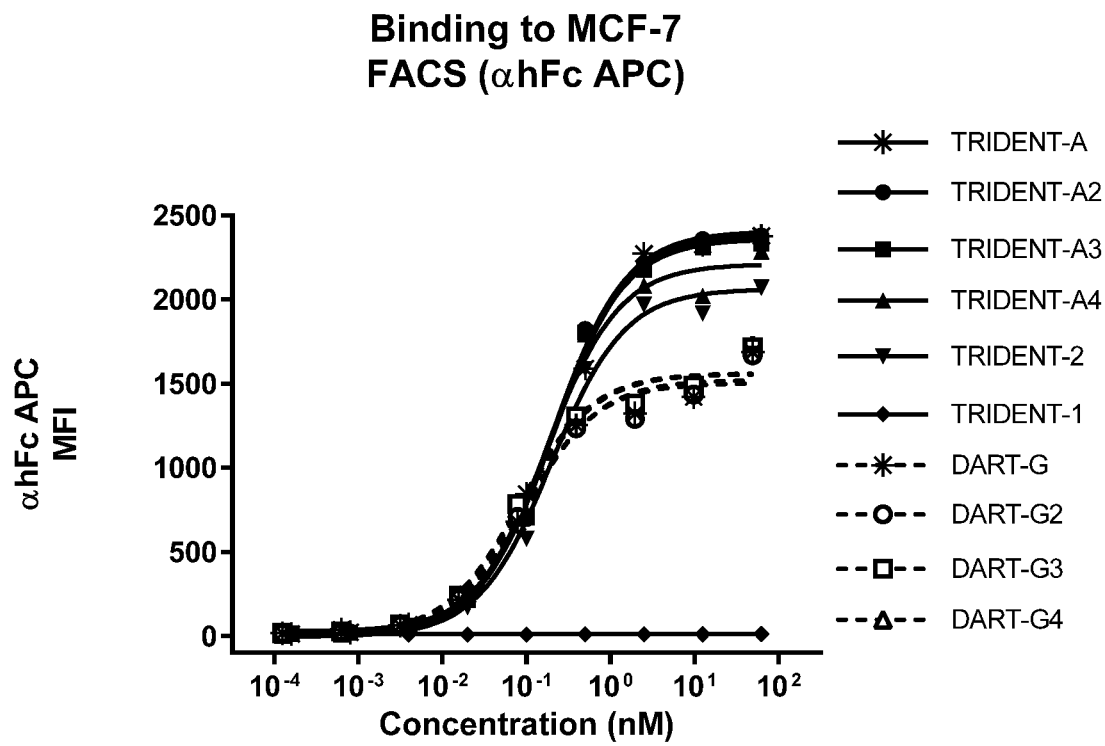

As noted above, CD137×TA Binding Molecules having one binding site for CD137 and one or more binding sites for HER2/neu did not exhibit any co-stimulatory activity in T cell cytokine release assays. This observation suggests that at least two CD137 binding sites may be required for co-stimulatory activity. To address this question, a set of exemplary Trivalent CD137×TA Binding Molecules capable of binding to CD137 and to the exemplary TA, HER2/neu, were generated. These molecules included four bispecific trivalent binding molecules "TRIDENT-A," "TRIDENT-A2," "TRIDENT-A3," and "TRIDENT-A4," respectively, each of which comprises two hCD137 MAB-3 domains and one hHER2 MAB-1 domain (CD137×CD137×HER2). The structure and sequences of these exemplary CD137×TA Binding Molecules are provided in detail above. In addition, two control molecules, "TRIDENT-1," each comprising one variant palivizumab domain and two optimized hCD137 MAB-3 domains (CD137×CD137×RSV), and "TRIDENT-2" comprising one hHER2 MAB-1 domain, one 4-4-20 domain, and one variant palivizumab domain (RSV×FITC×HER2) were generated. The trivalent molecules have the general structure shown in FIG. 6A, and were generated and characterized as detailed below for their ability to bind to HER2/neu present on the surface of target $N87(3^+)$, JIMT-$1(2^+)$ and MCF-$7(1^+)$ by FACS analysis essentially as described above. CD137×TA Binding Molecules having two binding sites for CD137 and two binding sites for HER2/neu (DART-G, DART-G2, DART-G3, and DART-G4), were also evaluated As shown in FIGS. 23A-23C, the molecules that comprised one or two HER2/neu binding domains bound to all three target cell types. It will be noted that the binding curves of molecules having two HER2/neu binding sites (DART-G, DART-G2, DART-G3, and DART-G4) reach saturation sooner particularly on cells having high levels of HER2/neu on their cell surface. This indicates that some molecules are exhibiting bivalent binding (i.e., binding two HER2/neu molecules on the surface). Bivalent bonding is more likely in the presence of high concentrations of target ligand.

Figure 24A:
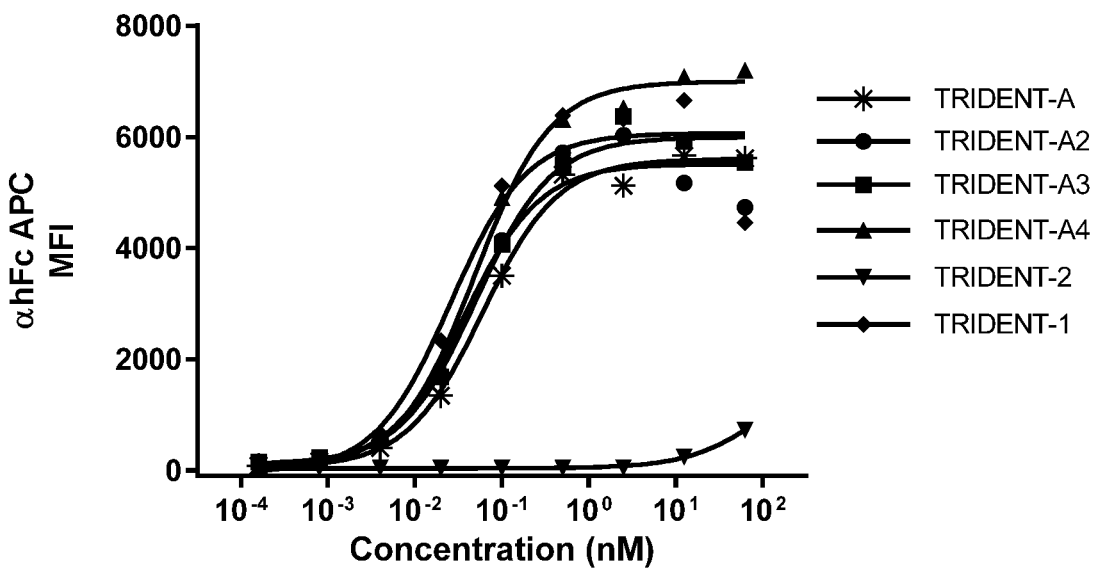
FIGS. 24A-24B show the ability of CD137×TA Binding Molecules to bind to CD137 expressed by activated CD8+ T cells.
Figure 24B:
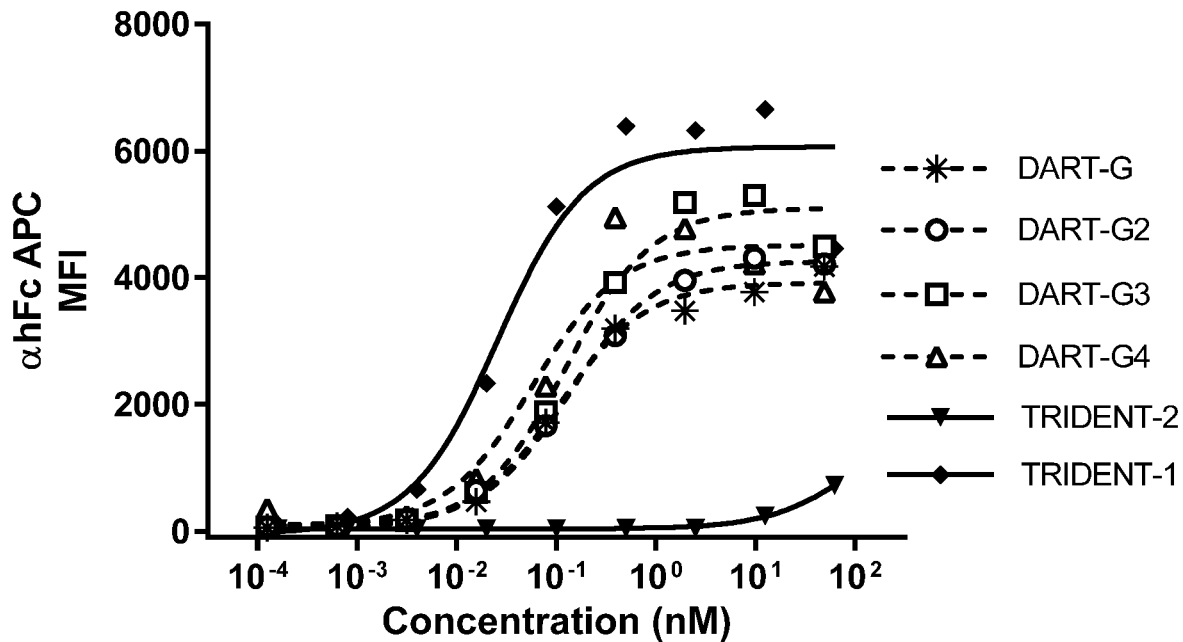

The CD137×TA Binding Molecules having two binding sites for CD137 and one binding site for HER2/neu (TRIDENT-A, TRIDENT-A2, TRIDENT-A3 and TRIDENT-A4), the CD137×CD137×RSV and TA×FITC×RSV control molecules (TRIDENT-1 and TRIDENT-2), and the CD137×TA Binding Molecules having two binding sites for CD137 and 2 binding sites for HER2/neu (DART-G, DART-G2, DART-G3, and DART-G4), were also evaluated by FACS analysis essentially as described in Example 2 above for their ability to bind CD137 present on the surface of activated $CD4^+$ (FIG. 24A) and $CD8^+$ (FIG. 24B) T cells. The molecules that comprised two CD137 binding domains exhibited strong binding to activated T-cells. Improved binding was observed for the exemplary HER2×CD137 diabodies comprising the optimized hCD137 MAB-3 VH domains described above. The TA×FITC×RSV control molecule (TRIDENT-2) did not exhibit any binding to activated T-cells, as expected.

Figure 25A:
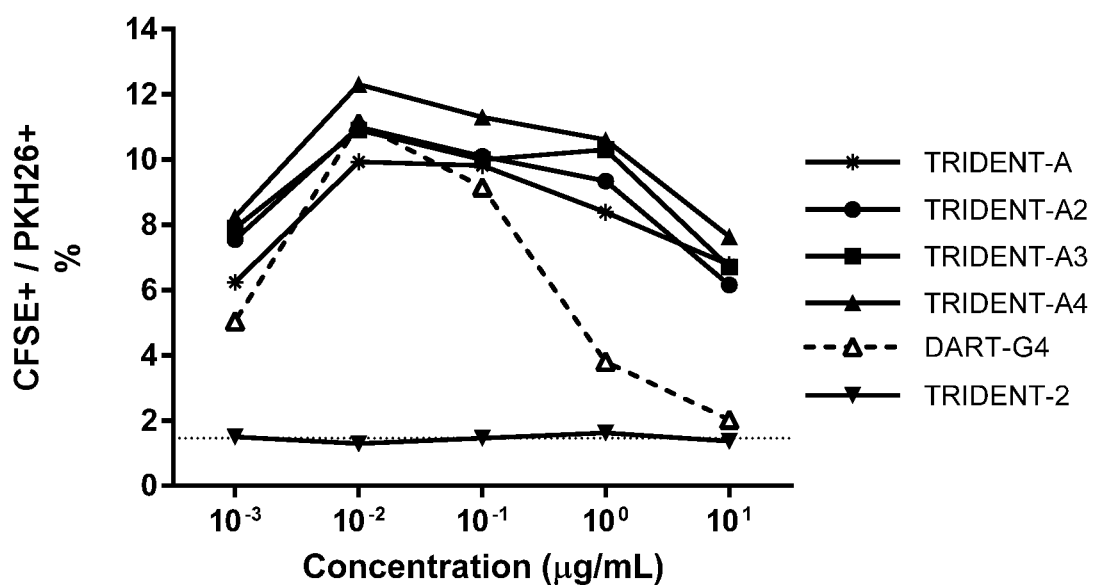
FIGS. 25A-25C show the ability of the CD137×TA Binding Molecules to mediate cell-cell conjugation between CHO cells expressing CD137 and cells expressing the illustrative TA, HER2/neu, FACS.
Figure 25B:
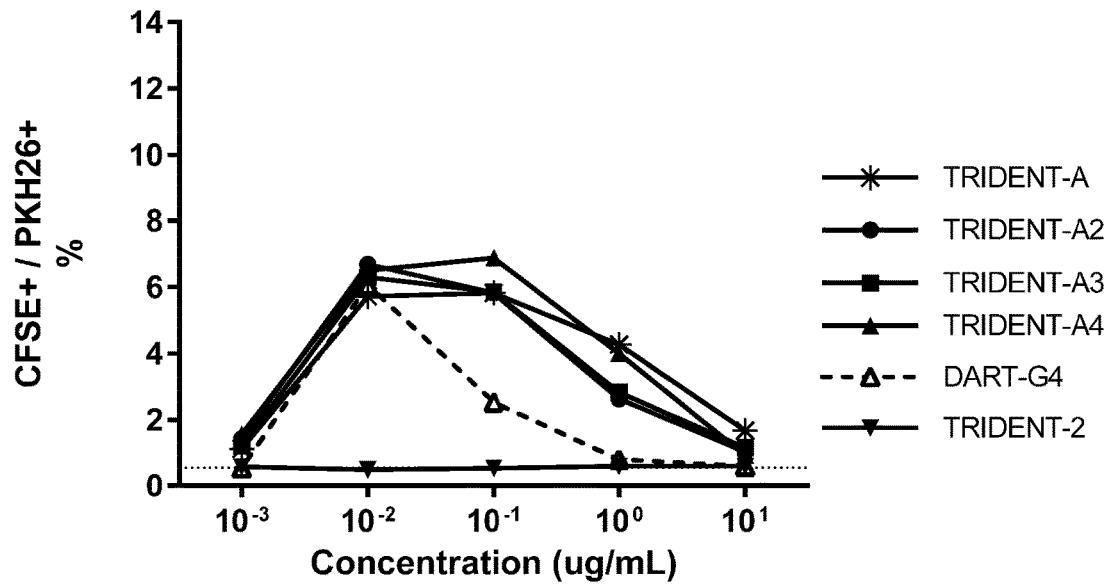
Figure 25C:
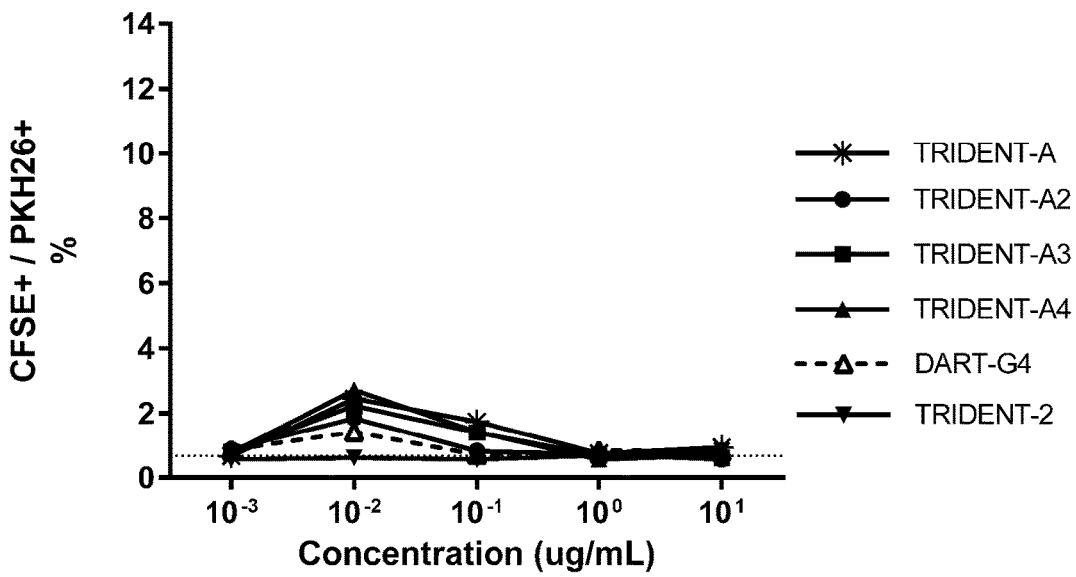

In another study, the CD137×TA Binding Molecules having two binding sites for CD137 and one binding site for HER2/neu (TRIDENT-A, TRIDENT-A2, TRIDENT-A3 and TRIDENT-A4), a CD137×TA Binding Molecule having two binding sites for CD137 and two binding sites for HER2/neu (DART-G4) and the TA×FITC×RSV control molecule (TRIDENT-2), were evaluated for their ability to mediate cell-cell conjugation between CD137 expressing cells and HER2/neu expressing target cells. For such evaluation, $1.5 \times 10^4$ CD137-expressing CHO cells labeled with PKH26 were co-incubated with $1.5 \times 10^4$ HER2/neu-expressing target cells (N87(HER2 expression level: $3^+$), JIMT-1 (HER2 expression level: $2^+$), or MCF-7(HER2 expression level: $1^+$)), labeled with CFSE in a 1:1 ratio in the presence of serially diluted (10-fold dilutions) test article for 30 min at room temperature. The samples were then analyzed by flow cytometry to determine the percentage of conjugated cells (CFSE+/PKH26+) as a readout for cell-cell conjugation. As shown in FIGS. 25A-25C, the molecules that comprised at least one HER2/neu binding domain and two CD137 binding domains were able to mediate cell-cell conjugation while the control molecule was inactive. For all active molecules, cell-cell conjugation activity correlated with the level of HER2/neu expression.

Figure 26A:
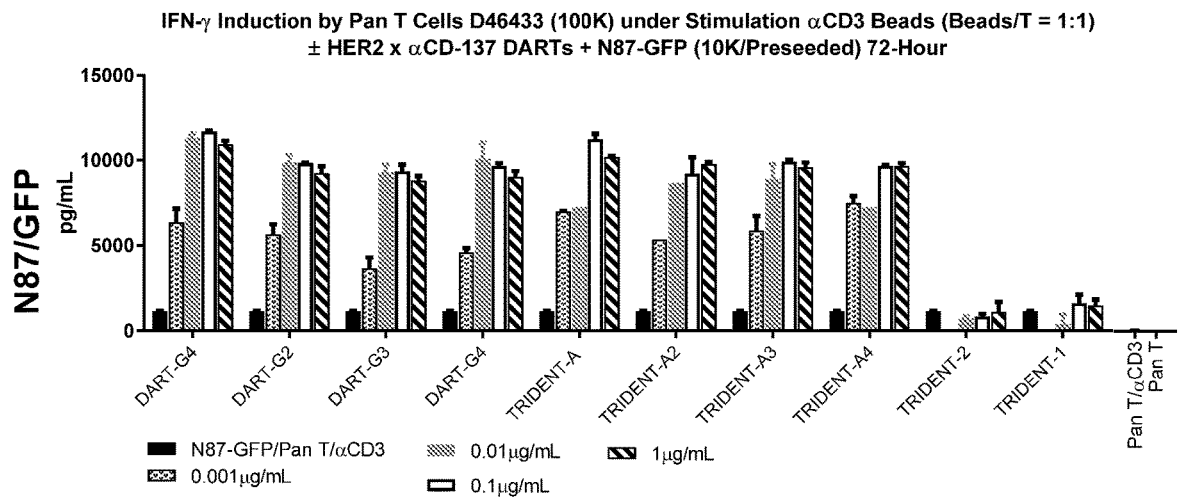
FIGS. 26A-26C show the results of a representative assay of the ability of CD137×TA Binding Molecules TRIDENT-A, TRIDENT-A2, TRIDENT-A3, TRIDENT-A4, DART-G, DART-G2, DART-G3, DART-G4, and the control binding molecules TRIDENT-1 and TRIDENT-2, to mediate co-stimulatory activity in a T cell cytokine release assay (exemplified by the release of IFN-γ). Cytokine release was measured in the presence of HER2/neu-expressing N87 target cells (FIG. 26A), JIMT-1 target cells (FIG. 26B), or with no target cells present (FIG. 26C).
Figure 26B:
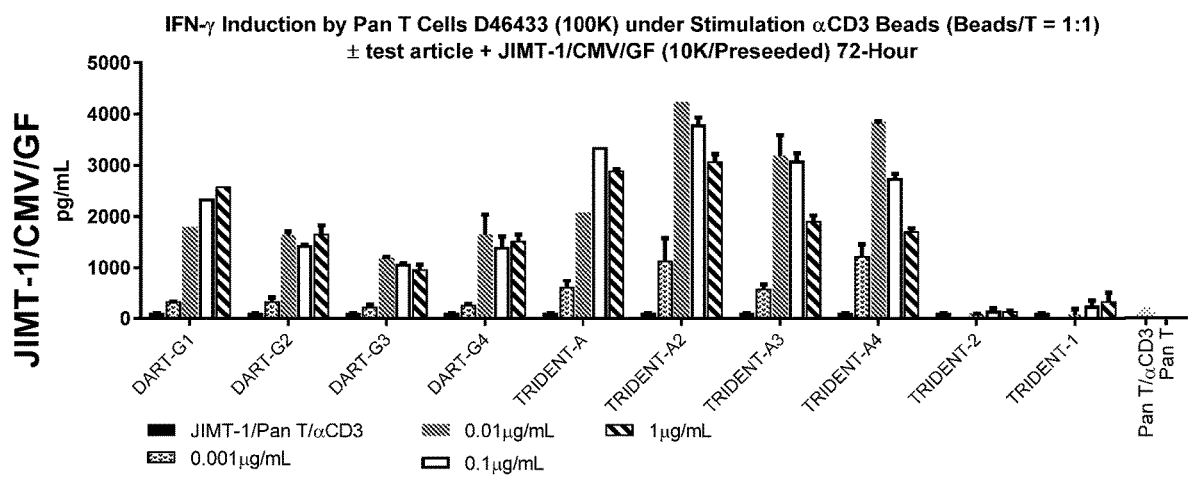
Figure 26C:
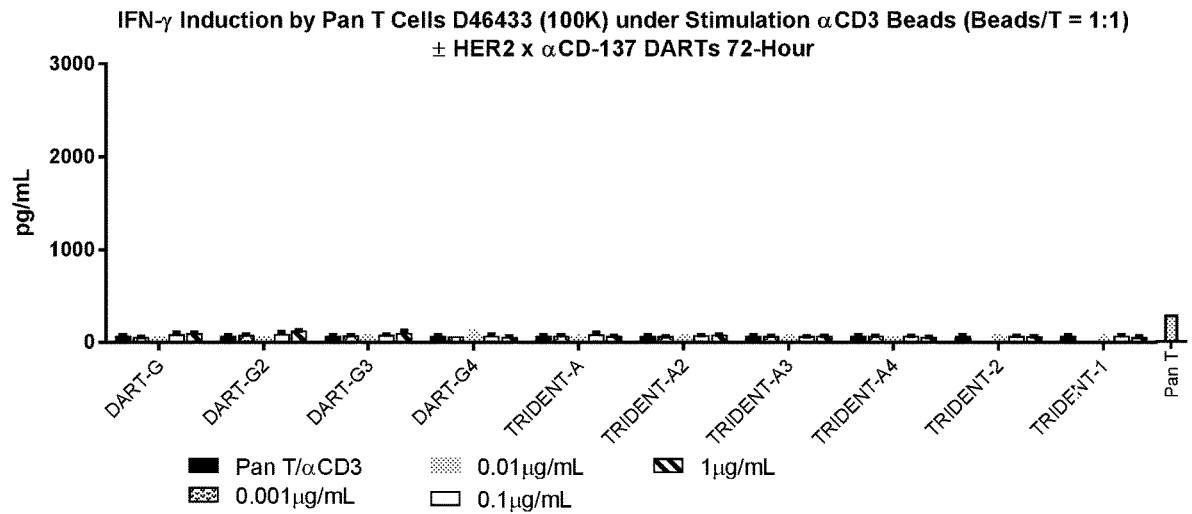

In another study, the CD137×TA Binding Molecules having two binding sites for CD137 and one binding site for HER2/neu (TRIDENT-A, TRIDENT-A2, TRIDENT-A3 and TRIDENT-A4), the CD137×RSV and TA×FITC×RSV control molecules (TRIDENT-1 and TRIDENT-2), and the CD137×TA Binding Molecules having two binding sites for CD137 and two binding sites for HER2/neu (DART-G, DART-G2, DART-G3, and DART-G4), were evaluated for their ability to mediate a co-stimulatory activity in a T cell cytokine release assay (performed essentially as described in Example 2 above, and exemplified by release of IFN-γ) in the presence or absence of target cells expressing the exemplary TA, HER2/neu. Cytokine release was measured as described above in the presence of HER2/neu-expressing N87 target cells (FIG. 26A), JIMT-1 target cells (FIG. 26B), or with no target cells present (FIG. 26C).

The results show that the exemplary CD137×TA Binding Molecules exhibited co-stimulatory activity in the presence of either target cell line, with activity correlated with the level of HER2/neu expression. TRIDENT-A, TRIDENT-A2, TRIDENT-A3 and TRIDENT-A4 (each having two binding sites for CD137 and one binding site for HER2/neu) exhibited higher co-stimulatory activity on JIMT-1 (HER2$^{++}$) cells than DART-G, DART-G2, DART-G3 or DART-G4 (having two binding sites for CD137 and 2 binding sites for HER2/neu). The CD137×TA Binding Molecules did not exhibit any observable co-stimulatory activity in the absence of target cells or with HER2/neu-negative target cells. the control molecules, TRIDENT-1 and TRIDENT-2, exhibited no co-stimulatory activity.

Example 7

CD137×TA Binding Molecules Enhance T-Cell Activation

As described above, the CD137×TA Binding Molecules of the present invention can enhance T-cell expansion and activation (see, e.g., FIGS. 17A-17O) and tumor targeting agent-mediated NK effector function (ADCC) (see, e.g., enhancement of Margetuximab-mediated ADCC, FIGS. 18A-18B). TA×CD3 bispecific molecules (e.g., DART diabodies, BiTE® molecules, etc.) which bind to a TA and to CD3 are known to mediate T-cell redirected killing of target cells expressing the TA, and stimulate T-cells expansion and activation (see, e.g., PCT Publication Nos. WO 2017/030926; WO 2016/048938; and WO 2015/026892). The ability of the CD137×TA Binding Molecules of the invention to enhance T-cell activation and T-cell redirected killing mediated by such tumor targeting agents was assessed in several studies using exemplary TA×CD3 bispecific molecules.

Figure 27:
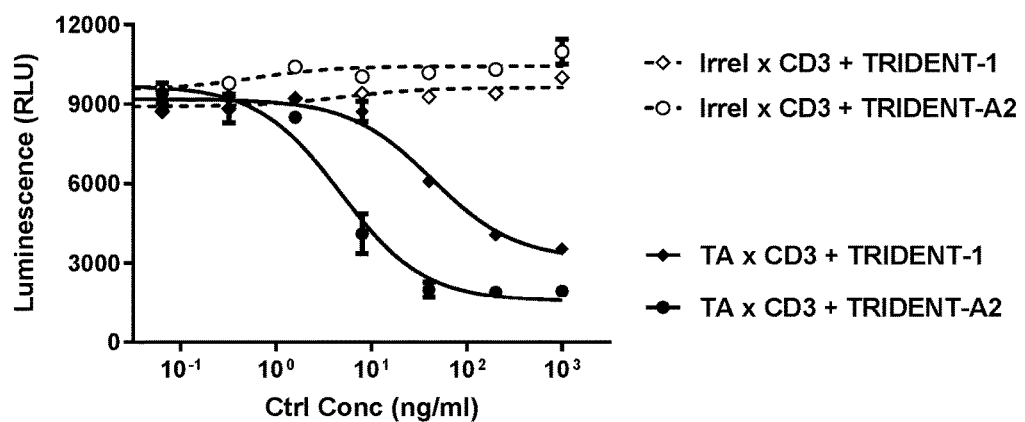
FIG. 27 shows the ability of an exemplary CD137×TA Binding Molecule (TRIDENT-A2) to enhance the TA×CD3 diabody-mediated redirected T-cell killing of Colo205/Luc target cells as measured by cell-associated luciferase as compared to the control molecule (TRIDENT-1)
Figure 28A:
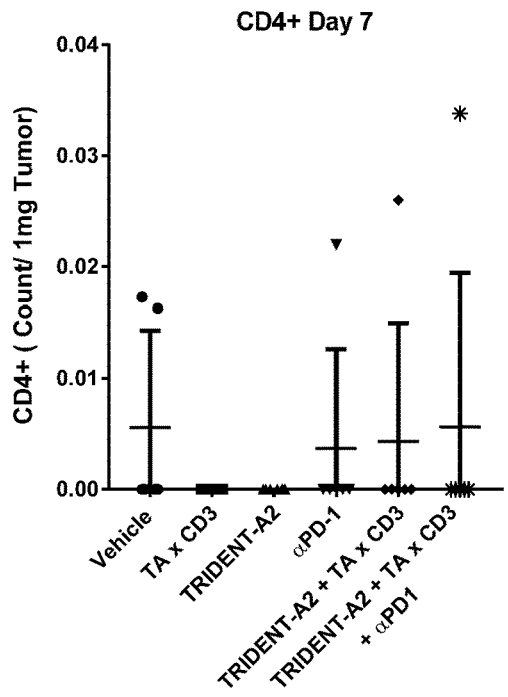
FIGS. 28A-28C show the expression of T-cell markers present in 1 mg of tumor sampled post-treatment with vehicle control (●); TRIDENT-A2 (▼); TA×CD3 diabody (■); combination of TRIDENT-A2 and TA×CD3 diabody (♦); anti-PD-1 mAb (▼); or the combination of TRIDENT-A2, TA×CD3 diabody, and anti-PD-1 mAb.
Figure 28B:
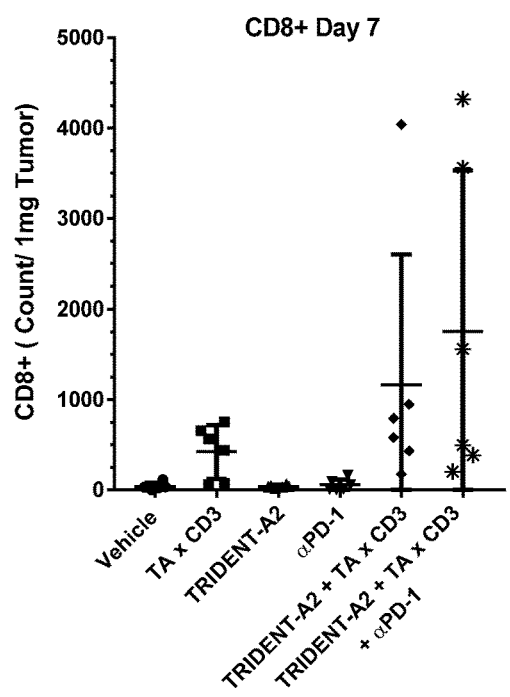
Figure 28C:
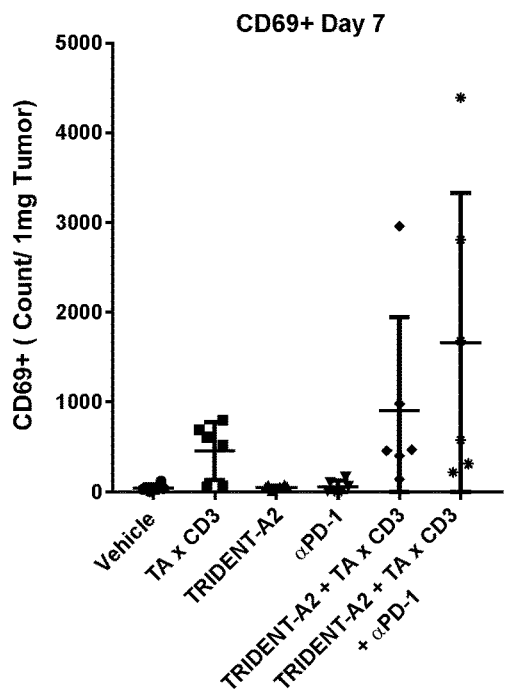
Figure 28D:
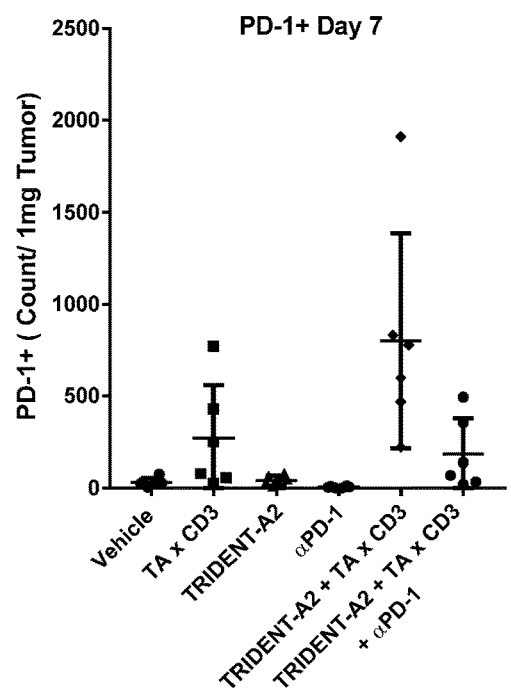
FIG. 28D: PD-1 expression.

In one such study, the ability of the exemplary CD137×TA Binding Molecule TRIDENT-A4 to enhance T-cell redirected cell killing mediated by a TA×CD3 diabody that binds to the illustrative TA gpA33 was assessed using a luciferase based cytotoxic T lymphocyte (CTL) assay. Briefly, pan T cells were incubated with Colo205 cells engineered to express luciferase (luc) reporter gene (Colo205/luc) target cells at an effector:target (E:T) ratio of 3:1 in the presence of TRIDENT-A4 or the control TRIDENT-1 in combination with a TA×CD3 diabody or a control Irrel×CD3 bispecific diabody (comprising an irrelevant binding domain (4-4-20 to fluorescein) in place of gpA33). At the end of the incubation, cytotoxicity was determined by luminescence (LUM) assay measuring cellular luciferase activity of the target cells with luminescence relative light unit (RLU) as the read-out (FIG. 27). The results of this study demonstrate that the CD137×TA Binding Molecules of the invention are able to enhance T-cell redirected killing mediated by TA×CD3 bispecific molecules.

In another study, the ability of the exemplary CD137×TA Binding Molecule TRIDENT-A2 to enhance T-cell expansion and anti-tumor activity in combination in vivo was assessed in an SK-OV3 ovarian carcinoma model (expressing the TAs HER2/neu and 5T4). In this study, the activity of TRIDENT-A2 was examined alone or in combination with a TA×CD3 diabody that binds to the illustrative TA 5T4 (5T4×CD3), and optionally in further combination with an anti-PD-1 mAb (hPD-1 mAb 7(1.2) IgG4 (P), see, e.g., SEQ ID NOs:264 and 266 of PCT Publication WO 2017/019846).

Briefly, freshly isolated PBMCs were injected retro-orbitally into NSG.MHCI$^{-/-}$ mice (female mice 7 per group for tumor monitoring; 3 per group for T-cell and tumor profiling) on study day 0. SK-OV3 cells (5×10$^6$) were mixed 1:1 with Matrigel and injected subcutaneously on study day 0. On study day 7, mice were treated with the anti-CD4 antibody OKT4 (initial dose 10 mg/kg subcutaneously, 5 mg/kg twice a week IP thereafter) to eliminate CD4$^+$ T-cells. Starting on day 22, mice were treated by intravenous (IV) injection with: vehicle control; TRIDENT-A2 (2.5 mg/kg, once per week); TA×CD3 diabody (0.01 mg/kg, twice per week); combination of TRIDENT-A2 (2.5 mg/kg, once per week) and TA×CD3 diabody (0.01 mg/kg, twice per week); anti-PD-1 mAb (5 mg/kg, once per week); or the combination of TRIDENT-A2 (2.5 mg/kg; once per week), TA×CD3 diabody (0.01 mg/kg, twice per week), and anti-PD-1 mAb (5 mg/kg, once per week).

T-cell markers were evaluated by FACS analysis 7 days post administration of the test articles and tumor growth was monitored over the course of the study. Expression of the T-cell markers CD4, CD8, CD69, and PD-1, present in 1 mg of tumor sampled at day 7 post-post treatment are plotted in FIG. 28A, FIG. 28B, FIG. 28C, and FIG. 28D, respectively. These data show that the CD137×TA Binding Molecule TRIDENT-A2 enhanced T-cell activation and expansion (as exemplified by increased expression of CD4, CD8 and CD69) mediated by the TA×CD3 diabody. Expression of the immune checkpoint molecule PD-1 was upregulated upon treatment with TA×CD3 diabody alone. Treatment with the combination of the CD137×TA Binding Molecule TRIDENT-A2 and the TA×CD3 diabody further enhanced the expression of the checkpoint molecule PD-1 observed upon treatment with TA×CD3 diabody alone and suggested that the activity of the combination could be enhanced by the addition of a checkpoint inhibitor. Indeed, addition of the anti-PD-1 mAb, an exemplary PD-1/PD-L1 check point inhibitor, to the TRIDENT-A2/TA×CD3 diabody combination inhibited the upregulation of PD-1 expression and further enhanced T-cell activation and proliferation.

Figure 29:
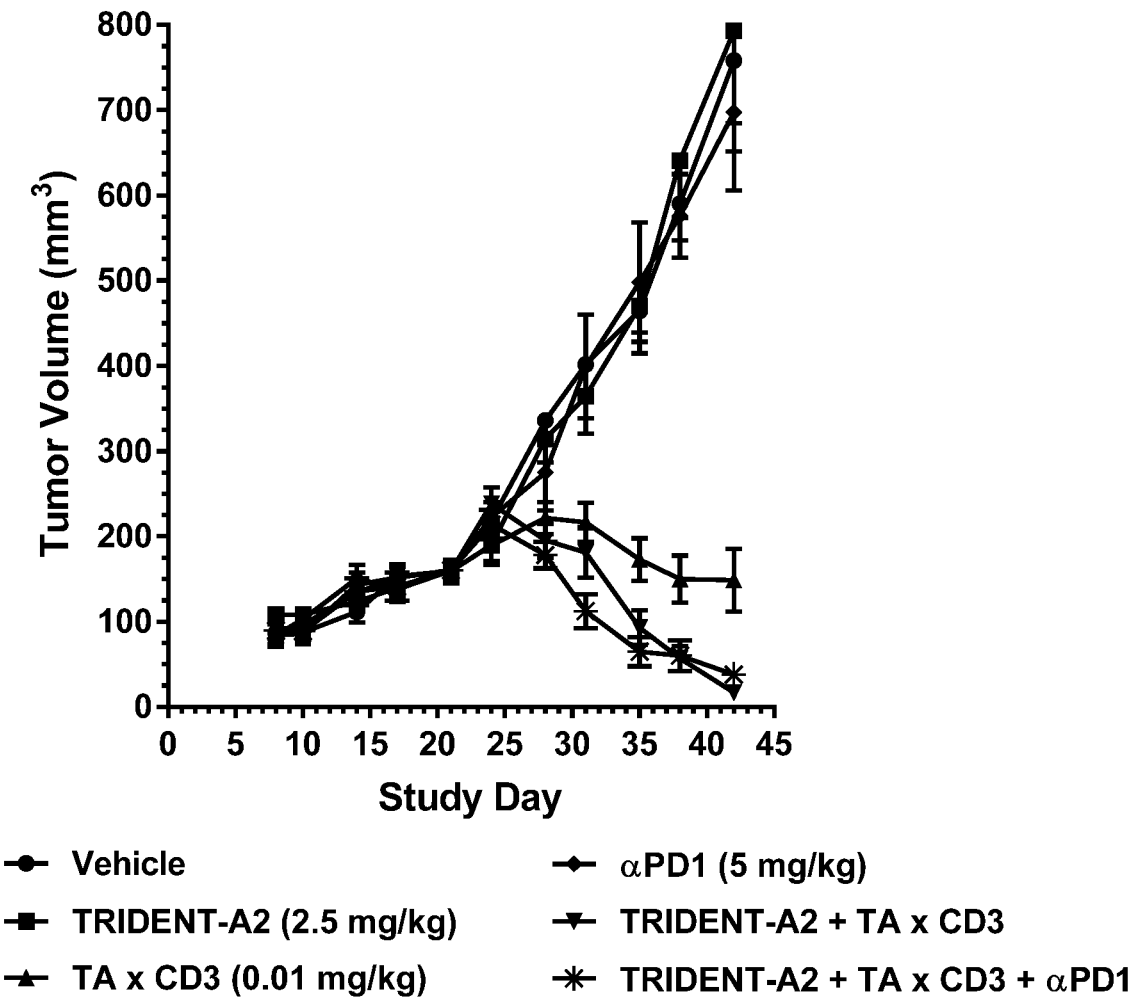
FIG. 29 shows the ability of vehicle control (●); TRIDENT-A2 (▼); TA×CD3 diabody (■); the combination of TRIDENT-A2 and TA×CD3 diabody (♦); anti-PD-1 mAb (▼); and the combination of TRIDENT-A2, TA×CD3 diabody, and anti-PD-1 mAb, to inhibit tumor growth or development of ovarian carcinoma cells in a PBMC-reconstituted murine xenograph model.

Tumor growth over the course of the study is plotted in FIG. 29, which shows that the CD137×TA Binding Molecule TRIDENT-A2 enhanced the anti-tumor activity of the TA×CD3 diabody. In addition, the addition of the PD-1/PD-L1 checkpoint inhibitor, anti-PD-1 mAb, to the combination further enhanced the anti-tumor activity of the combination. The results of this study demonstrate that the CD137×TA Binding Molecules of the invention, particularly those having two binding sites for CD137 and one binding site for a TA, enhance T-cell activation, proliferation and target cell killing in combination with a tumor targeting agent. Thus, CD137×TA Binding Molecules of the invention may advantageously be using in combination with tumor targeting agents, particularly those that mediate T cell activation, NK cell activation, and/or stimulate CD137 expression in such cells. Furthermore, these studies demonstrate that the addition of a PD-1/PD-L1 checkpoint inhibitor, such as an anti-PD-1 or anti-PD-L1 antibody, can further enhance T-cell activation, proliferation and target cell killing.

Example 8

Stability Studies

The melting temperature (Tm) and other stability parameters of the exemplary Trivalent CD137×TA Binding Molecules TRIDENT-A (comprising hCD137 MAB-3 (1.3)), and the optimized variants TRIDENT-A1 (comprising hCD137 MAB-3 (1A.3)), TRIDENT-A2 (comprising hCD137 MAB-3 (1B.3)), TRIDENT-A3 (comprising hCD137 MAB-3 (1C.3)), and TRIDENT-A4 (comprising hCD137 MAB-3 (1D.3)) were evaluated. The Tm of purified material (>95% percent as determined by High Pressure Size Exclusion Chromatography (HP-SEC)) was evaluated by differential scanning calorimetry (DSC). Briefly, purity levels were measured HPLC-SEC using an Agilent 1260 Infinity II HPLC connected to a Waters Acquity UPLC BEH Column (200 Å 1.7 μm 4.6×150 mm). The running buffer was 20 mM sodium phosphate, 0.5 M NaCl, 0.02% sodium azide, pH 7.2. The flow rate was 0.4 mi/minute for 5 minutes. The 0% purity is determined from the 0% area of the absorbance tracing at 280 nm of the monomer peak. Thermal stability measurements were performed on a MicroCal VP-Capillary DSC (Malverm Instruments, Inc.) between 15-95° C. and ramped at 1° C./minute.

To evaluate other stability parameters, purified CD137× TA Binding Molecules (1 mg/mL in PBS pH7.2 unless noted) were stressed and revaluated by HP-SEC and the values compared to those obtained from the unstressed molecule. The following stress conditions were utilized: three rounds of freeze (1 hr at −80° C.) followed by thaw; after 2 and 7 days of storage at 25° C. or 40° C.; after 0, 2, 7 days of storage at 25° C. in 20 mM Sodium Acetate pH 5.5; at 0, 2, 7 days of storage at 25° C. in 10 mM Histidine HCL pH 6.5. The results of these studies are summarized in Table 14.

both TRIDENT-A3 and TRIDENT-A4. Only TRIDENT-A2 was stable at 40° C. (Day 2 and Day 7) in PBS, the remaining molecules were sensitive to this storage condition. Both TRIDENT-A and TRIDENT-A2 were stable in Acetate pH 5.5, while TRIDENT-A3 and TRIDENT-A4 were both sensitive to Acetate pH 5.5 incubation. All the molecules tested were stable in Histidine at pH 6.5. Based on the results from these studies ranking for stability in the tested buffers is TRIDENT-A2>TRIDENT-A>TRIDENT-A3>TRIDENT-A4.

Example 9

Co-Stimulatory Activity with Cynomolgus T Cells

As noted above, molecules comprising the binding domains of CD137 MAB-3 (or humanized, optimized variants thereof) bind both human and cynomolgus monkey CD137. Representative CD137×TA Binding Molecules TRIDENT-A2 and TRIDENT-B2 having two binding sites for CD137 and one binding site for the for HER2/neu or 5T4 were evaluated for their ability to mediate a co-stimulatory activity in a cynomolgus T cell cytokine release assay. The structure and sequences of these exemplary CD137×TA Binding Molecules are provided in detail above. The control molecules, TRIDENT-1, and TRIDENT-2 were also included. The cytokine release assay was performed essentially as described in Example 2 above, and exemplified by release of IFN-γ) in the presence or absence of target cells except cynomolgus monkey pan T cells were utilized. For these studies JIMT-1 target cells expressing both HER2/neu and 5T4 were utilized.

Figure 30:
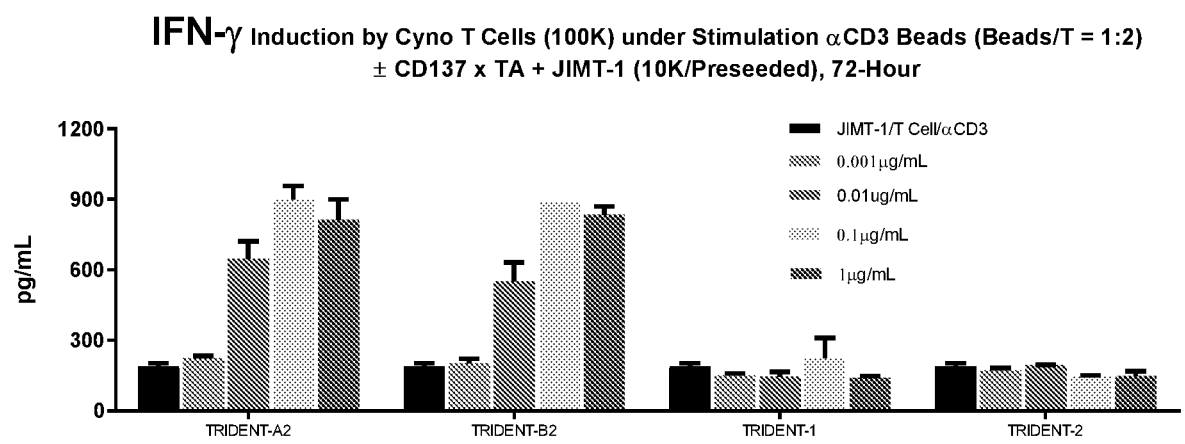
FIG. 30 shows the ability of CD137×TA Binding Molecules TRIDENT-A2, TRIDENT-B2, and the control binding molecules TRIDENT-1 and TRIDENT-2, to mediate co-stimulatory activity in a cynomolgus monkey T cell cytokine release assay (exemplified by the release of IFN-γ). Cytokine release was measured in the presence of JIMT-1 target cells expressing 5T4 and HER2/neu.
Figure 32A:
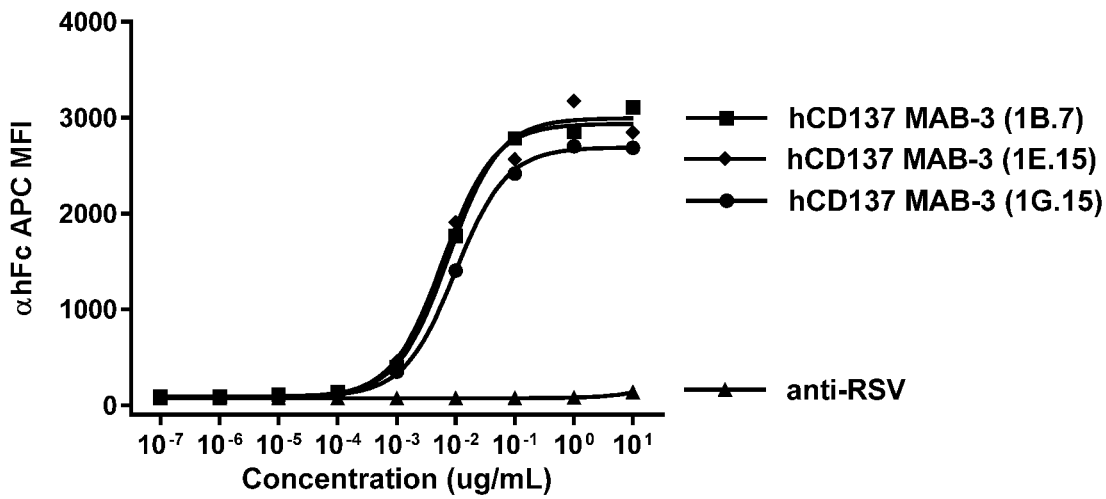
FIGS. 32A-32B show the ability anti-CD137 antibodies comprising deimmunized VH and VL Domains to bind to CD137 of activated CD4+ T cells or CD8+ T cells as measured by FACS using V510-labeled CD4+ and αhFc APC (FIG. 32A) or FITC-labeled CD8 and αhFc APC (FIG. 32B).
Figure 32B:
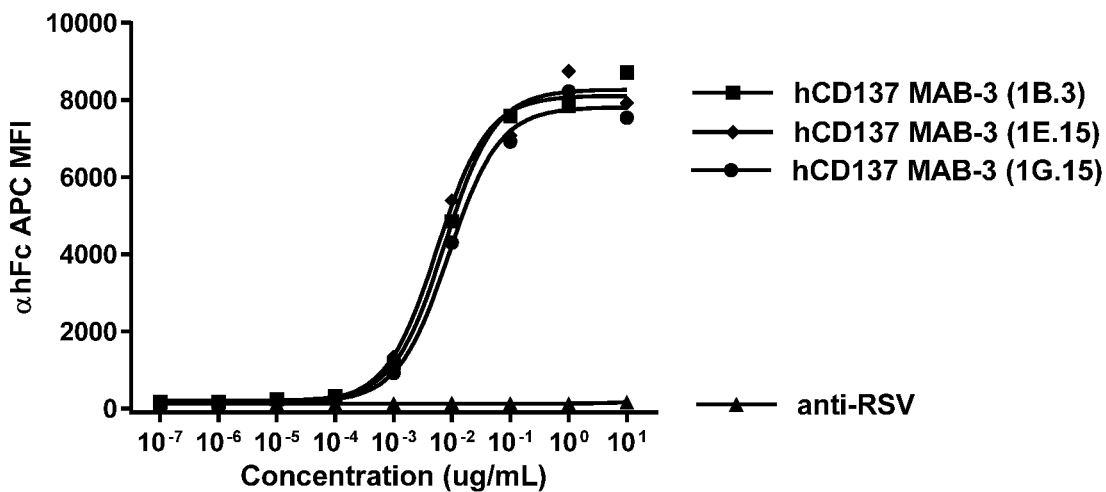
Figure 33A:
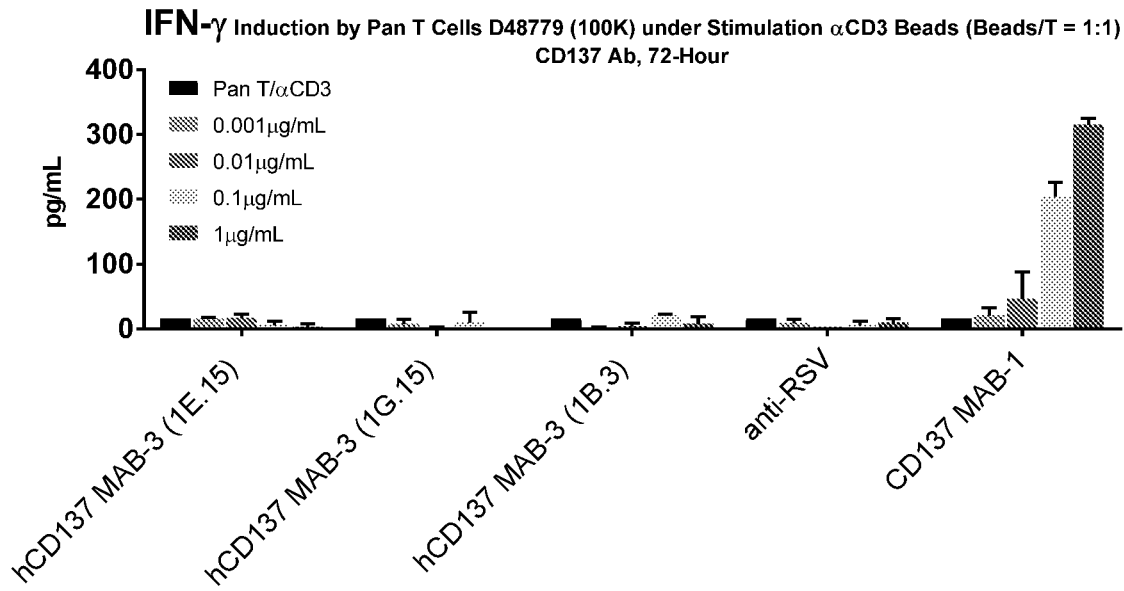
FIGS. 33A-33B show induction after 72 hours of IFN-γ by pan T cells upon stimulation with dry-coated anti-CD3 antibody (3 μg/mL-50 μg/mL) in the presence of the optimized/deimmunized anti-CD137 antibodies CD137 MAB-3 (1b.3), CD137 MAB-3 (1E.15) and CD137 MAB-3 (1G.15) in the absence of cross-linking (FIG. 33A) or cross-linked with 4×hFc F(ab)'$_2$ (FIG. 33B).
Figure 33B:
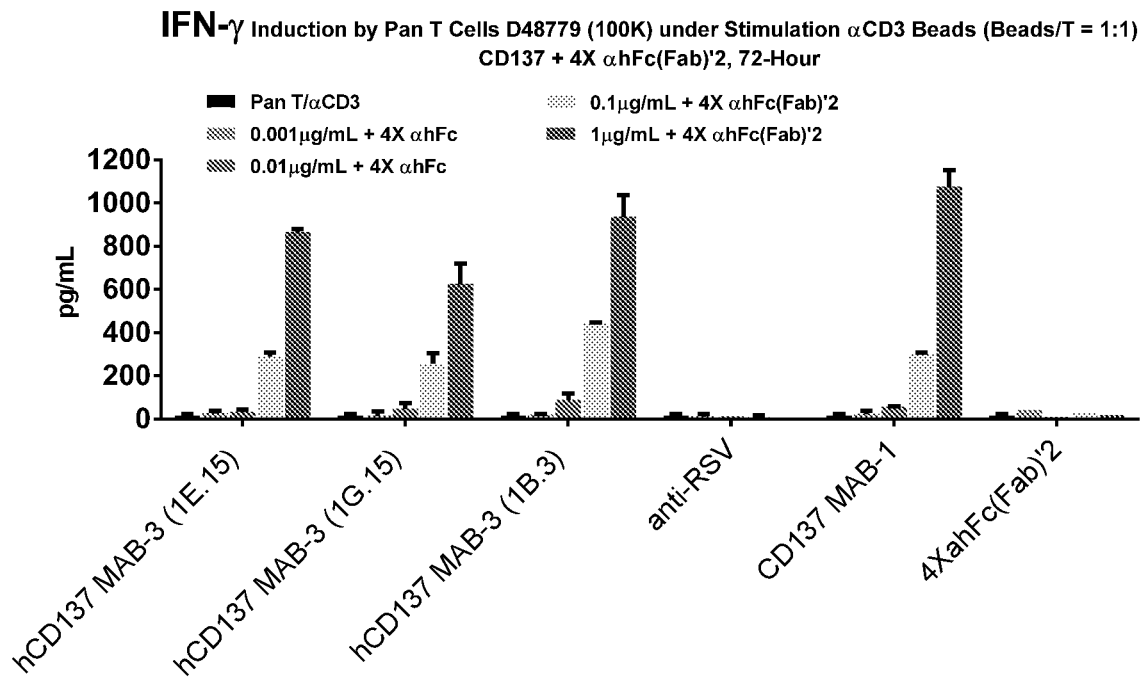
Figure 34A:
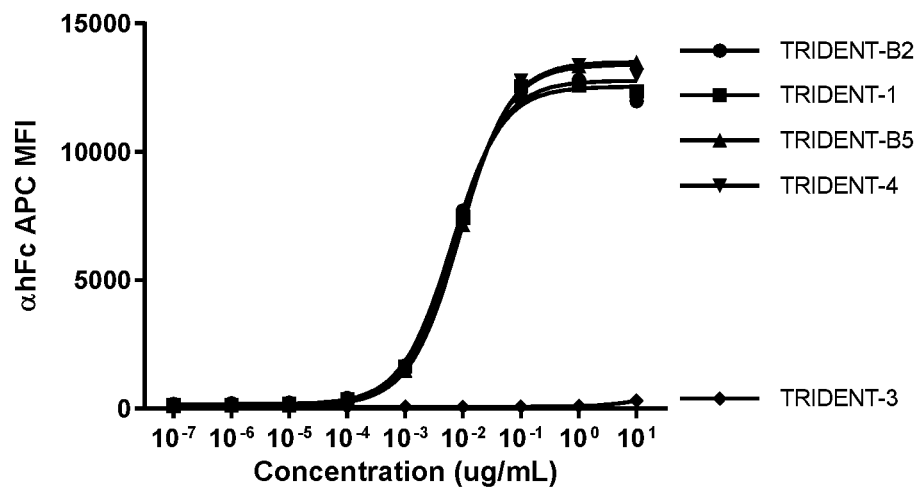
FIGS. 34A-34C show the ability of CD137×TA Binding Molecules TRIDENT-B2, TRIDENT-B5, and the control molecules TRIDENT-1, TRIDENT-3, and TRIDENT-4 to bind to CD137 on the surface of activated CD8+ T cells as measured by FACS using FITC-labeled CD8 and αhFc APC (FIG. 34A), and the illustrative TA, 5T4 on the surface of JIMT-1 ($5T4^{hi}$) (FIG. 34B) or SKOV-3 ($5T4^{lo}$) target cells (FIG. 34C).
Figure 34B:
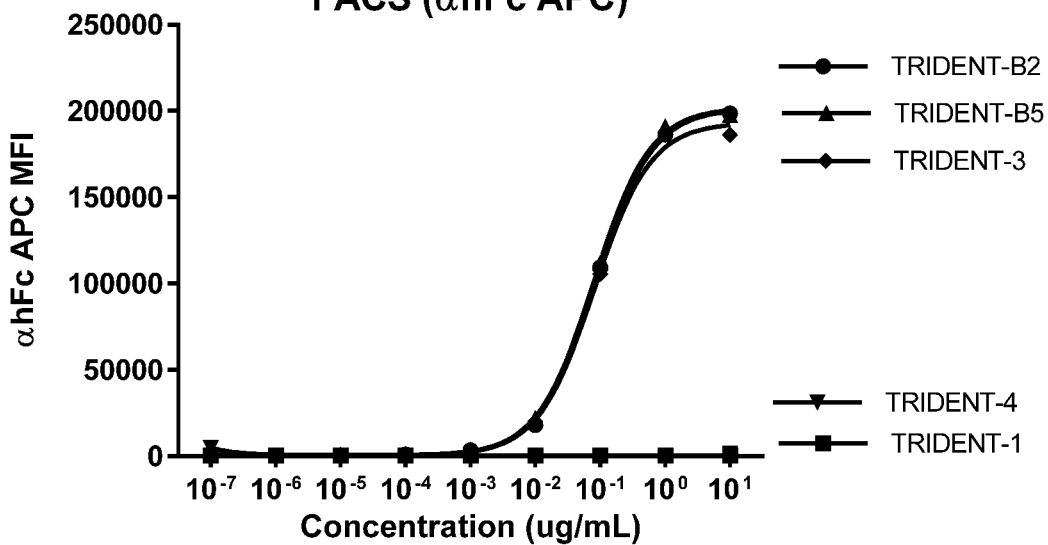
Figure 34C:
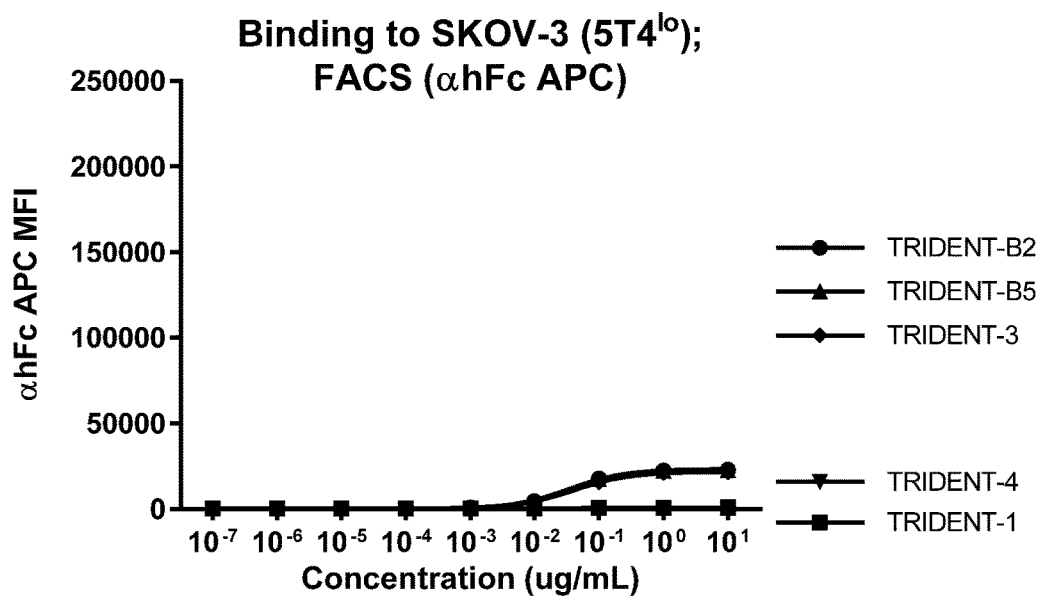

The results are plotted in FIG. 30, and show that the control molecules, TRIDENT-1 and TRIDENT-2 exhibited no co-stimulatory activity. While the CD137×TA Binding Molecules TRIDENT-A2 and TRIDENT-B2 (comprising the humanized/optimized anti-CD137 antibody hCD137 MAB-3 (1B.3)) both exhibited a dose dependent co-stimulatory activity.

Example 10

CD137 Deimmunization

In silico analysis of hCD137 MAB-3 (1B.3) identified two potential MHC class II binding peptides (T-cell

TABLE 14

| Assay | Stress Type | Optimal Value | TRIDENT- A | A2 | A3 | A4 |
|---|---|---|---|---|---|---|
| HP-SEC pure | none (4° C. storage) | >95%† | 99.4 | 96.6 | 97.1 | 99.6 |
| DSC | none | Tm Onset > 50° C. | 62.19 | 54.72 | 48.57 | 48.35 |
|  | none | Tm1 > 60° C. | 68.19 | 61.75 | 54.72 | 56.61 |
| Stability Assessed | Freeze Thaw 3× | no change | no change | no change | no change | no change |
|  | 25° C. | no change | no change | no change | no change | no change |
|  | 40° C. | no change | no change | sensitive | no change | sensitive | very sensitive |
|  | pH 5.5 Acetate | no change | no change | sensitive | no change | sensitive |
|  | pH 6.5 Histidine | no change | no change | no change | no change | no change |

Figure 35A:
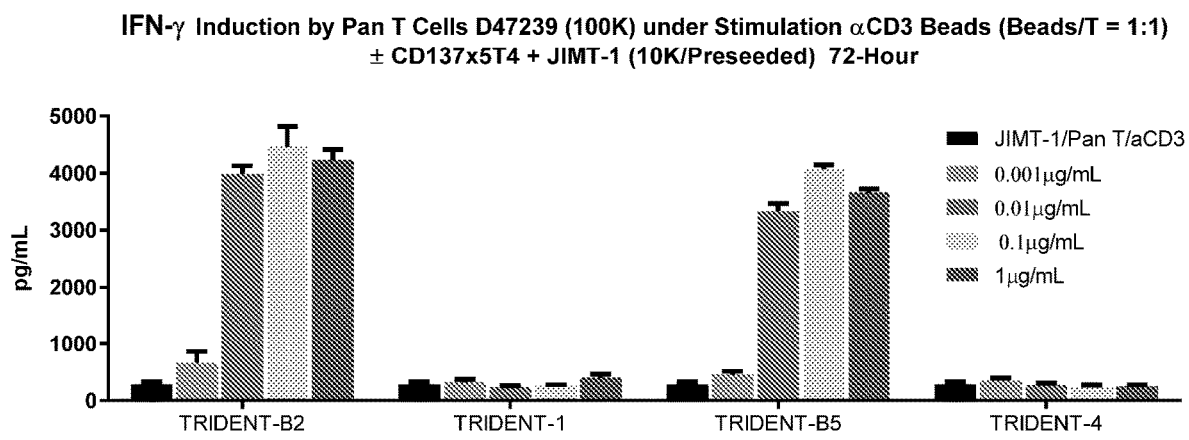
FIGS. 35A-35C show the ability of CD137×TA Binding Molecules to mediate a co-stimulatory activity in a T cell cytokine release assay (exemplified by release of IFN-γ). The Figures show results for TRIDENT-B2, TRIDENT-B5, and the control molecules TRIDENT-1, TRIDENT-3, and TRIDENT-4, tested in the presence of 5T4-expressing JIMT-1 ($5T4^{hi}$) (FIG. 35A) or SKOV-3 ($5T4^{lo}$) (FIG. 35B) target cells no co-stimulatory activity was seen in the absence of target cells (FIG. 35C).
Figure 35B:
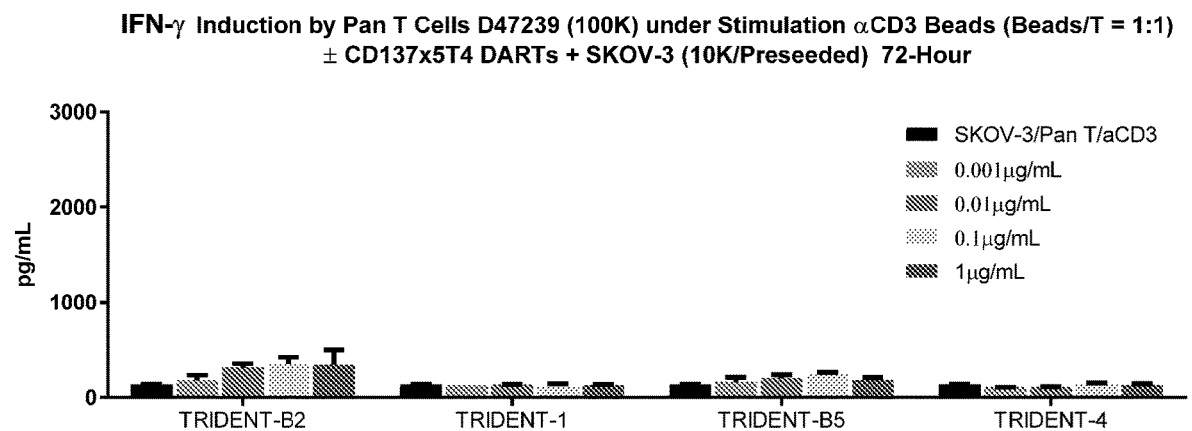
Figure 35C:
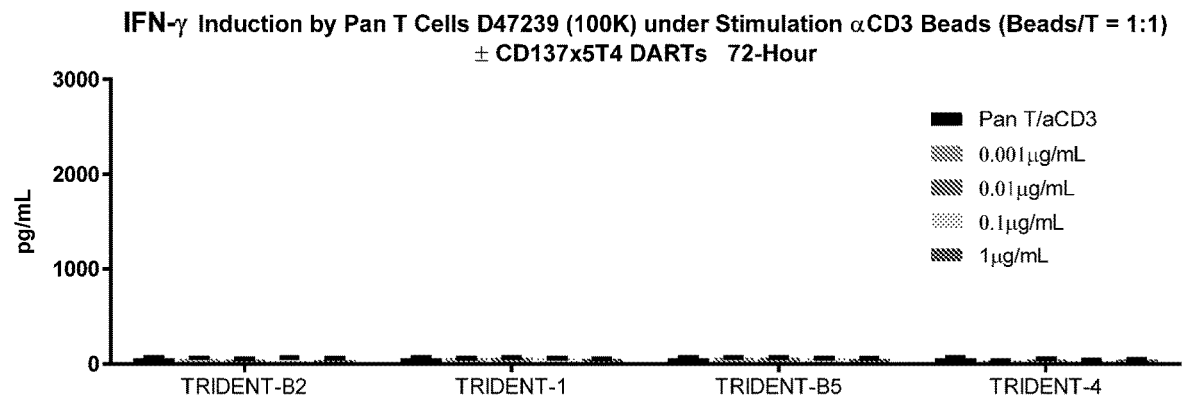

†indicates the percentage purity of the sample as measured by HP-SEC
sensitive: < 95% of desired product remains as measured by HP-SEC
very sensitive: < 90% desired product remains as measured by HP-SEC The Tm onset and Tm of the CD137 binding regions (Tm1) are in the optimal range for TRIDENT-A and TRIDENT-A2. However, the Tm onset and Tm1 are lower for epitopes) in the VH Domain and three potential MHC class II binding peptides in the VL Domain. A panel of amino acid substitutions to hCD137 MAB-3 (1B.3) were examined to identify substitutions (which may be single amino acid substitutions or sets of substitutions) to eliminate/reduce the potential immunogenicity of the identified T-cell epitopes. Specifically, amino acid substitutions were introduced at up to two positions (Kabat residues 38 and 48) for deimmunizing hCD137 MAB-3 VH1B and up to six positions (Kabat residues 24, 25, 44, 48, 52, and 54) for deimmunizing hCD137 MAB-3 VL3. The substituted amino acid residues in the VH and VL Domains are boxed and the Kabat numbering is indicated by arrows in FIGS. 31A and 31B, respectively. IgG1 antibodies (having 234A/235A Fc Domain (SEQ ID NO:40)) comprising the VH and/or VL variants of hCD137 MAB-3 (1B.3) having various substitutions at these positions, separately and/or in combination, were generated and characterized for their ability to bind CD137 by Attana Cell A200 QCM. Briefly, hCD137 MAB-3 (1B.3) and the deimmunized variants were independently captured on an Attana sensor chip coated with rabbit anti-human IgG Fc polyclonal antibody and soluble human CD137-His tagged fusion protein was passed over the chip at 11.1, 33.3, 100, and 300 mM. The sensograms of the deimmunized variants were compared to that of hCD137 MAB-3 (1B.3) and scored. The antibodies were also characterized for their thermal stability by DSC, performed essentially as described above in Example 8. The results for a number of such variants are summarized in Table 15, the amino acid sequences of these variants are provided above.

TABLE 15

| hCD137 MAB-3 Ref. | VH1B Substitutions^ | VL3 Substitutions^ | CD137 binding* | DSC‡ |
|---|---|---|---|---|
| (1B.3) | none | none | +++ | 64.7 |
| (1E.3) | K38R (VH1E) | none | +++ | 65 |
| (1F.3) | I48A (VH1F) | none | ++ | 55.0 |
| (1B.4) | none | R24Q/P25A (VL4) | +++ | 65.5 |
| (1B.5) | none | V44A (VL5) | +++ | 62.6 |
| (1B.6) | none | L54A (VL6) | +++ | 64.7 |
| (1G.7) | K38R/I48A (VH1G) | R24Q/P25A/V44A (VL7) | + | 45.2 |
| (1G.8) | K38R/I48A (VH1G) | R24Q/P25A/V44A/L54A (VL8) | + | n.d. |
| (1E.4) | K38R (VH1E) | R24Q/P25A (VL4) | +++ | 64.5 |
| (1G.4) | K38R/I48A (VH1G) | R24Q/P25A (VL4) | +++ | 55.1 |
| (1B.10) | none | S52T (VL10) | +++ | 65.2 |
| (1B.11) | none | S52G (VL11) | +++ | 64.4 |
| (1B.11) | none | I48A/S52T (VL12) | +++ | n.d. |
| (1B.13) | none | I48A/S52G (VL13) | ++− | n.d. |
| (1E.9) | K38R (VH1E) | R24Q/P25A/L54A (VL9) | +++ | 64 |
| (1E.14) | K38R (VH1E) | R24Q/P25A/S52T/L54A (VL14) | +++ | 64 |
| (1E.15) | K38R (VH1E) | R24Q/P25A/S52G/L54A (VL15) | +++ | 62.9 |
| (1G.14) | K38R/I48A (VH1G) | R24Q/P25A/S52T/L54A (VL14) | ++ | 51.9 |
| (1G.15) | K38R/I48A (VH1G) | R24Q/P25A/S52G/L54A (VL15) | + | 50 |

^substitution(s) relative to VH1B or VL3 are listed, the designation of the resulting variable region comprising the indicated substitutions is provided in parenthesis
*relative binding as compared to hCD137 MAB-3 (1B.3) (set to +++) determined by comparison of binding sensograms
‡Tm onset
"none" indicates no mutations are present
n.d. not determined A large number of deimmunized variants were identified that retain both CD137 binding activity and thermal stability. The majority of deimmunized variants comprising the VH Domain I48A substitution exhibited some reduction in both CD137 binding and in the onset of Tm.

Deimmunized hCD137 MAB-3 (1E.15) and hCD137 MAB-3 (1G.15), and the parental humanized hCD137 MAB-3 (1B.3) were tested for their ability to bind to activated $CD4^+$ and $CD8^+$ T cells essentially as described above. As shown in FIGS. 32A-32B the binding curve of the deimmunized antibody hCD137 MAB-3 (1E.15) was unchanged, while hCD137 MAB-3 (1G.15) exhibited slightly reduced binding to both $CD4^+$ and $CD8^+$ T cells.

The in vitro agonist activity hCD137 MAB-3 (1E.15) and hCD137 MAB-3 (1G.15) was evaluated in a T-cell cytokine release assay (performed essentially as described in Example 2 above, and exemplified by release of IFN-γ) in the absence of or with cross-linking. None of the hCD137 MAB-3 based antibodies exhibited activity was observed in the absence of cross-linking (FIG. 33A), with crossing linking hCD137 MAB-3 (1E.15) exhibited similar agonist activity to hCD137 MAB-3 (1B.3), while hCD137 MAB-3 (1G.15) exhibited a slight reduction in agonist activity likely due to the reduced binding for CD137 (FIG. 33B). As reported above CD137 MAB-1, exhibited agonist activity in the presence and absence of cross-linking.

Example 11

Trivalent CD137×TA Binding Molecules Having Deimmunized CD137 Binding Domains As described above the VH and VL Domains of hCD137 MAB-3 were humanized, optimized and deimmunized. Exemplary bispecific tetravalent and/or trivalent CD137×TA Binding Molecules are generated by incorporating such VH and VL Domains. One such bispecific trivalent binding molecule "TRIDENT-B5" comprising the CD137 binding domains of hCD137 MAB-3 (1E.15) was generated and evaluated in a number of assays. The structure and sequence of this exemplary CD137×TA Binding Molecule is provided in detail above. TRIDENT-B2 and one or more the control molecules. TRIDENT-1, TRIDENT-2, TRIDENT-3, TRIDENT-4 were included in these studies.

TRIDENT-B2, TRIDENT-B5, and the control molecules TRIDENT-1, TRIDENT-3, and TRIDENT-4 were evaluated for their ability to bind to activated $CD8^+$ T cells, and/or 5T4 present on the surface of target cells (high expressing JIMT-1 breast carcinoma cells and low expressing SKOV-3 ovarian carcinoma cells) essentially as described above. As shown in FIG. 34A, all the molecules comprising two CD137 binding domains (TRIDENT-B2, TRIDENT-B5, and the control molecules TRIDENT-1 and TRIDENT-4) exhibited similar binding to activated $CD8^+$ T cells, while the control molecule lacking any CD137 binding domains (TRIDENT-3) did not bind. Similarly, all the molecules having a 5T4 binding domain (TRIDENT-B2, TRIDENT-B5, and the control TRIDENT-3) exhibited similar strong binding to target cells expressing high levels of 5T4 (JIMT-1, FIG. 34B), and weaker binding to target cells expressing low levels of 5T4 (SKOV-3, FIG. 34C), while the control molecules lacking a 5T4 binding domain (TRIDENT-1 and TRIDENT-4) did not bind to either 5T4 expressing target cell.

The in vitro agonist activity of TRIDENT-B2, TRIDENT-B5, and the control molecules TRIDENT-1, TRIDENT-3, and TRIDENT-4 were evaluated in a T-cell cytokine release assay (performed essentially as described in Example 2 above, and exemplified by release of IFN-γ) in the presence or absence of target cells expressing different levels of the exemplary TA, 5T4 (JIMT-1 ($5T4^{hi}$) cells, or SKOV-3 ($5T4^{lo}$) cells).

As shown in FIGS. 35A-35C, TRIDENT-1, TRIDENT-4 (lacking a 5T4 binding domain) exhibited no co-stimulatory activity. TRIDENT-3 (lacking CD137 binding domains) was also found to lack any co-stimulatory activity. TRIDENT-B2, and TRIDENT-B5 exhibited similar a dose dependent co-stimulatory activity in the presence of high 5T4-expressing JIMT-1 target cells (FIG. 35A) but little or no co-stimulatory activity in the presence of low 5T4-expressing SKOV-3 target cells (FIG. 35B), or no target cells (FIG. 35C).

The results of these studies indicate that CD137×TA Binding Molecules comprising the deimmunized VH and VL Domains of hCD137 MAB-3 (1E.15) exhibit comparable binding and co-stimulatory activity profiles as CD137× TA Binding Molecules comprising the optimized VH and VL Domains of hCD137 MAB-3 (1B.3).

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A CD137×TA Binding Molecule capable of specific binding to an epitope of CD137 and an epitope of a tumor antigen (TA), comprising a CD137 binding domain and a TA binding domain, wherein the CD137 binding domain comprises:
a first Light Chain Variable Domain that comprises a $CDR_L1$, $CDR_L2$ and $CDR_L3$, and
a first Heavy Chain Variable Domain that comprises a $CDR_H1$, $CDR_H2$ and $CDR_H3$; wherein:
(A) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(B) (1) said first Light Chain Variable Domain $CDR_L1$, $CDR_L2$, and $CDR_L3$ are the Light Chain CDRs of CD137 MAB-3 VL15 (SEQ ID NO:222); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(C) (1) said first Light Chain Variable Domain $CDR_L1$, $CDR_L2$, and $CDR_L3$ are the Light Chain CDRs of CD137 MAB-3 VL14 (SEQ ID NO:221); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(D) (1) said first Light Chain Variable Domain $CDR_L1$, $CDR_L2$, and $CDR_L3$ are the Light Chain CDRs of CD137 MAB-3 VL11 (SEQ ID NO:218); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(E) (1) said first Light Chain Variable Domain $CDR_L1$, $CDR_L2$, and $CDR_L3$ are the Light Chain CDRs of CD137 MAB-3 VL10 (SEQ ID NO:217); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(F) (1) said first Light Chain Variable Domain $CDR_L1$, $CDR_L2$, and $CDR_L3$ are the Light Chain CDRs of CD137 MAB-3 VL6 (SEQ ID NO:213); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(G) (1) said first Light Chain Variable Domain $CDR_L1$, $CDR_L2$, and $CDR_L3$ are the Light Chain CDRs of CD137 MAB-3 VL4 (SEQ ID NO:211); and
(2) said first Heavy Chain Variable Domain $CDR_H1$, $CDR_H2$, and $CDR_H3$ are the Heavy Chain CDRs of CD137 MAB-3 VH1B (SEQ ID NO:84);
(H) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH (SEQ ID NO:74);
(I) (1) said first Light Chain Variable Domain $CDR_L1$, $CDR_L2$, and $CDR_L3$ are the Light Chain CDRs of CD137 MAB-4 VL (SEQ ID NO:91); and
(2) said first Heavy Chain Variable Domain $CDR_H1$, $CDR_H2$, and $CDR_H3$ are the Heavy Chain CDRs of CD137 MAB-4 VH (SEQ ID NO:90);
(J) (1) said first Light Chain Variable Domain $CDR_L1$, $CDR_L2$, and $CDR_L3$ are the Light Chain CDRs of CD137 MAB-5 VL (SEQ ID NO:97); and
(2) said first Heavy Chain Variable Domain $CDR_H1$, $CDR_H2$, and $CDR_H3$ are the Heavy Chain CDRs of CD137 MAB-5 VH (SEQ ID NO:96);
(K) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1A (SEQ ID NO:83);
(L) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1C (SEQ ID NO:85);
or
(M) (1) said first Light Chain Variable Domain $CDR_L1$, $CDR_L2$, and $CDR_L3$ are the Light Chain CDRs of CD137 MAB-3 VL (SEQ ID NO:75); and
(2) said first Heavy Chain Variable Domain $CDR_H1$, $CDR_H2$, and $CDR_H3$ are the Heavy Chain CDRs of CD137 MAB-3 VH1D (SEQ ID NO:86),
and wherein the TA binding domain comprises:
a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$.

2. The CD137×TA Binding Molecule of claim 1, wherein:
(A) said first Light Chain Variable Domain comprises the amino acid sequence of CD137 MAB-3 VL15 (SEQ ID NO:222), and said first Heavy Chain Variable Domain comprises the amino acid sequence of hCD137 MAB-3 VH1B (SEQ ID NO:84); or
(B) said first Light Chain Variable Domain comprises the amino acid sequence of CD137 MAB-3 VL14 (SEQ ID NO:221), and said first Heavy Chain Variable Domain comprises the amino acid sequence of hCD137 MAB-3 VH1B (SEQ ID NO:84); or
(C) said first Light Chain Variable Domain comprises the amino acid sequence of CD137 MAB-3 11 (SEQ ID NO:218), and said first Heavy Chain Variable Domain comprises the amino acid sequence of hCD137 MAB-3 VH1B (SEQ ID NO:84); or
(D) said first Light Chain Variable Domain comprises the amino acid sequence of CD137 MAB-3 VL10 (SEQ ID NO:217), and said first Heavy Chain Variable Domain comprises the amino acid sequence of hCD137 MAB-3 VH1B (SEQ ID NO:84); or
(E) said first Light Chain Variable Domain comprises the amino acid sequence of CD137 MAB-3 VL6 (SEQ ID NO:213), and said first Heavy Chain Variable Domain comprises the amino acid sequence of hCD137 MAB-3 VH1B (SEQ ID NO:84); or
(F) said first Light Chain Variable Domain comprises the amino acid sequence of CD137 MAB-3 VL4 (SEQ ID NO:211), and said first Heavy Chain Variable Domain comprises the amino acid sequence of hCD137 MAB-3 VH1B (SEQ ID NO:84).

3. The CD137×TA Binding Molecule of claim 1, wherein: said tumor antigen (TA) is selected from the group of tumor antigens consisting of: 19.9; oncofetal protein 5T4; A33; AFP; ALCAM; BAGE; beta-catenin; CA125; Carboxypeptidase M; B1; CD5; CD19; CD20; CD22; CD23; CD25; CD27; CD30; CD33; CD36; CD46; CD52; CD79a/CD79b; CD123; CD317; CEA; CEACAM5; CEACAM6; CO-43; CO-514; CTLA-1; CTLA-4; Cytokeratin 8; EGF-R; an Ephrin receptor;

Erb; F3; FC10.2; a GAGE GD2; GD3; GD49; GM2; GM3; GICA 19-9; gp37; gp75; gp100; HER-2/neu; human B-lymphoma antigen-CD20; human milk fat globule antigen; human papillomavirus-E6; human papillomavirus-E7; HMW-MAA; I antigen; ITGB6; IL13Rα2; JAM-3; KID3; KID31; KS 1/4 pan-carcinoma antigen; KS 1/4; KSA; L6; L20; LEA; LUCA-2; M1:22:25:8; M18; M39; a MAGE; MART; Myl; MUC-1; MUM-1; N-acetylglucosaminyltransferase; neoglycoprotein; NS-10; OFA-1; OFA-2; Oncostatin M; p15; PSA; PSMA; PEMA; PIPA; prostatic acid phosphate; ROR1; SSEA-1; SSEA-3; SSEA-4; sTn; T cell receptor derived peptide; TAG-72; TL5; TNF-α receptor; TNF-ß receptor; TNF-γ receptor; TRA-1-85; Transferrin Receptor; TSTA; and VEGF-R.

4. The CD137×TA Binding Molecule of claim 3, wherein: said tumor antigen (TA) is HER2/neu; and
   (A) said second Light Chain Variable Domain $CDR_L1$, $CDR_L2$, and $CDR_L3$ are the Light Chain CDRs of HER2 MAB-1 VL (SEQ ID NO:63); and
   (B) said second Heavy Chain Variable Domain $CDR_H1$, $CDR_H2$, and $CDR_H3$ are the Heavy Chain CDRs of HER2 MAB-1 VH (SEQ ID NO:62).

5. The CD137×TA Binding Molecule of claim 4, wherein: said second Heavy Chain Variable Domain comprises the amino acid sequence of:
   (A) hHER2 MAB-1 VH1 (SEQ ID NO:64);
   (B) hHER2 MAB-1 VH2 (SEQ ID NO:65); or
   (C) hHER2 MAB-1 VH3 (SEQ ID NO:66); and
said second Light Chain Variable Domain comprises the amino acid sequence of:
   (A) hHER2 MAB-1 VL1 (SEQ ID NO:67);
   (B) hHER2 MAB-1 VL2 (SEQ ID NO:68); or
   (C) hHER2 MAB-1 VL3 (SEQ ID NO:69).

6. The CD137×TA Binding Molecule of claim 3, wherein: the tumor antigen (TA) is 5T4; and
   (I) (A) the second Light Chain Variable Domain $CDR_L1$, $CDR_L2$, and $CDR_L3$ are the Light Chain CDRs of 5T4 MAB-1 VL (SEQ ID NO:135); and
   (B) the second Heavy Chain Variable Domain $CDR_H1$, $CDR_H2$, and $CDR_H3$ are the Heavy Chain CDRs of 5T4 MAB-1 VH (SEQ ID NO:134); or
   (II) (A) the second Light Chain Variable Domain $CDR_L1$, $CDR_L2$, and $CDR_L3$ are the Light Chain CDRs of 5T4 MAB-2 VL (SEQ ID NO:137); and
   (B) the second Heavy Chain Variable Domain $CDR_H1$, $CDR_H2$, and $CDR_H3$ are the Heavy Chain CDRs of 5T4 MAB-2 VH (SEQ ID NO:136).

7. A pharmaceutical composition comprising the CD137× TA Binding Molecule of claim 1, and a physiologically acceptable carrier.

8. The CD137×TA Binding Molecule of claim 1, wherein said tumor antigen (TA) is selected from the group of tumor antigens consisting of: HER-2/neu, EphA2, 5T4, B7-H3, gpA33, CEACAM5, CEACAM6, CD19 and CD123.

* * * * *

SEQUENCE LISTING

```
<160> NUMBER OF SEQ ID NOS: 232

<210> SEQ ID NO 1
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG CL Kappa Domain

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Human IgG CL Lambda Domain

<400> SEQUENCE: 2

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80
```

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 3
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 4
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 5
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG3 CH1 Domain -continued

<400> SEQUENCE: 5

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 6
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 7
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Human IgG1 Hinge Region

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG2 Hinge Region

```
<400> SEQUENCE: 8

Glu Arg Lys Cys Cys Val Glu Cys Pro Pro Cys Pro
1               5                   10

<210> SEQ ID NO 9
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: Human IgG3 Hinge Region

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 10
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG4 Hinge Region

<400> SEQUENCE: 10

Glu Ser Lys Tyr Gly Pro Pro Cys Pro Ser Cys Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Human IgG4 Hinge Region Variant Comprising
      S228P Substitution

<400> SEQUENCE: 11

Glu Ser Lys Tyr Gly Pro Pro Cys Pro Pro Cys Pro
1               5                   10

<210> SEQ ID NO 12
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Exemplary Human IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 12

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                20                  25                  30
Val Val Asp Val Ser His Glu Asp Pro Glu Val Lys Phe Asn Trp Tyr
            35                  40                  45
Val Asp Gly Val Glu Val His Asn Ala Lys Thr Lys Pro Arg Glu Glu
        50                  55                  60
Gln Tyr Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Xaa
    210                 215

<210> SEQ ID NO 13
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: Exemplary Human IgG2 CH2-CH3 Domain
<220> FEATURE:
<221> NAME/KEY: MISC_FEATURE
<222> LOCATION: (216)..(216)
<223> OTHER INFORMATION: Xaa is Lysine (K) or Is Absent

<400> SEQUENCE: 13

Ala Pro Pro Val Ala Gly Pro Ser Val Phe Leu Phe Pro Pro Lys Pro
 1               5                  10                  15
Lys Asp Thr Leu Met Ile Ser Arg Thr Pro Glu Val Thr Cys Val Val
            20                  25                  30
Val Asp Val Ser His Glu Asp Pro Glu Val Gln Phe Asn Trp Tyr Val
        35                  40                  45
Asp Gly Val Glu Val His Asn Ala Lys Thr Lys Pro Arg Glu Glu Gln
    50                  55                  60
Phe Asn Ser Thr Phe Arg Val Val Ser Val Leu Thr Val His Gln
 65                  70                  75                  80
Asp Trp Leu Asn Gly Lys Glu Tyr Lys Cys Lys Val Ser Asn Lys Gly
                85                  90                  95
Leu Pro Ala Pro Ile Glu Lys Thr Ile Ser Lys Thr Lys Gly Gln Pro
            100                 105                 110
Arg Glu Pro Gln Val Tyr Thr Leu Pro Pro Ser Arg Glu Glu Met Thr
        115                 120                 125
Lys Asn Gln Val Ser Leu Thr Cys Leu Val Lys Gly Phe Tyr Pro Ser
```

```
                130                 135                 140
Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
                195                 200                 205

Ser Leu Ser Leu Ser Pro Gly Xaa
                210                 215

<210> SEQ ID NO 14
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Exemplary Human IgG3 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
                35                  40                  45

Val Asp Gly Val Glu Val His Asn Ala Lys Thr Lys Pro Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
                100                 105                 110

Pro Arg Glu Pro Gln Val Tyr Thr Leu Pro Pro Ser Arg Glu Glu Met
                115                 120                 125

Thr Lys Asn Gln Val Ser Leu Thr Cys Leu Val Lys Gly Phe Tyr Pro
                130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
                180                 185                 190

Phe Ser Cys Ser Val Met His Glu Ala Leu His Asn Arg Phe Thr Gln
                195                 200                 205

Lys Ser Leu Ser Leu Ser Pro Gly Xaa
                210                 215

<210> SEQ ID NO 15
<211> LENGTH: 217
<212> TYPE: PRT
```

```
<213> ORGANISM: Homo sapiens
<220> FEATURE:
<221> NAME/KEY: MISC_FEATURE
<222> LOCATION: (1)..(217)
<223> OTHER INFORMATION: Exemplary Human IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 15

Ala Pro Glu Phe Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 16
<211> LENGTH: 8
<212> TYPE: PRT
<213> ORGANISM: Artificial Sequence
<220> FEATURE:
<223> OTHER INFORMATION: Preferred Intervening Spacer Peptide (Linker 1)

<400> SEQUENCE: 16

Gly Gly Gly Ser Gly Gly Gly Gly
1               5

<210> SEQ ID NO 17
<211> LENGTH: 15
<212> TYPE: PRT
<213> ORGANISM: Artificial Sequence
<220> FEATURE:
<223> OTHER INFORMATION: Intervening Spacer Peptide (Linker 1) for scFv
      Molecules

<400> SEQUENCE: 17

Gly Gly Gly Gly Ser Gly Gly Gly Gly Ser Gly Gly Gly Gly Ser
```

-continued

```
1               5               10              15
```

<210> SEQ ID NO 18
<211> LENGTH: 6
<212> TYPE: PRT
<213> ORGANISM: Artificial Sequence
<220> FEATURE:
<223> OTHER INFORMATION: Preferred Intervening Spacer Peptide (Linker 2)

<400> SEQUENCE: 18

Gly Gly Cys Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Alternative Intervening Spacer Peptide (Linker
      2)

<400> SEQUENCE: 19

Ala Ser Thr Lys Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Preferred Heterodimer-Promoting Domain (Linker
      3)

<400> SEQUENCE: 20

Asp Lys Thr His Thr Cys Pro Pro Cys Pro
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Alternative Heterodimer-Promoting Domain
      (Linker 3)

<400> SEQUENCE: 21

Gly Gly Gly Asp Lys Thr His Thr Cys Pro Pro Cys Pro
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Preferred Intervening Spacer Peptide (Linker 4)

<400> SEQUENCE: 22

Ala Pro Ser Ser Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Alternative Preferred Intervening Spacer
      Peptide (Linker 4)

```
<400> SEQUENCE: 23

Ala Pro Ser Ser Pro Met Glu
1               5

<210> SEQ ID NO 24
<211> LENGTH: 11
<212> TYPE: PRT
<213> ORGANISM: Artificial Sequence
<220> FEATURE:
<223> OTHER INFORMATION: Alternative Preferred Intervening Spacer
      Peptide (Linker 4)

<400> SEQUENCE: 24

Gly Gly Gly Ser Gly Gly Gly Ser Gly Gly Gly
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Alternative Linker

<400> SEQUENCE: 25

Leu Gly Gly Gly Ser Gly
1               5

<210> SEQ ID NO 26
<211> LENGTH: 4
<212> TYPE: PRT
<213> ORGANISM: Artificial Sequence
<220> FEATURE:
<223> OTHER INFORMATION: Alternative Linker

<400> SEQUENCE: 26

Gly Gly Gly Ser
1

<210> SEQ ID NO 27
<211> LENGTH: 6
<212> TYPE: PRT
<213> ORGANISM: Artificial Sequence
<220> FEATURE:
<223> OTHER INFORMATION: Alternative Linker

<400> SEQUENCE: 27

Leu Glu Pro Lys Ser Ser
1               5

<210> SEQ ID NO 28
<211> LENGTH: 16
<212> TYPE: PRT
<213> ORGANISM: Artificial Sequence
<220> FEATURE:
<223> OTHER INFORMATION: Alternative Linker

<400> SEQUENCE: 28

Val Glu Pro Lys Ser Ala Asp Lys Thr His Thr Cys Pro Pro Cys Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Alternative Linker
```

```
<400> SEQUENCE: 29

Leu Glu Pro Lys Ser Ala Asp Lys Thr His Thr Cys Pro Pro Cys Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Alternative Linker

<400> SEQUENCE: 30

Leu Glu Pro Lys Ser Ser Asp Lys Thr His Thr Cys Pro Pro Cys Pro
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: Preferred Heterodimer-Promoting Domain

<400> SEQUENCE: 31

Gly Val Glu Pro Lys Ser Cys
1               5

<210> SEQ ID NO 32
<211> LENGTH: 6
<212> TYPE: PRT
<213> ORGANISM: Artificial Sequence
<220> FEATURE:
<223> OTHER INFORMATION: Preferred Heterodimer-Promoting Domain

<400> SEQUENCE: 32

Val Glu Pro Lys Ser Cys
1               5

<210> SEQ ID NO 33
<211> LENGTH: 6
<212> TYPE: PRT
<213> ORGANISM: Artificial Sequence
<220> FEATURE:
<223> OTHER INFORMATION: Preferred Heterodimer-Promoting Domain

<400> SEQUENCE: 33

Ala Glu Pro Lys Ser Cys
1               5

<210> SEQ ID NO 34
<211> LENGTH: 7
<212> TYPE: PRT
<213> ORGANISM: Artificial Sequence
<220> FEATURE:
<223> OTHER INFORMATION: Preferred Heterodimer-Promoting Domain

<400> SEQUENCE: 34

Gly Phe Asn Arg Gly Glu Cys
1               5

<210> SEQ ID NO 35
<211> LENGTH: 6
<212> TYPE: PRT
<213> ORGANISM: Artificial Sequence
<220> FEATURE:
<223> OTHER INFORMATION: Preferred Heterodimer-Promoting Domain

<400> SEQUENCE: 35
```

```
Phe Asn Arg Gly Glu Cys
1               5

<210> SEQ ID NO 36
<211> LENGTH: 28
<212> TYPE: PRT
<213> ORGANISM: Artificial Sequence
<220> FEATURE:
<223> OTHER INFORMATION: E-Coil Heterodimer-Promoting Domain

<400> SEQUENCE: 36

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 37
<211> LENGTH: 28
<212> TYPE: PRT
<213> ORGANISM: Artificial Sequence
<220> FEATURE:
<223> OTHER INFORMATION: K-Coil Heterodimer-Promoting Domain

<400> SEQUENCE: 37

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 38
<211> LENGTH: 28
<212> TYPE: PRT
<213> ORGANISM: Artificial Sequence
<220> FEATURE:
<223> OTHER INFORMATION: Cysteine-Containing E-Coil Heterodimer-
      Promoting Domain

<400> SEQUENCE: 38

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 39
<211> LENGTH: 28
<212> TYPE: PRT
<213> ORGANISM: Artificial Sequence
<220> FEATURE:
<223> OTHER INFORMATION: Cysteine-Containing K-Coil Heterodimer-
      Promoting Domain

<400> SEQUENCE: 39

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 40
<211> LENGTH: 217
<212> TYPE: PRT
<213> ORGANISM: Artificial Sequence
<220> FEATURE:
<223> OTHER INFORMATION: Human IgG1 CH2-CH3 Domain Variant Comprising
      Kabat L234A and L235A Substitutions
<220> FEATURE:
```

<221> NAME/KEY: MISC_FEATURE
<222> LOCATION: (217)..(217)
<223> OTHER INFORMATION: Xaa is Lysine (K) or Is Absent

<400> SEQUENCE: 40

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 41
<211> LENGTH: 217
<212> TYPE: PRT
<213> ORGANISM: Artificial Sequence
<220> FEATURE:
<223> OTHER INFORMATION: Human IgG1 CH2-CH3 Domain Variant Comprising
      Kabat M252Y, S254T and T256E Substitutions
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 41

```
Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                    85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 42
<211> LENGTH: 217
<212> TYPE: PRT
<213> ORGANISM: Artificial Sequence
<220> FEATURE:
<223> OTHER INFORMATION: Human IgG1 CH2-CH3 Domain Variant Comprising
      Kabat L234A, L235A, M252Y, S254T and T256E Substitutions
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 42

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Xaa
        210                 215

<210> SEQ ID NO 43
<211> LENGTH: 217
<212> TYPE: PRT
<213> ORGANISM: Artificial Sequence
<220> FEATURE:
<223> OTHER INFORMATION: Human IgG4 CH2-CH3 Domain Variant Comprising
      Kabat M252Y, S254T and T256E Substitutions
<220> FEATURE:
<221> NAME/KEY: misc_feature
<222> LOCATION: (217)..(217)
<223> OTHER INFORMATION: Xaa can be any naturally occurring amino acid

<400> SEQUENCE: 43

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
        210                 215

<210> SEQ ID NO 44
<211> LENGTH: 217
<212> TYPE: PRT
<213> ORGANISM: Artificial Sequence
<220> FEATURE:
<223> OTHER INFORMATION: Exemplary "Knob-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 44

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                    20                  25                  30
Val Val Asp Val Ser His Glu Asp Pro Glu Val Lys Phe Asn Trp Tyr
            35                  40                  45
Val Asp Gly Val Glu Val His Asn Ala Lys Thr Lys Pro Arg Glu Glu
        50                  55                  60
Gln Tyr Asn Ser Thr Tyr Arg Val Val Ser Val Leu Thr Val Leu His
 65                 70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Trp Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Xaa
    210                 215

<210> SEQ ID NO 45
<211> LENGTH: 217
<212> TYPE: PRT
<213> ORGANISM: Artificial Sequence
<220> FEATURE:
<223> OTHER INFORMATION: Exemplary "Knob-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 45

Ala Pro Glu Phe Leu Gly Gly Pro Ser Val Phe Leu Phe Pro Pro Lys
 1               5                  10                  15
Pro Lys Asp Thr Leu Tyr Ile Thr Arg Glu Pro Glu Val Thr Cys Val
            20                  25                  30
Val Val Asp Val Ser Gln Glu Asp Pro Glu Val Gln Phe Asn Trp Tyr
        35                  40                  45
Val Asp Gly Val Glu Val His Asn Ala Lys Thr Lys Pro Arg Glu Glu
    50                  55                  60
Gln Phe Asn Ser Thr Tyr Arg Val Val Ser Val Leu Thr Val Leu His
 65                 70                  75                  80
Gln Asp Trp Leu Asn Gly Lys Glu Tyr Lys Cys Lys Val Ser Asn Lys
                85                  90                  95
Gly Leu Pro Ser Ser Ile Glu Lys Thr Ile Ser Lys Ala Lys Gly Gln
            100                 105                 110
Pro Arg Glu Pro Gln Val Tyr Thr Leu Pro Pro Ser Gln Glu Glu Met
        115                 120                 125
Thr Lys Asn Gln Val Ser Leu Trp Cys Leu Val Lys Gly Phe Tyr Pro
    130                 135                 140
```

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 46
<211> LENGTH: 217
<212> TYPE: PRT
<213> ORGANISM: Artificial Sequence
<220> FEATURE:
<223> OTHER INFORMATION: Exemplary "Knob-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 46

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 47
<211> LENGTH: 217
<212> TYPE: PRT
<213> ORGANISM: Artificial Sequence
<220> FEATURE:
<223> OTHER INFORMATION: Exemplary "Hole-Bearing" IgG1 CH2-CH3 Domain
<220> FEATURE:
```

```
<221> NAME/KEY: MISC_FEATURE
<222> LOCATION: (217)..(217)
<223> OTHER INFORMATION: Xaa is Lysine (K) or Is Absent

<400> SEQUENCE: 47

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215

<210> SEQ ID NO 48
<211> LENGTH: 217
<212> TYPE: PRT
<213> ORGANISM: Artificial Sequence
<220> FEATURE:
<223> OTHER INFORMATION: Exemplary "Hole-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 48

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Arg Leu Thr Val Asp Lys Ser Arg Trp Gln Glu Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Leu Gly Xaa
        210                 215

<210> SEQ ID NO 49
<211> LENGTH: 217
<212> TYPE: PRT
<213> ORGANISM: Artificial Sequence
<220> FEATURE:
<223> OTHER INFORMATION: Exemplary "Hole-Bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or Is Absent

<400> SEQUENCE: 49

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
```

<210> SEQ ID NO 50
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus Strain G148

<400> SEQUENCE: 50

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 51
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus Strain G148

<400> SEQUENCE: 51

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 52
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus Strain G148

<400> SEQUENCE: 52

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 53
<211> LENGTH: 46
<212> TYPE: PRT
<213> ORGANISM: Artificial Sequence
<220> FEATURE:
<223> OTHER INFORMATION: Deimmunized Albumin-Binding Domain 3 (ABD3) of
      Protein G of Streptococcus Strain G148

<400> SEQUENCE: 53

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu

```
                 20                  25                  30

Gly Val Lys Ala Leu Ile Ala Glu Ile Leu Ala Ala Leu Pro
            35                  40                  45

<210> SEQ ID NO 54
<211> LENGTH: 120
<212> TYPE: PRT
<213> ORGANISM: Artificial Sequence
<220> FEATURE:
<223> OTHER INFORMATION: VH Domain of Margetuximab

<400> SEQUENCE: 54

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120

<210> SEQ ID NO 55
<211> LENGTH: 107
<212> TYPE: PRT
<213> ORGANISM: Artificial Sequence
<220> FEATURE:
<223> OTHER INFORMATION: VL Domain of Margetuximab

<400> SEQUENCE: 55

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys
            100                 105

<210> SEQ ID NO 56
<211> LENGTH: 120
<212> TYPE: PRT
<213> ORGANISM: Artificial Sequence
<220> FEATURE:
<223> OTHER INFORMATION: VH Domain of Trastuzumab

<400> SEQUENCE: 56
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 57
<211> LENGTH: 107
<212> TYPE: PRT
<213> ORGANISM: Artificial Sequence
<220> FEATURE:
<223> OTHER INFORMATION: VL Domain of Trastuzumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys
            100                 105

<210> SEQ ID NO 58
<211> LENGTH: 119
<212> TYPE: PRT
<213> ORGANISM: Artificial Sequence
<220> FEATURE:
<223> OTHER INFORMATION: VH Domain of Pertuzumab

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Asn Leu Gly Pro Ser Phe Tyr Phe Asp Tyr Trp Gly Gln Gly
                100                 105                 110

Thr Leu Val Thr Val Ser Ser
            115

<210> SEQ ID NO 59
<211> LENGTH: 107
<212> TYPE: PRT
<213> ORGANISM: Artificial Sequence
<220> FEATURE:
<223> OTHER INFORMATION: VL Domain of Pertuzumab

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
                100                 105

<210> SEQ ID NO 60
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Murine Anti-HER2/neu Monoclonal Antibody HER2-
      MAB-1 VH Domain

<400> SEQUENCE: 60

Glu Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Asn Ile Gly Glu Pro Thr Tyr Thr Glu Glu Phe
    50                  55                  60

Lys Gly Arg Phe Ala Phe Ser Leu Gly Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Asp Asp Gly Tyr Gly Asn Arg Val Ser Tyr Trp Gly Gln Gly
                100                 105                 110

Thr Leu Val Thr Val Ser Ala
            115
```

```
<210> SEQ ID NO 61
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Murine Anti-HER2/neu Monoclonal Antibody HER2-
      MAB-1 VL Domain

<400> SEQUENCE: 61

Asp Ile Leu Met Thr Gln Ser Pro Leu Ser Met Tyr Thr Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln His Asp Glu Phe Pro Trp
                85                  90                  95

Thr Phe Gly Gly Gly Thr Lys Leu Glu Ile Lys
            100                 105

<210> SEQ ID NO 62
<211> LENGTH: 119
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VH Domain
<220> FEATURE:
<221> NAME/KEY: MISC_FEATURE
<222> LOCATION: (100)..(100)
<223> OTHER INFORMATION: Xaa is Asparatate (D) or Glutamate (E)
<220> FEATURE:
<221> NAME/KEY: MISC_FEATURE
<222> LOCATION: (101)..(101)
<223> OTHER INFORMATION: Xaa is Glycine (G) or Isoleucine (I)

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Xaa Xaa Tyr Gly Asn Arg Val Ser Tyr Trp Gly Gln Gly
            100                 105                 110

Thr Leu Val Thr Val Ser Ser
        115

<210> SEQ ID NO 63
```

```
<211> LENGTH: 107
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VL Domain
<220> FEATURE:
<221> NAME/KEY: MISC_FEATURE
<222> LOCATION: (30)..(30)
<223> OTHER INFORMATION: Xaa is Asparagine (N) or Serine (S)
<220> FEATURE:
<221> NAME/KEY: MISC_FEATURE
<222> LOCATION: (31)..(31)
<223> OTHER INFORMATION: Xaa is Serine (S), Threonine (T) or Asparagine
      (N)
<220> FEATURE:
<221> NAME/KEY: MISC_FEATURE
<222> LOCATION: (55)..(55)
<223> OTHER INFORMATION: Xaa is Valine (V) or Glutamine (Q)
<220> FEATURE:
<221> NAME/KEY: MISC_FEATURE
<222> LOCATION: (56)..(56)
<223> OTHER INFORMATION: Xaa is Aspartate (D), Glutamate (E) or Serine
      (S)

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Xaa Xaa Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Xaa Xaa Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105

<210> SEQ ID NO 64
<211> LENGTH: 119
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VH1 Domain

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110
```

Thr Leu Val Thr Val Ser Ser
        115

<210> SEQ ID NO 65
<211> LENGTH: 119
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VH2 Domain

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Glu Gly Tyr Gly Asn Arg Val Ser Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VH3 Domain

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Ile Tyr Gly Asn Arg Val Ser Tyr Trp Gly Gln Gly
            100                 105                 110

Thr Leu Val Thr Val Ser Ser
        115

<210> SEQ ID NO 67
<211> LENGTH: 107
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VL1 Domain

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VL2 Domain

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105

<210> SEQ ID NO 69
<211> LENGTH: 107
<212> TYPE: PRT
<213> ORGANISM: Artificial Sequence
<220> FEATURE:
<223> OTHER INFORMATION: Humanized Anti-HER2/neu Monoclonal Antibody
      hHER2-MAB-1 VL3 Domain

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105

<210> SEQ ID NO 70
<211> LENGTH: 121
<212> TYPE: PRT
<213> ORGANISM: Artificial Sequence
<220> FEATURE:
<223> OTHER INFORMATION: VH Domain of CD137 MAB-1 (CD137 MAB-1 VH)

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120

<210> SEQ ID NO 71
<211> LENGTH: 109
<212> TYPE: PRT
<213> ORGANISM: Artificial Sequence
<220> FEATURE:
<223> OTHER INFORMATION: VL Domain of CD137 MAB-1 (CD137 MAB-1 VL)

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 72

-continued

```
<211> LENGTH: 116
<212> TYPE: PRT
<213> ORGANISM: Artificial Sequence
<220> FEATURE:
<223> OTHER INFORMATION: VH Domain of CD137 MAB-2 (CD137 MAB-2 VH)

<400> SEQUENCE: 72
```

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

```
<210> SEQ ID NO 73
<211> LENGTH: 108
<212> TYPE: PRT
<213> ORGANISM: Artificial Sequence
<220> FEATURE:
<223> OTHER INFORMATION: VL Domain of CD137 MAB-2 (CD137 MAB-2 VL)

<400> SEQUENCE: 73
```

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

```
<210> SEQ ID NO 74
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of CD137 MAB-3 (CD137 MAB-3 VH)

<400> SEQUENCE: 74
```

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr

-continued

```
                    20                  25                  30
Trp Ile Asn Trp Val Lys Gln Arg Pro Gly Gln Gly Leu Glu Trp Ile
                35                  40                  45
Gly Asn Ile Tyr Pro Ser Asp Ser Tyr Thr Asn Tyr Asn Gln Lys Phe
            50                  55                  60
Lys Asp Lys Ala Thr Leu Thr Val Asp Lys Ser Ser Thr Ala Tyr
65                  70                  75                  80
Met Gln Leu Ser Ser Pro Thr Ser Glu Asp Ser Ala Val Tyr Tyr Cys
                85                  90                  95
Thr Arg Asp Tyr Gly Ser Ser Tyr Ser Phe Asp Tyr Trp Gly Gln Gly
                100                 105                 110
Thr Thr Leu Thr Val Ser Ser
            115

<210> SEQ ID NO 75
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of CD137 MAB-3 (CD137 MAB-3 VL)

<400> SEQUENCE: 75

Asp Ile Gln Met Thr Gln Thr Thr Ser Ser Leu Ser Ala Ser Leu Gly
1               5                   10                  15
Asp Arg Val Thr Ile Ser Cys Arg Pro Ser Gln Asp Ile Ser Asn Tyr
                20                  25                  30
Leu Asn Trp Tyr Gln Gln Lys Pro Asp Gly Thr Val Lys Leu Leu Ile
                35                  40                  45
Tyr Tyr Thr Ser Arg Leu Arg Ser Gly Val Pro Ser Arg Phe Ser Gly
            50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asp Thr Leu Pro Tyr
                85                  90                  95
Thr Phe Gly Gly Gly Thr Lys Leu Glu Ile Lys
                100                 105

<210> SEQ ID NO 76
<211> LENGTH: 119
<212> TYPE: PRT
<213> ORGANISM: Artificial Sequence
<220> FEATURE:
<223> OTHER INFORMATION: VH Domain of Humanized CD137 MAB-3 (hCD137
      MAB-3 VH1)

<400> SEQUENCE: 76

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Trp Ile Asn Trp Val Lys Gln Ala Pro Gly Gln Gly Leu Glu Trp Ile
                35                  40                  45
Gly Asn Ile Tyr Pro Ser Asp Ser Tyr Thr Asn Tyr Asn Gln Lys Phe
            50                  55                  60
Lys Asp Lys Ala Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                 85                  90                  95

Thr Arg Asp Tyr Gly Ser Ser Tyr Ser Phe Asp Tyr Trp Gly Gln Gly
            100                 105                 110

Thr Thr Val Thr Val Ser Ser
        115

<210> SEQ ID NO 77
<211> LENGTH: 119
<212> TYPE: PRT
<213> ORGANISM: Artificial Sequence
<220> FEATURE:
<223> OTHER INFORMATION: VH Domain of Optimized Humanized CD137 MAB-3
      (hCD137 MAB-3 VH1)
<220> FEATURE:
<221> NAME/KEY: MISC_FEATURE
<222> LOCATION: (103)..(103)
<223> OTHER INFORMATION: Xaa is Alanine (A) or Serine (S)
<220> FEATURE:
<221> NAME/KEY: MISC_FEATURE
<222> LOCATION: (104)..(104)
<223> OTHER INFORMATION: Xaa is Tyrosine (Y)
<220> FEATURE:
<221> NAME/KEY: MISC_FEATURE
<222> LOCATION: (105)..(105)
<223> OTHER INFORMATION: Xaa is Serine (S)
<220> FEATURE:
<221> NAME/KEY: MISC_FEATURE
<222> LOCATION: (106)..(106)
<223> OTHER INFORMATION: Xaa is Phenylalanine (F), Methionine (M) or
      Tyrosine (Y)
<220> FEATURE:
<221> NAME/KEY: MISC_FEATURE
<222> LOCATION: (107)..(107)
<223> OTHER INFORMATION: Xaa is Histidine (H), Serine (S) or Asparagine
      (N)
<220> FEATURE:
<221> NAME/KEY: MISC_FEATURE
<222> LOCATION: (108)..(108)
<223> OTHER INFORMATION: Xaa is Proline (P), Threonine (T), Leucine or
      Valine (V)

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Lys Gln Ala Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Thr Arg Asp Tyr Gly Ser Xaa Xaa Xaa Xaa Xaa Xaa Trp Gly Gln Gly
            100                 105                 110

Thr Thr Val Thr Val Ser Ser
        115

<210> SEQ ID NO 78
<211> LENGTH: 6
<212> TYPE: PRT
<213> ORGANISM: Artificial Sequence
<220> FEATURE:
<223> OTHER INFORMATION: Preferred Residues 103-108 of SEQ ID NO:77
      Variant 1A
```

<400> SEQUENCE: 78

Ala Tyr Ser Phe His Pro
1               5

<210> SEQ ID NO 79
<211> LENGTH: 6
<212> TYPE: PRT
<213> ORGANISM: Artificial Sequence
<220> FEATURE:
<223> OTHER INFORMATION: Preferred Residues 103-108 of SEQ ID NO:77
      Variant 1B

<400> SEQUENCE: 79

Ala Tyr Ser Met Ser Thr
1               5

<210> SEQ ID NO 80
<211> LENGTH: 6
<212> TYPE: PRT
<213> ORGANISM: Artificial Sequence
<220> FEATURE:
<223> OTHER INFORMATION: Preferred Residues 103-108 of SEQ ID NO:77
      Variant 1C

<400> SEQUENCE: 80

Ala Tyr Ser Tyr Ser Leu
1               5

<210> SEQ ID NO 81
<211> LENGTH: 6
<212> TYPE: PRT
<213> ORGANISM: Artificial Sequence
<220> FEATURE:
<223> OTHER INFORMATION: Preferred Residues 103-108 of SEQ ID NO:77
      Variant 1D

<400> SEQUENCE: 81

Ser Tyr Ser Tyr Asn Val
1               5

<210> SEQ ID NO 82
<211> LENGTH: 107
<212> TYPE: PRT
<213> ORGANISM: Artificial Sequence
<220> FEATURE:
<223> OTHER INFORMATION: VL Domain of Optimized Humanized Antibody
      hCD137 MAB-3 (hCD137 MAB-3 VL)
<220> FEATURE:
<221> NAME/KEY: MISC_FEATURE
<222> LOCATION: (41)..(41)
<223> OTHER INFORMATION: Xaa is Asparatate (D) or Glycine (G)
<220> FEATURE:
<221> NAME/KEY: MISC_FEATURE
<222> LOCATION: (42)..(42)
<223> OTHER INFORMATION: Xaa is Glycine (G) or Lysine (K)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Xaa Xaa Thr Val Lys Leu Leu Ile
        35                  40                  45

Tyr Tyr Thr Ser Arg Leu Arg Ser Gly Val Pro Ser Arg Phe Ser Gly
    50                  55                  60

-continued

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 83
<211> LENGTH: 119
<212> TYPE: PRT
<213> ORGANISM: Artificial Sequence
<220> FEATURE:
<223> OTHER INFORMATION: hCD137 MAB-3 VH1A

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Lys Gln Ala Pro Gly Gln Gly Leu Glu Trp Ile
            35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ala Tyr Ser Phe His Pro Trp Gly Gln Gly
            100                 105                 110

Thr Thr Val Thr Val Ser Ser
        115

<210> SEQ ID NO 84
<211> LENGTH: 119
<212> TYPE: PRT
<213> ORGANISM: Artificial Sequence
<220> FEATURE:
<223> OTHER INFORMATION: hCD137 MAB-3 VH1B

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile Asn Trp Val Lys Gln Ala Pro Gly Gln Gly Leu Glu Trp Ile
            35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ala Tyr Ser Met Ser Thr Trp Gly Gln Gly
            100                 105                 110

Thr Thr Val Thr Val Ser Ser
        115

<210> SEQ ID NO 85

```
<211> LENGTH: 119
<212> TYPE: PRT
<213> ORGANISM: Artificial Sequence
<220> FEATURE:
<223> OTHER INFORMATION: hCD137 MAB-3 VH1C

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Lys Gln Ala Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ala Tyr Ser Tyr Ser Leu Trp Gly Gln Gly
            100                 105                 110

Thr Thr Val Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: hCD137 MAB-3 VH1D

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Lys Gln Ala Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ser Tyr Ser Tyr Asn Val Trp Gly Gln Gly
            100                 105                 110

Thr Thr Val Thr Val Ser Ser
        115

<210> SEQ ID NO 87
<211> LENGTH: 107
<212> TYPE: PRT
<213> ORGANISM: Artificial Sequence
<220> FEATURE:
<223> OTHER INFORMATION: hCD137 MAB-3 VL1

<400> SEQUENCE: 87

Asp Ile Gln Met Thr Gln Ser Pro Ser Ser Leu Ser Ala Ser Val Gly
1               5                   10                  15
```

Asp Arg Val Thr Ile Thr Cys Arg Pro Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: hCD137 MAB-3 VL2

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Gly Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: hCD137 MAB-3 VL3

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 90
<211> LENGTH: 123
<212> TYPE: PRT
<213> ORGANISM: Mus musculus
<220> FEATURE:
<221> NAME/KEY: MISC_FEATURE
<222> LOCATION: (1)..(123)
<223> OTHER INFORMATION: VH Domain of CD137 MAB-4 (CD137 MAB-4 VH)

<400> SEQUENCE: 90

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asp Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Lys Ser Gly Glu Tyr Gly Lys Ile Gly Tyr Tyr Ala Met Asp Tyr
            100                 105                 110

Trp Gly Gln Gly Thr Ser Val Thr Val Ser Ser
        115                 120

<210> SEQ ID NO 91
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of CD137 MAB-4 (CD137 MAB-4 VL)

<400> SEQUENCE: 91

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 92
<211> LENGTH: 123
<212> TYPE: PRT
<213> ORGANISM: Artificial Sequence
<220> FEATURE:
<223> OTHER INFORMATION: VH Domain of Humanized CD137 MAB-4 (hCD137 MAB-4 VH1)

```
<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asp Ser Tyr Thr Asn Tyr Asp Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Lys Ser Gly Glu Tyr Gly Lys Ile Gly Tyr Tyr Ala Met Asp Tyr
            100                 105                 110

Trp Gly Gln Gly Thr Thr Val Thr Val Ser Ser
        115                 120

<210> SEQ ID NO 93
<211> LENGTH: 107
<212> TYPE: PRT
<213> ORGANISM: Artificial Sequence
<220> FEATURE:
<223> OTHER INFORMATION: VL Domain of Humanized CD137 MAB-4 (hCD137
      MAB-4 VL)
<220> FEATURE:
<221> NAME/KEY: MISC_FEATURE
<222> LOCATION: (87)..(87)
<223> OTHER INFORMATION: Xaa is Phenylalanine (F) or Tyrosine (Y)

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Xaa Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: VL Domain of Humanized CD137 MAB-4 (hCD137
      MAB-4 VL1)

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

```
Leu Asn Trp Tyr Gln Gln Lys Pro Asp Lys Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Phe Cys Gln Gln Gly Asn Thr Leu Pro Tyr
                 85                  90                  95

Thr Phe Gly Gln Gly Thr Lys Leu Glu Ile Lys
                100                 105

<210> SEQ ID NO 95
<211> LENGTH: 107
<212> TYPE: PRT
<213> ORGANISM: Artificial Sequence
<220> FEATURE:
<223> OTHER INFORMATION: VL Domain of Humanized CD137 MAB-4 (hCD137
      MAB-4 VL2)

<400> SEQUENCE: 95

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Asp Lys Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Tyr Cys Gln Gln Gly Asn Thr Leu Pro Tyr
                 85                  90                  95

Thr Phe Gly Gln Gly Thr Lys Leu Glu Ile Lys
                100                 105

<210> SEQ ID NO 96
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VH Domain of CD137 MAB-5 (CD137 MAB-5 VH)

<400> SEQUENCE: 96

Gln Val Gln Leu Lys Glu Ser Gly Pro Gly Leu Val Ala Pro Ser Gln
1               5                  10                  15

Ser Leu Ser Ile Thr Cys Thr Val Ser Gly Phe Ser Leu Thr Ser Tyr
                 20                  25                  30

Asp Ile Ser Trp Ile Arg Gln Pro Pro Gly Lys Gly Leu Glu Trp Leu
         35                  40                  45

Gly Val Val Trp Thr Gly Gly Gly Thr Asn Tyr Asn Ser Ala Phe Met
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Ile Tyr Tyr Cys Glu
                 85                  90                  95

Arg Val Asp Tyr Trp Gly Gln Gly Thr Ser Val Thr Val Ser Ser
                100                 105                 110
```

<210> SEQ ID NO 97
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of CD137 MAB-5 (CD137 MAB-5 VL)

<400> SEQUENCE: 97

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 98
<211> LENGTH: 500
<212> TYPE: PRT
<213> ORGANISM: Artificial Sequence
<220> FEATURE:
<223> OTHER INFORMATION: First and Third Polypeptide Chains of DART-A

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ser Tyr Ser Phe Asp Tyr Trp
210                 215                 220

Gly Gln Gly Thr Thr Val Thr Val Ser Ser Gly Gly Cys Gly Gly Gly
225                 230                 235                 240

Glu Val Ala Ala Cys Glu Lys Glu Val Ala Ala Leu Glu Lys Glu Val
                245                 250                 255

Ala Ala Leu Glu Lys Glu Val Ala Ala Leu Glu Lys Leu Glu Pro Lys
            260                 265                 270

Ser Ala Asp Lys Thr His Thr Cys Pro Pro Cys Pro Ala Pro Glu Ala
            275                 280                 285

Ala Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
            370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
            450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly
            500

<210> SEQ ID NO 99
<211> LENGTH: 268
<212> TYPE: PRT
<213> ORGANISM: Artificial Sequence
<220> FEATURE:
<223> OTHER INFORMATION: Second and Fourth Polypeptide Chains of DART-A

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

```
Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Asn Tyr Gly Met Asn Trp Val Arg Gln Ala Pro Gly Gln Gly Leu
145                 150                 155                 160

Glu Trp Met Gly Trp Ile Asn Thr Asn Ile Gly Glu Pro Thr Tyr Thr
                165                 170                 175

Glu Glu Phe Lys Gly Arg Val Thr Met Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Asp Asp Gly Tyr Gly Asn Arg Val Ser Tyr Trp
    210                 215                 220

Gly Gln Gly Thr Leu Val Thr Val Ser Ser Gly Gly Cys Gly Gly Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 100
<211> LENGTH: 500
<212> TYPE: PRT
<213> ORGANISM: Artificial Sequence
<220> FEATURE:
<223> OTHER INFORMATION: First and Third Polypeptide Chain of DART-B

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140
```

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ser Tyr Ser Phe Asp Tyr Trp
210                 215                 220

Gly Gln Gly Thr Thr Val Thr Val Ser Ser Gly Gly Cys Gly Gly Gly
225                 230                 235                 240

Glu Val Ala Ala Cys Glu Lys Glu Val Ala Ala Leu Glu Lys Glu Val
                245                 250                 255

Ala Ala Leu Glu Lys Glu Val Ala Ala Leu Glu Lys Leu Glu Pro Lys
            260                 265                 270

Ser Ala Asp Lys Thr His Thr Cys Pro Pro Cys Pro Ala Pro Glu Ala
        275                 280                 285

Ala Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly
            500

<210> SEQ ID NO 101
<211> LENGTH: 268
<212> TYPE: PRT
<213> ORGANISM: Artificial Sequence
<220> FEATURE:
<223> OTHER INFORMATION: Second and Fourth Polypeptide Chain of DART-B

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
            85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Asn Tyr Gly Met Asn Trp Val Arg Gln Ala Pro Gly Gln Gly Leu
145                 150                 155                 160

Glu Trp Met Gly Trp Ile Asn Thr Asn Ile Gly Glu Pro Thr Tyr Thr
            165                 170                 175

Glu Glu Phe Lys Gly Arg Val Thr Met Thr Arg Asp Thr Ser Ile Ser
            180                 185                 190

Thr Ala Tyr Met Glu Leu Ser Arg Leu Arg Ser Asp Asp Thr Ala Val
            195                 200                 205

Tyr Tyr Cys Ala Arg Asp Asp Gly Tyr Gly Asn Arg Val Ser Tyr Trp
210                 215                 220

Gly Gln Gly Thr Leu Val Thr Val Ser Ser Gly Gly Cys Gly Gly Gly
225                 230                 235                 240

Lys Val Ala Ala Cys Lys Glu Lys Val Ala Ala Leu Lys Glu Lys Val
            245                 250                 255

Ala Ala Leu Lys Glu Lys Val Ala Ala Leu Lys Glu
            260                 265

<210> SEQ ID NO 102
<211> LENGTH: 500
<212> TYPE: PRT
<213> ORGANISM: Artificial Sequence
<220> FEATURE:
<223> OTHER INFORMATION: First and Third Polypeptide Chains of DART-C

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
            85                  90                  95

-continued

```
Thr Phe Gly Gln Gly Thr Lys Leu Glu Ile Lys Gly Gly Ser Gly
            100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
            130                 135                 140

Thr Asn Tyr Gly Met Asn Trp Val Arg Gln Ala Pro Gly Gln Gly Leu
145                 150                 155                 160

Glu Trp Met Gly Trp Ile Asn Thr Asn Ile Gly Glu Pro Thr Tyr Thr
                    165                 170                 175

Glu Glu Phe Lys Gly Arg Val Thr Met Thr Arg Asp Thr Ser Ile Ser
            180                 185                 190

Thr Ala Tyr Met Glu Leu Ser Arg Leu Arg Ser Asp Asp Thr Ala Val
            195                 200                 205

Tyr Tyr Cys Ala Arg Asp Asp Gly Tyr Gly Asn Arg Val Ser Tyr Trp
210                 215                 220

Gly Gln Gly Thr Leu Val Thr Val Ser Ser Gly Gly Cys Gly Gly Gly
225                 230                 235                 240

Glu Val Ala Ala Cys Glu Lys Glu Val Ala Ala Leu Glu Lys Glu Val
                    245                 250                 255

Ala Ala Leu Glu Lys Glu Val Ala Ala Leu Glu Lys Leu Glu Pro Lys
            260                 265                 270

Ser Ala Asp Lys Thr His Thr Cys Pro Pro Cys Pro Ala Pro Glu Ala
            275                 280                 285

Ala Gly Gly Pro Ser Val Phe Leu Phe Pro Pro Lys Pro Lys Asp Thr
            290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                    325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                    405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
            450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                    485                 490                 495

Leu Ser Pro Gly
            500
```

```
<210> SEQ ID NO 103
<211> LENGTH: 268
<212> TYPE: PRT
<213> ORGANISM: Artificial Sequence
<220> FEATURE:
<223> OTHER INFORMATION: Second and Fourth Polypeptide Chains of DART-C

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ser Tyr Ser Phe Asp Tyr Trp
    210                 215                 220

Gly Gln Gly Thr Thr Val Thr Val Ser Ser Gly Gly Cys Gly Gly Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 104
<211> LENGTH: 449
<212> TYPE: PRT
<213> ORGANISM: Artificial Sequence
<220> FEATURE:
<223> OTHER INFORMATION: First Polypeptide Chain of DART-D

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45
```

```
Gly Trp Ile Asn Thr Asn Ile Gly Glu Pro Thr Tyr Thr Glu Glu Phe
     50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Asp Gly Tyr Gly Asn Arg Val Ser Tyr Trp Gly Gln Gly
                100                 105                 110

Thr Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro Gly
        435                 440                 445

Lys
```

```
<210> SEQ ID NO 105
<211> LENGTH: 214
<212> TYPE: PRT
<213> ORGANISM: Artificial Sequence
<220> FEATURE:
<223> OTHER INFORMATION: Second and Fifth Polypeptide Chains of DART-D

<400> SEQUENCE: 105
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 106
<211> LENGTH: 727
<212> TYPE: PRT
<213> ORGANISM: Artificial Sequence
<220> FEATURE:
<223> OTHER INFORMATION: Third Polypeptide Chain of DART-D

<400> SEQUENCE: 106
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

-continued

```
Ala Arg Asp Asp Gly Tyr Gly Asn Arg Val Ser Tyr Trp Gly Gln Gly
             100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Ser Gly Gly Gly Ser Gly Gly Gly Asp Ile Gln Met Thr
    450                 455                 460

Gln Thr Thr Ser Ser Leu Ser Ala Ser Leu Gly Asp Arg Val Thr Ile
465                 470                 475                 480

Ser Cys Arg Pro Ser Gln Asp Ile Ser Asn Tyr Leu Asn Trp Tyr Gln
                485                 490                 495

Gln Lys Pro Asp Gly Thr Val Lys Leu Leu Ile Tyr Tyr Thr Ser Arg
            500                 505                 510

Leu Arg Ser Gly Val Pro Ser Arg Phe Ser Gly Ser Gly Ser Gly Thr
```

```
            515                 520                 525
Asp Tyr Ser Leu Thr Ile Ser Asn Leu Glu Gln Glu Asp Ile Ala Thr
        530                 535                 540

Tyr Phe Cys Gln Gln Gly Asp Thr Leu Pro Tyr Thr Phe Gly Gly Gly
545                 550                 555                 560

Thr Lys Leu Glu Ile Lys Gly Gly Gly Ser Gly Gly Gly Gly Gln Val
                565                 570                 575

Gln Leu Gln Gln Pro Gly Ala Glu Leu Val Arg Pro Gly Ala Ser Val
            580                 585                 590

Lys Leu Ser Cys Lys Ala Ser Gly Tyr Thr Phe Thr Ser Tyr Trp Ile
        595                 600                 605

Asn Trp Val Lys Gln Arg Pro Gly Gln Gly Leu Glu Trp Ile Gly Asn
    610                 615                 620

Ile Tyr Pro Ser Asp Ser Tyr Thr Asn Tyr Asn Gln Lys Phe Lys Asp
625                 630                 635                 640

Lys Ala Thr Leu Thr Val Asp Lys Ser Ser Thr Ala Tyr Met Gln
                645                 650                 655

Leu Ser Ser Pro Thr Ser Glu Asp Ser Ala Val Tyr Tyr Cys Thr Arg
                660                 665                 670

Asp Tyr Gly Ser Ser Tyr Ser Phe Asp Tyr Trp Gly Gln Gly Thr Thr
            675                 680                 685

Leu Thr Val Ser Ser Gly Gly Cys Gly Gly Glu Val Ala Ala Leu
        690                 695                 700

Glu Lys Glu Val Ala Ala Leu Glu Lys Glu Val Ala Ala Leu Glu Lys
705                 710                 715                 720

Glu Val Ala Ala Leu Glu Lys
                725

<210> SEQ ID NO 107
<211> LENGTH: 268
<212> TYPE: PRT
<213> ORGANISM: Artificial Sequence
<220> FEATURE:
<223> OTHER INFORMATION: Fourth Polypeptide Chain of DART-D

<400> SEQUENCE: 107

Asp Ile Gln Met Thr Gln Thr Thr Ser Ser Leu Ser Ala Ser Leu Gly
1               5                   10                  15

Asp Arg Val Thr Ile Ser Cys Arg Pro Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys Gly Gly Gly Ser Gly
            100                 105                 110

Gly Gly Gly Gln Val Gln Leu Gln Gln Pro Gly Ala Glu Leu Val Arg
        115                 120                 125

Pro Gly Ala Ser Val Lys Leu Ser Cys Lys Ala Ser Gly Tyr Thr Phe
    130                 135                 140

Thr Ser Tyr Trp Ile Asn Trp Val Lys Gln Arg Pro Gly Gln Gly Leu
```

```
                145                 150                 155                 160
Glu Trp Ile Gly Asn Ile Tyr Pro Ser Asp Ser Tyr Thr Asn Tyr Asn
                    165                 170                 175
Gln Lys Phe Lys Asp Lys Ala Thr Leu Thr Val Asp Lys Ser Ser Ser
                180                 185                 190
Thr Ala Tyr Met Gln Leu Ser Ser Pro Thr Ser Glu Asp Ser Ala Val
                195                 200                 205
Tyr Tyr Cys Thr Arg Asp Tyr Gly Ser Ser Tyr Ser Phe Asp Tyr Trp
            210                 215                 220
Gly Gln Gly Thr Thr Leu Thr Val Ser Ser Gly Gly Cys Gly Gly Gly
225                 230                 235                 240
Lys Val Ala Ala Leu Lys Glu Lys Val Ala Ala Leu Lys Glu Lys Val
                    245                 250                 255
Ala Ala Leu Lys Glu Lys Val Ala Ala Leu Lys Glu
                260                 265

<210> SEQ ID NO 108
<211> LENGTH: 449
<212> TYPE: PRT
<213> ORGANISM: Artificial Sequence
<220> FEATURE:
<223> OTHER INFORMATION: First Polypeptide Chain of DART-E

<400> SEQUENCE: 108

Gln Val Gln Leu Gln Gln Pro Gly Ala Glu Leu Val Arg Pro Gly Ala
1               5                   10                  15
Ser Val Lys Leu Ser Cys Lys Ala Ser Gly Tyr Thr Phe Thr Ser Tyr
                20                  25                  30
Trp Ile Asn Trp Val Lys Gln Arg Pro Gly Gln Gly Leu Glu Trp Ile
            35                  40                  45
Gly Asn Ile Tyr Pro Ser Asp Ser Tyr Thr Asn Tyr Asn Gln Lys Phe
        50                  55                  60
Lys Asp Lys Ala Thr Leu Thr Val Asp Lys Ser Ser Ser Thr Ala Tyr
65                  70                  75                  80
Met Gln Leu Ser Ser Pro Thr Ser Glu Asp Ser Ala Val Tyr Tyr Cys
                85                  90                  95
Thr Arg Asp Tyr Gly Ser Ser Tyr Ser Phe Asp Tyr Trp Gly Gln Gly
                100                 105                 110
Thr Thr Leu Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
```

```
                     245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
                355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro Gly
        435                 440                 445

Lys
```

<210> SEQ ID NO 109
<211> LENGTH: 214
<212> TYPE: PRT
<213> ORGANISM: Artificial Sequence
<220> FEATURE:
<223> OTHER INFORMATION: Second and Fifth Polypeptide Chain of DART-E

<400> SEQUENCE: 109

```
Asp Ile Gln Met Thr Gln Thr Thr Ser Ser Leu Ser Ala Ser Leu Gly
1               5                   10                  15

Asp Arg Val Thr Ile Ser Cys Arg Pro Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 110
<211> LENGTH: 727
<212> TYPE: PRT
<213> ORGANISM: Artificial Sequence
<220> FEATURE:
<223> OTHER INFORMATION: Third Polypeptide Chain of DART-E

<400> SEQUENCE: 110

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Asp Tyr Gly Ser Ser Tyr Ser Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Ser Gly Gly Gly Ser Gly Gly Gly Asp Ile Gln Met Thr
    450                 455                 460

Gln Ser Pro Ser Ser Leu Ser Ala Ser Val Gly Asp Arg Val Thr Ile
465                 470                 475                 480

Thr Cys Lys Ala Ser Gln Asp Ile Ser Asn Tyr Leu Ser Trp Phe Gln
                485                 490                 495

Gln Lys Pro Gly Lys Ala Pro Lys Thr Leu Ile Tyr Arg Ala Asn Arg
            500                 505                 510

Leu Gln Ser Gly Val Pro Ser Arg Phe Ser Gly Ser Gly Ser Gly Thr
        515                 520                 525

Asp Phe Thr Leu Thr Ile Ser Ser Leu Gln Pro Glu Asp Phe Ala Thr
    530                 535                 540

Tyr Tyr Cys Leu Gln His Asp Glu Phe Pro Trp Thr Phe Gly Gln Gly
545                 550                 555                 560

Thr Lys Leu Glu Ile Lys Gly Gly Gly Ser Gly Gly Gly Gly Gln Val
                565                 570                 575

Gln Leu Val Gln Ser Gly Ala Glu Val Lys Lys Pro Gly Ala Ser Val
            580                 585                 590

Lys Val Ser Cys Lys Ala Ser Gly Tyr Thr Phe Thr Asn Tyr Gly Met
        595                 600                 605

Asn Trp Val Arg Gln Ala Pro Gly Gln Gly Leu Glu Trp Met Gly Trp
    610                 615                 620

Ile Asn Thr Asn Ile Gly Glu Pro Thr Tyr Thr Glu Glu Phe Lys Gly
625                 630                 635                 640

Arg Val Thr Met Thr Arg Asp Thr Ser Ile Ser Thr Ala Tyr Met Glu
                645                 650                 655

Leu Ser Arg Leu Arg Ser Asp Asp Thr Ala Val Tyr Tyr Cys Ala Arg
            660                 665                 670

Asp Asp Gly Tyr Gly Asn Arg Val Ser Tyr Trp Gly Gln Gly Thr Leu
        675                 680                 685

Val Thr Val Ser Ser Gly Gly Cys Gly Gly Gly Glu Val Ala Ala Leu
    690                 695                 700

Glu Lys Glu Val Ala Ala Leu Glu Lys Glu Val Ala Ala Leu Glu Lys
705                 710                 715                 720
```

Glu Val Ala Ala Leu Glu Lys
            725

<210> SEQ ID NO 111
<211> LENGTH: 268
<212> TYPE: PRT
<213> ORGANISM: Artificial Sequence
<220> FEATURE:
<223> OTHER INFORMATION: Fourth Polypeptide Chain of DART-E

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Asn Tyr Gly Met Asn Trp Val Arg Gln Ala Pro Gly Gln Gly Leu
145                 150                 155                 160

Glu Trp Met Gly Trp Ile Asn Thr Asn Ile Gly Glu Pro Thr Tyr Thr
                165                 170                 175

Glu Glu Phe Lys Gly Arg Val Thr Met Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Asp Asp Gly Tyr Gly Asn Arg Val Ser Tyr Trp
    210                 215                 220

Gly Gln Gly Thr Leu Val Thr Val Ser Ser Gly Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 112
<211> LENGTH: 731
<212> TYPE: PRT
<213> ORGANISM: Artificial Sequence
<220> FEATURE:
<223> OTHER INFORMATION: Third Polypeptide Chain of DART-F

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
         35                  40                  45

Gly Trp Ile Asn Thr Asn Ile Gly Glu Pro Thr Tyr Thr Glu Glu Phe
     50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                 85                  90                  95

Ala Arg Asp Asp Gly Tyr Gly Asn Arg Val Ser Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
             130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
             195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Trp
             355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
             435                 440                 445

Gly Gly Gly Ser Gly Gly Ser Gly Gly Gly Asp Ile Gln Met Thr
            450             455             460

Gln Thr Thr Ser Ser Leu Ser Ala Ser Leu Gly Asp Arg Val Thr Ile
465             470             475             480

Ser Cys Arg Ala Ser Gln Asp Ile Ser Asn Tyr Leu Asn Trp Tyr Gln
                485             490             495

Gln Lys Pro Asp Gly Thr Val Lys Leu Leu Ile Tyr Tyr Thr Ser Arg
            500             505             510

Leu His Ser Gly Val Pro Ser Arg Phe Ser Gly Ser Gly Ser Gly Thr
            515             520             525

Asp Tyr Ser Leu Thr Ile Ser Asn Leu Glu Gln Glu Asp Ile Ala Thr
530             535             540

Tyr Phe Cys Gln Gln Gly Asn Thr Leu Pro Tyr Thr Phe Gly Gly Gly
545             550             555             560

Thr Lys Leu Glu Ile Lys Gly Gly Gly Ser Gly Gly Gly Gly Gln Val
                565             570             575

Gln Leu Gln Gln Pro Gly Ala Glu Leu Val Arg Pro Gly Ala Ser Val
            580             585             590

Lys Leu Ser Cys Lys Ala Ser Gly Tyr Thr Phe Thr Ser Tyr Trp Ile
            595             600             605

Asn Trp Val Lys Gln Arg Pro Gly Gln Gly Leu Glu Trp Ile Gly Asn
610             615             620

Ile Tyr Pro Ser Asp Ser Tyr Thr Asn Tyr Asp Gln Lys Phe Lys Asp
625             630             635             640

Lys Ala Thr Leu Thr Val Asp Lys Ser Ser Ser Thr Ala Tyr Met Gln
                645             650             655

Leu Ser Ser Pro Thr Ser Glu Asp Ser Ala Val Tyr Tyr Cys Thr Lys
            660             665             670

Ser Gly Glu Tyr Gly Lys Ile Gly Tyr Tyr Ala Met Asp Tyr Trp Gly
            675             680             685

Gln Gly Thr Ser Val Thr Val Ser Ser Gly Gly Cys Gly Gly Gly Glu
            690             695             700

Val Ala Ala Leu Glu Lys Glu Val Ala Ala Leu Glu Lys Glu Val Ala
705             710             715             720

Ala Leu Glu Lys Glu Val Ala Ala Leu Glu Lys
                725             730

<210> SEQ ID NO 113
<211> LENGTH: 272
<212> TYPE: PRT
<213> ORGANISM: Artificial Sequence
<220> FEATURE:
<223> OTHER INFORMATION: Fourth Polypeptide Chain of DART-F

<400> SEQUENCE: 113

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Gly Thr Lys Leu Glu Ile Lys Gly Gly Gly Ser Gly
            100                 105                 110

Gly Gly Gly Gln Val Gln Leu Gln Gln Pro Gly Ala Glu Leu Val Arg
            115                 120                 125

Pro Gly Ala Ser Val Lys Leu Ser Cys Lys Ala Ser Gly Tyr Thr Phe
            130                 135                 140

Thr Ser Tyr Trp Ile Asn Trp Val Lys Gln Arg Pro Gly Gln Gly Leu
145                 150                 155                 160

Glu Trp Ile Gly Asn Ile Tyr Pro Ser Asp Ser Tyr Thr Asn Tyr Asp
            165                 170                 175

Gln Lys Phe Lys Asp Lys Ala Thr Leu Thr Val Asp Lys Ser Ser Ser
            180                 185                 190

Thr Ala Tyr Met Gln Leu Ser Ser Pro Thr Ser Glu Asp Ser Ala Val
            195                 200                 205

Tyr Tyr Cys Thr Lys Ser Gly Glu Tyr Gly Lys Ile Gly Tyr Tyr Ala
            210                 215                 220

Met Asp Tyr Trp Gly Gln Gly Thr Ser Val Thr Val Ser Ser Gly Gly
225                 230                 235                 240

Cys Gly Gly Lys Val Ala Ala Leu Lys Glu Lys Val Ala Ala Leu
            245                 250                 255

Lys Glu Lys Val Ala Ala Leu Lys Glu Lys Val Ala Ala Leu Lys Glu
            260                 265                 270

<210> SEQ ID NO 114
<211> LENGTH: 727
<212> TYPE: PRT
<213> ORGANISM: Artificial Sequence
<220> FEATURE:
<223> OTHER INFORMATION: Third Polypeptide Chain of DART-G

<400> SEQUENCE: 114

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Asn Ile Gly Glu Pro Thr Tyr Thr Glu Glu Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

```
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Trp
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Gly Gly Gly Ser Gly Gly Gly Ser Gly Gly Gly Asp Ile Gln Met Thr
    450                 455                 460
Gln Ser Pro Ser Ser Leu Ser Ala Ser Val Gly Asp Arg Val Thr Ile
465                 470                 475                 480
Thr Cys Arg Pro Ser Gln Asp Ile Ser Asn Tyr Leu Asn Trp Tyr Gln
                485                 490                 495
Gln Lys Pro Asp Lys Thr Val Lys Leu Leu Ile Tyr Tyr Thr Ser Arg
            500                 505                 510
Leu Arg Ser Gly Val Pro Ser Arg Phe Ser Gly Ser Gly Ser Gly Thr
        515                 520                 525
Asp Phe Thr Phe Thr Ile Ser Ser Leu Gln Pro Glu Asp Ile Ala Thr
    530                 535                 540
Tyr Phe Cys Gln Gln Gly Asp Thr Leu Pro Tyr Thr Phe Gly Gln Gly
545                 550                 555                 560
Thr Lys Leu Glu Ile Lys Gly Gly Gly Ser Gly Gly Gly Gly Gln Val
                565                 570                 575
Gln Leu Val Gln Ser Gly Ala Glu Val Lys Lys Pro Gly Ala Ser Val
            580                 585                 590
Lys Val Ser Cys Lys Ala Ser Gly Tyr Thr Phe Thr Ser Tyr Trp Ile
```

```
                595                 600                 605
Asn Trp Val Lys Gln Ala Pro Gly Gln Gly Leu Glu Trp Ile Gly Asn
            610                 615                 620

Ile Tyr Pro Ser Asp Ser Tyr Thr Asn Tyr Asn Gln Lys Phe Lys Asp
625                 630                 635                 640

Lys Ala Thr Ile Thr Ala Asp Lys Ser Thr Ser Thr Ala Tyr Met Glu
                645                 650                 655

Leu Ser Ser Leu Arg Ser Glu Asp Thr Ala Val Tyr Tyr Cys Thr Arg
            660                 665                 670

Asp Tyr Gly Ser Ser Tyr Ser Phe Asp Tyr Trp Gly Gln Gly Thr Thr
                675                 680                 685

Val Thr Val Ser Ser Gly Gly Cys Gly Gly Gly Val Ala Ala Leu
            690                 695                 700

Glu Lys Glu Val Ala Ala Leu Glu Lys Glu Val Ala Ala Leu Glu Lys
705                 710                 715                 720

Glu Val Ala Ala Leu Glu Lys
                725

<210> SEQ ID NO 115
<211> LENGTH: 729
<212> TYPE: PRT
<213> ORGANISM: Artificial Sequence
<220> FEATURE:
<223> OTHER INFORMATION: Third Polypeptide Chain of Optimized DART-G1

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Asn Ile Gly Glu Pro Thr Tyr Thr Glu Glu Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
```

```
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Trp
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Gly Gly Gly Ser Gly Gly Gly Ser Gly Gly Gly Asp Ile Gln Met Thr
    450                 455                 460
Gln Ser Pro Ser Ser Leu Ser Ala Ser Val Gly Asp Arg Val Thr Ile
465                 470                 475                 480
Thr Cys Arg Pro Ser Gln Asp Ile Ser Asn Tyr Leu Asn Trp Tyr Gln
                485                 490                 495
Gln Lys Pro Asp Lys Thr Val Lys Leu Leu Ile Tyr Tyr Thr Ser Arg
            500                 505                 510
Leu Arg Ser Gly Val Pro Ser Arg Phe Ser Gly Ser Gly Ser Gly Thr
        515                 520                 525
Asp Phe Thr Phe Thr Ile Ser Ser Leu Gln Pro Glu Asp Ile Ala Thr
    530                 535                 540
Tyr Phe Cys Gln Gln Gly Asp Thr Leu Pro Tyr Thr Phe Gly Gln Gly
545                 550                 555                 560
Thr Lys Leu Glu Ile Lys Gly Gly Gly Ser Gly Gly Gly Gly Gln Val
                565                 570                 575
Gln Val Gln Leu Val Gln Ser Gly Ala Glu Val Lys Lys Pro Gly Ala
            580                 585                 590
Ser Val Lys Val Ser Cys Lys Ala Ser Gly Tyr Thr Phe Thr Ser Tyr
        595                 600                 605
Trp Ile Asn Trp Val Lys Gln Ala Pro Gly Gln Gly Leu Glu Trp Ile
    610                 615                 620
Gly Asn Ile Tyr Pro Ser Asp Ser Tyr Thr Asn Tyr Asn Gln Lys Phe
625                 630                 635                 640
Lys Asp Lys Ala Thr Ile Thr Ala Asp Lys Ser Thr Ser Thr Ala Tyr
                645                 650                 655
```

```
Met Glu Leu Ser Ser Leu Arg Ser Glu Asp Thr Ala Val Tyr Tyr Cys
            660                 665                 670

Thr Arg Asp Tyr Gly Ser Ala Tyr Ser Phe His Pro Trp Gly Gln Gly
            675                 680                 685

Thr Thr Val Thr Val Ser Ser Gly Gly Cys Gly Gly Gly Glu Val Ala
            690                 695                 700

Ala Leu Glu Lys Glu Val Ala Ala Leu Glu Lys Glu Val Ala Ala Leu
705                 710                 715                 720

Glu Lys Glu Val Ala Ala Leu Glu Lys
                    725

<210> SEQ ID NO 116
<211> LENGTH: 729
<212> TYPE: PRT
<213> ORGANISM: Artificial Sequence
<220> FEATURE:
<223> OTHER INFORMATION: Third Polypeptide Chain of Optimized DART-G2

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Asn Ile Gly Glu Pro Thr Tyr Thr Glu Glu Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Ser Gly Gly Gly Ser Gly Gly Gly Asp Ile Gln Met Thr
    450                 455                 460

Gln Ser Pro Ser Ser Leu Ser Ala Ser Val Gly Asp Arg Val Thr Ile
465                 470                 475                 480

Thr Cys Arg Pro Ser Gln Asp Ile Ser Asn Tyr Leu Asn Trp Tyr Gln
                485                 490                 495

Gln Lys Pro Asp Lys Thr Val Lys Leu Leu Ile Tyr Tyr Thr Ser Arg
            500                 505                 510

Leu Arg Ser Gly Val Pro Ser Arg Phe Ser Gly Ser Gly Ser Gly Thr
        515                 520                 525

Asp Phe Thr Phe Thr Ile Ser Ser Leu Gln Pro Glu Asp Ile Ala Thr
    530                 535                 540

Tyr Phe Cys Gln Gln Gly Asp Thr Leu Pro Tyr Thr Phe Gly Gln Gly
545                 550                 555                 560

Thr Lys Leu Glu Ile Lys Gly Gly Gly Ser Gly Gly Gly Gly Gln Val
                565                 570                 575

Gln Val Gln Leu Val Gln Ser Gly Ala Glu Val Lys Lys Pro Gly Ala
            580                 585                 590

Ser Val Lys Val Ser Cys Lys Ala Ser Gly Tyr Thr Phe Thr Ser Tyr
        595                 600                 605

Trp Ile Asn Trp Val Lys Gln Ala Pro Gly Gln Gly Leu Glu Trp Ile
    610                 615                 620

Gly Asn Ile Tyr Pro Ser Asp Ser Tyr Thr Asn Tyr Asn Gln Lys Phe
625                 630                 635                 640

Lys Asp Lys Ala Thr Ile Thr Ala Asp Lys Ser Thr Ser Thr Ala Tyr
                645                 650                 655

Met Glu Leu Ser Ser Leu Arg Ser Glu Asp Thr Ala Val Tyr Tyr Cys
            660                 665                 670

Thr Arg Asp Tyr Gly Ser Ala Tyr Ser Met Ser Thr Trp Gly Gln Gly
        675                 680                 685

Thr Thr Val Thr Val Ser Ser Gly Gly Cys Gly Gly Gly Glu Val Ala
    690                 695                 700
```

Ala Leu Glu Lys Glu Val Ala Ala Leu Glu Lys Glu Val Ala Ala Leu
705                 710                 715                 720

Glu Lys Glu Val Ala Ala Leu Glu Lys
                725

<210> SEQ ID NO 117
<211> LENGTH: 729
<212> TYPE: PRT
<213> ORGANISM: Artificial Sequence
<220> FEATURE:
<223> OTHER INFORMATION: Third Polypeptide Chain of Optimized DART-G3

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Trp
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Gly Gly Gly Ser Gly Gly Ser Gly Gly Gly Asp Ile Gln Met Thr
    450                 455                 460
Gln Ser Pro Ser Ser Leu Ser Ala Ser Val Gly Asp Arg Val Thr Ile
465                 470                 475                 480
Thr Cys Arg Pro Ser Gln Asp Ile Ser Asn Tyr Leu Asn Trp Tyr Gln
                485                 490                 495
Gln Lys Pro Asp Lys Thr Val Lys Leu Leu Ile Tyr Tyr Thr Ser Arg
            500                 505                 510
Leu Arg Ser Gly Val Pro Ser Arg Phe Ser Gly Ser Gly Ser Gly Thr
        515                 520                 525
Asp Phe Thr Phe Thr Ile Ser Ser Leu Gln Pro Glu Asp Ile Ala Thr
530                 535                 540
Tyr Phe Cys Gln Gln Gly Asp Thr Leu Pro Tyr Thr Phe Gly Gln Gly
545                 550                 555                 560
Thr Lys Leu Glu Ile Lys Gly Gly Ser Gly Gly Gly Gln Val
                565                 570                 575
Gln Val Gln Leu Val Gln Ser Gly Ala Glu Val Lys Lys Pro Gly Ala
            580                 585                 590
Ser Val Lys Val Ser Cys Lys Ala Ser Gly Tyr Thr Phe Thr Ser Tyr
        595                 600                 605
Trp Ile Asn Trp Val Lys Gln Ala Pro Gly Gln Gly Leu Glu Trp Ile
610                 615                 620
Gly Asn Ile Tyr Pro Ser Asp Ser Tyr Thr Asn Tyr Asn Gln Lys Phe
625                 630                 635                 640
Lys Asp Lys Ala Thr Ile Thr Ala Asp Lys Ser Thr Ser Thr Ala Tyr
                645                 650                 655
Met Glu Leu Ser Ser Leu Arg Ser Glu Asp Thr Ala Val Tyr Tyr Cys
            660                 665                 670
Thr Arg Asp Tyr Gly Ser Ala Tyr Ser Tyr Ser Leu Trp Gly Gln Gly
        675                 680                 685
Thr Thr Val Thr Val Ser Ser Gly Gly Cys Gly Gly Gly Glu Val Ala
690                 695                 700
Ala Leu Glu Lys Glu Val Ala Ala Leu Glu Lys Glu Val Ala Ala Leu
705                 710                 715                 720
Glu Lys Glu Val Ala Ala Leu Glu Lys
                725
```

<210> SEQ ID NO 118
<211> LENGTH: 729
<212> TYPE: PRT

<213> ORGANISM: Artificial Sequence
<220> FEATURE:
<223> OTHER INFORMATION: Third Polypeptide Chain of Optimized DART-G4

<400> SEQUENCE: 118

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

Asp Ser Asp Gly Ser Phe Phe Leu Tyr Ser Lys Leu Thr Val Asp Lys
            385                 390                 395                 400

Ser Arg Trp Gln Gln Gly Asn Val Phe Ser Cys Ser Val Met His Glu
            405                 410                 415

Ala Leu His Asn His Tyr Thr Gln Lys Ser Leu Ser Leu Ser Pro Gly
        420                 425                 430

Gly Gly Gly Ser Gly Gly Gly Ser Gly Gly Gly Asp Ile Gln Met Thr
    435                 440                 445

Gln Ser Pro Ser Ser Leu Ser Ala Ser Val Gly Asp Arg Val Thr Ile
450                 455                 460

465                 470                 475                 480

Thr Cys Arg Pro Ser Gln Asp Ile Ser Asn Tyr Leu Asn Trp Tyr Gln
            485                 490                 495

Gln Lys Pro Asp Lys Thr Val Lys Leu Leu Ile Tyr Tyr Thr Ser Arg
        500                 505                 510

Leu Arg Ser Gly Val Pro Ser Arg Phe Ser Gly Ser Gly Ser Gly Thr
    515                 520                 525

Asp Phe Thr Phe Thr Ile Ser Ser Leu Gln Pro Glu Asp Ile Ala Thr
530                 535                 540

Tyr Phe Cys Gln Gln Gly Asp Thr Leu Pro Tyr Thr Phe Gly Gln Gly
545                 550                 555                 560

Thr Lys Leu Glu Ile Lys Gly Gly Gly Ser Gly Gly Gly Gly Gln Val
            565                 570                 575

Gln Val Gln Leu Val Gln Ser Gly Ala Glu Val Lys Lys Pro Gly Ala
        580                 585                 590

Ser Val Lys Val Ser Cys Lys Ala Ser Gly Tyr Thr Phe Thr Ser Tyr
    595                 600                 605

Trp Ile Asn Trp Val Lys Gln Ala Pro Gly Gln Gly Leu Glu Trp Ile
610                 615                 620

Gly Asn Ile Tyr Pro Ser Asp Ser Tyr Thr Asn Tyr Asn Gln Lys Phe
625                 630                 635                 640

Lys Asp Lys Ala Thr Ile Thr Ala Asp Lys Ser Thr Ser Thr Ala Tyr
            645                 650                 655

Met Glu Leu Ser Ser Leu Arg Ser Glu Asp Thr Ala Val Tyr Tyr Cys
        660                 665                 670

Thr Arg Asp Tyr Gly Ser Ser Tyr Ser Tyr Asn Val Trp Gly Gln Gly
    675                 680                 685

Thr Thr Val Thr Val Ser Ser Gly Cys Gly Gly Gly Glu Val Ala
690                 695                 700

Ala Leu Glu Lys Glu Val Ala Ala Leu Glu Lys Glu Val Ala Ala Leu
705                 710                 715                 720

Glu Lys Glu Val Ala Ala Leu Glu Lys
            725

<210> SEQ ID NO 119
<211> LENGTH: 268
<212> TYPE: PRT
<213> ORGANISM: Artificial Sequence
<220> FEATURE:
<223> OTHER INFORMATION: Fourth Polypeptide Chain of DART-G

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr

```
                    20                  25                  30
Leu Asn Trp Tyr Gln Gln Lys Pro Asp Lys Thr Val Lys Leu Leu Ile
                35                  40                  45

Tyr Tyr Thr Ser Arg Leu Arg Ser Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
            130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ser Tyr Ser Phe Asp Tyr Trp
            210                 215                 220

Gly Gln Gly Thr Thr Val Thr Val Ser Ser Gly Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 120
<211> LENGTH: 268
<212> TYPE: PRT
<213> ORGANISM: Artificial Sequence
<220> FEATURE:
<223> OTHER INFORMATION: Fourth Polypeptide Chain of Optimized DART-G1

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
                35                  40                  45

Tyr Tyr Thr Ser Arg Leu Arg Ser Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
```

```
                115                 120                 125
Pro Gly Ala Ser Val Lys Val Ser Cys Lys Ala Ser Gly Tyr Thr Phe
            130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Phe His Pro Trp
    210                 215                 220

Gly Gln Gly Thr Thr Val Thr Val Ser Ser Gly Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 121
<211> LENGTH: 268
<212> TYPE: PRT
<213> ORGANISM: Artificial Sequence
<220> FEATURE:
<223> OTHER INFORMATION: Fourth Polypeptide Chain of Optimized DART-G2

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Met Ser Thr Trp
```

Gly Gln Gly Thr Thr Val Thr Val Ser Ser Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 122
<211> LENGTH: 268
<212> TYPE: PRT
<213> ORGANISM: Artificial Sequence
<220> FEATURE:
<223> OTHER INFORMATION: Fourth Polypeptide Chain of Optimized DART-G3

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Tyr Ser Leu Trp
210                 215                 220

Gly Gln Gly Thr Thr Val Thr Val Ser Ser Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 123
<211> LENGTH: 268
<212> TYPE: PRT
<213> ORGANISM: Artificial Sequence
<220> FEATURE:
<223> OTHER INFORMATION: Fourth Polypeptide Chain of Optimized DART-G4

```
<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65              70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Lys Gln Ala Pro Gly Gln Gly Leu
145             150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ser Tyr Ser Tyr Asn Val Trp
210                 215                 220

Gly Gln Gly Thr Thr Val Thr Val Ser Ser Gly Gly Cys Gly Gly Gly
225                 230                 235                 240

Lys Val Ala Ala Leu Lys Glu Lys Val Ala Ala Leu Lys Glu Lys Val
                245                 250                 255

Ala Ala Leu Lys Glu Lys Val Ala Ala Leu Lys Glu
                260                 265

<210> SEQ ID NO 124
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of Anti-Fluorescein Antibody 4-4-20

<400> SEQUENCE: 124

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
50                  55                  60

Ser Val Lys Gly Arg Phe Thr Ile Ser Arg Asp Asp Ser Lys Ser Ser
```

```
                65                  70                  75                  80
Val Tyr Leu Gln Met Asn Asn Leu Arg Val Glu Asp Met Gly Ile Tyr
                    85                  90                  95

Tyr Cys Thr Gly Ser Tyr Tyr Gly Met Asp Tyr Trp Gly Gln Gly Thr
                100                 105                 110

Ser Val Thr Val Ser Ser
        115

<210> SEQ ID NO 125
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of Anti-Fluorescein Antibody 4-4-20

<400> SEQUENCE: 125

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110

<210> SEQ ID NO 126
<211> LENGTH: 120
<212> TYPE: PRT
<213> ORGANISM: Artificial Sequence
<220> FEATURE:
<223> OTHER INFORMATION: VH Domain of Palivizumab

<400> SEQUENCE: 126

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser
        115                 120
```

```
<210> SEQ ID NO 127
<211> LENGTH: 106
<212> TYPE: PRT
<213> ORGANISM: Artificial Sequence
<220> FEATURE:
<223> OTHER INFORMATION: VL Domain of Palivizumab

<400> SEQUENCE: 127
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

```
<210> SEQ ID NO 128
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of EphA2 MAB-1

<400> SEQUENCE: 128
```

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Lys His Gly Asn Tyr Tyr Thr Met Asp Tyr Trp Gly Gln Gly Thr
            100                 105                 110

Ser Val Thr Val Ser Ser
        115

```
<210> SEQ ID NO 129
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of EphA2 MAB-1

<400> SEQUENCE: 129
```

Asp Ile Gln Met Thr Gln Thr Thr Ser Ser Leu Ser Ala Ser Leu Gly

```
                1               5                  10                 15
Asp Arg Ile Thr Ile Ser Cys Arg Ala Ser Gln Asp Ile Ser Asn Tyr
                    20                  25                 30

Leu Asn Trp Tyr Gln Gln Lys Pro Asp Gly Thr Val Lys Leu Leu Ile
            35                  40                      45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
                    85                  90                  95

Phe Gly Gly Gly Thr Lys Leu Glu Ile Lys
                100                 105

<210> SEQ ID NO 130
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of EphA2 MAB-2

<400> SEQUENCE: 130

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
                    20                  25                  30

Gly Met Asn Trp Val Lys Gln Ala Pro Gly Lys Gly Leu Lys Trp Met
            35                  40                  45

Gly Trp Ile Asn Thr Tyr Ile Gly Glu Pro Thr Tyr Ala Asp Asp Phe
        50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                    85                  90                  95

Ala Arg Glu Leu Gly Pro Tyr Tyr Phe Asp Tyr Trp Gly Gln Gly Thr
                100                 105                 110

Thr Leu Thr Val Ser Ser
        115

<210> SEQ ID NO 131
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of EphA2 MAB-2

<400> SEQUENCE: 131

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                    20                  25                  30

Ser Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys
            100                 105                 110
```

<210> SEQ ID NO 132
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of EphA2 MAB-3

<400> SEQUENCE: 132

```
Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Thr Asp His
                20                  25                  30

Tyr Met Tyr Trp Val Arg Gln Thr Pro Glu Lys Arg Leu Glu Trp Val
            35                  40                  45

Ala Thr Ile Ser Asp Gly Gly Ser Phe Thr Ser Tyr Pro Asp Ser Val
50                  55                  60

Lys Gly Arg Phe Thr Ile Ser Arg Asp Ile Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Asp Glu Ser Asp Arg Pro Phe Pro Tyr Trp Gly Gln Gly Thr
            100                 105                 110

Leu Val Thr Val Ser Ser
        115
```

<210> SEQ ID NO 133
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of EphA2 MAB-3

<400> SEQUENCE: 133

```
Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
                20                  25                  30

Val Ala Trp Tyr Gln Gln Lys Pro Gly Gln Ser Pro Lys Leu Leu Ile
            35                  40                  45

Phe Trp Ala Ser Thr Arg His Ala Gly Val Pro Asp Arg Phe Thr Gly
50                  55                  60

Ser Gly Ser Gly Thr Asp Phe Thr Leu Thr Ile Ser Ser Val Gln Ala
65                  70                  75                  80

Gly Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105
```

<210> SEQ ID NO 134
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of 5T4 MAB-1

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
    50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser
        115

<210> SEQ ID NO 135
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of 5T4 MAB-1

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys
            100                 105

<210> SEQ ID NO 136
<211> LENGTH: 127
<212> TYPE: PRT
<213> ORGANISM: Mus musculus
<220> FEATURE:
<221> NAME/KEY: MISC_FEATURE
<222> LOCATION: (1)..(127)
<223> OTHER INFORMATION: VH Domain of 5T4 MAB-2

<400> SEQUENCE: 136

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Arg Ala Asn Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Asn Cys
                85                  90                  95

Ala Arg Tyr Gly Pro Leu Phe Thr Val Val Asp Pro Asn Ser Tyr
            100                 105                 110

Ala Met Asp Tyr Trp Gly Gln Gly Thr Ser Val Thr Val Ser Ser
        115                 120                 125

<210> SEQ ID NO 137
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of 5T4 MAB-2

<400> SEQUENCE: 137

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 138
<211> LENGTH: 122
<212> TYPE: PRT
<213> ORGANISM: Artificial Sequence
<220> FEATURE:
<223> OTHER INFORMATION: VH Domain of Fc-Optimized Anti-Human B7-H3
      Antibody Enoblituzumab

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Gly Arg Gly Arg Glu Asn Ile Tyr Tyr Gly Ser Arg Leu Asp Tyr Trp
                100                 105                 110

Gly Gln Gly Thr Thr Val Thr Val Ser Ser
            115                 120

<210> SEQ ID NO 139
<211> LENGTH: 107
<212> TYPE: PRT
<213> ORGANISM: Artificial Sequence
<220> FEATURE:
<223> OTHER INFORMATION: VL Domain of Fc-Optimized Anti-Human B7-H3
      Antibody Enoblituzumab

<400> SEQUENCE: 139

Asp Ile Gln Leu Thr Gln Ser Pro Ser Phe Leu Ser Ala Ser Val Gly
 1               5                  10                  15

Asp Arg Val Thr Ile Thr Cys Lys Ala Ser Gln Asn Val Asp Thr Asn
                 20                  25                  30

Val Ala Trp Tyr Gln Gln Lys Pro Gly Lys Ala Pro Lys Ala Leu Ile
             35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Phe
                 85                  90                  95

Thr Phe Gly Gln Gly Thr Lys Leu Glu Ile Lys
                100                 105

<210> SEQ ID NO 140
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of Anti-Human B7-H3 Antibody BRCA69D

<400> SEQUENCE: 140

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
                 20                  25                  30

Trp Met Gln Trp Val Lys Gln Arg Pro Gly Gln Gly Leu Glu Trp Ile
             35                  40                  45

Gly Thr Ile Tyr Pro Gly Asp Gly Asp Thr Arg Tyr Thr Gln Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Ala Ser Glu Asp Ser Ala Val Tyr Tyr Cys
                 85                  90                  95

Ala Arg Arg Gly Ile Pro Arg Leu Trp Tyr Phe Asp Val Trp Gly Ala
                100                 105                 110

```
Gly Thr Thr Val Thr Val Ser Ser
        115                 120

<210> SEQ ID NO 141
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of Anti-Human B7-H3 Antibody BRCA69D

<400> SEQUENCE: 141

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 142
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
      Antibody BRCA69D (hBRCA69D VH1)

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Asp Gly Asp Thr Arg Tyr Thr Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120

<210> SEQ ID NO 143
<211> LENGTH: 120
<212> TYPE: PRT
<213> ORGANISM: Artificial Sequence
<220> FEATURE:
<223> OTHER INFORMATION: VH Domain of Humanized Anti-Human B7-H3
```

-continued

Antibody BRCA69D (hBRCA69D VH2)

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Gly Asp Thr Arg Tyr Thr Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
            115                 120

<210> SEQ ID NO 144
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody BRCA69D (hBRCA69D VL1)

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 145
<211> LENGTH: 107
<212> TYPE: PRT
<213> ORGANISM: Artificial Sequence
<220> FEATURE:
<223> OTHER INFORMATION: VL Domain of Humanized Anti-Human B7-H3
      Antibody BRCA69D (hBRCA69D VL2)

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 146
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of Anti-Human B7-H3 Antibody PRCA157

<400> SEQUENCE: 146

Glu Val Gln Gln Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
            115

<210> SEQ ID NO 147
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: VL Domain of Anti-Human B7-H3 Antibody PRCA157

<400> SEQUENCE: 147

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Ser Ile Tyr Ser Tyr
            20                  25                  30

Leu Ala Trp Tyr Gln Gln Lys Gln Gly Lys Ser Pro Gln Leu Leu Val
            35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
 65                  70                  75                  80

Glu Asp Phe Gly Arg Tyr Tyr Cys Gln His His Tyr Gly Thr Pro Pro
                85                  90                  95

```
Trp Thr Phe Gly Gly Gly Thr Asn Leu Glu Ile Lys
            100                 105
```

<210> SEQ ID NO 148
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of Anti-gpA33 Antibody gpA33 MAB-1

<400> SEQUENCE: 148

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser
        115
```

<210> SEQ ID NO 149
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of Anti-gpA33 Antibody gpA33 MAB-1

<400> SEQUENCE: 149

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105
```

<210> SEQ ID NO 150
<211> LENGTH: 121
<212> TYPE: PRT
<213> ORGANISM: Artificial Sequence
<220> FEATURE:
<223> OTHER INFORMATION: VH Domain of Humanized Anti-CEACAM5/CEACAM6

-continued

Antibody 16C3

<400> SEQUENCE: 150

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 151
<211> LENGTH: 107
<212> TYPE: PRT
<213> ORGANISM: Artificial Sequence
<220> FEATURE:
<223> OTHER INFORMATION: VL Domain of Humanized Anti-CEACAM5/CEACAM6
      Antibody 16C3

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Trp Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 152
<211> LENGTH: 121
<212> TYPE: PRT
<213> ORGANISM: Artificial Sequence
<220> FEATURE:
<223> OTHER INFORMATION: VH Domain of Humanized Anti-CEACAM5/CEACAM6
      Antibody hMN15

<400> SEQUENCE: 152

Gln Val Gln Leu Val Glu Ser Gly Gly Gly Val Val Gln Pro Gly Arg
1               5                   10                  15

Ser Leu Arg Leu Ser Cys Ser Ser Ser Gly Phe Ala Leu Thr Asp Tyr
            20                  25                  30

Tyr Met Ser Trp Val Arg Gln Ala Pro Gly Lys Gly Leu Glu Trp Leu
        35                  40                  45

Gly Phe Ile Ala Asn Lys Ala Asn Gly His Thr Thr Asp Tyr Ser Pro
            50                  55                  60

Ser Val Lys Gly Arg Phe Thr Ile Ser Arg Asp Asn Ser Lys Asn Thr
 65                  70                  75                  80

Leu Phe Leu Gln Met Asp Ser Leu Arg Pro Glu Asp Thr Gly Val Tyr
                 85                  90                  95

Phe Cys Ala Arg Asp Met Gly Ile Arg Trp Asn Phe Asp Val Trp Gly
             100                 105                 110

Gln Gly Thr Pro Val Thr Val Ser Ser
         115                 120

<210> SEQ ID NO 153
<211> LENGTH: 107
<212> TYPE: PRT
<213> ORGANISM: Artificial Sequence
<220> FEATURE:
<223> OTHER INFORMATION: VL Domain of Humanized Anti-CEACAM5/CEACAM6
      Antibody hMN15

<400> SEQUENCE: 153

Asp Ile Gln Leu Thr Gln Ser Pro Ser Ser Leu Ser Ala Ser Val Gly
  1               5                  10                  15

Asp Arg Val Thr Met Thr Cys Ser Ala Ser Ser Arg Val Ser Tyr Ile
                 20                  25                  30

His Trp Tyr Gln Gln Lys Pro Gly Lys Ala Pro Lys Arg Trp Ile Tyr
             35                  40                  45

Gly Thr Ser Thr Leu Ala Ser Gly Val Pro Ala Arg Phe Ser Gly Ser
     50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Tyr Asn Pro Pro Thr
                 85                  90                  95

Phe Gly Gln Gly Thr Lys Val Glu Ile Lys Arg
            100                 105

<210> SEQ ID NO 154
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of Murine Anti-CD137 Monoclonal Antibody
      (CD137 MAB-3 VH)

<400> SEQUENCE: 154

Ser Tyr Trp Ile Asn
 1               5

<210> SEQ ID NO 155
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of Murine Anti-CD137 Monoclonal Antibody
      (CD137 MAB-3 VH)

<400> SEQUENCE: 155

Asn Ile Tyr Pro Ser Asp Ser Tyr Thr Asn Tyr Asn Gln Lys Phe Lys
 1               5                  10                  15

Asp

<210> SEQ ID NO 156
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDRH3 of Murine Anti-CD137 Monoclonal Antibody
      (CD137 MAB-3 VH)

<400> SEQUENCE: 156

Asp Tyr Gly Ser Ser Tyr Ser Phe Asp Tyr
1               5                   10

<210> SEQ ID NO 157
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of Murine Anti-CD137 Monoclonal Antibody
      (CD137 MAB-3 VL)

<400> SEQUENCE: 157

Arg Pro Ser Gln Asp Ile Ser Asn Tyr Leu Asn
1               5                   10

<210> SEQ ID NO 158
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of Murine Anti-CD137 Monoclonal Antibody
      (CD137 MAB-3 VL)

<400> SEQUENCE: 158

Tyr Thr Ser Arg Leu Arg Ser
1               5

<210> SEQ ID NO 159
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of Murine Anti-CD137 Monoclonal Antibody
      (CD137 MAB-3 VL)

<400> SEQUENCE: 159

Gln Gln Gly Asp Thr Leu Pro Tyr Thr
1               5

<210> SEQ ID NO 160
<211> LENGTH: 6
<212> TYPE: PRT
<213> ORGANISM: Mus musculus
<220> FEATURE:
<221> NAME/KEY: 1MISC_FEATURE
<222> LOCATION: (1)..(6)
<223> OTHER INFORMATION: Residues 103-108 of SEQ ID NO:74

<400> SEQUENCE: 160

```
Ser Tyr Ser Phe Asp Tyr
1               5

<210> SEQ ID NO 161
<211> LENGTH: 10
<212> TYPE: PRT
<213> ORGANISM: Artificial Sequence
<220> FEATURE:
<223> OTHER INFORMATION: CDRH3 of hCD137 MAB-3 VH1A

<400> SEQUENCE: 161

Asp Tyr Gly Ser Ala Tyr Ser Phe His Pro
1               5                   10

<210> SEQ ID NO 162
<211> LENGTH: 10
<212> TYPE: PRT
<213> ORGANISM: Artificial Sequence
<220> FEATURE:
<223> OTHER INFORMATION: CDRH3 of hCD137 MAB-3 VH1B

<400> SEQUENCE: 162

Asp Tyr Gly Ser Ala Tyr Ser Met Ser Thr
1               5                   10

<210> SEQ ID NO 163
<211> LENGTH: 10
<212> TYPE: PRT
<213> ORGANISM: Artificial Sequence
<220> FEATURE:
<223> OTHER INFORMATION: CDRH3 of hCD137 MAB-3 VH1C

<400> SEQUENCE: 163

Asp Tyr Gly Ser Ala Tyr Ser Tyr Ser Leu
1               5                   10

<210> SEQ ID NO 164
<211> LENGTH: 10
<212> TYPE: PRT
<213> ORGANISM: Artificial Sequence
<220> FEATURE:
<223> OTHER INFORMATION: CDRH3 of hCD137 MAB-3 VH1D

<400> SEQUENCE: 164

Asp Tyr Gly Ser Ser Tyr Ser Tyr Asn Val
1               5                   10

<210> SEQ ID NO 165
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of CD137 MAB-4 VH

<400> SEQUENCE: 165

Ser Tyr Trp Ile Asn
1               5

<210> SEQ ID NO 166
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of CD137 MAB-4 VH
```

-continued

<400> SEQUENCE: 166

Asn Ile Tyr Pro Ser Asp Ser Tyr Thr Asn Tyr Asp Gln Lys Phe Lys
1               5                   10                  15
Asp

<210> SEQ ID NO 167
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDRH3 of CD137 MAB-4 VH

<400> SEQUENCE: 167

Ser Gly Glu Tyr Gly Lys Ile Gly Tyr Tyr Ala Met Asp Tyr
1               5                   10

<210> SEQ ID NO 168
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of CD137 MAB-4 VL

<400> SEQUENCE: 168

Arg Ala Ser Gln Asp Ile Ser Asn Tyr Leu Asn
1               5                   10

<210> SEQ ID NO 169
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of CD137 MAB-4 VL

<400> SEQUENCE: 169

Tyr Thr Ser Arg Leu His Ser
1               5

<210> SEQ ID NO 170
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of CD137 MAB-4 VL

<400> SEQUENCE: 170

Gln Gln Gly Asn Thr Leu Pro Tyr Thr
1               5

<210> SEQ ID NO 171
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of CD137 MAB-5 VH

<400> SEQUENCE: 171

```
Ser Tyr Asp Ile Ser
1               5

<210> SEQ ID NO 172
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRH2 of CD137 MAB-5 VH

<400> SEQUENCE: 172

Val Val Trp Thr Gly Gly Gly Thr Asn Tyr Asn Ser Ala Phe Met Ser
1               5                   10                  15

<210> SEQ ID NO 173
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: CD137 MAB-5 (CD137 MAB-5

<400> SEQUENCE: 173

Val Asp Tyr
1

<210> SEQ ID NO 174
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of CD137 MAB-5 VL

<400> SEQUENCE: 174

Arg Ser Ser Gln Ser Leu Val His Ser Asn Gly Asn Thr Tyr Leu His
1               5                   10                  15

<210> SEQ ID NO 175
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of CD137 MAB-5 VL

<400> SEQUENCE: 175

Lys Val Ser Asn Arg Phe Ser
1               5

<210> SEQ ID NO 176
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of CD137 MAB-5 VL

<400> SEQUENCE: 176

Ser Gln Ser Thr His Val Pro Trp Thr
1               5
```

<210> SEQ ID NO 177
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of Murine Anti-HER2/neu Monoclonal
      Antibody HER2 MAB-1 VH

<400> SEQUENCE: 177

Asn Tyr Gly Met Asn
1               5

<210> SEQ ID NO 178
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of Murine Anti-HER2/neu Monoclonal
      Antibody HER2 MAB-1 VH

<400> SEQUENCE: 178

Trp Ile Asn Thr Asn Ile Gly Glu Pro Thr Tyr Thr Glu Glu Phe Lys
1               5                   10                  15

Gly

<210> SEQ ID NO 179
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDRH3 of Murine Anti-HER2/neu Monoclonal
      Antibody HER2 MAB-1 VH

<400> SEQUENCE: 179

Asp Asp Gly Tyr Gly Asn Arg Val Ser Tyr
1               5                   10

<210> SEQ ID NO 180
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of Murine Anti-HER2/neu Monoclonal
      Antibody HER2 MAB-1 VL

<400> SEQUENCE: 180

Lys Ala Ser Gln Asp Ile Asn Ser Tyr Leu Ser
1               5                   10

<210> SEQ ID NO 181
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of Murine Anti-HER2/neu Monoclonal
      Antibody HER2 MAB-1 VL

<400> SEQUENCE: 181

Arg Ala Asn Arg Leu Val Asp
1               5

<210> SEQ ID NO 182
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of Murine Anti-HER2/neu Monoclonal
      Antibody HER2 MAB-1 VL

<400> SEQUENCE: 182

Leu Gln His Asp Glu Phe Pro Trp Thr
1               5

<210> SEQ ID NO 183
<211> LENGTH: 10
<212> TYPE: PRT
<213> ORGANISM: Artificial Sequence
<220> FEATURE:
<223> OTHER INFORMATION: CDRH3 of VH Domain of Humanized Anti-Human
      HER2/neu Antibody (hHER2 MAB-1 VH1)

<400> SEQUENCE: 183

Asp Asp Gly Tyr Gly Asn Arg Val Ser Tyr
1               5                   10

<210> SEQ ID NO 184
<211> LENGTH: 10
<212> TYPE: PRT
<213> ORGANISM: Artificial Sequence
<220> FEATURE:
<223> OTHER INFORMATION: CDRH3 of VH Domain of Humanized Anti-Human
      HER2/neu Antibody (hHER2 MAB-1 VH2)

<400> SEQUENCE: 184

Asp Glu Gly Tyr Gly Asn Arg Val Ser Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: CDRH3 of VH Domain of Humanized Anti-Human
      HER2/neu Antibody (hHER2 MAB-1 VH3)

<400> SEQUENCE: 185

Asp Asp Ile Tyr Gly Asn Arg Val Ser Tyr
1               5                   10

<210> SEQ ID NO 186
<211> LENGTH: 11
<212> TYPE: PRT
<213> ORGANISM: Artificial Sequence
<220> FEATURE:
<223> OTHER INFORMATION: CDRL1 of VL Domain of Humanized Anti-Human
      HER2/neu Antibody (hHER2 MAB-1 VL1)

<400> SEQUENCE: 186

Lys Ala Ser Gln Asp Ile Asn Ser Tyr Leu Ser
1               5                   10

<210> SEQ ID NO 187
<211> LENGTH: 11
<212> TYPE: PRT

```
<213> ORGANISM: Artificial Sequence
<220> FEATURE:
<223> OTHER INFORMATION: CDRL1 of VL Domain of Humanized Anti-Human
      HER2/neu Antibody (hHER2 MAB-1 VL2)

<400> SEQUENCE: 187

Lys Ala Ser Gln Asp Ile Asn Thr Tyr Leu Ser
1               5                   10

<210> SEQ ID NO 188
<211> LENGTH: 11
<212> TYPE: PRT
<213> ORGANISM: Artificial Sequence
<220> FEATURE:
<223> OTHER INFORMATION: CDRL1 of VL Domain of Humanized Anti-Human
      HER2/neu Antibody (hHER2 MAB-1 VL3)

<400> SEQUENCE: 188

Lys Ala Ser Gln Asp Ile Ser Asn Tyr Leu Ser
1               5                   10

<210> SEQ ID NO 189
<211> LENGTH: 7
<212> TYPE: PRT
<213> ORGANISM: Artificial Sequence
<220> FEATURE:
<223> OTHER INFORMATION: CDRL2 of VL Domain of Humanized Anti-Human
      HER2/neu Antibody (hHER2 MAB-1 VL1)

<400> SEQUENCE: 189

Arg Ala Asn Arg Leu Val Asp
1               5

<210> SEQ ID NO 190
<211> LENGTH: 7
<212> TYPE: PRT
<213> ORGANISM: Artificial Sequence
<220> FEATURE:
<223> OTHER INFORMATION: CDRL2 of VL Domain of Humanized Anti-Human
      HER2/neu Antibody (hHER2 MAB-1 VL2)

<400> SEQUENCE: 190

Arg Ala Asn Arg Leu Val Glu
1               5

<210> SEQ ID NO 191
<211> LENGTH: 7
<212> TYPE: PRT
<213> ORGANISM: Artificial Sequence
<220> FEATURE:
<223> OTHER INFORMATION: CDRL2 of VL Domain of Humanized Anti-Human
      HER2/neu Antibody (hHER2 MAB-1 VL3)

<400> SEQUENCE: 191

Arg Ala Asn Arg Leu Gln Ser
1               5

<210> SEQ ID NO 192
<211> LENGTH: 497
<212> TYPE: PRT
<213> ORGANISM: Artificial Sequence
<220> FEATURE:
<223> OTHER INFORMATION: First Polypeptide Chain of TRIDENT-A

<400> SEQUENCE: 192

Asp Ile Gln Met Thr Gln Ser Pro Ser Ser Leu Ser Ala Ser Val Gly
1               5                   10                  15
```

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
        130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ser Tyr Ser Phe Asp Tyr Trp
210                 215                 220

Gly Gln Gly Thr Thr Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu

```
                     435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 193
<211> LENGTH: 497
<212> TYPE: PRT
<213> ORGANISM: Artificial Sequence
<220> FEATURE:
<223> OTHER INFORMATION: First Polypeptide Chain of TRIDENT-A1

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Phe His Pro Trp
    210                 215                 220

Gly Gln Gly Thr Thr Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
    290                 295                 300
```

```
Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
            325                 330                 335

Ala Lys Thr Lys Pro Arg Glu Glu Gln Tyr Asn Ser Thr Tyr Arg Val
        340                 345                 350

Val Ser Val Leu Thr Val Leu His Gln Asp Trp Leu Asn Gly Lys Glu
    355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
            405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 194
<211> LENGTH: 497
<212> TYPE: PRT
<213> ORGANISM: Artificial Sequence
<220> FEATURE:
<223> OTHER INFORMATION: First Polypeptide Chain of TRIDENT-A2

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160
```

```
Glu Trp Ile Gly Asn Ile Tyr Pro Ser Asp Ser Tyr Thr Asn Tyr Asn
                165                 170                 175
Gln Lys Phe Lys Asp Lys Ala Thr Ile Thr Ala Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Thr Arg Asp Tyr Gly Ala Tyr Ser Met Ser Thr Trp
    210                 215                 220
Gly Gln Gly Thr Thr Val Thr Val Ser Ser Ala Ser Thr Lys Gly Glu
225                 230                 235                 240
Val Ala Ala Cys Glu Lys Glu Val Ala Ala Leu Glu Lys Glu Val Ala
                245                 250                 255
Ala Leu Glu Lys Glu Val Ala Ala Leu Glu Lys Gly Gly Gly Asp Lys
            260                 265                 270
Thr His Thr Cys Pro Pro Cys Pro Ala Pro Glu Ala Ala Gly Gly Pro
        275                 280                 285
Ser Val Phe Leu Phe Pro Lys Pro Lys Asp Thr Leu Met Ile Ser
    290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
        355                 360                 365
Tyr Lys Cys Lys Val Ser Asn Lys Ala Leu Pro Ala Pro Ile Glu Lys
    370                 375                 380
Thr Ile Ser Lys Ala Lys Gly Gln Pro Arg Glu Pro Gln Val Tyr Thr
385                 390                 395                 400
Leu Pro Pro Ser Arg Glu Glu Met Thr Lys Asn Gln Val Ser Leu Trp
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
        435                 440                 445
Asp Ser Asp Gly Ser Phe Phe Leu Tyr Ser Lys Leu Thr Val Asp Lys
    450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys

<210> SEQ ID NO 195
<211> LENGTH: 497
<212> TYPE: PRT
<213> ORGANISM: Artificial Sequence
<220> FEATURE:
<223> OTHER INFORMATION: First Polypeptide Chain of TRIDENT-A3

<400> SEQUENCE: 195

Asp Ile Gln Met Thr Gln Ser Pro Ser Ser Leu Ser Ala Ser Val Gly
1               5                   10                  15
Asp Arg Val Thr Ile Thr Cys Arg Pro Ser Gln Asp Ile Ser Asn Tyr
```

-continued

```
                20                  25                  30
Leu Asn Trp Tyr Gln Gln Lys Pro Asp Lys Thr Val Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
            130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ala Tyr Ser Tyr Ser Leu Trp
            210                 215                 220

Gly Gln Gly Thr Thr Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
            275                 280                 285

Ser Val Phe Leu Phe Pro Pro Lys Pro Lys Asp Thr Leu Met Ile Ser
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445
```

```
Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
            485                 490                 495

Lys

<210> SEQ ID NO 196
<211> LENGTH: 497
<212> TYPE: PRT
<213> ORGANISM: Artificial Sequence
<220> FEATURE:
<223> OTHER INFORMATION: First Polypeptide Chain of TRIDENT-A4

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ser Tyr Ser Tyr Asn Val Trp
210                 215                 220

Gly Gln Gly Thr Thr Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
    290                 295                 300
```

```
Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 197
<211> LENGTH: 267
<212> TYPE: PRT
<213> ORGANISM: Artificial Sequence
<220> FEATURE:
<223> OTHER INFORMATION: Second Polypeptide Chain of TRIDENT-A

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
```

```
                    165                 170                 175
Gln Lys Phe Lys Asp Lys Ala Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ser Tyr Ser Phe Asp Tyr Trp
210                 215                 220

Gly Gln Gly Thr Thr Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
                260                 265

<210> SEQ ID NO 198
<211> LENGTH: 267
<212> TYPE: PRT
<213> ORGANISM: Artificial Sequence
<220> FEATURE:
<223> OTHER INFORMATION: Second Polypeptide Chain of TRIDENT-A1

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
                20                  25                  30

Leu Asn Trp Tyr Gln Gln Lys Pro Asp Lys Thr Val Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ala Tyr Ser Phe His Pro Trp
210                 215                 220

Gly Gln Gly Thr Thr Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
```

<210> SEQ ID NO 199
<211> LENGTH: 267
<212> TYPE: PRT
<213> ORGANISM: Artificial Sequence
<220> FEATURE:
<223> OTHER INFORMATION: Second Polypeptide Chain of TRIDENT-A2

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Met Ser Thr Trp
    210                 215                 220

Gly Gln Gly Thr Thr Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265

<210> SEQ ID NO 200
<211> LENGTH: 267
<212> TYPE: PRT
<213> ORGANISM: Artificial Sequence
<220> FEATURE:
<223> OTHER INFORMATION: Second Polypeptide Chain of TRIDENT-A3

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
                35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
    130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Tyr Ser Leu Trp
    210                 215                 220

Gly Gln Gly Thr Val Thr Val Ser Ser Ala Ser Thr Lys Gly Lys Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265

<210> SEQ ID NO 201
<211> LENGTH: 267
<212> TYPE: PRT
<213> ORGANISM: Artificial Sequence
<220> FEATURE:
<223> OTHER INFORMATION: Second Polypeptide Chain of TRIDENT-A4

<400> SEQUENCE: 201

Asp Ile Gln Met Thr Gln Ser Pro Ser Ser Leu Ser Ala Ser Val Gly
 1               5                  10                  15

Asp Arg Val Thr Ile Thr Cys Arg Pro Ser Gln Asp Ile Ser Asn Tyr
                 20                  25                  30

Leu Asn Trp Tyr Gln Gln Lys Pro Asp Lys Thr Val Lys Leu Leu Ile
                35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
            130                 135                 140

Thr Ser Tyr Trp Ile Asn Trp Val Lys Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Thr Arg Asp Tyr Gly Ser Ser Tyr Ser Tyr Asn Val Trp
210                 215                 220

Gly Gln Gly Thr Thr Val Thr Val Ser Ser Ala Ser Thr Lys Gly Lys
225                 230                 235                 240

Val Ala Ala Cys Lys Glu Lys Val Ala Ala Leu Lys Glu Lys Val Ala
            245                 250                 255

Ala Leu Lys Glu Lys Val Ala Ala Leu Lys Glu
            260                 265

<210> SEQ ID NO 202
<211> LENGTH: 117
<212> TYPE: PRT
<213> ORGANISM: Artificial Sequence
<220> FEATURE:
<223> OTHER INFORMATION: VH Domain of hPRCA157 VH1

<400> SEQUENCE: 202

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Gly Gly Ala Met Asp Tyr Trp Gly Gln Gly Thr Thr
            100                 105                 110

Val Thr Val Ser Ser
        115

<210> SEQ ID NO 203
<211> LENGTH: 108
<212> TYPE: PRT
<213> ORGANISM: Artificial Sequence
<220> FEATURE:
<223> OTHER INFORMATION: VL Domain of hPRCA157 VL1

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

```
Tyr Asn Thr Lys Thr Leu Pro Glu Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Gly Thr Pro Pro
                 85                  90                  95

Trp Thr Phe Gly Gln Gly Thr Arg Leu Glu Ile Lys
                100                 105
```

<210> SEQ ID NO 204
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of CD19 MAB-1

<400> SEQUENCE: 204

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Trp Trp Asp Asp Lys Arg Tyr Asn Pro Ala
 50                  55                  60

Leu Lys Ser Arg Leu Thr Ile Ser Lys Asp Thr Ser Lys Asn Gln Val
 65                  70                  75                  80

Phe Leu Thr Met Thr Asn Met Asp Pro Val Asp Thr Ala Thr Tyr Tyr
                 85                  90                  95

Cys Ala Arg Met Glu Leu Trp Ser Tyr Tyr Phe Asp Tyr Trp Gly Gln
                100                 105                 110

Gly Thr Thr Val Thr Val Ser Ser
        115                 120
```

<210> SEQ ID NO 205
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of CD19 MAB-1

<400> SEQUENCE: 205

```
Glu Asn Val Leu Thr Gln Ser Pro Ala Thr Leu Ser Val Thr Pro Gly
 1               5                  10                  15

Glu Lys Ala Thr Ile Thr Cys Arg Ala Ser Gln Ser Val Ser Tyr Met
             20                  25                  30

His Trp Tyr Gln Gln Lys Pro Gly Gln Ala Pro Arg Leu Leu Ile Tyr
         35                  40                  45

Asp Ala Ser Asn Arg Ala Ser Gly Val Pro Ser Arg Phe Ser Gly Ser
 50                  55                  60

Gly Ser Gly Thr Asp His Thr Leu Thr Ile Ser Ser Leu Glu Ala Glu
 65                  70                  75                  80

Asp Ala Ala Thr Tyr Tyr Cys Phe Gln Gly Ser Val Tyr Pro Phe Thr
                 85                  90                  95
```

```
Phe Gly Gln Gly Thr Lys Leu Glu Ile Lys
            100                 105
```

<210> SEQ ID NO 206
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: VH Domain of CD123 MAB-1

<400> SEQUENCE: 206

```
Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Lys Trp Val Arg Gln Ala Pro Gly Gln Gly Leu Glu Trp Ile
            35                  40                  45

Gly Asp Ile Ile Pro Ser Asn Gly Ala Thr Phe Tyr Asn Gln Lys Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 207
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: VL Domain of CD123 MAB-1

<400> SEQUENCE: 207

```
Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys
```

<210> SEQ ID NO 208
<211> LENGTH: 119
<212> TYPE: PRT
<213> ORGANISM: Artificial Sequence

```
<220> FEATURE:
<223> OTHER INFORMATION: VH Domain oif of hCD137 MAB-3 VH1E

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ala Tyr Ser Met Ser Thr Trp Gly Gln Gly
            100                 105                 110

Thr Thr Val Thr Val Ser Ser
        115

<210> SEQ ID NO 209
<211> LENGTH: 119
<212> TYPE: PRT
<213> ORGANISM: Artificial Sequence
<220> FEATURE:
<223> OTHER INFORMATION: VH Domain oif of hCD137 MAB-3 VH1F

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Lys Gln Ala Pro Gly Gln Gly Leu Glu Trp Ala
        35                  40                  45

Gly Asn Ile Tyr Pro Ser Asp Ser Tyr Thr Asn Tyr Asn Gln Lys Phe
    50                  55                  60

Lys Asp Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Tyr Gly Ser Ala Tyr Ser Met Ser Thr Trp Gly Gln Gly
            100                 105                 110

Thr Thr Val Thr Val Ser Ser
        115

<210> SEQ ID NO 210
<211> LENGTH: 119
<212> TYPE: PRT
<213> ORGANISM: Artificial Sequence
<220> FEATURE:
<223> OTHER INFORMATION: VH Domain oif of hCD137 MAB-3 VH1G

<400> SEQUENCE: 210

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Ile Asn Trp Val Arg Gln Ala Pro Gly Gln Gly Leu Glu Trp Ala
             35                  40                  45

Gly Asn Ile Tyr Pro Ser Asp Ser Tyr Thr Asn Tyr Asn Gln Lys Phe
 50                  55                  60

Lys Asp Lys Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Asp Tyr Gly Ser Ala Tyr Ser Met Ser Thr Trp Gly Gln Gly
                100                 105                 110

Thr Thr Val Thr Val Ser Ser
            115
```

<210> SEQ ID NO 211
<211> LENGTH: 107
<212> TYPE: PRT
<213> ORGANISM: Artificial Sequence
<220> FEATURE:
<223> OTHER INFORMATION: VL Domain oif of hCD137 MAB-3 VL4

<400> SEQUENCE: 211

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Asp Lys Thr Val Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys
                100                 105
```

<210> SEQ ID NO 212
<211> LENGTH: 107
<212> TYPE: PRT
<213> ORGANISM: Artificial Sequence
<220> FEATURE:
<223> OTHER INFORMATION: VL Domain oif of hCD137 MAB-3 VL5

<400> SEQUENCE: 212

```
Asp Ile Gln Met Thr Gln Ser Pro Ser Ser Leu Ser Ala Ser Val Gly
 1               5                  10                  15

Asp Arg Val Thr Ile Thr Cys Arg Pro Ser Gln Asp Ile Ser Asn Tyr
             20                  25                  30

Leu Asn Trp Tyr Gln Gln Lys Pro Asp Lys Thr Ala Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln Gln Gly Asp Thr Leu Pro Tyr
                 85                  90                  95

Thr Phe Gly Gln Gly Thr Lys Leu Glu Ile Lys
                100                 105
```

<210> SEQ ID NO 213
<211> LENGTH: 107
<212> TYPE: PRT
<213> ORGANISM: Artificial Sequence
<220> FEATURE:
<223> OTHER INFORMATION: VL Domain oif of hCD137 MAB-3 VL6

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Ser Arg Ala Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 214
<211> LENGTH: 107
<212> TYPE: PRT
<213> ORGANISM: Artificial Sequence
<220> FEATURE:
<223> OTHER INFORMATION: VL Domain oif of hCD137 MAB-3 VL7

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Ala Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 215
<211> LENGTH: 107
<212> TYPE: PRT
<213> ORGANISM: Artificial Sequence
<220> FEATURE:
<223> OTHER INFORMATION: VL Domain oif of hCD137 MAB-3 VL8

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Ala Lys Leu Leu Ile
                35                  40                  45

Tyr Tyr Thr Ser Arg Ala Arg Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
                100                 105

<210> SEQ ID NO 216
<211> LENGTH: 107
<212> TYPE: PRT
<213> ORGANISM: Artificial Sequence
<220> FEATURE:
<223> OTHER INFORMATION: VL Domain oif of hCD137 MAB-3 VL9

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Asp Lys Thr Val Lys Leu Leu Ile
                35                  40                  45

Tyr Tyr Thr Ser Arg Ala Arg Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
                100                 105

<210> SEQ ID NO 217
<211> LENGTH: 107
<212> TYPE: PRT
<213> ORGANISM: Artificial Sequence
<220> FEATURE:
<223> OTHER INFORMATION: VL Domain oif of hCD137 MAB-3 VL10

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
                20                  25                  30

Leu Asn Trp Tyr Gln Gln Lys Pro Asp Lys Thr Val Lys Leu Leu Ile
                35                  40                  45

Tyr Tyr Thr Thr Arg Leu Arg Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
                100                 105

<210> SEQ ID NO 218

```
<211> LENGTH: 107
<212> TYPE: PRT
<213> ORGANISM: Artificial Sequence
<220> FEATURE:
<223> OTHER INFORMATION: VL Domain oif of hCD137 MAB-3 VL11

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Gly Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 219
<211> LENGTH: 107
<212> TYPE: PRT
<213> ORGANISM: Artificial Sequence
<220> FEATURE:
<223> OTHER INFORMATION: VL Domain oif of hCD137 MAB-3 VL12

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ala
        35                  40                  45

Tyr Tyr Thr Thr Arg Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: VL Domain oif of hCD137 MAB-3 VL13

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Ser Asn Tyr
            20                  25                  30

Leu Asn Trp Tyr Gln Gln Lys Pro Asp Lys Thr Val Lys Leu Leu Ala
        35                  40                  45
```

-continued

Tyr Tyr Thr Gly Arg Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 221
<211> LENGTH: 107
<212> TYPE: PRT
<213> ORGANISM: Artificial Sequence
<220> FEATURE:
<223> OTHER INFORMATION: VL Domain oif of hCD137 MAB-3 VL14

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Thr Arg Ala Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 222
<211> LENGTH: 107
<212> TYPE: PRT
<213> ORGANISM: Artificial Sequence
<220> FEATURE:
<223> OTHER INFORMATION: VL Domain oif of hCD137 MAB-3 VL15

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Gly Arg Ala Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys
            100                 105

<210> SEQ ID NO 223
<211> LENGTH: 11
<212> TYPE: PRT
<213> ORGANISM: Artificial Sequence

```
<220> FEATURE:
<223> OTHER INFORMATION: CDRL1 of hCD137 MAB-3 VL4, hCD137 MAB-3 VL7,
      hCD137 MAB-3 VL8, hCD137 MAB-3 VL9, hCD137 MAB-3 VL14 and hCD137
      MAB-3 VL15

<400> SEQUENCE: 223

Gln Ala Ser Gln Asp Ile Ser Asn Tyr Leu Asn
1               5                   10

<210> SEQ ID NO 224
<211> LENGTH: 7
<212> TYPE: PRT
<213> ORGANISM: Artificial Sequence
<220> FEATURE:
<223> OTHER INFORMATION: CDRL2 of hCD137 MAB-3 VL6, hCD137 MAB-3 VL8 and
      hCD137 MAB-3 VL9

<400> SEQUENCE: 224

Tyr Thr Ser Arg Ala Arg Ser
1               5

<210> SEQ ID NO 225
<211> LENGTH: 7
<212> TYPE: PRT
<213> ORGANISM: Artificial Sequence
<220> FEATURE:
<223> OTHER INFORMATION: CDRL2 of hCD137 MAB-3 VL10 and hCD137 MAB-3
      VL12

<400> SEQUENCE: 225

Tyr Thr Thr Arg Leu Arg Ser
1               5

<210> SEQ ID NO 226
<211> LENGTH: 7
<212> TYPE: PRT
<213> ORGANISM: Artificial Sequence
<220> FEATURE:
<223> OTHER INFORMATION: CDRL2 of hCD137 MAB-3 VL11 and hCD137 MAB-3
      VL13

<400> SEQUENCE: 226

Tyr Thr Gly Arg Leu Arg Ser
1               5

<210> SEQ ID NO 227
<211> LENGTH: 7
<212> TYPE: PRT
<213> ORGANISM: Artificial Sequence
<220> FEATURE:
<223> OTHER INFORMATION: CDRL2 of hCD137 MAB-3 VL14

<400> SEQUENCE: 227

Tyr Thr Thr Arg Ala Arg Ser
1               5

<210> SEQ ID NO 228
<211> LENGTH: 7
<212> TYPE: PRT
<213> ORGANISM: Artificial Sequence
<220> FEATURE:
<223> OTHER INFORMATION: CDRL2 of hCD137 MAB-3 VL15

<400> SEQUENCE: 228

Tyr Thr Gly Arg Ala Arg Ser
1               5
```

<210> SEQ ID NO 229
<211> LENGTH: 497
<212> TYPE: PRT
<213> ORGANISM: Artificial Sequence
<220> FEATURE:
<223> OTHER INFORMATION: First Polypeptide Chain of TRIDENT-A5

<400> SEQUENCE: 229

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Gly Arg Ala Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Arg Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Met Ser Thr Trp
210                 215                 220

Gly Gln Gly Thr Thr Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
```

|  | 370 |  |  | 375 |  |  | 380 |  |  |  |
|---|---|---|---|---|---|---|---|---|---|---|

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 230
<211> LENGTH: 267
<212> TYPE: PRT
<213> ORGANISM: Artificial Sequence
<220> FEATURE:
<223> OTHER INFORMATION: Second Polypeptide Chain of TRIDENT-A5

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Asp Lys Thr Val Lys Leu Leu Ile
        35                  40                  45

Tyr Tyr Thr Gly Arg Ala Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Gly Asp Thr Leu Pro Tyr
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Ser Tyr Trp Ile Asn Trp Val Arg Gln Ala Pro Gly Gln Gly Leu
145                 150                 155                 160

Glu Trp Ile Gly Asn Ile Tyr Pro Ser Asp Ser Tyr Thr Asn Tyr Asn
                165                 170                 175

Gln Lys Phe Lys Asp Lys Ala Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Thr Arg Asp Tyr Gly Ser Ala Tyr Ser Met Ser Thr Trp
210                 215                 220

Gly Gln Gly Thr Thr Val Thr Val Ser Ser Ala Ser Thr Lys Gly Lys
225                 230                 235                 240

Val Ala Ala Cys Lys Glu Lys Val Ala Leu Lys Glu Lys Val Ala
                245                 250                 255

Ala Leu Lys Glu Lys Val Ala Ala Leu Lys Glu
                260                 265

<210> SEQ ID NO 231
<211> LENGTH: 448
<212> TYPE: PRT
<213> ORGANISM: Artificial Sequence
<220> FEATURE:
<223> OTHER INFORMATION: Third Polypeptide Chain of TRIDENT-B

<400> SEQUENCE: 231

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Trp Met His Trp Val Arg Gln Ala Pro Gly Gln Gly Leu Glu Trp Met
            35                  40                  45

Gly Arg Ile Asp Pro Asn Arg Gly Gly Thr Glu Tyr Asn Glu Lys Ala
        50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Ser Cys
            355                 360                 365

Ala Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445
```

<210> SEQ ID NO 232
<211> LENGTH: 214
<212> TYPE: PRT
<213> ORGANISM: Artificial Sequence
<220> FEATURE:
<223> OTHER INFORMATION: Fourth Polypeptide Chain of TRIDENT-B

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```